US012464945B2

(12) United States Patent
Xia et al.

(10) Patent No.: US 12,464,945 B2
(45) **Date of Patent: *Nov. 4, 2025**

(54) ORGANIC ELECTROLUMINESCENT MATERIALS AND DEVICES

(71) Applicant: UNIVERSAL DISPLAY CORPORATION, Ewing, NJ (US)

(72) Inventors: Chuanjun Xia, Lawrenceville, NJ (US); Raymond Kwong, Plainsboro, NJ (US); Ken-Tsung Wong, Tapei County (TW); Ming-Cheng Kuo, Taichung County (TW)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 277 days.

This patent is subject to a terminal disclaimer.

(21) Appl. No.: 17/692,444

(22) Filed: Mar. 11, 2022

(65) Prior Publication Data

US 2022/0216421 A1 Jul. 7, 2022

Related U.S. Application Data

(63) Continuation of application No. 15/915,199, filed on Mar. 8, 2018, now Pat. No. 11,316,113, which is a continuation of application No. 13/816,407, filed as application No. PCT/US2010/046218 on Aug. 20, 2010, now Pat. No. 9,954,180.

(51) Int. Cl.

| | |
|---|---|
| ***H10K 85/60*** | (2023.01) |
| ***C07D 401/14*** | (2006.01) |
| ***C07D 403/14*** | (2006.01) |
| ***C07D 405/14*** | (2006.01) |
| ***C07D 409/14*** | (2006.01) |
| ***C09K 11/06*** | (2006.01) |
| ***H10K 50/11*** | (2023.01) |
| ***H10K 85/30*** | (2023.01) |
| ***H10K 101/00*** | (2023.01) |
| ***H10K 101/10*** | (2023.01) |

(52) U.S. Cl.

CPC ......... *H10K 85/654* (2023.02); *C07D 401/14* (2013.01); *C07D 403/14* (2013.01); *C07D 405/14* (2013.01); *C07D 409/14* (2013.01); *C09K 11/06* (2013.01); *H10K 85/615* (2023.02); *H10K 85/622* (2023.02); *H10K 85/626* (2023.02); *H10K 85/6572* (2023.02); *H10K 85/6574* (2023.02); *H10K 85/6576* (2023.02); *C09K 2211/1007* (2013.01); *C09K 2211/1011* (2013.01); *C09K 2211/1029* (2013.01); *C09K 2211/1059* (2013.01); *C09K 2211/1088* (2013.01); *C09K 2211/1092* (2013.01); *H10K 50/11* (2023.02); *H10K 85/342* (2023.02); *H10K 85/655* (2023.02); *H10K 2101/10* (2023.02); *H10K 2101/27* (2023.02)

(58) Field of Classification Search

CPC ............ H01L 51/0072; H01L 51/0052; H01L 51/0054; H01L 51/0055; H01L 51/0058; H01L 51/0067; H01L 51/0085; H01L 51/50; H01L 51/5012; H01L 51/5016; H01L 51/5056; H01L 51/5072; H01L 51/5092; H01L 51/005; H01L 51/0051; H01L 51/0062; H01L 51/0071; C09K 11/06; C09K 2211/1018; C09K 2211/1029; C09K 2211/1059; C09K 2211/1007; C09K 2211/1011; C09K 2211/1044; C09K 2211/185; C09K 11/025; C07D 251/00; C07D 251/02; C07D 251/14; C07D 251/24; C07D 209/00; C07D 209/82; C07D 209/86; C07D 401/14; C07D 403/04; C07D 403/14; C07D 405/14; C07D 209/60; C07D 209/80; C07D 209/88; H10K 85/657; H10K 85/6572; H10K 50/11

USPC ................. 544/180, 194, 211, 212; 548/440; 257/40, E51.024, E51.025, E51.047, 257/E51.048, E51.049, E51.05, 88–104, 257/51.001–51.052; 428/690, 917, 313, 428/504, 505, 506, 691, 411; 427/58, 66; 313/500–512; 252/301.16–301.35

See application file for complete search history.

(56) References Cited

U.S. PATENT DOCUMENTS

| | | | |
|---|---|---|---|
| 4,769,292 | A | 9/1988 | Tang et al. |
| 5,061,569 | A | 10/1991 | VanSlyke et al. |
| 5,247,190 | A | 9/1993 | Friend et al. |
| 5,703,436 | A | 12/1997 | Forrest et al. |

(Continued)

FOREIGN PATENT DOCUMENTS

| | | |
|---|---|---|
| EP | 0650955 | 5/1995 |
| EP | 1725079 | 11/2006 |

(Continued)

OTHER PUBLICATIONS

Hong et al., "Effect of Substituents on the Electronic Structure and Degradation Process in Carbazole Derivatives for Blue OLED Host Materials," Chemistry of Materials, vol. 28 (2016) pp. 5791-5798. (Year: 2016)*

(Continued)

*Primary Examiner* — Dylan C Kershner

(74) *Attorney, Agent, or Firm* — DUANE MORRIS LLP

(57) ABSTRACT

Novel organic compounds comprising a bicarbazole core are provided. In particular, the compounds has a 3,3'-bicarbazole core substituted at the 9-position with a triazine or pyrimidine. The compounds may be used in organic light emitting devices to provide devices having improved efficiency and improved lifetime.

20 Claims, 3 Drawing Sheets

(56) References Cited

U.S. PATENT DOCUMENTS

| | | | | |
|---|---|---|---|---|
| 5,707,745 | A | 1/1998 | Forrest et al. | |
| 5,834,893 | A | 11/1998 | Bulovic et al. | |
| 5,844,363 | A | 12/1998 | Gu et al. | |
| 6,013,982 | A | 1/2000 | Thompson et al. | |
| 6,087,196 | A | 7/2000 | Sturm et al. | |
| 6,091,195 | A | 7/2000 | Forrest et al. | |
| 6,097,147 | A * | 8/2000 | Baldo | H10K 50/18 428/917 |
| 6,294,398 | B1 | 9/2001 | Kim et al. | |
| 6,303,238 | B1 | 10/2001 | Thompson et al. | |
| 6,337,102 | B1 | 1/2002 | Forrest et al. | |
| 6,468,819 | B1 | 10/2002 | Kim et al. | |
| 6,528,187 | B1 | 3/2003 | Okada | |
| 6,687,266 | B1 | 2/2004 | Ma et al. | |
| 6,835,469 | B2 | 12/2004 | Kwong et al. | |
| 6,921,915 | B2 | 7/2005 | Takiguchi et al. | |
| 7,087,321 | B2 | 8/2006 | Kwong et al. | |
| 7,090,928 | B2 | 8/2006 | Thompson et al. | |
| 7,154,114 | B2 | 12/2006 | Brooks et al. | |
| 7,250,226 | B2 | 7/2007 | Tokito et al. | |
| 7,279,704 | B2 | 10/2007 | Walters et al. | |
| 7,332,232 | B2 | 2/2008 | Ma et al. | |
| 7,338,722 | B2 | 3/2008 | Thompson et al. | |
| 7,393,599 | B2 | 7/2008 | Thompson et al. | |
| 7,396,598 | B2 | 7/2008 | Takeuchi et al. | |
| 7,431,968 | B1 | 10/2008 | Shtein et al. | |
| 7,445,855 | B2 | 11/2008 | Mackenzie et al. | |
| 7,534,505 | B2 | 5/2009 | Lin et al. | |
| 9,954,180 | B2 * | 4/2018 | Xia | H10K 85/6572 |
| 11,316,113 | B2 * | 4/2022 | Xia | H10K 85/6572 |
| 2002/0034656 | A1 | 3/2002 | Thompson et al. | |
| 2002/0134984 | A1 | 9/2002 | Igarashi | |
| 2002/0158242 | A1 | 10/2002 | Son et al. | |
| 2003/0138657 | A1 | 7/2003 | Li et al. | |
| 2003/0162053 | A1 | 8/2003 | Marks et al. | |
| 2003/0162802 | A1 | 8/2003 | Tsuboyama et al. | |
| 2003/0175553 | A1 | 9/2003 | Thompson et al. | |
| 2003/0230980 | A1 | 12/2003 | Forrest et al. | |
| 2004/0036077 | A1 | 2/2004 | Ise | |
| 2004/0110031 | A1 * | 6/2004 | Fukuda | C09K 11/06 313/506 |
| 2004/0137267 | A1 | 7/2004 | Igarashi et al. | |
| 2004/0137268 | A1 | 7/2004 | Igarashi et al. | |
| 2004/0174116 | A1 | 9/2004 | Lu et al. | |
| 2005/0025993 | A1 | 2/2005 | Thompson et al. | |
| 2005/0112407 | A1 | 5/2005 | Ogasawara et al. | |
| 2005/0238919 | A1 | 10/2005 | Ogasawara | |
| 2005/0244673 | A1 | 11/2005 | Satoh et al. | |
| 2005/0260441 | A1 | 11/2005 | Thompson et al. | |
| 2005/0260449 | A1 | 11/2005 | Walters et al. | |
| 2006/0008670 | A1 | 1/2006 | Lin et al. | |
| 2006/0202194 | A1 | 9/2006 | Jeong et al. | |
| 2006/0240279 | A1 | 10/2006 | Adamovich et al. | |
| 2006/0251923 | A1 | 11/2006 | Lin et al. | |
| 2006/0263635 | A1 | 11/2006 | Ise | |
| 2006/0280965 | A1 | 12/2006 | Kwong | |
| 2007/0190359 | A1 | 8/2007 | Knowles et al. | |
| 2007/0278938 | A1 | 12/2007 | Yabunouchi et al. | |
| 2008/0015355 | A1 | 1/2008 | Schafer et al. | |
| 2008/0018221 | A1 | 1/2008 | Egen et al. | |
| 2008/0066235 | A1 | 3/2008 | Rubio | |
| 2008/0106190 | A1 | 5/2008 | Yabunouchi et al. | |
| 2008/0124572 | A1 | 5/2008 | Mizuki et al. | |
| 2008/0220265 | A1 | 9/2008 | Xia et al. | |
| 2008/0297033 | A1 | 12/2008 | Knowles et al. | |
| 2009/0008605 | A1 | 1/2009 | Kawamura et al. | |
| 2009/0009065 | A1 | 1/2009 | Nishimura et al. | |
| 2009/0017330 | A1 | 1/2009 | Iwakuma et al. | |
| 2009/0030202 | A1 | 1/2009 | Iwakuma et al. | |
| 2009/0039776 | A1 | 2/2009 | Yamada et al. | |
| 2009/0045730 | A1 | 2/2009 | Nishimura et al. | |
| 2009/0045731 | A1 | 2/2009 | Nishimura et al. | |
| 2009/0066235 | A1 | 3/2009 | Yabunouchi | |
| 2009/0101870 | A1 | 4/2009 | Pakash et al. | |
| 2009/0108737 | A1 | 4/2009 | Kwong et al. | |
| 2009/0115316 | A1 | 5/2009 | Zheng et al. | |
| 2009/0165846 | A1 | 7/2009 | Johannes et al. | |
| 2009/0167162 | A1 | 7/2009 | Lin et al. | |
| 2009/0179554 | A1 | 7/2009 | Kuma et al. | |
| 2009/0242876 | A1 | 10/2009 | Brunner et al. | |
| 2009/0302745 | A1 | 12/2009 | Otsu | |
| 2010/0044695 | A1 | 2/2010 | Kai | |
| 2010/0237339 | A1 | 9/2010 | Nomura | |
| 2011/0279020 | A1 * | 11/2011 | Inoue | C07D 403/14 548/440 |
| 2012/0235123 | A1 * | 9/2012 | Lee | C07D 471/14 546/159 |
| 2014/0131665 | A1 | 5/2014 | Xia et al. | |
| 2014/0231783 | A1 | 8/2014 | Bae et al. | |

FOREIGN PATENT DOCUMENTS

| | | |
|---|---|---|
| EP | 2034538 | 3/2009 |
| EP | 2568030 | 3/2013 |
| JP | 2003133075 | 5/2003 |
| JP | 200511610 | 1/2005 |
| JP | 2007123392 | 5/2007 |
| JP | 2007254287 | 10/2007 |
| JP | 2008074939 | 4/2008 |
| JP | 2008135498 | 6/2008 |
| KR | 20120013173 | 2/2012 |
| TW | 201120186 | 6/2011 |
| TW | 201130805 | 9/2011 |
| WO | 01/39234 | 5/2001 |
| WO | 02/02714 | 1/2002 |
| WO | 02015654 | 2/2002 |
| WO | 03040257 | 5/2003 |
| WO | 03060956 | 7/2003 |
| WO | 2004093207 | 10/2004 |
| WO | 04107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2007119816 | 10/2007 |
| WO | 2008056746 | 5/2008 |
| WO | 2008101842 | 8/2008 |
| WO | 2008123189 | 10/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009021126 | 2/2009 |
| WO | 2009050290 | 4/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |
| WO | 2011055934 | 5/2011 |
| WO | 2011071255 | 6/2011 |
| WO | 2011132683 | 10/2011 |

(56) References Cited

FOREIGN PATENT DOCUMENTS

| | | |
|---|---|---|
| WO | 2011139055 | 11/2011 |
| WO | 2011162162 | 12/2011 |

OTHER PUBLICATIONS

Montalti et al., Handbook of Photochemistry, Marco Montalti, Alberto Credi, Luca Prodi, and M. Teresa Gandolfi, 3rd edition.

Vaitkeviciene et al., "Well-defined [3,3] bicarbazolyl-based electroactive compounds for optoelectronics" Synthetic Metals, 2008, vol. 158, pp. 383-390.

Tominaga et al., Machine Translation of JP 2003-133075, Date of Japanese Language publication: 2003, pp. 1-15.

Adachi, Chihaya et al., "Organic Electroluminescent Device Having a Hole Conductor as an Emitting Layer," Appl. Phys. Lett., 55(15): 1489-1491 (1989).

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., 90, Apr. 30, 2007, 183503-1-183503-3.

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 1, 4-6 (1999).

Gao, Zhigiang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 1: 15-20 (2000).

Hamada, Yuji et al., "High Luminance in Organic Electroluminescent Devices with Bis(10-hydroxybenzo[h]quinolinato)beryllium as an Emitter," Chem, Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).

Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv, Mater., 19:739-743 (2007).

Huang, Wei-Sheng et al., "Highly Phosphorescent Bis-Cyclometalated Iridium Complexes Containing Benzoimidazole-Based Ligands," Chem. Mater., 16(12):2480-2488 (2004).

Hung, L.S. et al., "Anode Modification in Organic Light-Emitting Diodes by Low-Frequency Plasma Polymerization of CHF3," Appl. Phys. Lett., 78(5):673-675 (2001).

Ikai, Masamichi et al., "Highly Efficient Phosphorescence From Organic Light-Emitting Devices with an Exciton-Block Layer," Appl. Phys. Lett., 79(2):156-158 (2001).

Ikeda, Hisao et al., "P-185 Low-Drive-Voltage OLEDs with a Buffer Layer Having Molybdenum Oxide," SID Symposium Digest, 37:923-926 (2006).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).

Kanno, Hiroshi et al., "Highly Efficient and Stable Red Phosphorescent Organic Light-Emitting Device Using bis[2-(2-benzothiazoyl)phenolato]zinc(II) as host material." Appl. Phys. Lett., 90;123509-1-123509-3 (2007).

Kido, Junji et al., 1,2,4-Triazole Derivative as an Electron Transport Layer in Organic Electroluminescent Devices, Jpn. J. Appl. Phys., 32:L917-L920 (1993).

Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).

Kwong, Raymond C. et al., "High Operational Stability of Electrophosphorescent Devices," Appl. Phys. Lett., 81(1)162-164 (2002).

Lamansky, Sergey et al., "Synthesis and Characterization of Phosphorescent Cyclometalated Iridium Complexes," Inorg. Chem., 40(7):1704-1711 (2001).

Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).

Lo, Shih-Chun et al., "Blue Phosphorescence from Iridium(III) Complexes at Room Temperature," Chem. Mater., 18 (21)5119-5129 (2006).

Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).

Mi, Bao-Xiu et al., "Thermally Stable Hole-Transporting Material for Organic Light-Emitting Diode an Isoindole Derivative," Chem. Mater., 15(16):3148-3151 (2003).

Nishida, Jun-ichi et al., "Preparation, Characterization, and Electroluminescence Characteristics of α-Dilmine-type Platinum(II) Complexes with Perfluorinated Phenyl Groups as Ligands," Chem. Lett., 34(4): 592-593 (2005).

Niu, Yu-Hua et al., "Highly Efficient Electrophosphorescent Devices with Saturated Red Emission from a Neutral Osmium Complex," Chem. Mater., 17(13):3532-3536 (2005).

Noda, Tetsuya and Shirota, Yasuhiko, "5,5'-Bis(dimesitylboryl)-2,2'-bithiophene and 5,5"-Bis (dimesitylboryl)-2,2'5',2Δ-terthiophene as a Novel Family of Electron-Transporting Amorphous Molecular Materials," J. Am. Chem. Soc., 120 (37):9714-9715 (1998).

Okumoto, Kenji et al., "Green Fluorescent Organic Light-Emitting Device with External Quantum Efficiency of Nearly 10%," Appl. Phys. Lett., 89:063604-1-063504-3 (2006).

Palilis, Leonidas C., "High Efficiency Molecular Organic Light-Emitting Diodes Based On Silole Derivatives And Their Exciplexes," Organic Electronics, 4:113-121 (2003).

Paulose, Betty Marie Jennifer S. et al., "First Examples of Alkenyl Pyridines as Organic Ligands for Phosphorescent Iridium Complexes," Adv. Mater., 16(22):2003-2007 (2004).

Ranjan, Sudhir et al., "Realizing Green Phosphorescent Light-Emitting Materials from Rhenium(I) Pyrazolato Diimine Complexes," Inorg. Chem., 42(4):1248-1255 (2003).

Sakamoto, Youichi et al., "Synthesis, Characterization, and Electron-Transport Property of Perfluorinated Phenylene Dendrimers," J. Am. Chem. Soc., 122(8):1832-1833 (2000).

Salbeck, J. et al., "Low Molecular Organic Glasses for Blue Electroluminescence," Synthetic Metals, 91: 209-215 (1997).

Shirota, Yasuhiko et al., "Starburst Molecules Based on pi-Electron Systems as Materials for Organic Electroluminescent Devices," Journal of Luminescence, 72-74:985-991 (1997).

Sotoyama, Wataru et al., "Efficient Organic Light-Emitting Diodes with Phosphorescent Platinum Complexes Containing NCN-Coordinating Tridentate Ligand," Appl. Phys, Lett., 86:153505-1-153505-3 (2005).

Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).

T. Östergård et al., "Langmuir-Blodgett Light-Emitting Diodes Of Poly(3-Hexylthiophene) Electro-Optical Characteristics Related to Structure," Synthetic Metals, 88:171-177 (1997).

Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).

Tang, C.W. and VanSlyke, S.A., "Organic Electroluminescent Diodes," Appl. Phys. Lett., 51(12):913-915 (1987).

(56) References Cited

OTHER PUBLICATIONS

Tung, Yung-Liang et al., "Organic Light-Emitting Diodes Based on Charge-Neutral Ru II PHosphorescent Emitters," Adv, Mater., 17(8)1058-1064 (2005).
Van Slyke, S. A. et al., "Organic Electroluminescent Devices with Improved Stability," Appl. Phys. Lett., 69 (15):2160-2162 (1996).
Wang, Y. et al., "Highly Efficient Electroluminescent Materials Based on Fluorinated Organometallic Iridium Compounds," Appl. Phys, Lett., 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).

* cited by examiner

ORGANIC ELECTROLUMINESCENT MATERIALS AND DEVICES

CROSS REFERENCE TO RELATED APPLICATIONS

This application is a continuation of U.S. application Ser. No. 15/915,199, filed Mar. 8, 2018, which is a continuation of U.S. application Ser. No. 13/816,407, filed Feb. 11, 2013, now U.S. Pat. No. 9,954,180, which is a U.S. national phase application filed under 35 U.S.C. § 371 of International Application No. PCT/US2010/046218, filed Aug. 20, 2010, the entireties of which are included herein.

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to organic light emitting devices (OLEDs). More specifically, the present invention pertains to phosphorescent organic materials comprising a bicarbazole having a nitrogen-containing heterocycle at the 9 position.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted $Ir(ppy)_3$, which has the structure:

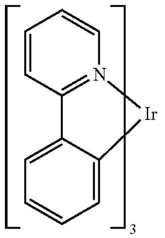

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher"

HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

Compounds comprising a bicarbazole are provided. The compounds have the formula:

Formula I

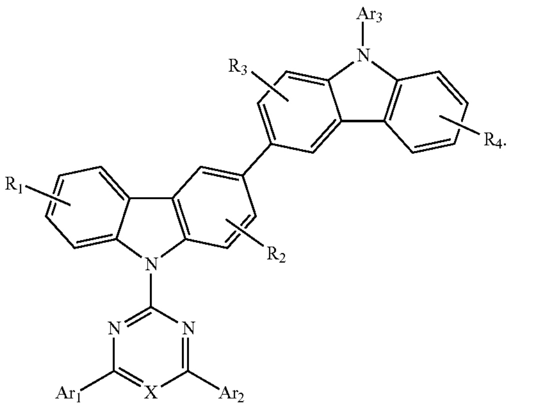

$R_1$, $R_2$, $R_3$, and $R_4$ may represent mono, di, tri, or tetra substitutions. $R_1$, $R_2$, $R_3$, and $R_4$ are independently selected from the group consisting of hydrogen, alkyl, alkoxy, amino, alkenyl, alkynyl, aryl and heteroaryl. $Ar_1$, $Ar_2$, and $Ar_3$ are independently selected from aryl or heteroaryl. $Ar_1$, $Ar_2$, and $Ar_3$ may be further substituted. X is C or N.

In one aspect, $Ar_1$, $Ar_2$, and $Ar_3$ are independently selected from the group consisting of phenyl, pyridine, naphthalene, biphenyl, terphenyl, fluorene, dibenzofuran, dibenzothiophene, phenanthrene, and triphenylene. $Ar_1$, $Ar_2$, and $Ar_3$ are independently further substituted with a substituent selected from the group consisting of hydrogen, alkyl, alkoxy, amino, alkenyl, alkynyl, aryl and heteroaryl, but the substituent is not an aryl or heteroaryl fused directly to $Ar_1$, $Ar_2$, and $Ar_3$. Preferably, $Ar_1$ and $Ar_2$ are independently selected from the group consisting of phenyl, pyridine, and naphthalene. Preferably, $Ar_3$ is selected from the group consisting of phenyl, biphenyl, dibenzofuran, and dibenzothiophene.

In another aspect, $R_1$, $R_2$, $R_3$, and $R_4$ are hydrogen.

Specific examples of compounds comprising bicarbazole are also provided. In particular, the compound is selected from the group consisting of Compound 1 to Compound 184 as defined herein.

A first device comprising an organic light emitting device is also provided. The device further comprises an anode, a cathode, and an organic layer, disposed between the anode and the cathode. The organic layer comprises a compound having Formula I, as described above.

$R_1$, $R_2$, $R_3$, and $R_4$ may represent mono, di, tri, or tetra substitutions. $R_1$, $R_2$, $R_3$, and $R_4$ are independently selected from the group consisting of hydrogen, alkyl, alkoxy, amino, alkenyl, alkynyl, aryl and heteroaryl. $Ar_1$, $Ar_2$, and $Ar_3$ are independently selected from aryl or heteroaryl. $Ar_1$, $Ar_2$, and $Ar_3$ may be further substituted. X is C or N.

In one aspect, $Ar_1$, $Ar_2$, and $Ar_3$ are independently selected from the group consisting of phenyl, pyridine, naphthalene, biphenyl, terphenyl, fluorene, dibenzofuran, dibenzothiophene, phenanthrene, and triphenylene. $Ar_1$, $Ar_2$, and $Ar_3$ are independently further substituted with a substituent selected from the group consisting of hydrogen, alkyl, alkoxy, amino, alkenyl, alkynyl, aryl and heteroaryl, but the substituent is not an aryl or heteroaryl fused directly to $Ar_1$, $Ar_2$, and $Ar_3$. Preferably, $Ar_1$ and $Ar_2$ are independently selected from the group consisting of phenyl, pyridine, and naphthalene. Preferably, $Ar_3$ is selected from the group consisting of phenyl, biphenyl, dibenzofuran, and dibenzothiophene.

In another aspect, $R_1$, $R_2$, $R_3$, and $R_4$ are hydrogen.

Specific examples of devices containing compounds comprising bicarbazole are also provided. In particular, the compound is selected from the group consisting of Compound 1-Compound 184.

In one aspect, the organic layer is deposited using solution processing.

In one aspect, the organic layer is an emissive layer and the compound having Formula I is a host.

In another aspect, the organic layer further comprises an emissive dopant having the formula:

D1

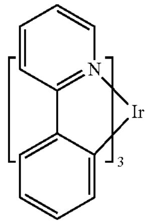

D2

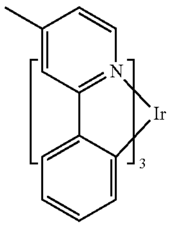

D3

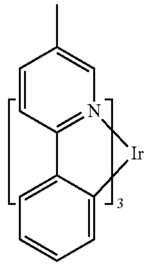

-continued
D4
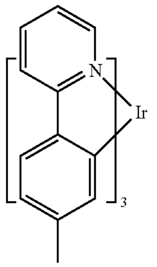
D5
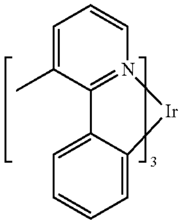
D6
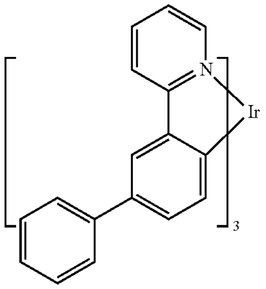
D7
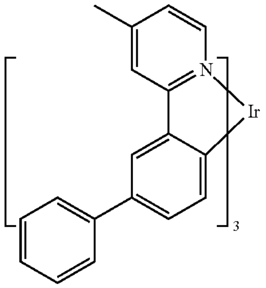
D8
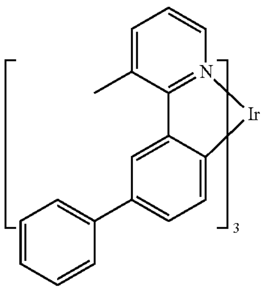
-continued
D9
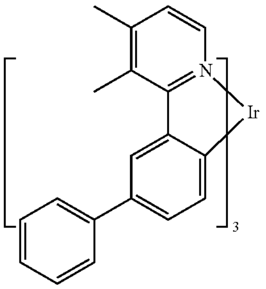
D10
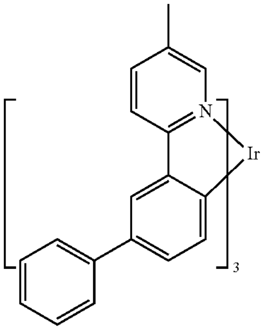
D11
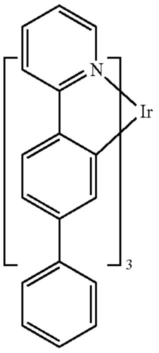
D12
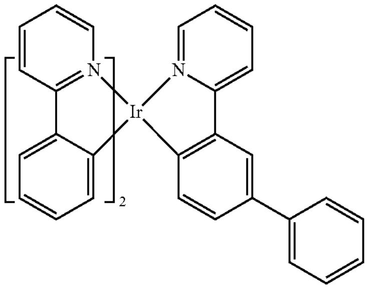
D13
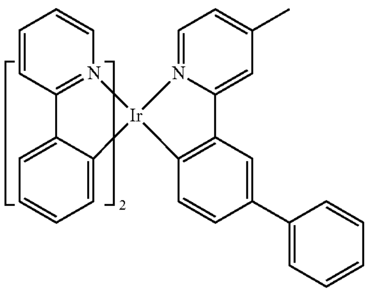

D14
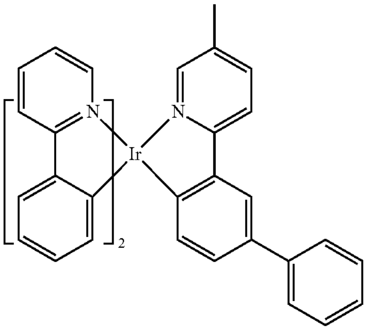
D15
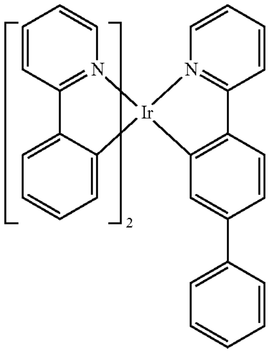
D16
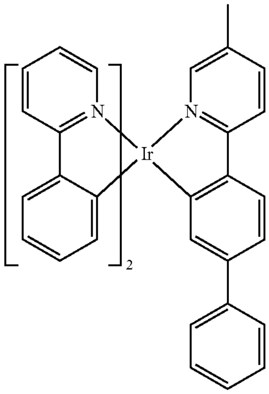
D17
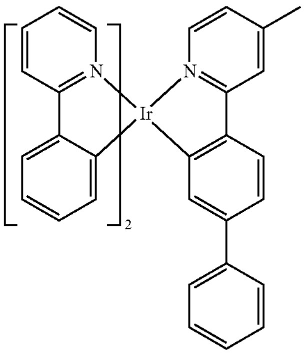
D18
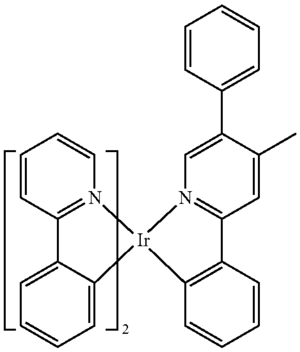
D19
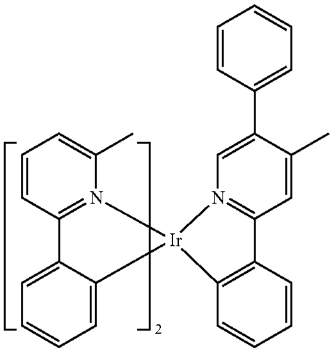
D20
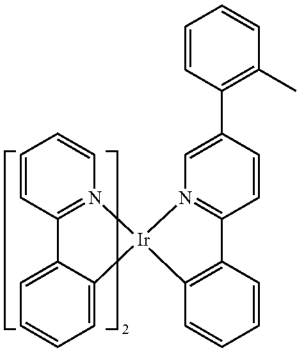
D21
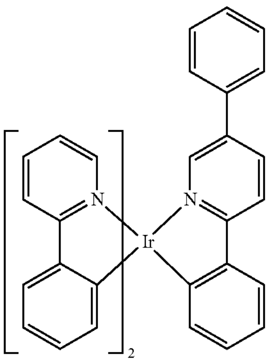

-continued
D22
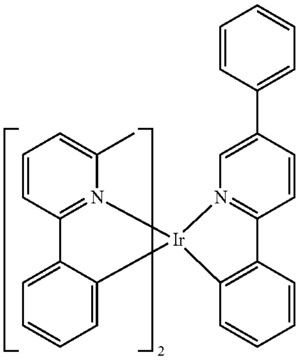
D23
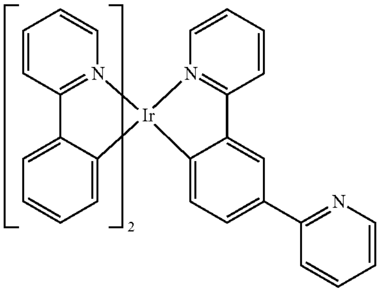
D24
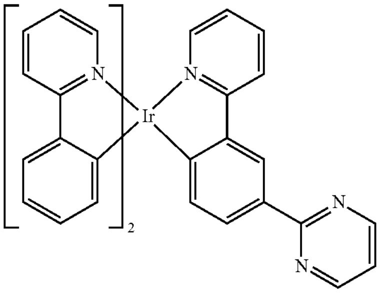
D25
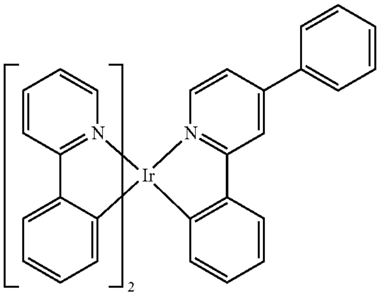
D26
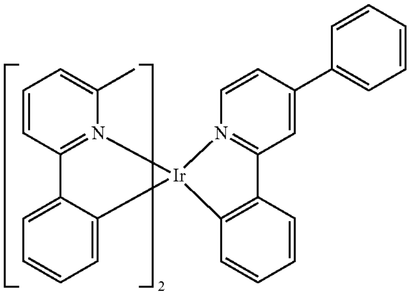
-continued
D27
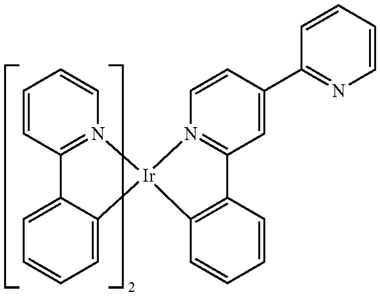
D28
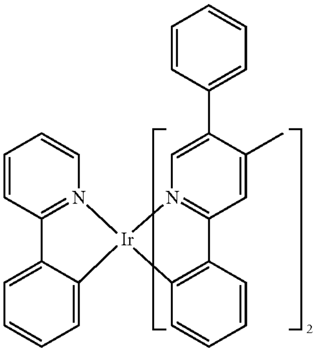
D29
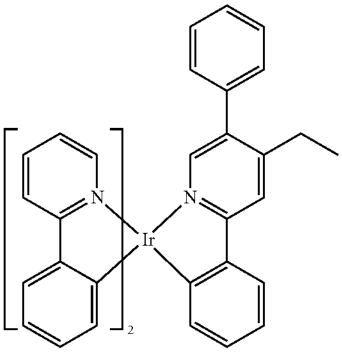
D30
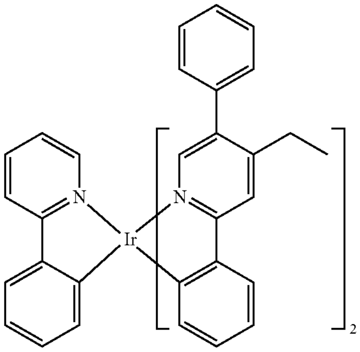
D31
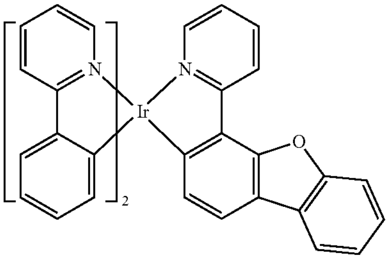

-continued
D32
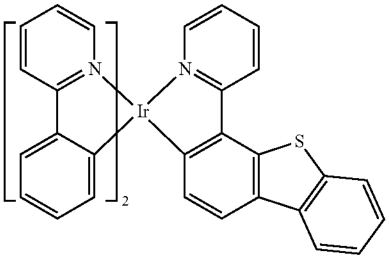
D33
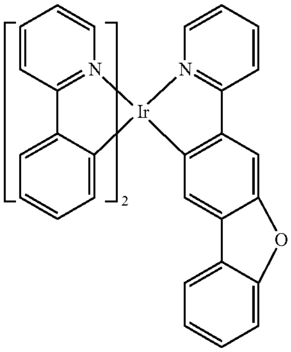
D34
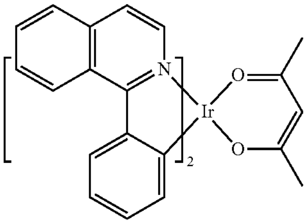
D35
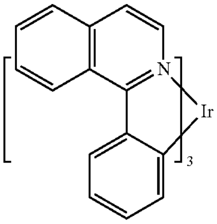
D36
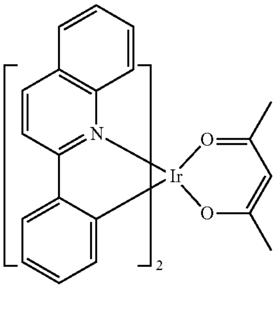
-continued
D37
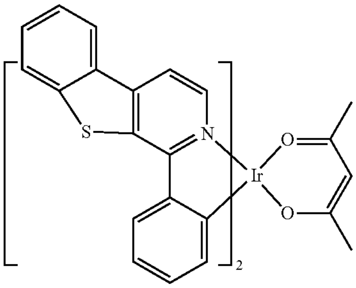
D38
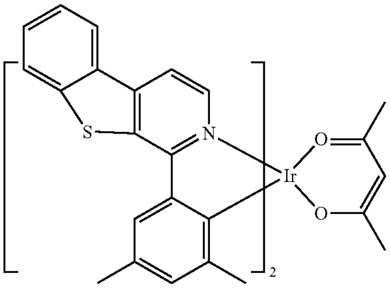
D39
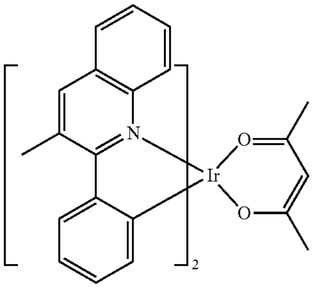
D40
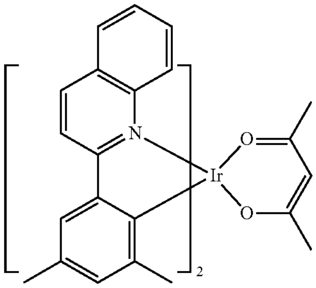
D41
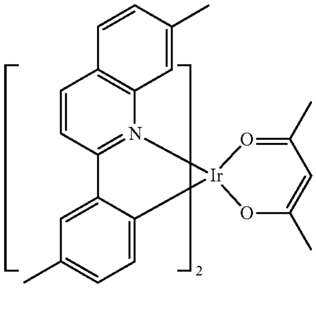

-continued

D42

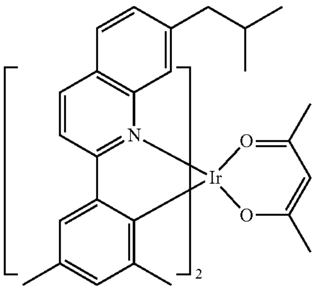

D43

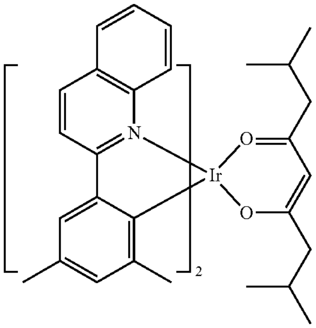

D44

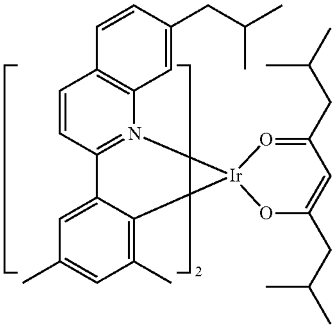

D45

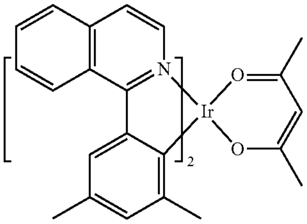

D46

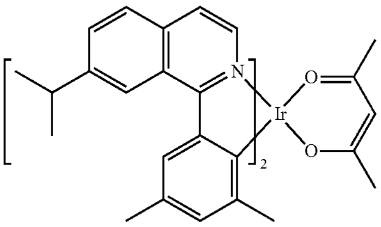

-continued

D47

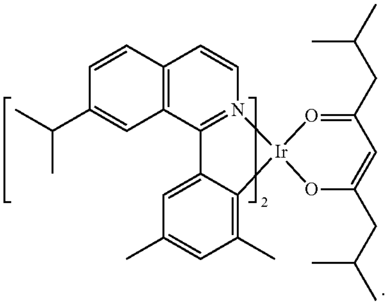

In one aspect, the first device is a consumer product. In another aspect, the first device is an organic light emitting device.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
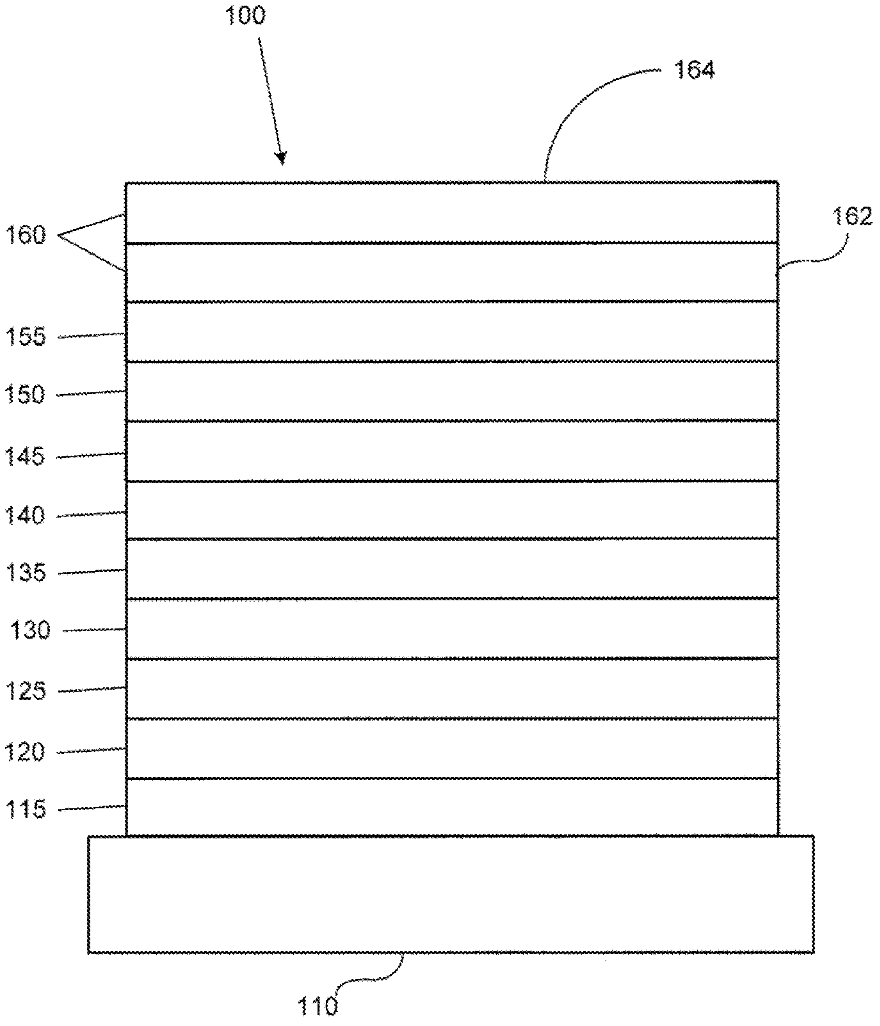
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F.sub.4-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
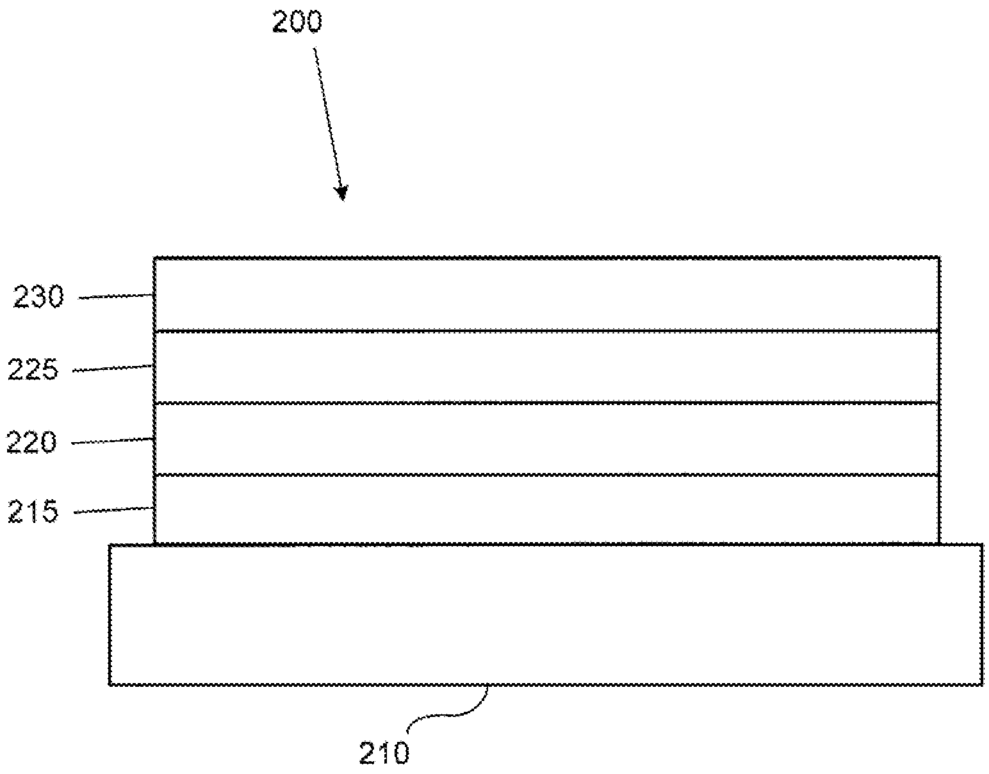
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

Figure 3:
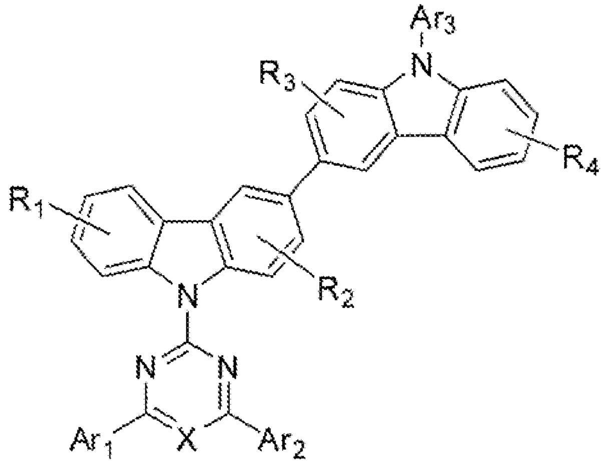
FIG. 3 shows a bicarbazole compound with a nitrogen-containing heterocycle substitution at the 9-position.

Novel bicarbazole containing compounds are provided (illustrated in FIG. 3). More specifically, these compounds contain a 3,3'-bicarbazole core and triazine or pyrimidine substitution at the 9-position. These compounds may be used as hosts for phosphorescent OLEDs.

Carbazole containing compounds for use as OLED materials have been previously described. In particular, 3,3'-bicarbazole compounds have good hole transporting properties, but have poor stability toward electrons. Alkyl and aryl substituted 3,3'-bicarbazole compounds have been used as hole transporting materials and hosts in OLEDs; however, these compounds also have imbalanced charge transporting properties and poor electron stability and may provide devices with low efficiency and limited lifetime. For example, a diaryl substituted 3,3'-bicarbazole, i.e. H1, has a HOMO around 5.6 eV, very good for hole transporting but poor for electron transporting and stability. Therefore, the 3,3'-bicarbazole compounds reported in the literature may have limited use.

In the present invention, nitrogen containing electron deficient heterocycles were introduced to 3,3'-bicarbazole compounds. In particular, the compounds contain a 3,3'-bicarbazole core and triazine or pyrimidine substitution at the 9 position. The nitrogen containing heterocycle tunes the HOMO/LUMO levels as well as increases the compound's stability toward electrons. In addition, these compounds contain a donor part, i.e. bicarbazole, and an acceptor part, i.e. electron deficient nitrogen heterocycle. Without being bound by theory, it is believed that these donor-acceptor type molecules can shrink singlet and triplet gap and improve stability to both hole and electrons. Therefore, these 3,3'-bicarbazole compounds containing a nitrogen heterocycle may provide devices having better stability and lower operating voltage.

Compounds comprising a bicarbazole are provided. The compounds have the formula:

Formula I

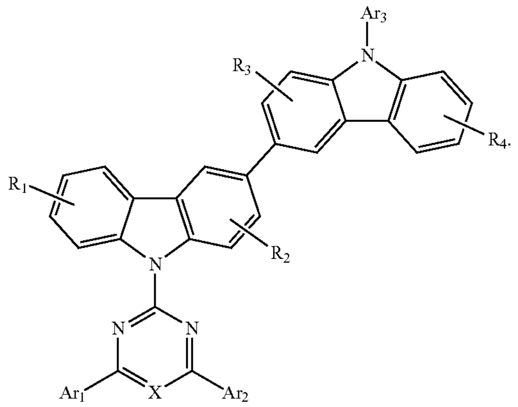

$R_1$, $R_2$, $R_3$, and $R_4$ may represent mono, di, tri, or tetra substitutions. $R_1$, $R_2$, $R_3$, and $R_4$ are independently selected from the group consisting of hydrogen, alkyl, alkoxy, amino, alkenyl, alkynyl, aryl and heteroaryl. $Ar_1$, $Ar_2$, and $Ar_3$ are independently selected from aryl or heteroaryl. $Ar_1$, $Ar_2$, and $Ar_3$ may be further substituted. X is C or N.

In one aspect, $Ar_1$, $Ar_2$, and $Ar_3$ are independently selected from the group consisting of phenyl, pyridine, naphthalene, biphenyl, terphenyl, fluorene, dibenzofuran, dibenzothiophene, phenanthrene, and triphenylene, and $Ar_1$, $Ar_2$, and $Ar_3$ are independently further substituted with a substituent selected from the group consisting of hydrogen, alkyl, alkoxy, amino, alkenyl, alkynyl, aryl and heteroaryl, but the substituent is not an aryl or heteroaryl fused directly to $Ar_1$, $Ar_2$, and $Ar_3$. Preferably, $Ar_1$ and $Ar_2$ are independently selected from the group consisting of phenyl, pyridine, and naphthalene. Preferably, $Ar_3$ is selected from the group consisting of phenyl, biphenyl, dibenzofuran, and dibenzothiophene.

In another aspect, $R_1$, $R_2$, $R_3$, and $R_4$ are hydrogen.

Specific examples of compounds comprising bicarbazole are also provided. In particular, the compound is selected from the group consisting of:

Compound 1

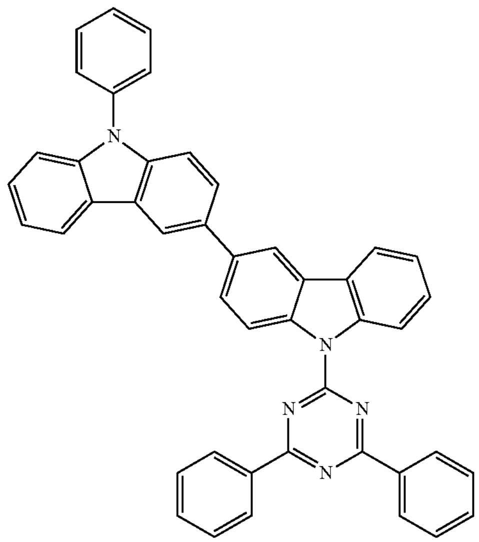

-continued
Compound 2
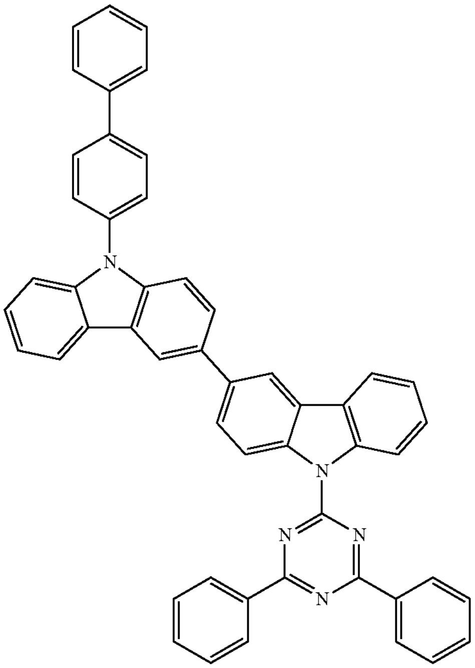
Compound 3
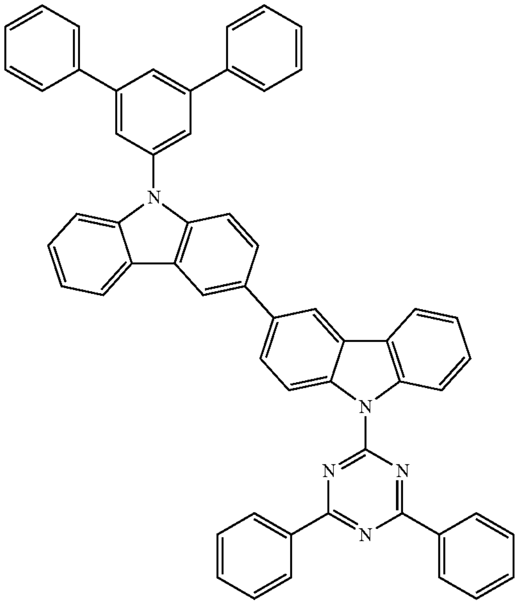
-continued
Compound 4
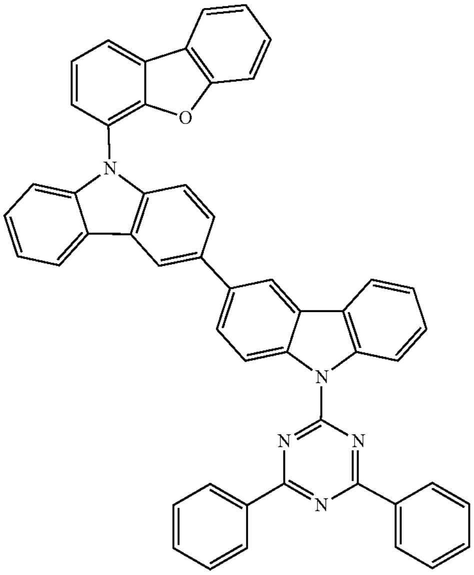
Compound 5
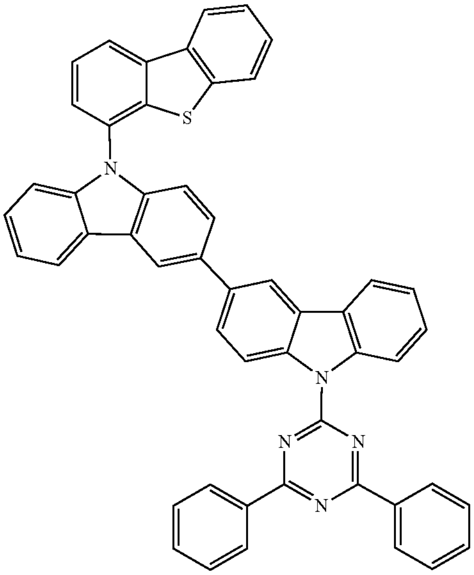

-continued
Compound 6
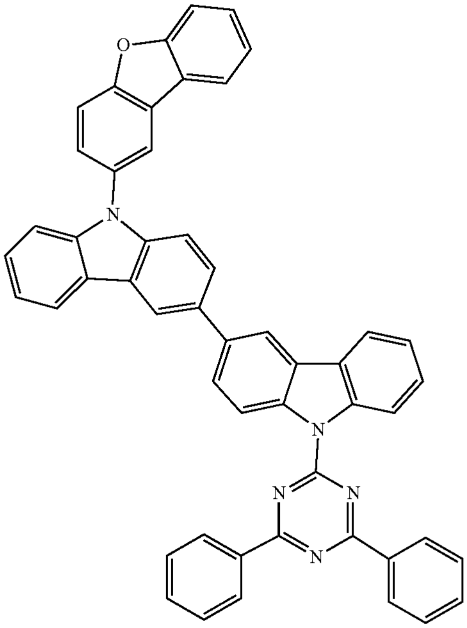
Compound 7
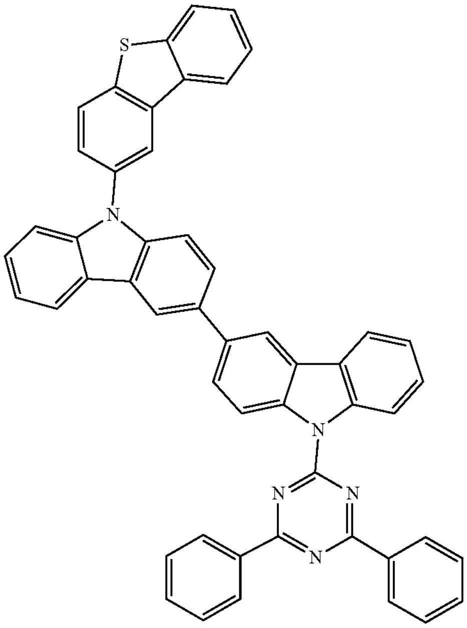
-continued
Compound 8
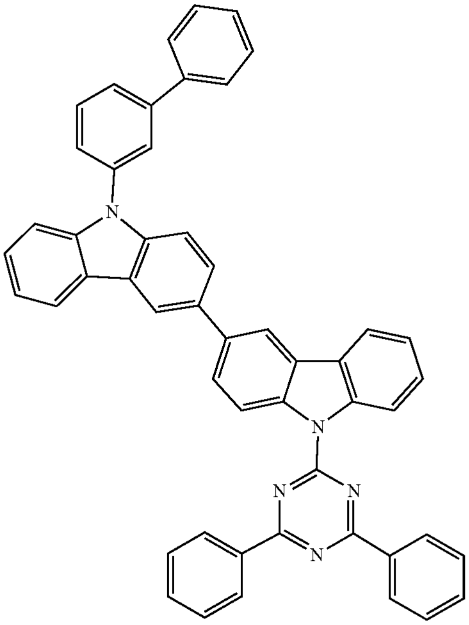
Compound 9
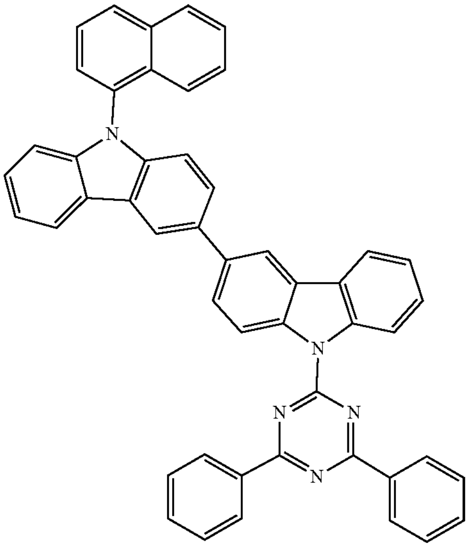

-continued
Compound 10
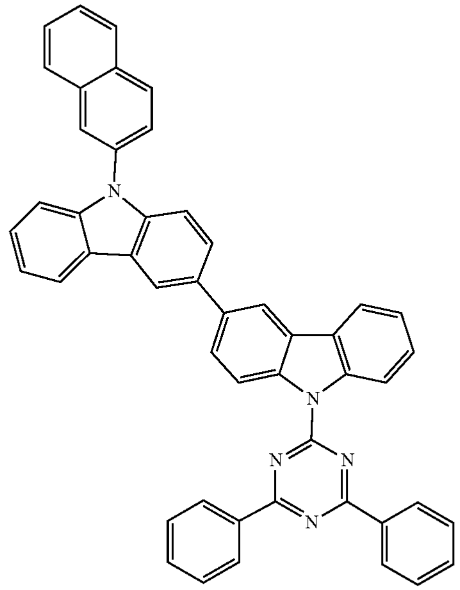
Compound 11
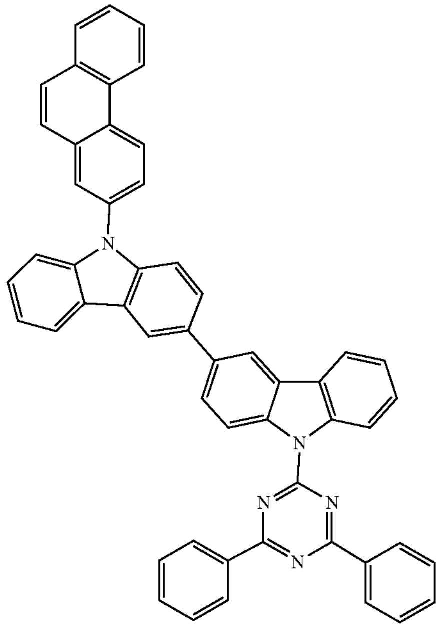
-continued
Compound 12
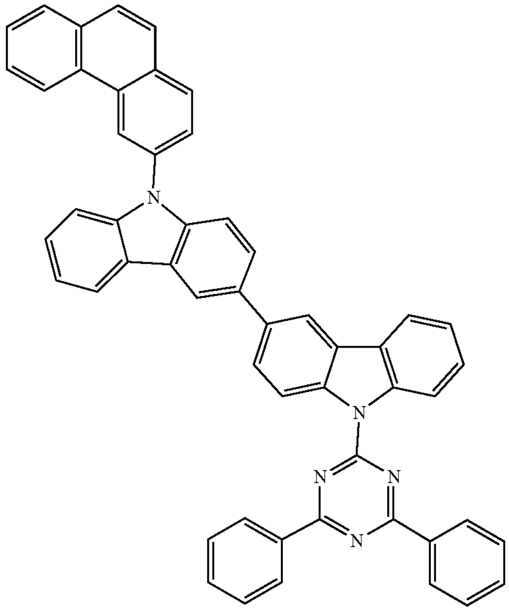
Compound 13
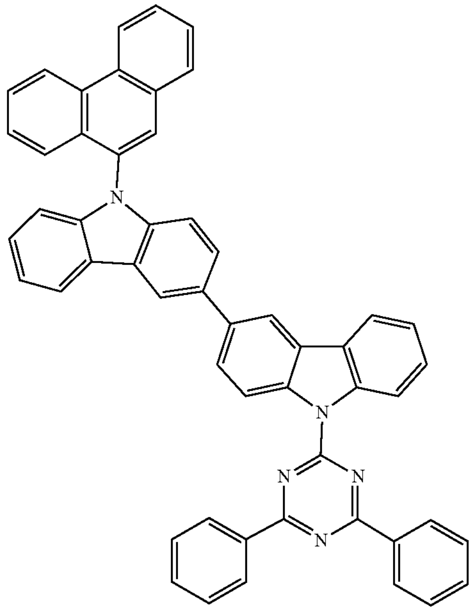

-continued
Compound 14
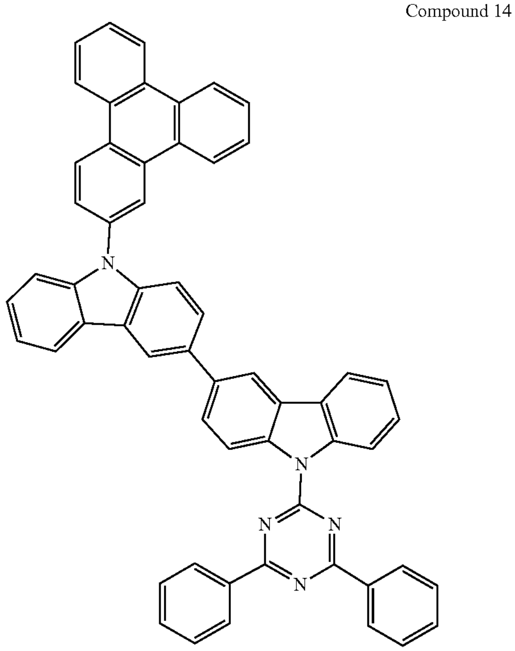
Compound 15
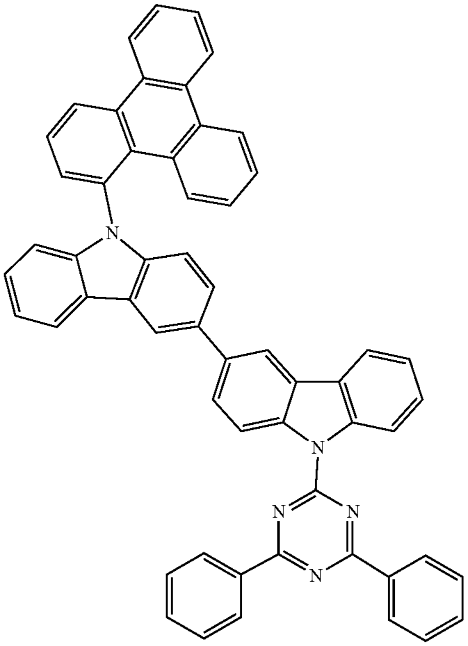
-continued
Compound 16
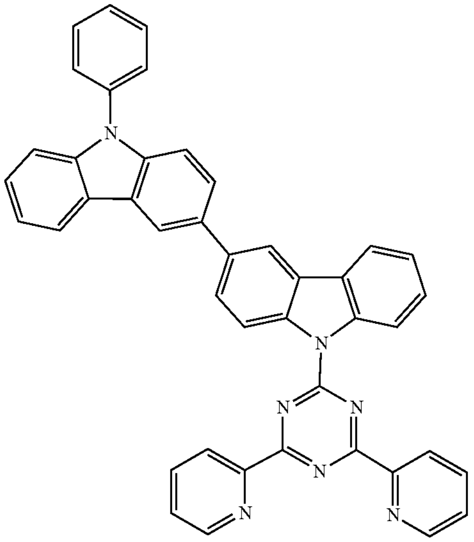
Compound 17
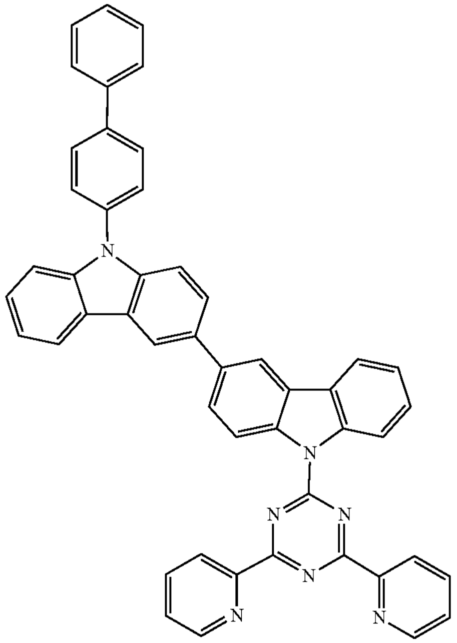

-continued
Compound 18
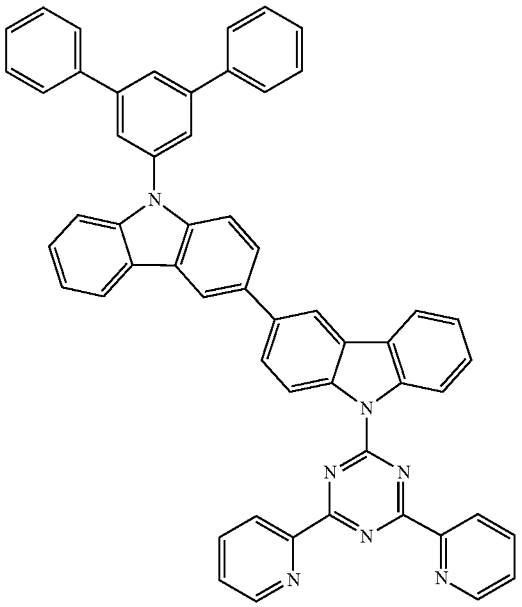
Compound 19
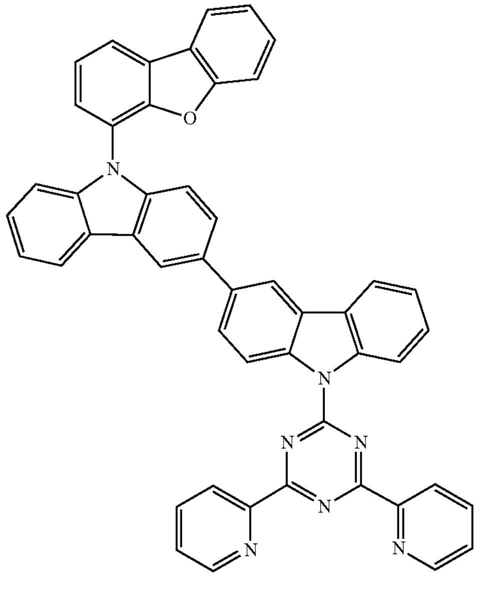
-continued
Compound 20
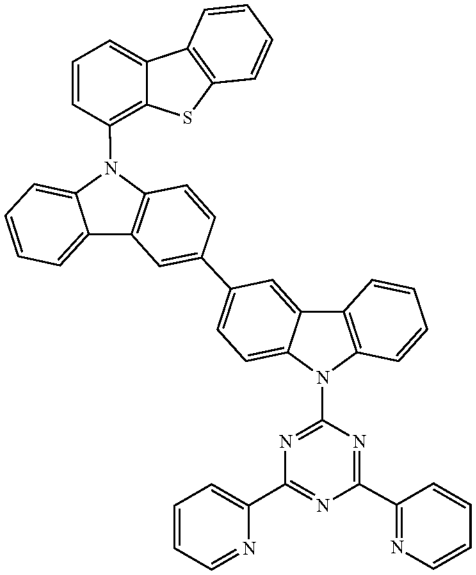
Compound 21
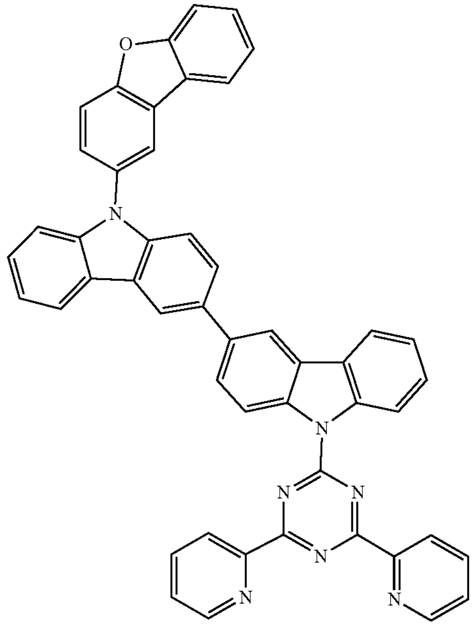

-continued
Compound 22
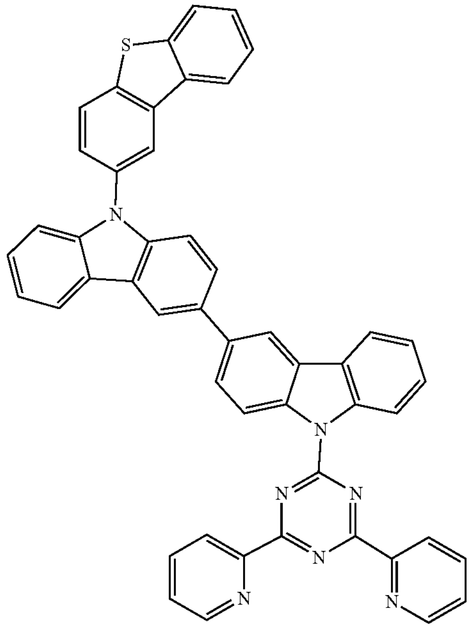
Compound 23
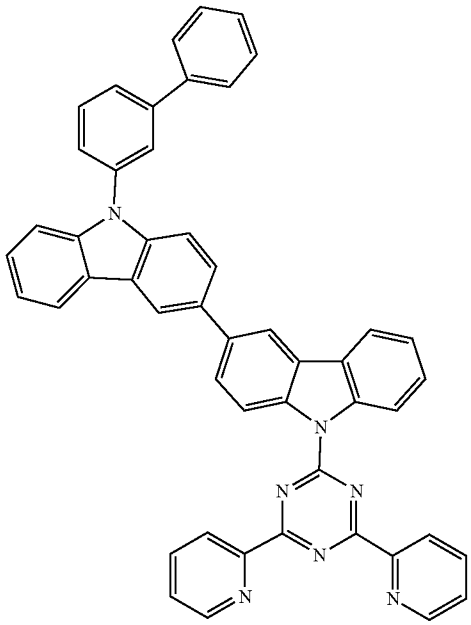
-continued
Compound 24
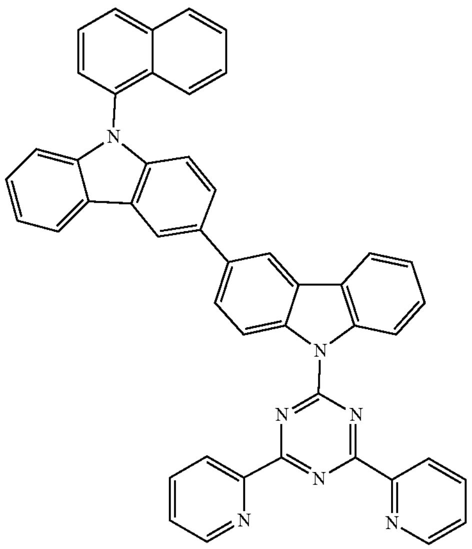
Compound 25
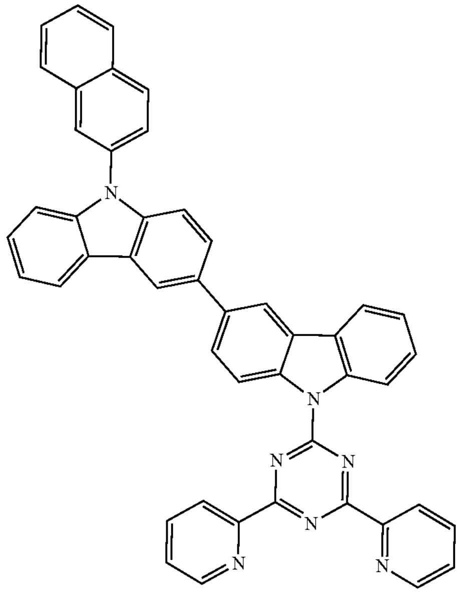

-continued
Compound 26
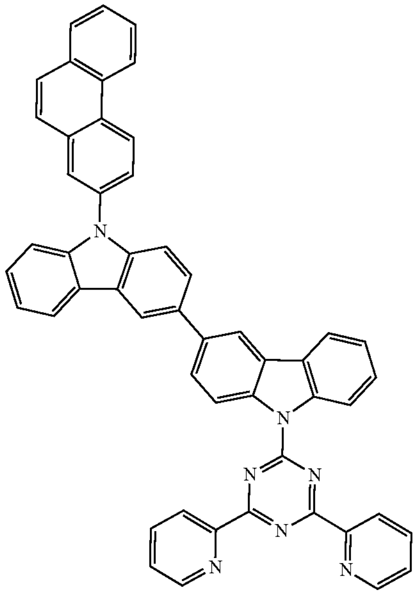
Compound 27
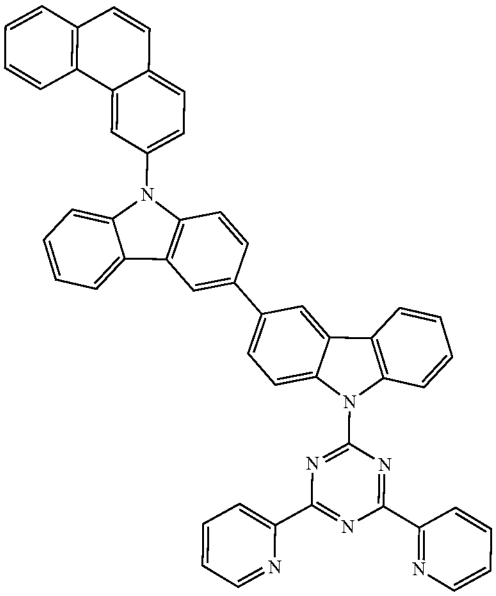
-continued
Compound 28
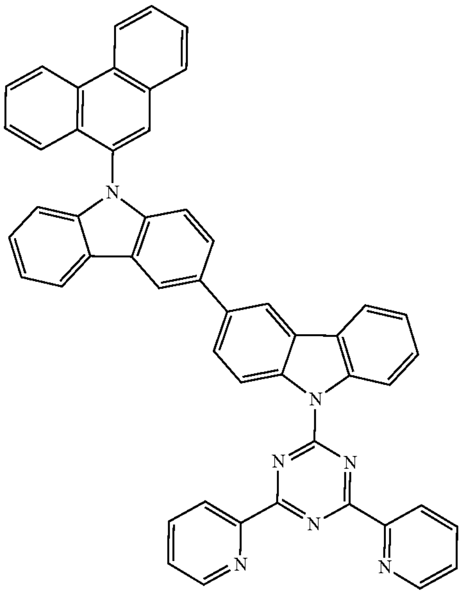
Compound 29
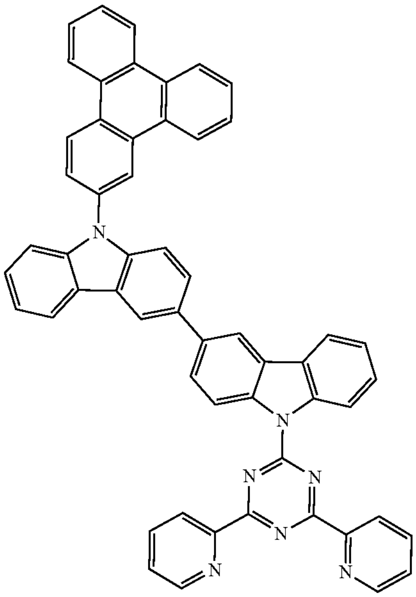

-continued
Compound 30
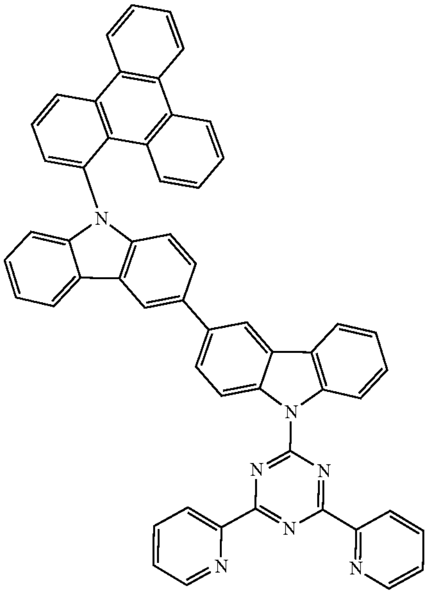
Compound 31
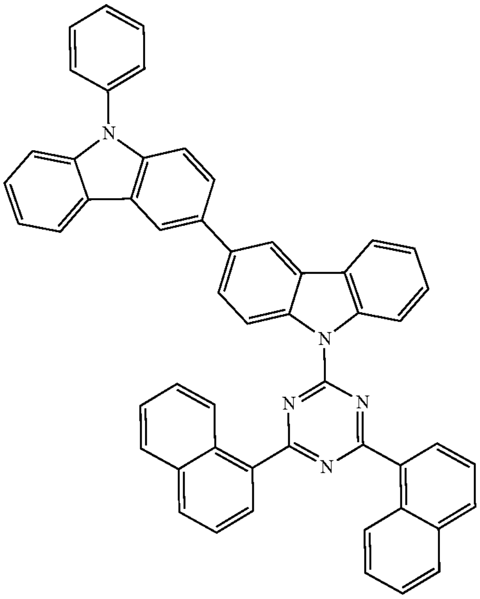
-continued
Compound 32
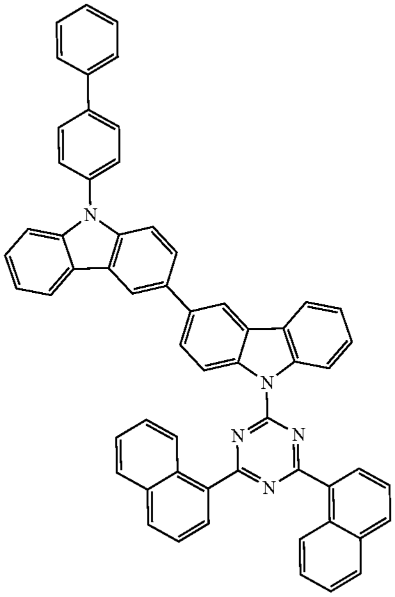
Compound 33
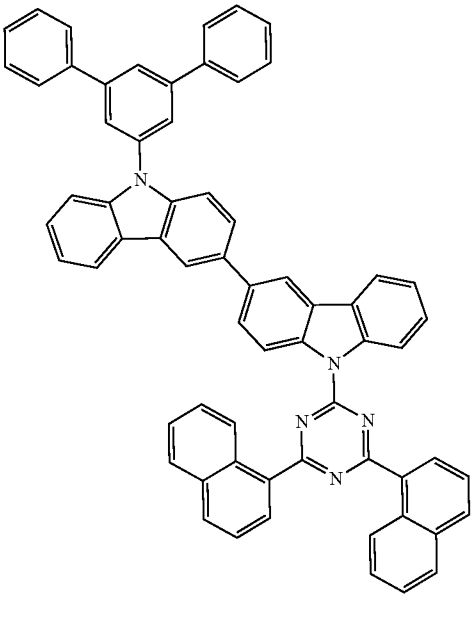

-continued
Compound 34
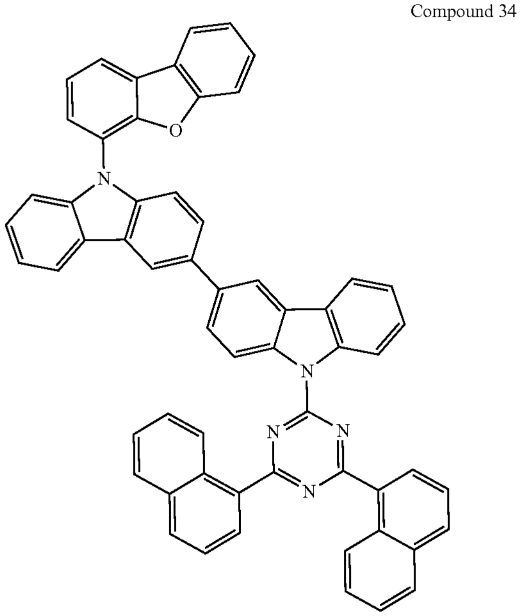
Compound 35
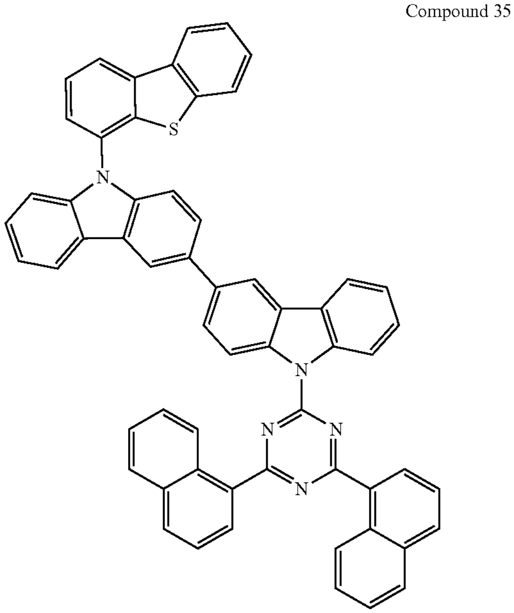
-continued
Compound 36
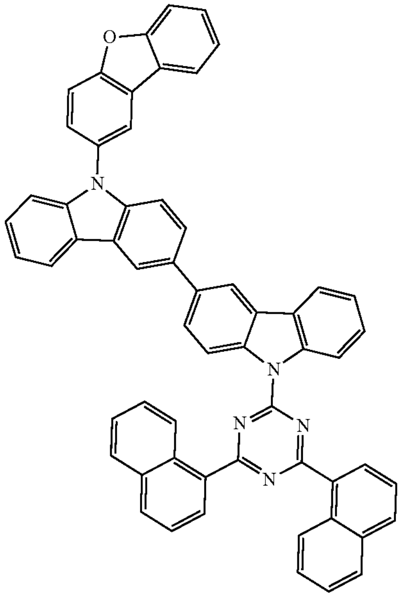
Compound 37
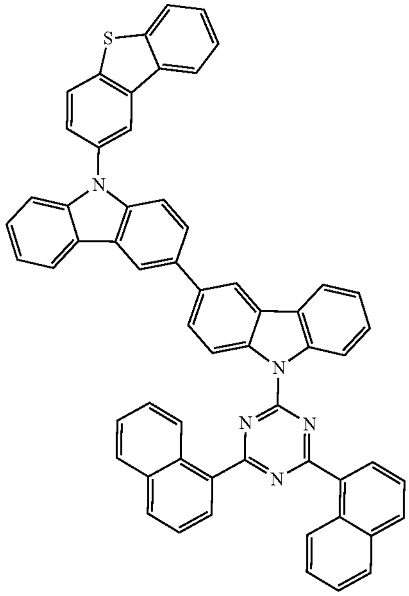

-continued
Compound 38
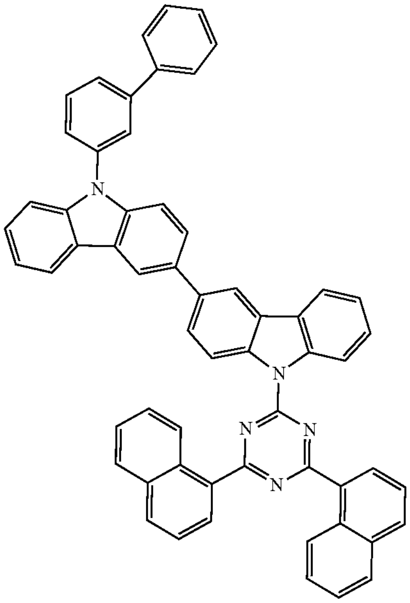
-continued
Compound 40
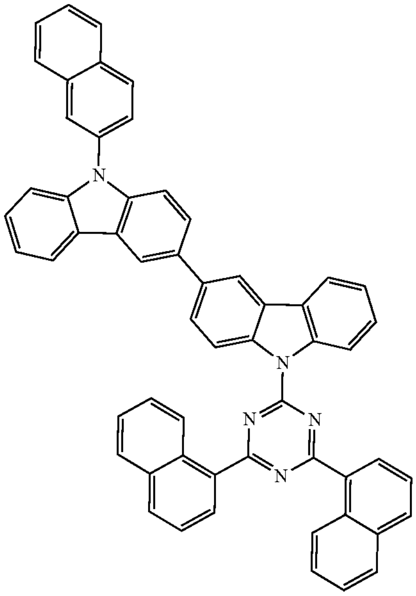
Compound 39
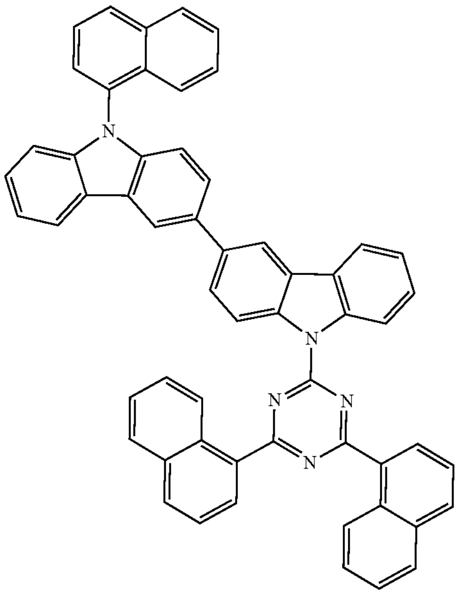
Compound 41
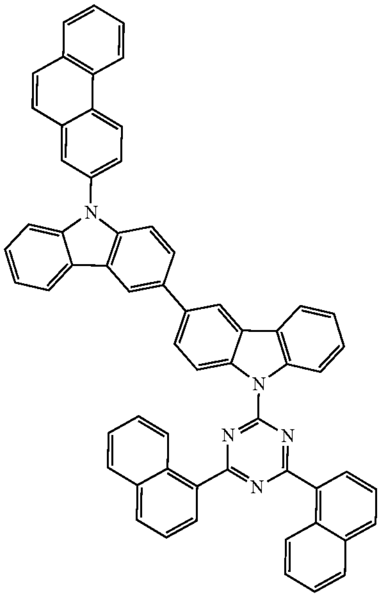

-continued
Compound 42
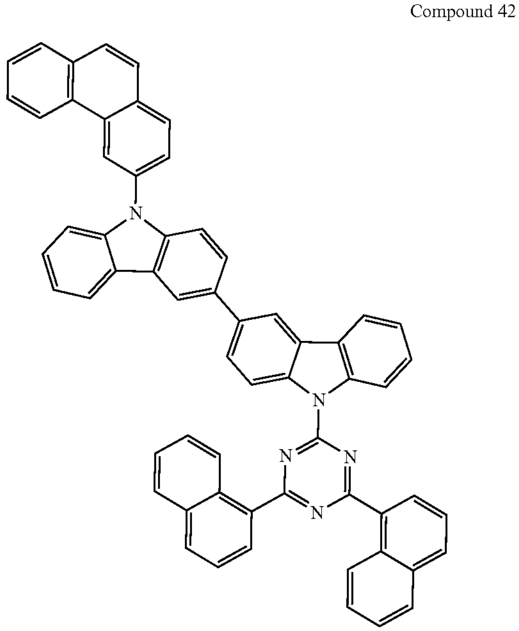
Compound 43
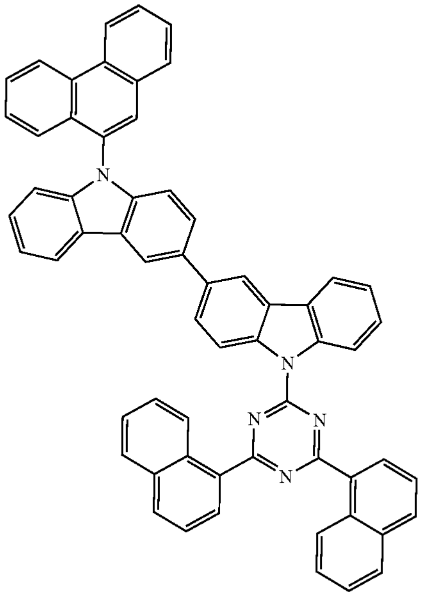
-continued
Compound 44
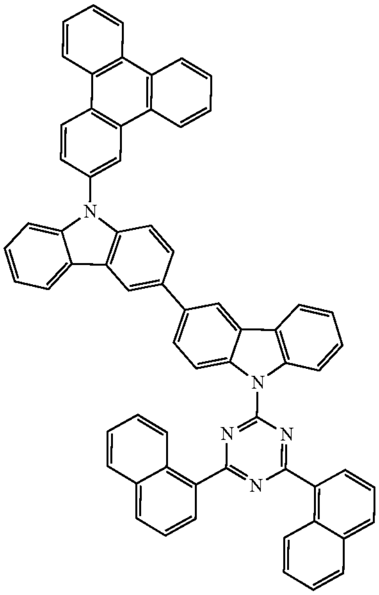
Compound 45
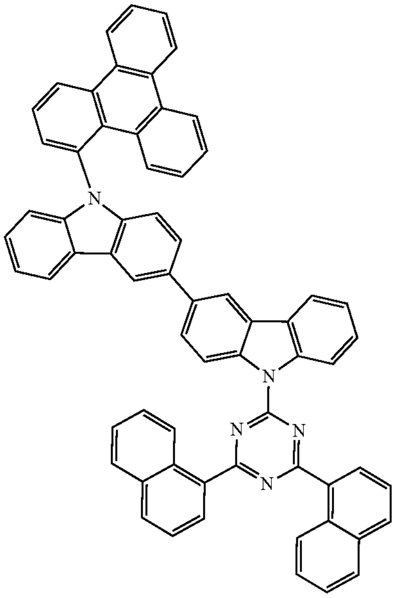

-continued
Compound 46
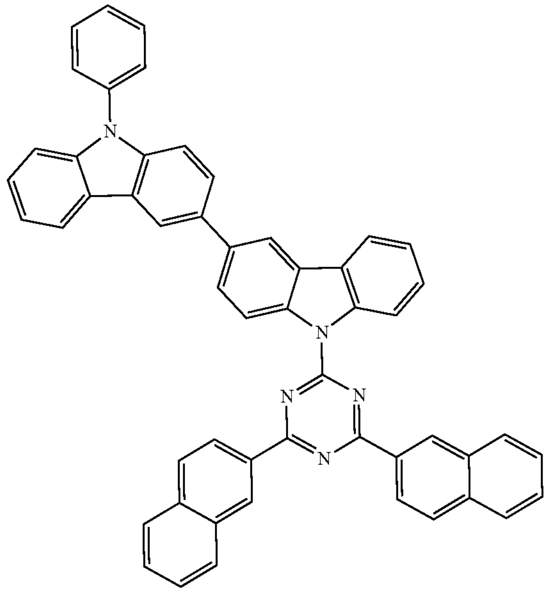
Compound 47
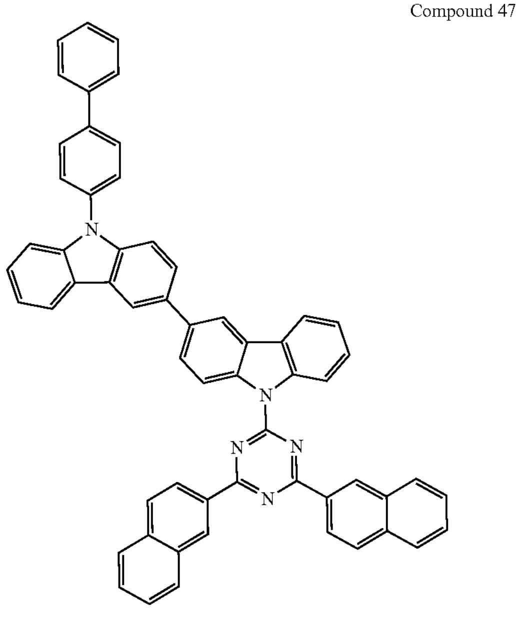
-continued
Compound 48
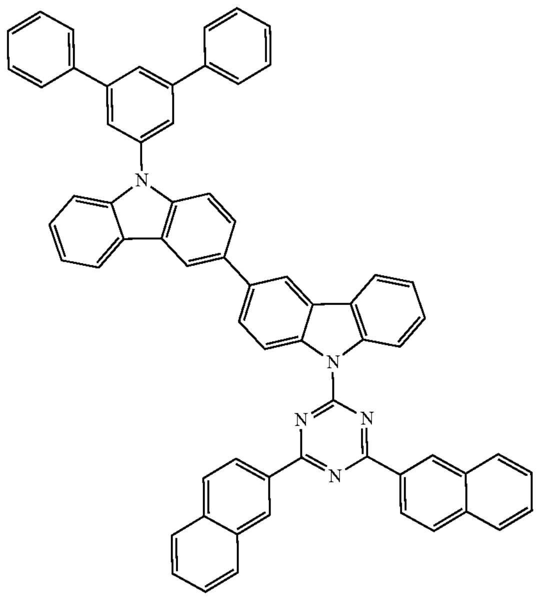
Compound 49
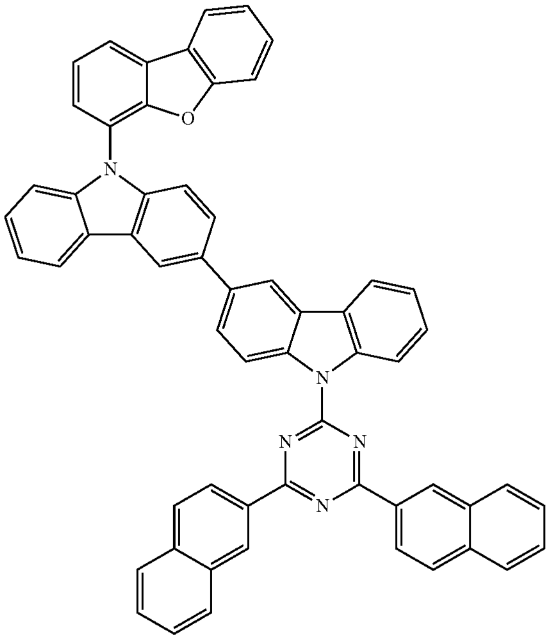

-continued
Compound 50
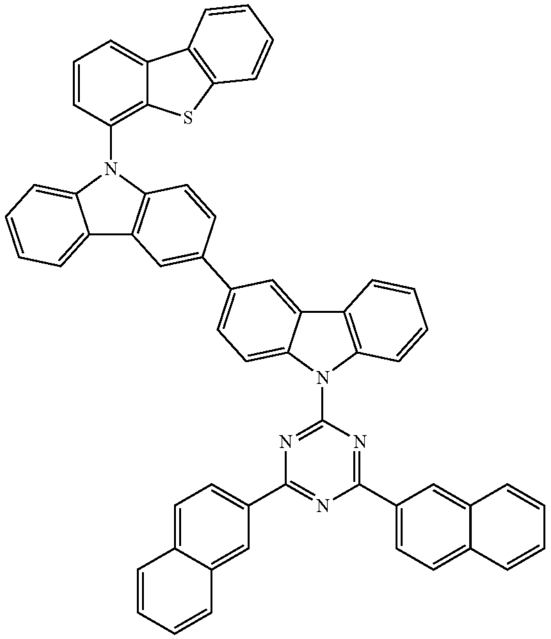
Compound 51
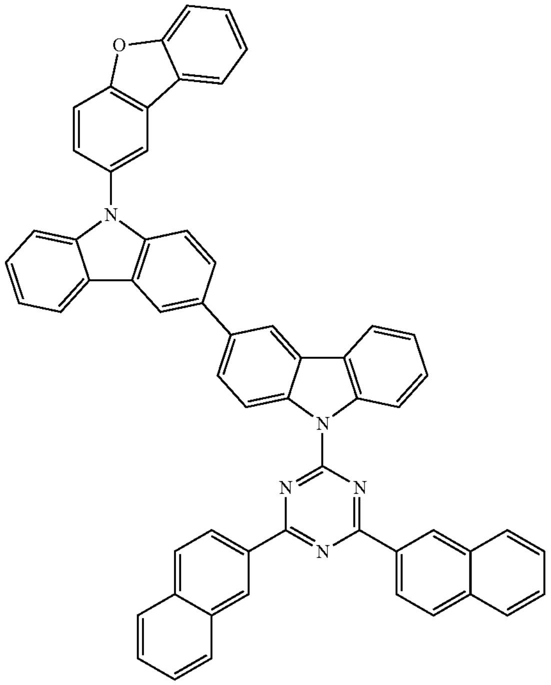
-continued
Compound 52
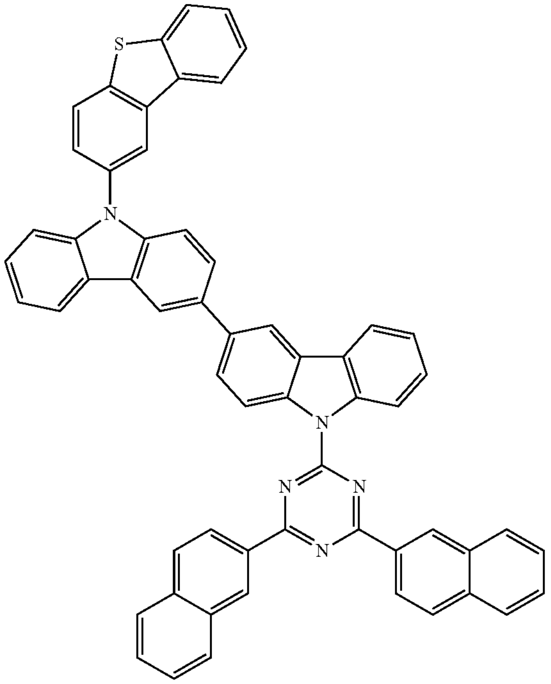
Compound 53
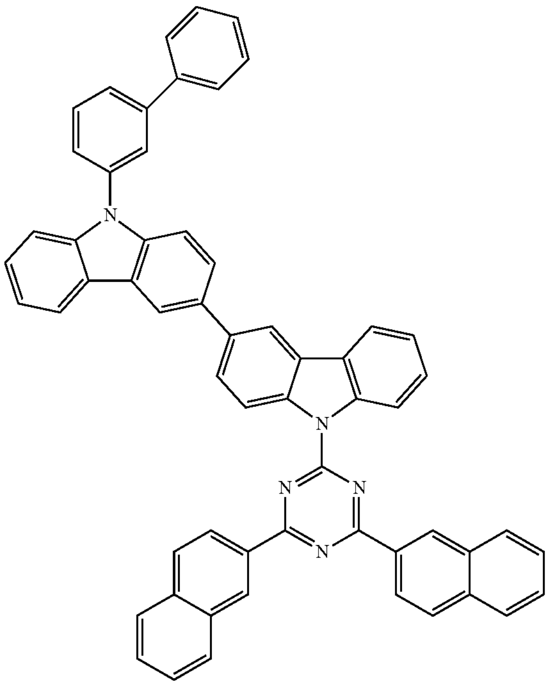

Compound 54
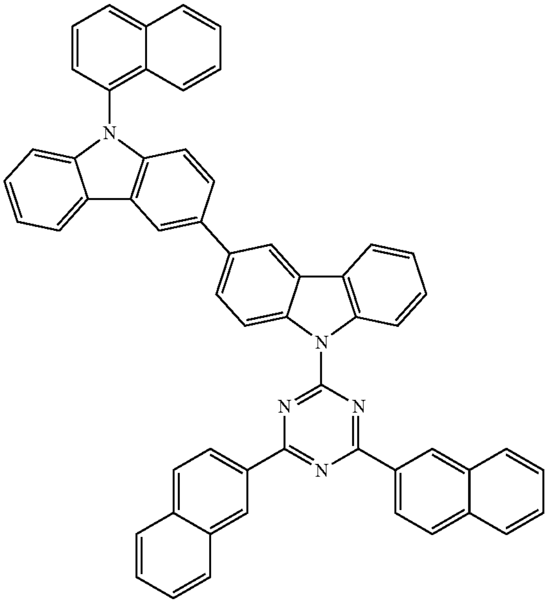
Compound 55
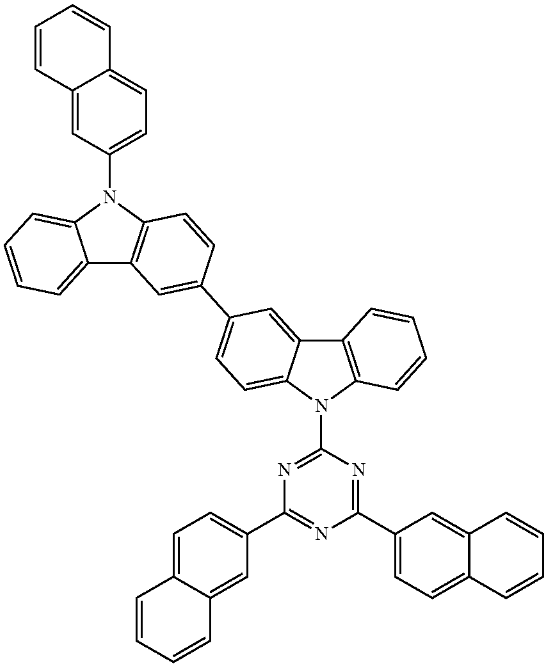
Compound 56
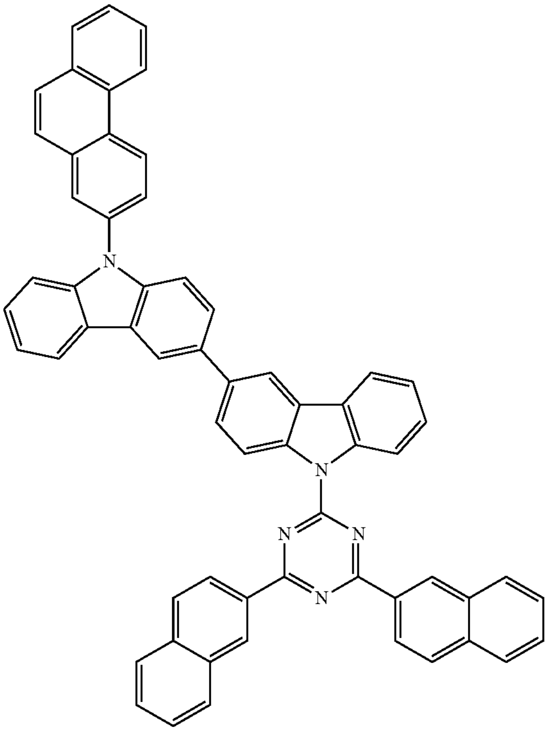
Compound 57
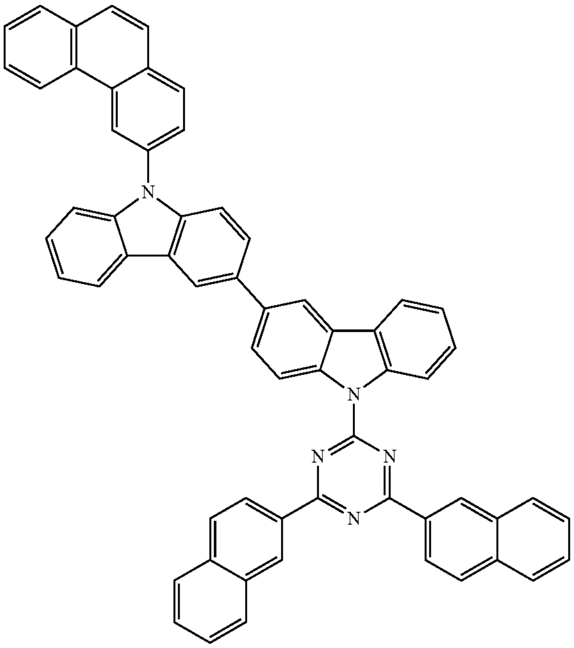

-continued
Compound 58
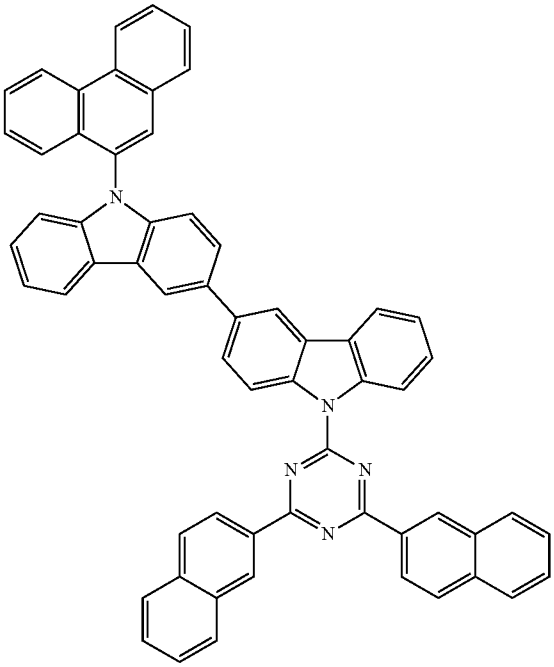
Compound 59
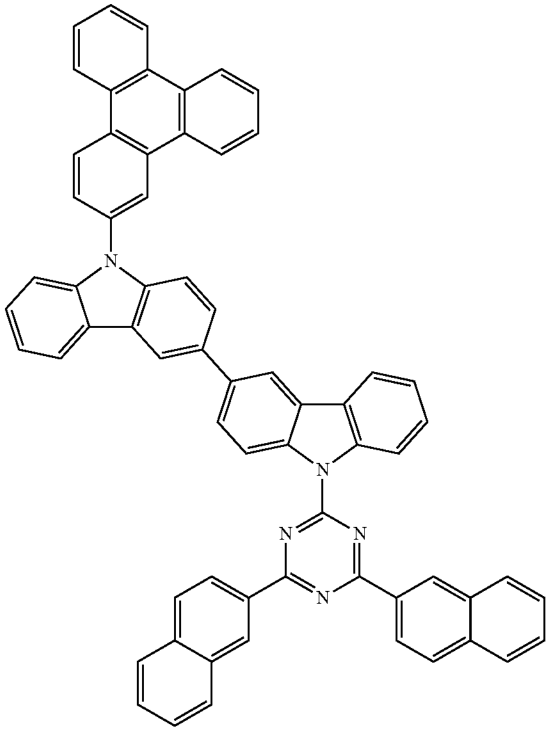
-continued
Compound 60
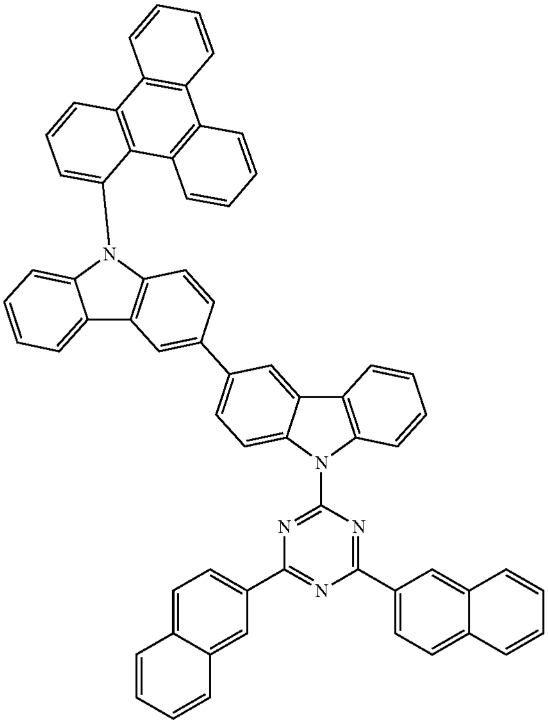
Compound 61
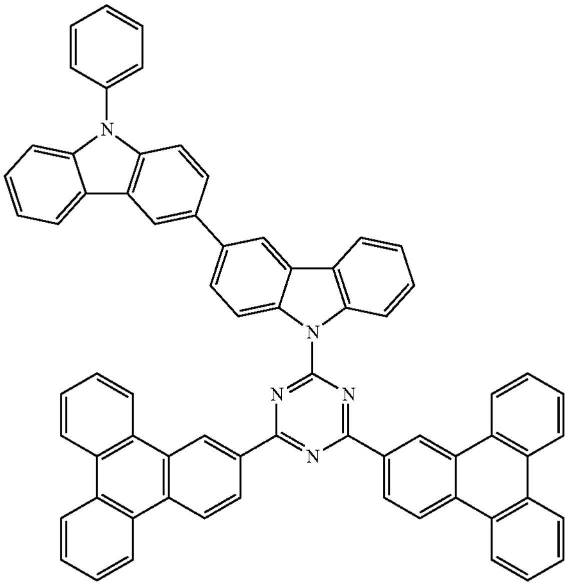

-continued
Compound 62
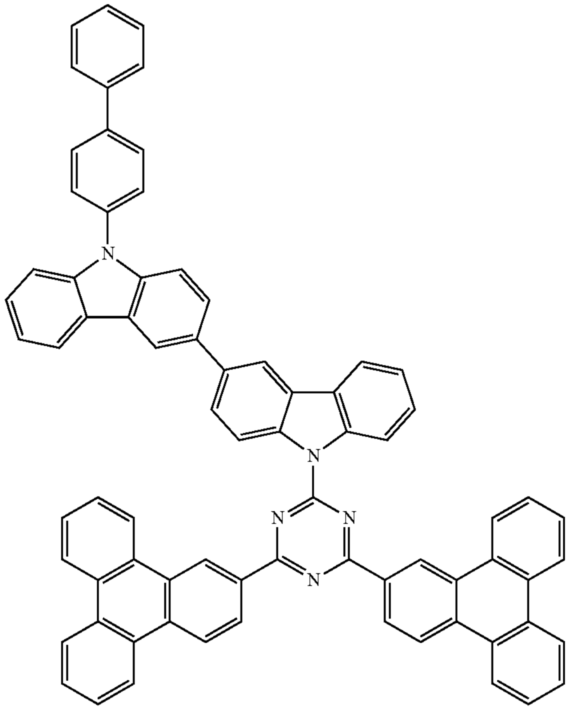
Compound 63
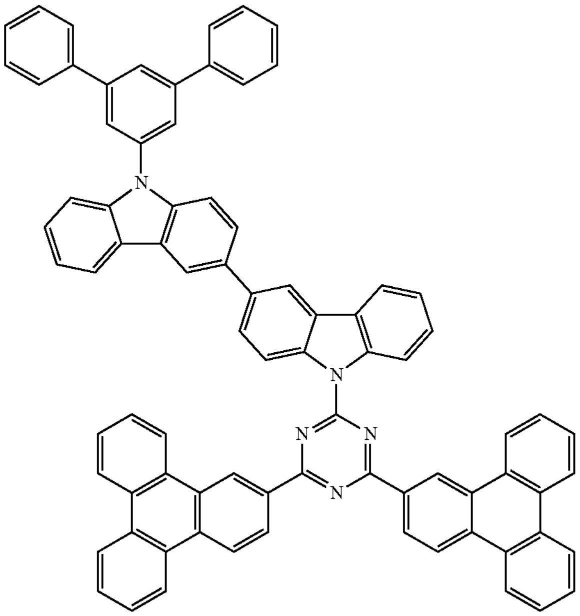
-continued
Compound 64
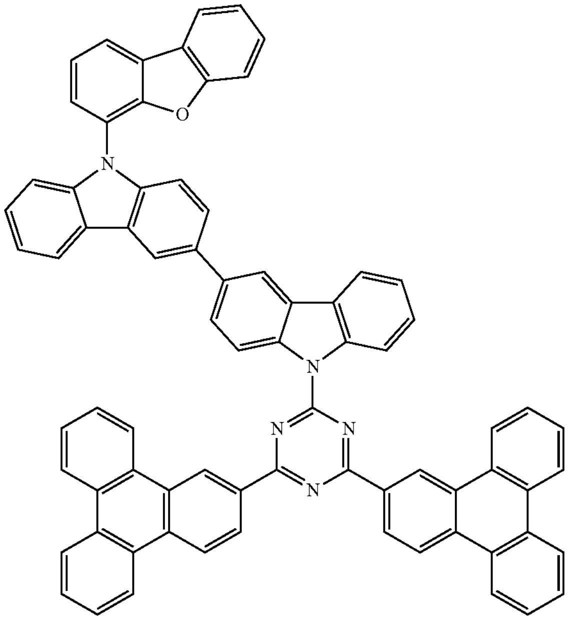
Compound 65
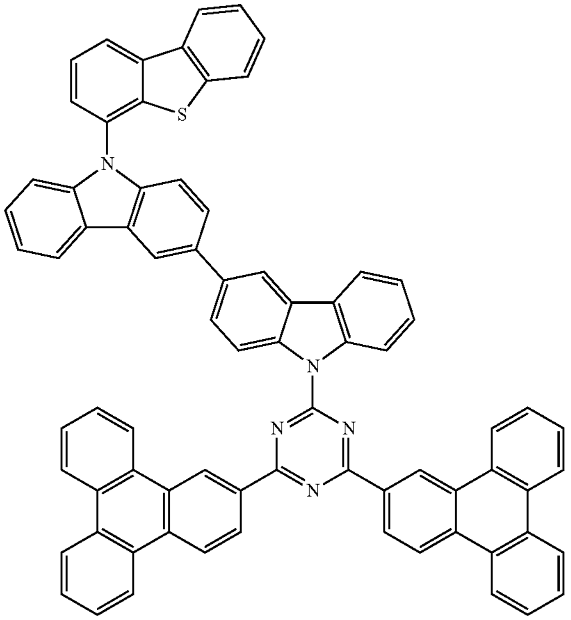

-continued
Compound 66
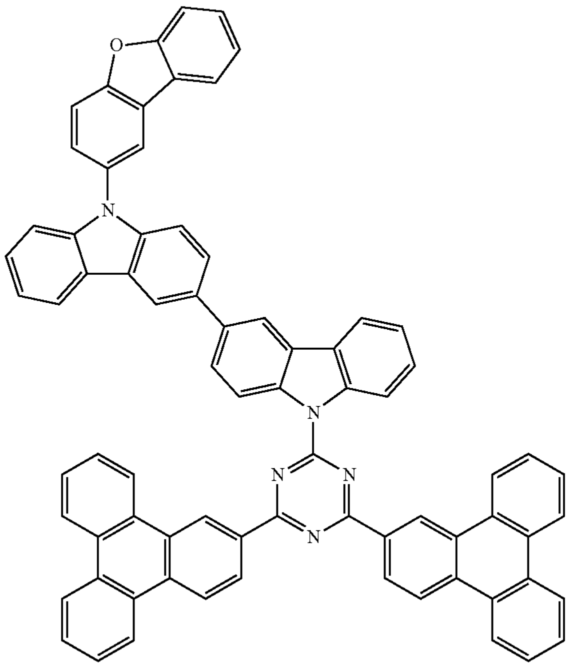
Compound 67
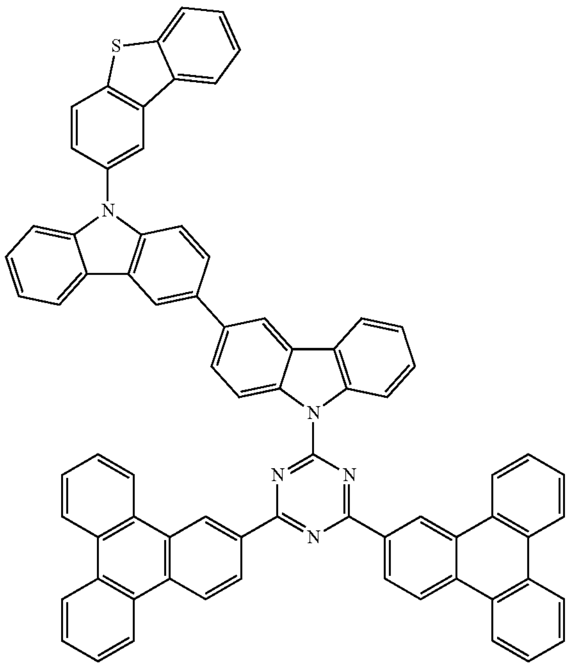
-continued
Compound 68
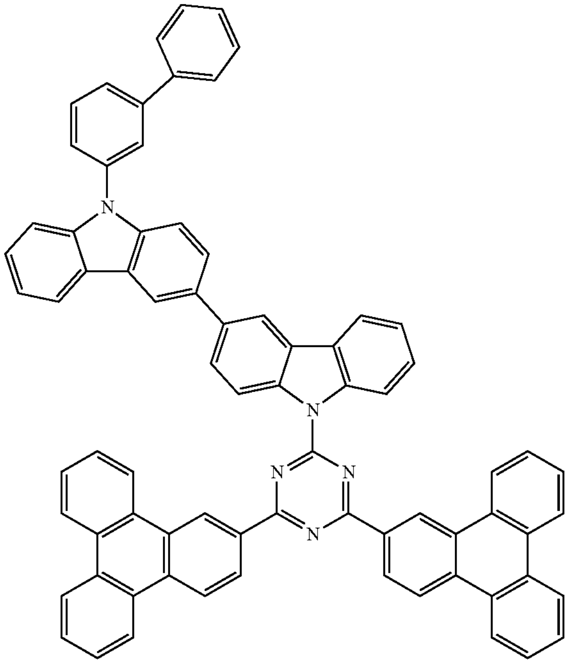
Compound 69
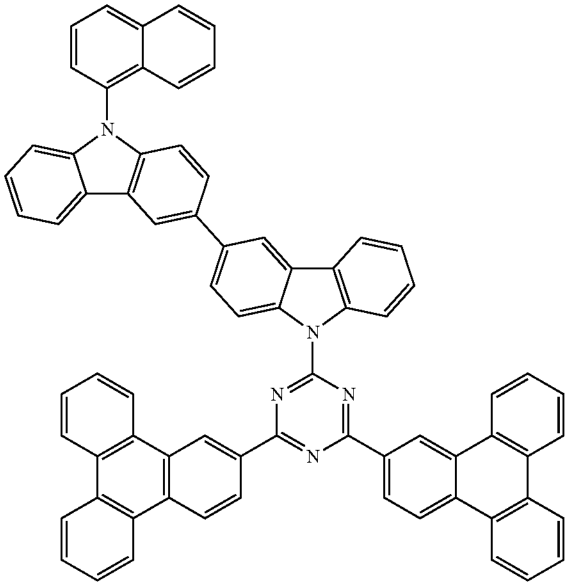

-continued
Compound 70
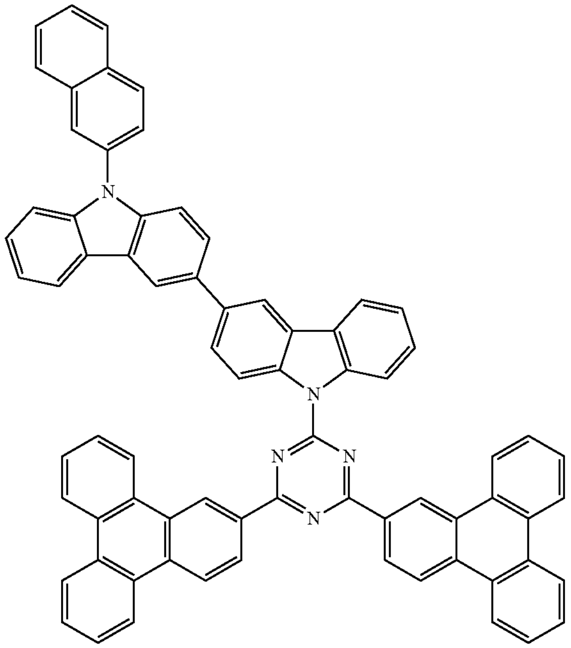
Compound 71
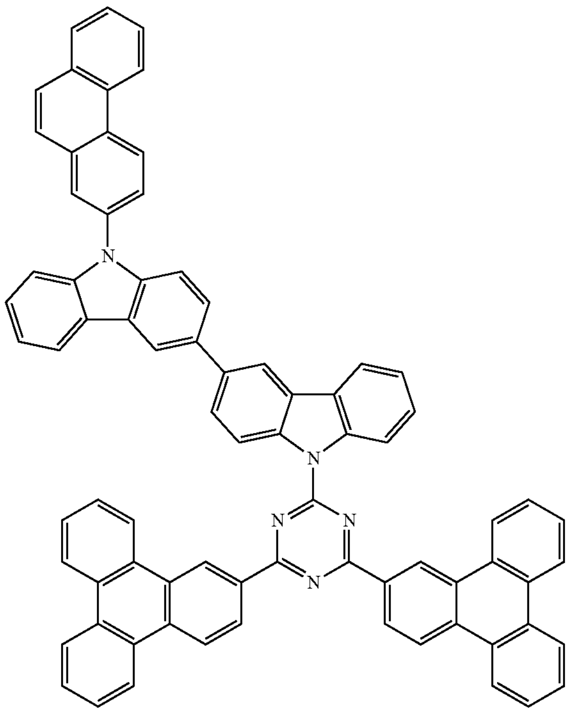
-continued
Compound 72
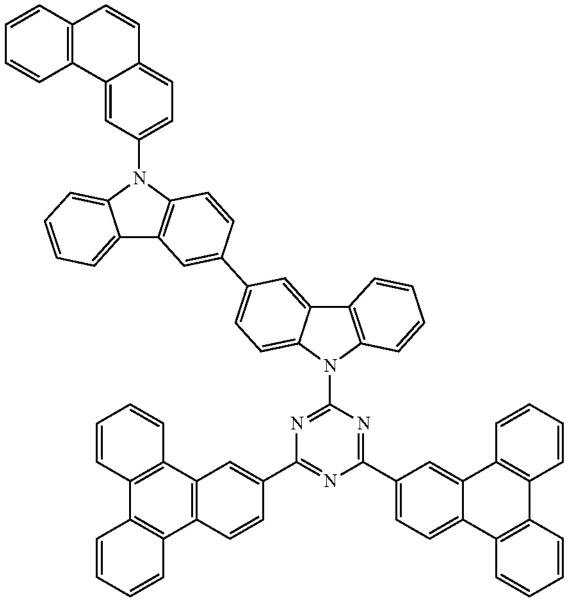
Compound 73
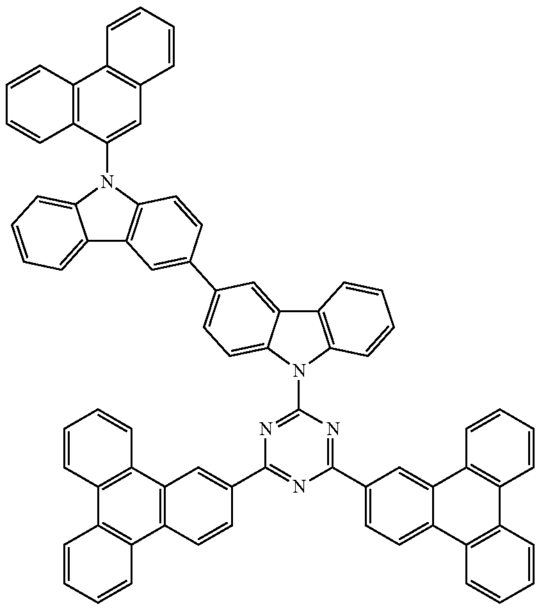

-continued
Compound 74
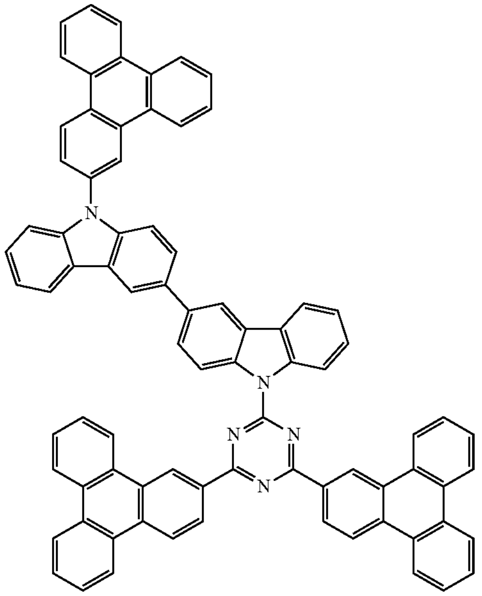
Compound 75
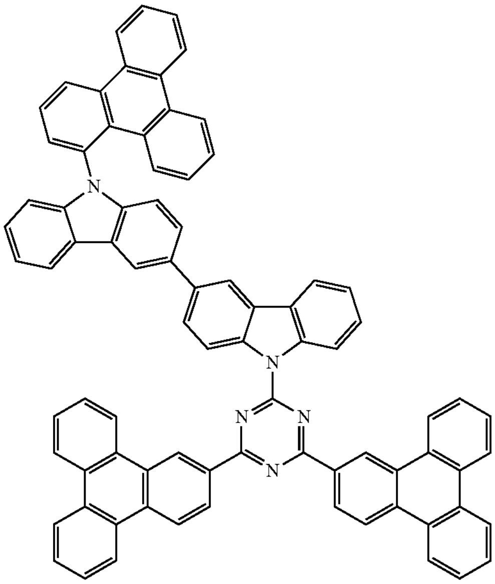
-continued
Compound 76
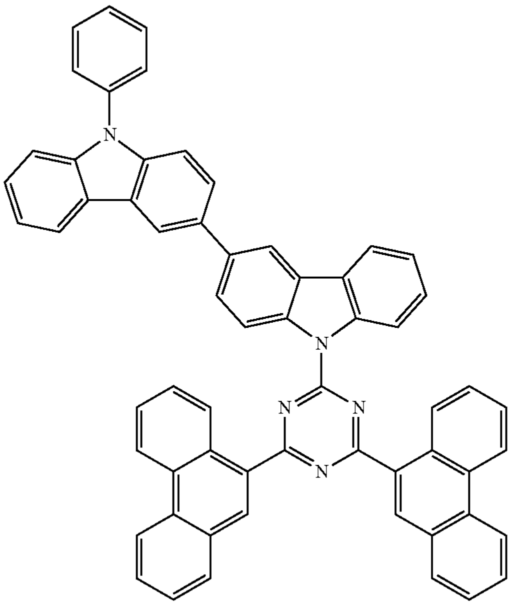
Compound 77
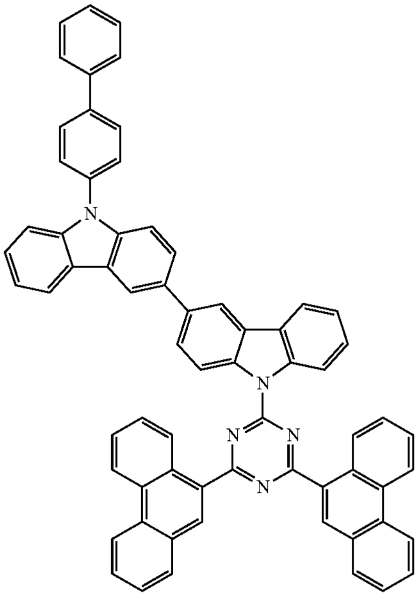

-continued
Compound 78
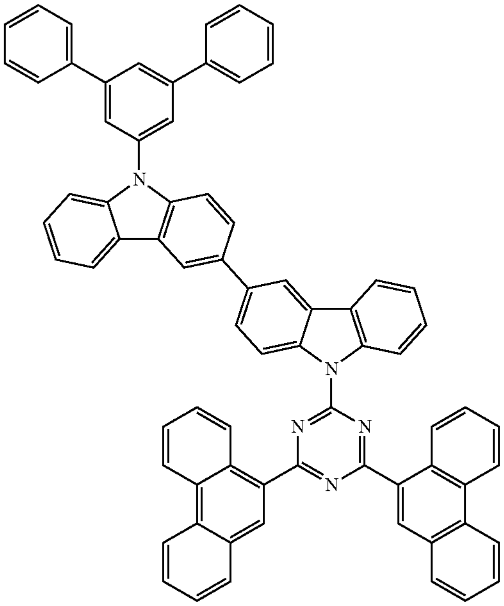
Compound 79
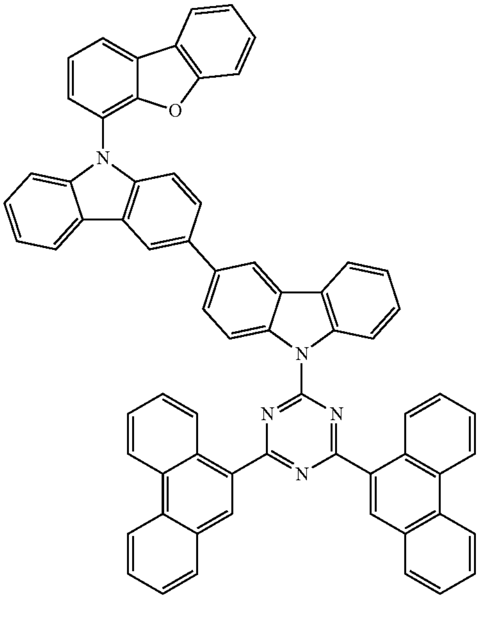
-continued
Compound 80
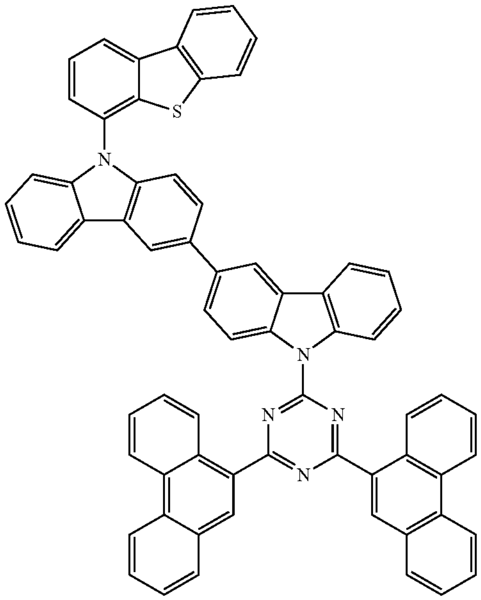
Compound 81
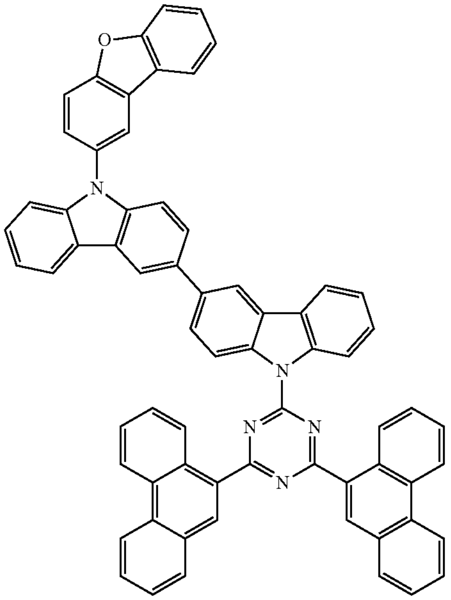

Compound 82
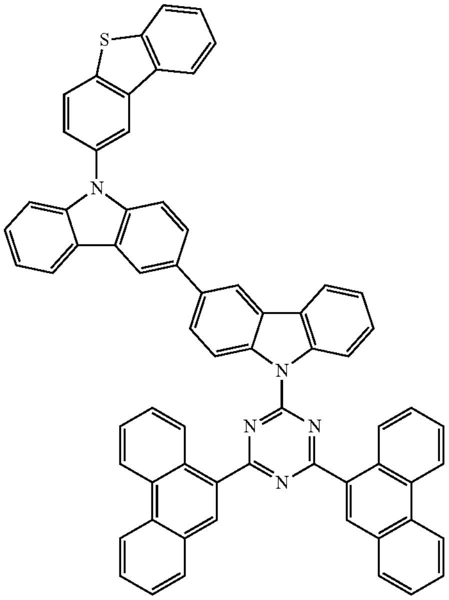
Compound 83
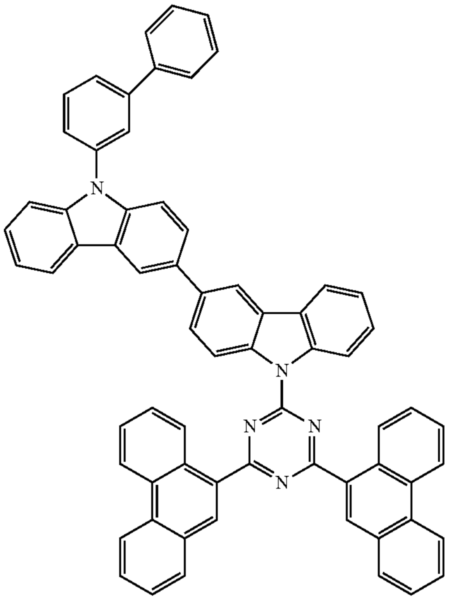
Compound 84
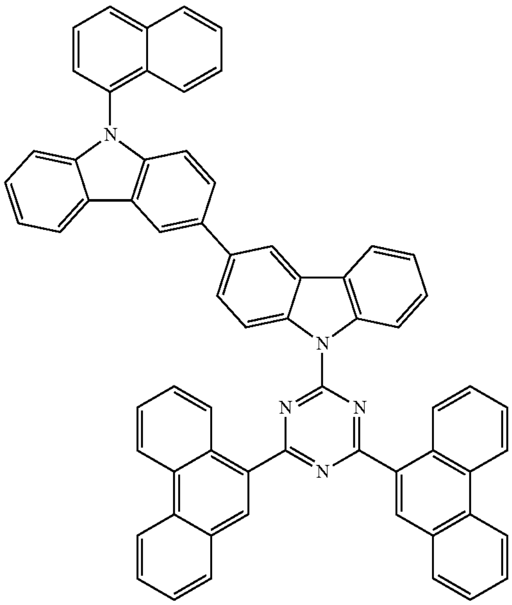
Compound 85
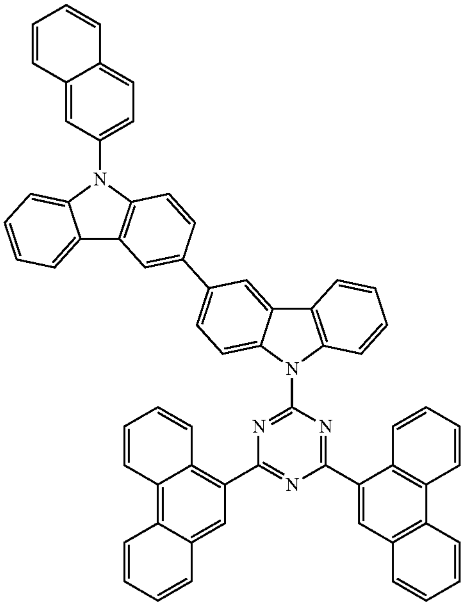

-continued
Compound 86
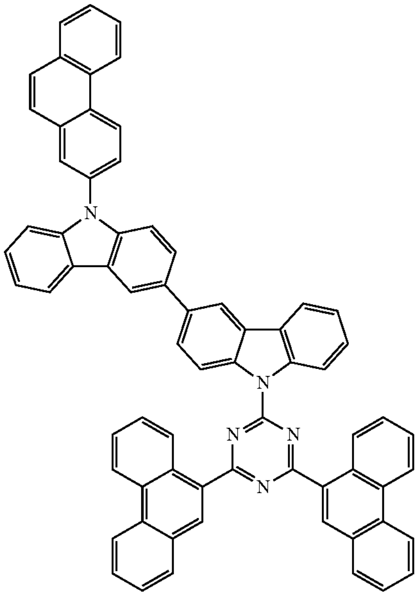
Compound 87
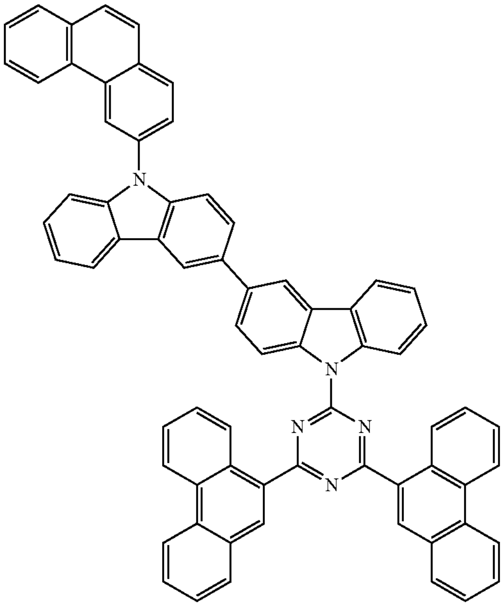
-continued
Compound 88
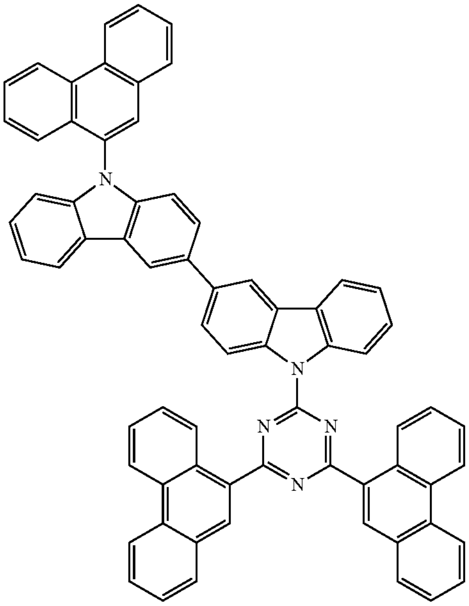
Compound 89
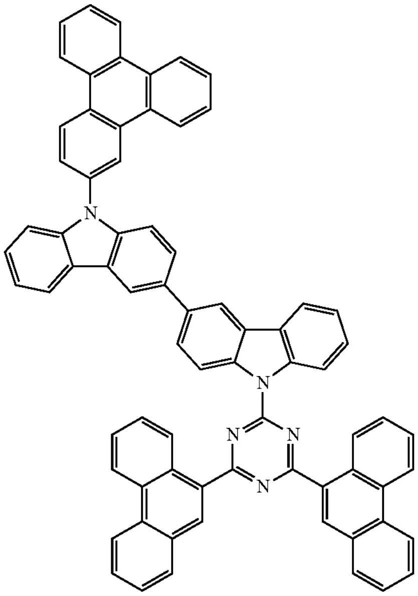

Compound 90
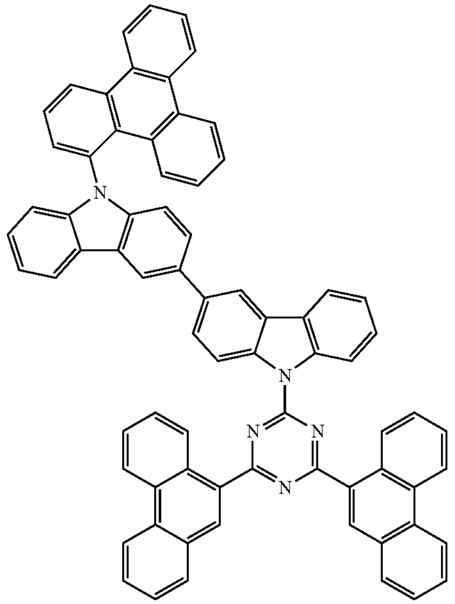
Compound 91
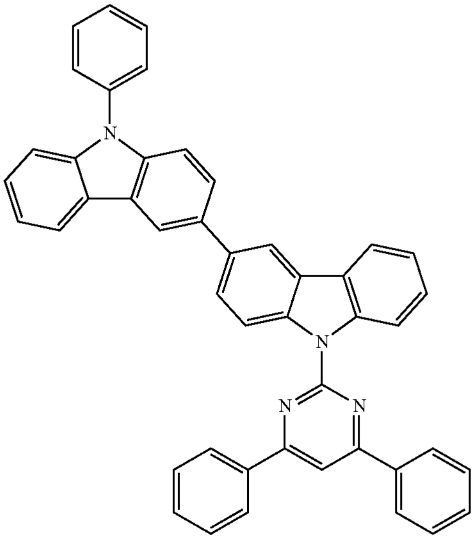
Compound 92
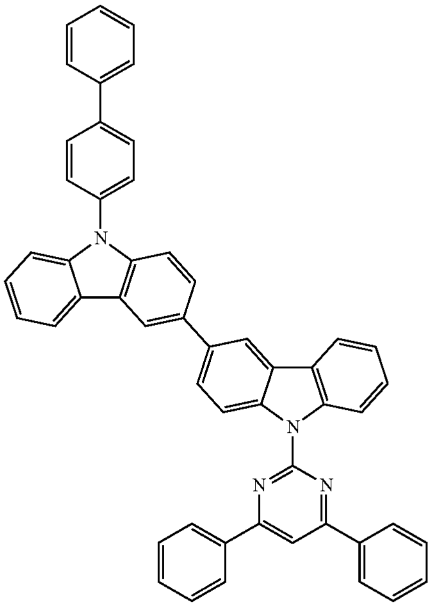
Compound 93
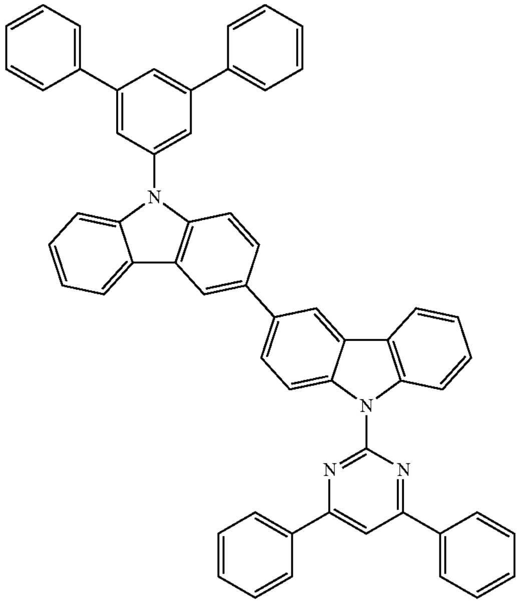

-continued
Compound 94
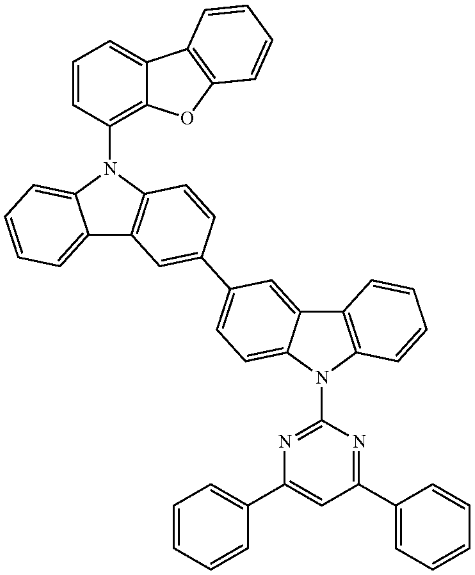
Compound 95
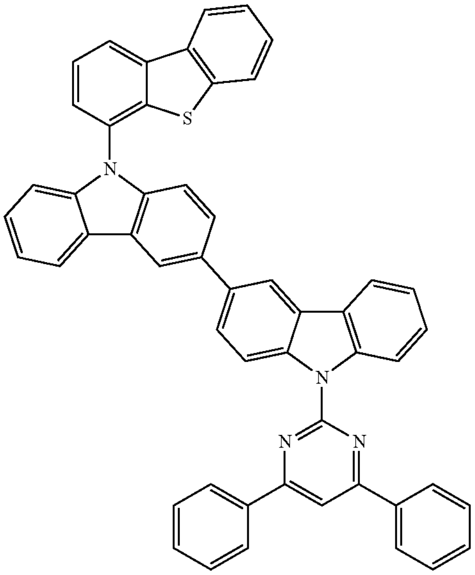
-continued
Compound 96
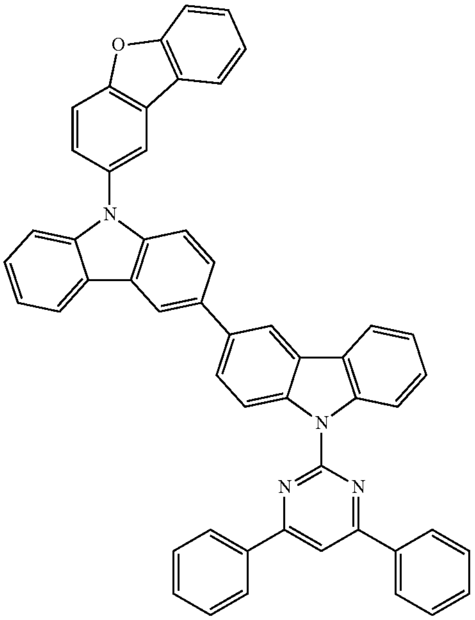
Compound 97
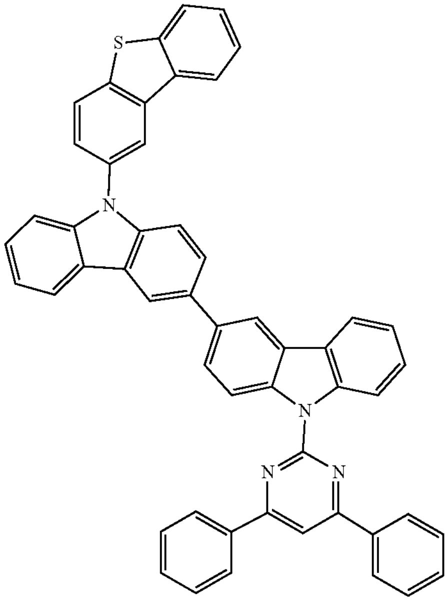

Compound 98
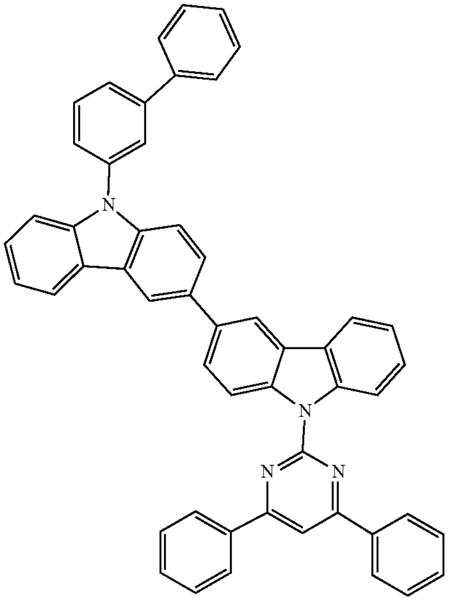
Compound 99
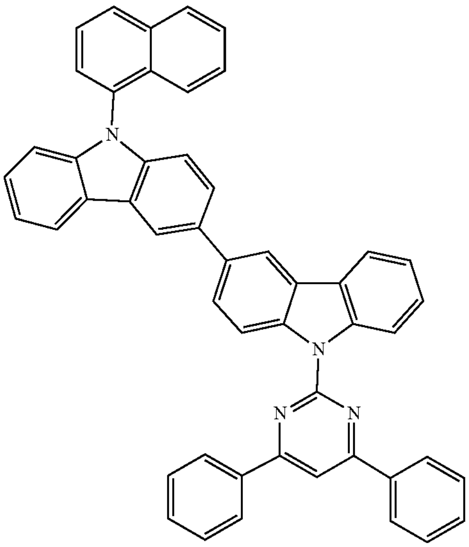
Compound 100
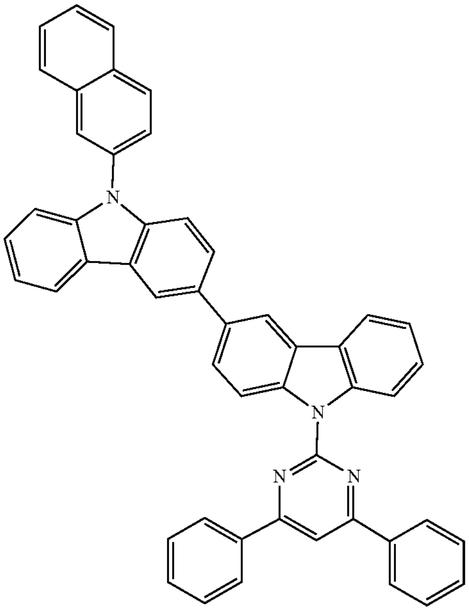
Compound 101
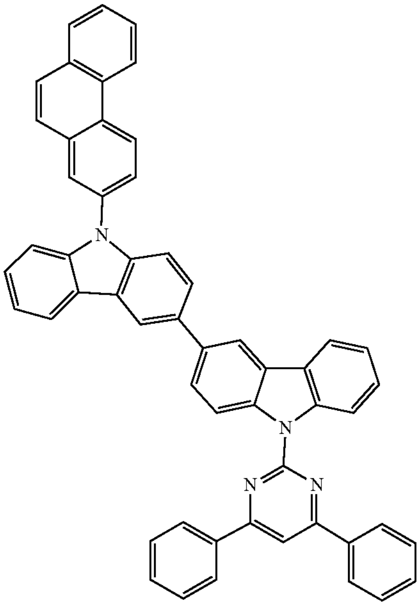

-continued
Compound 102
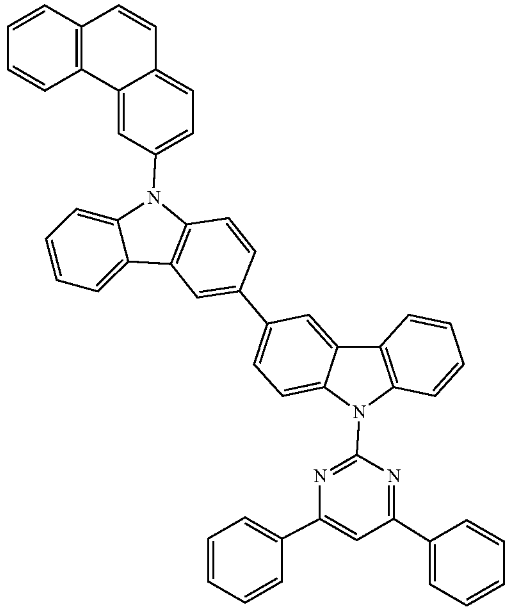
Compound 103
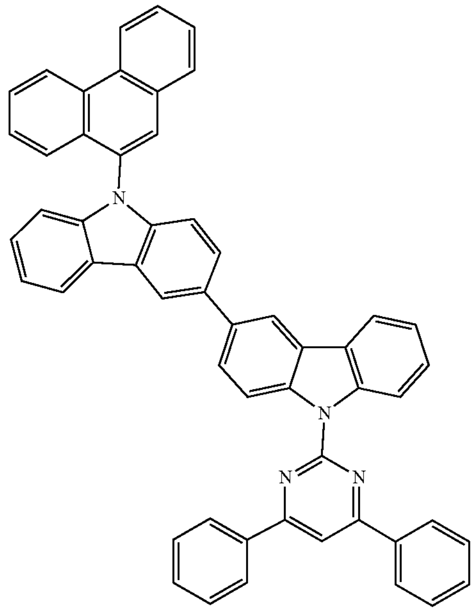
-continued
Compound 104
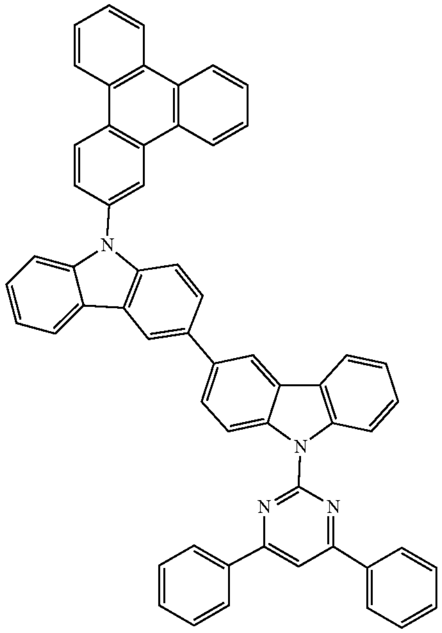
Compound 105
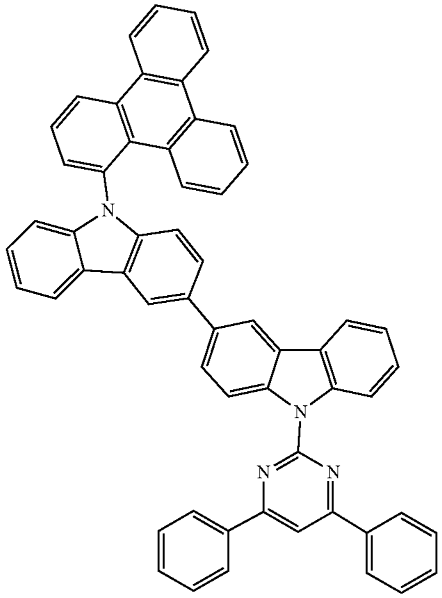

Compound 106
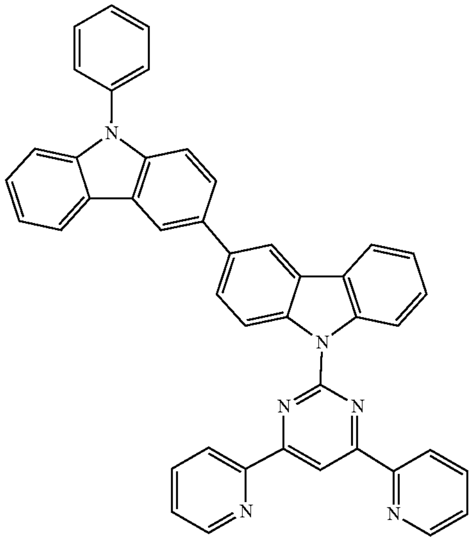
Compound 107
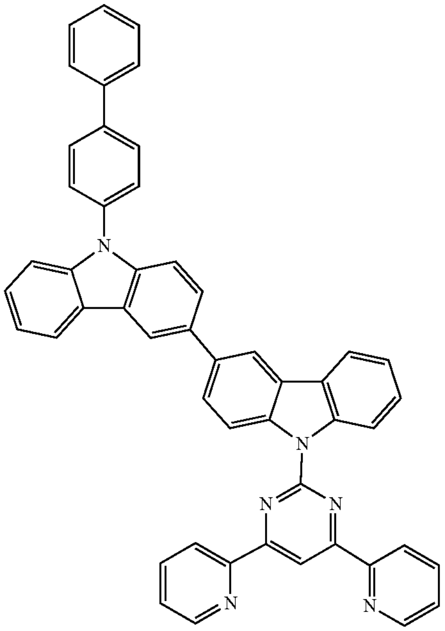
Compound 108
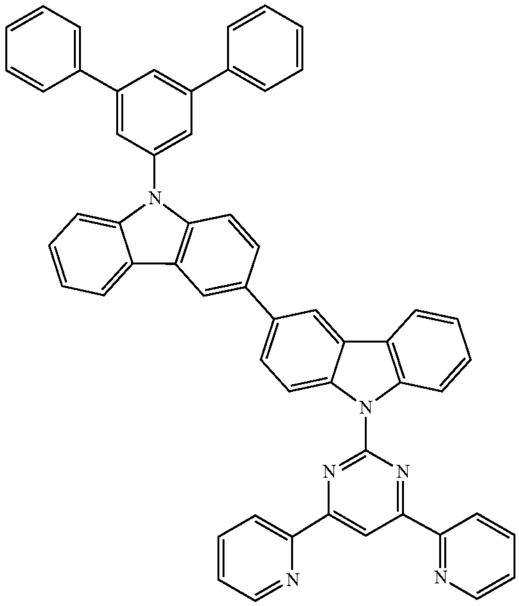
Compound 109
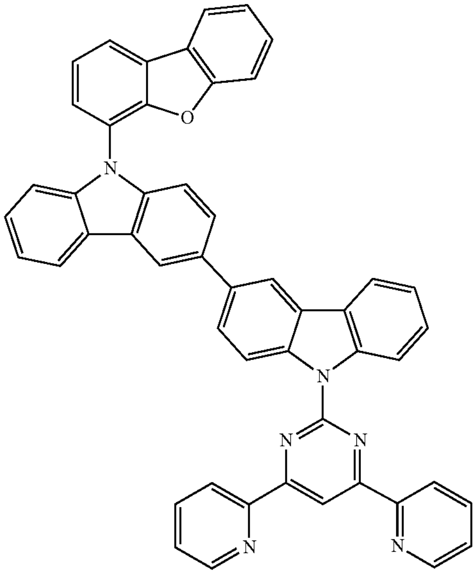

Compound 110
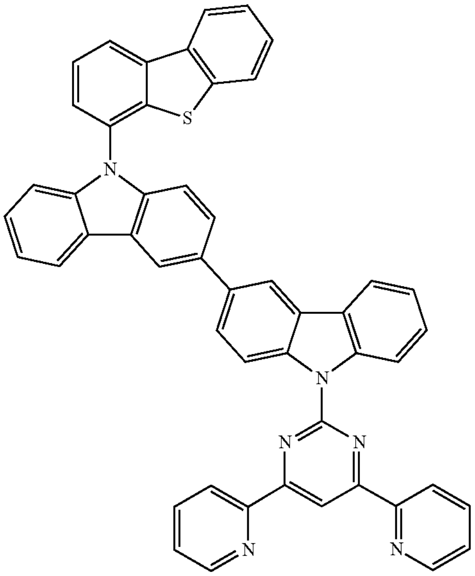
Compound 111
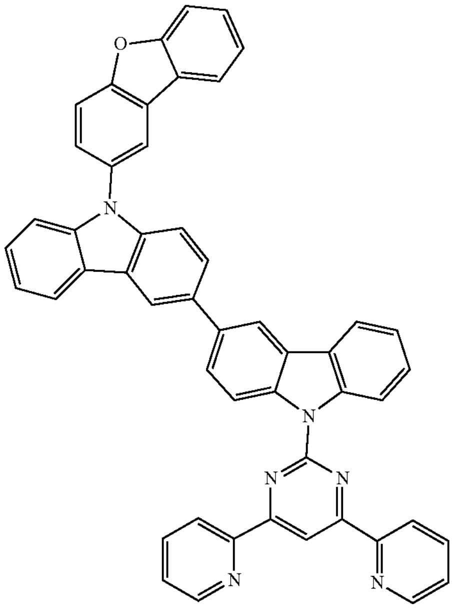
Compound 112
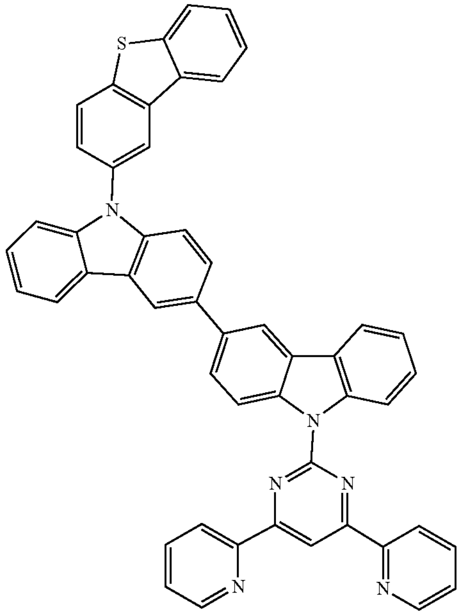
Compound 113
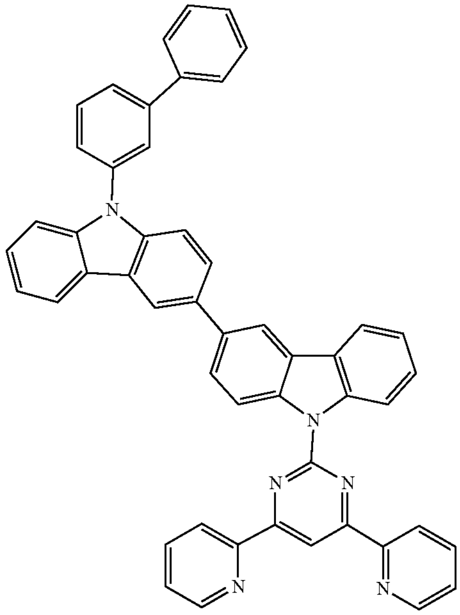

Compound 114
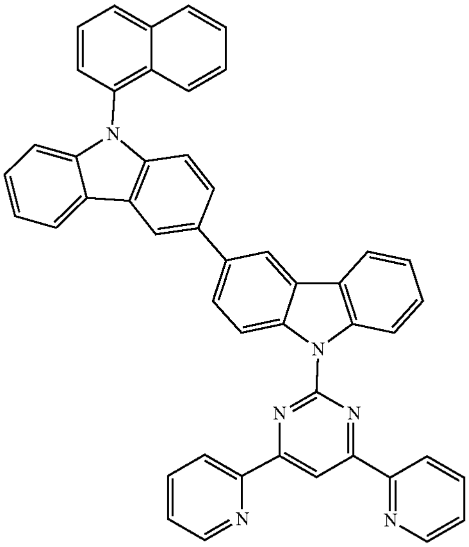
Compound 115
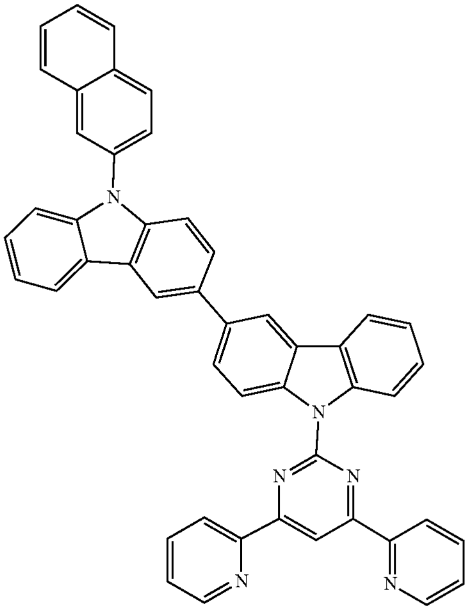
Compound 116
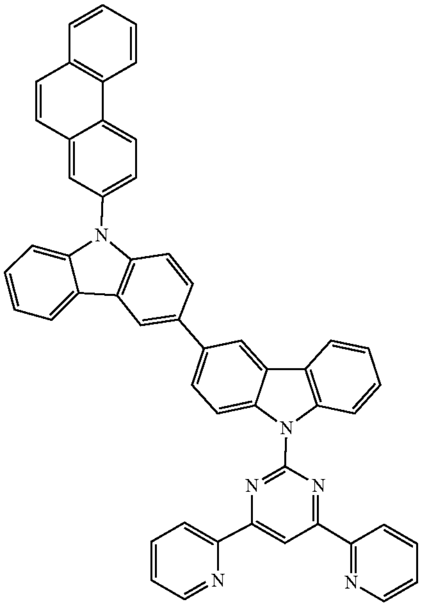
Compound 117
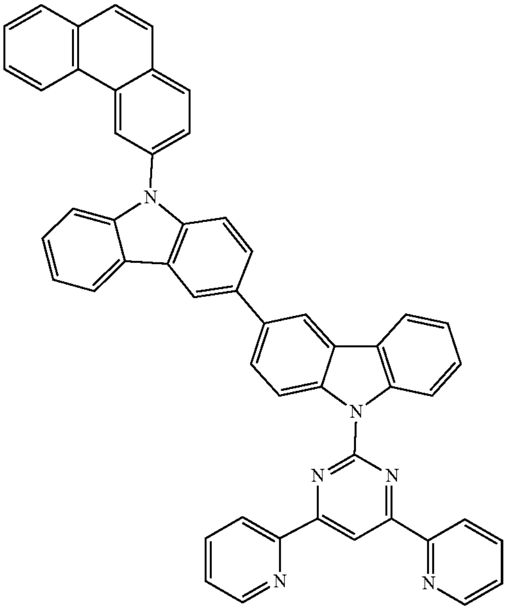

-continued
Compound 118
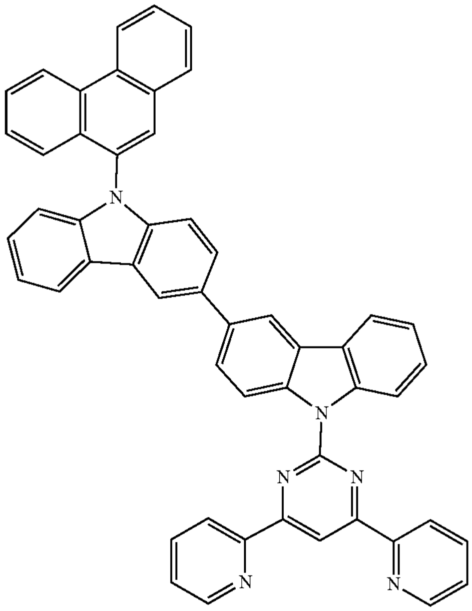
Compound 119
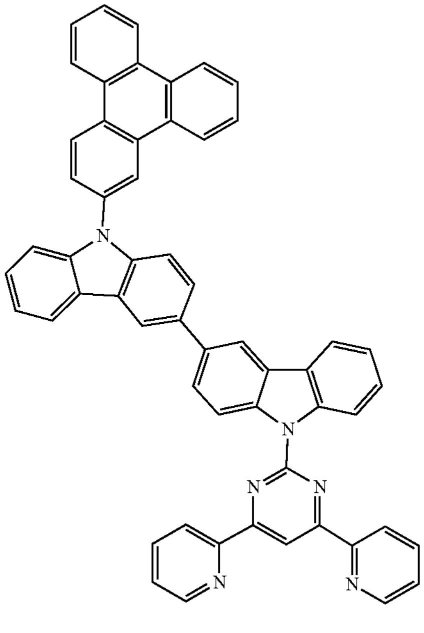
-continued
Compound 120
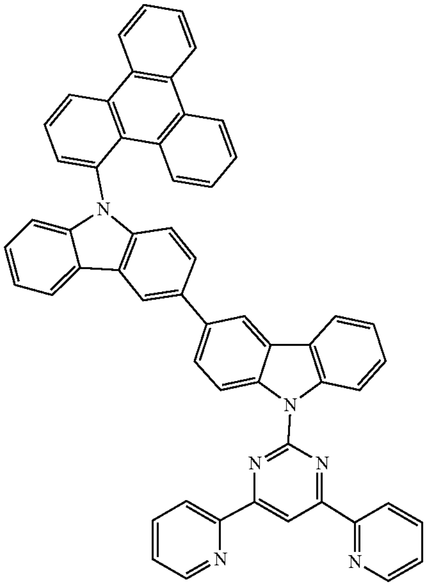
Compound 121
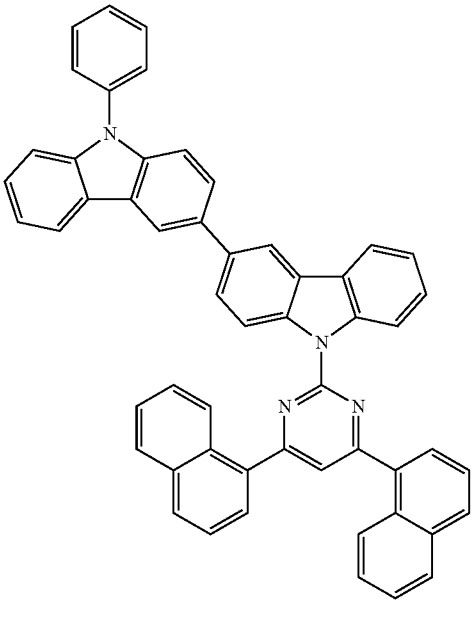

-continued
Compound 122
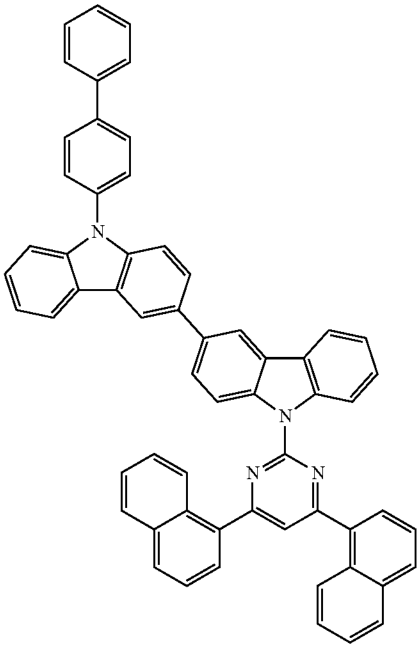
Compound 123
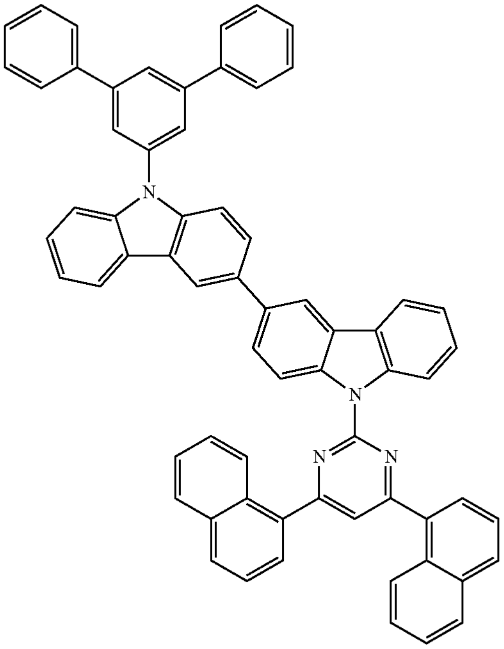
-continued
Compound 124
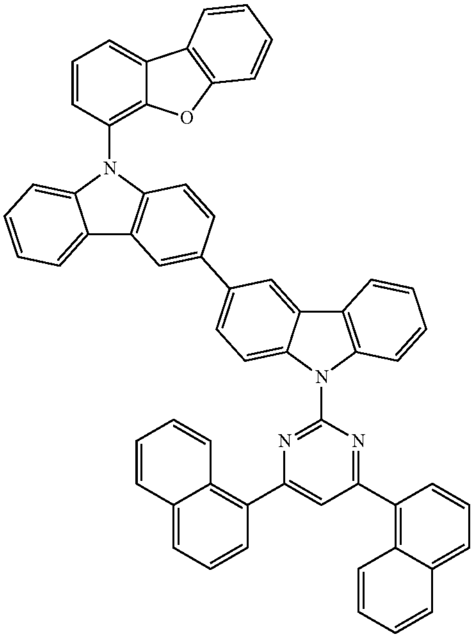
Compound 125
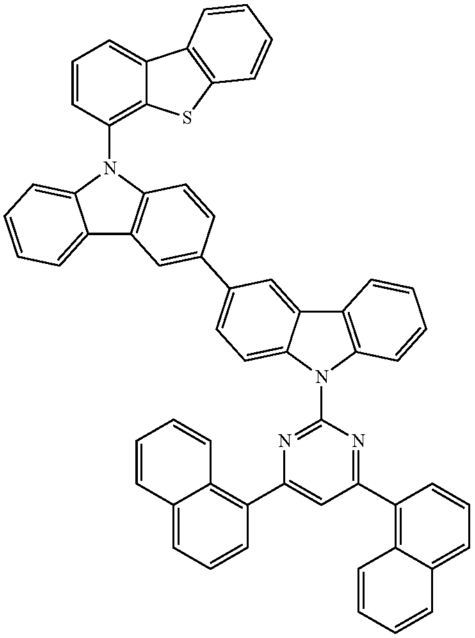

-continued
Compound 126
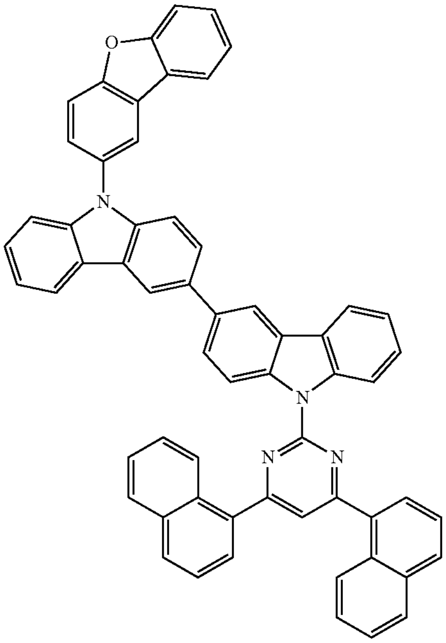
Compound 127
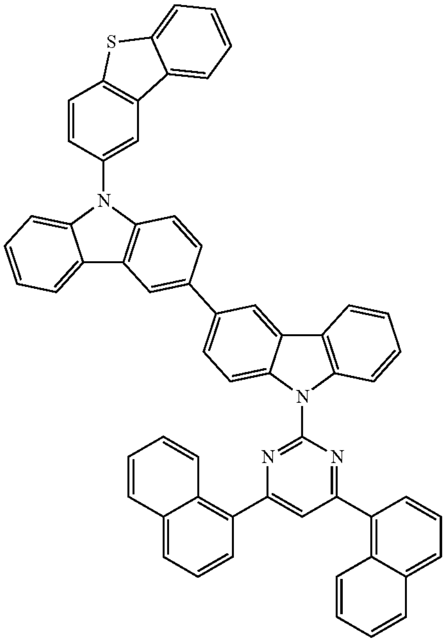
-continued
Compound 128
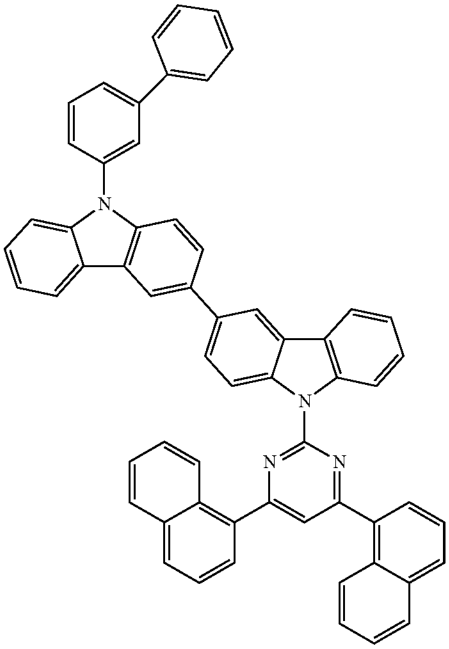
Compound 129
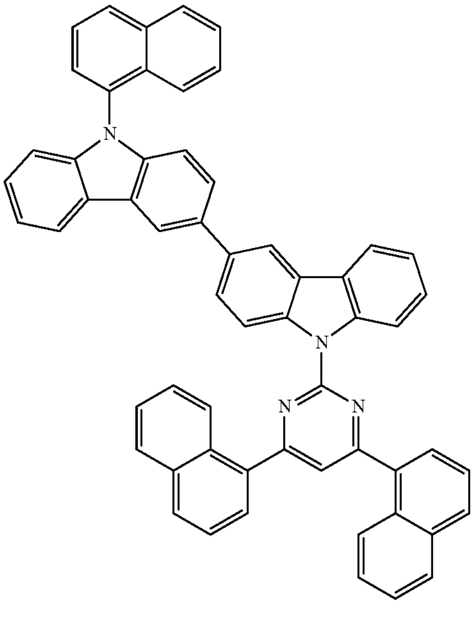

-continued
Compound 130
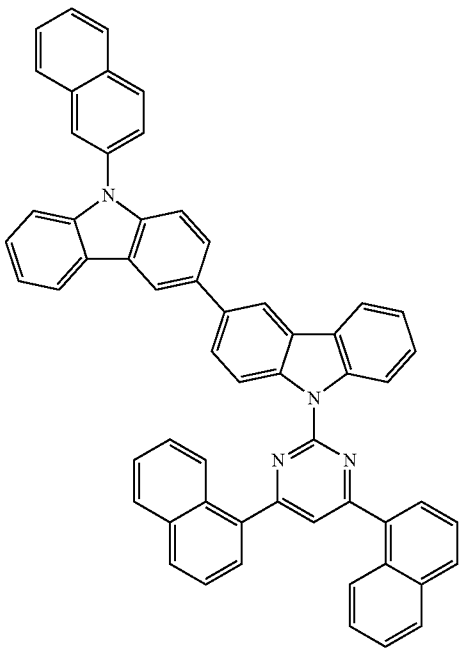
Compound 132
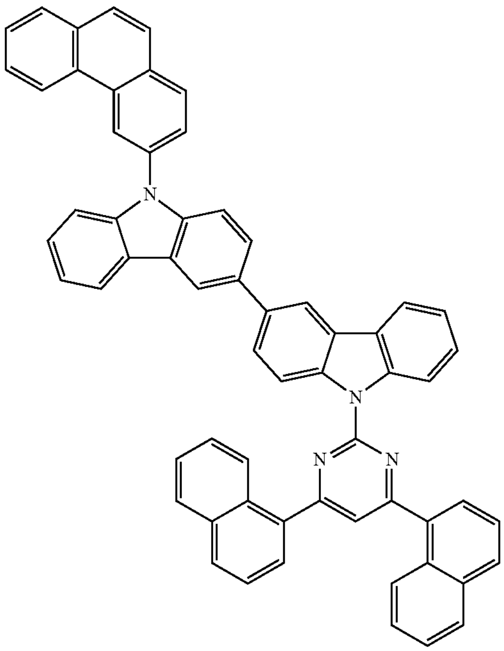
Compound 131
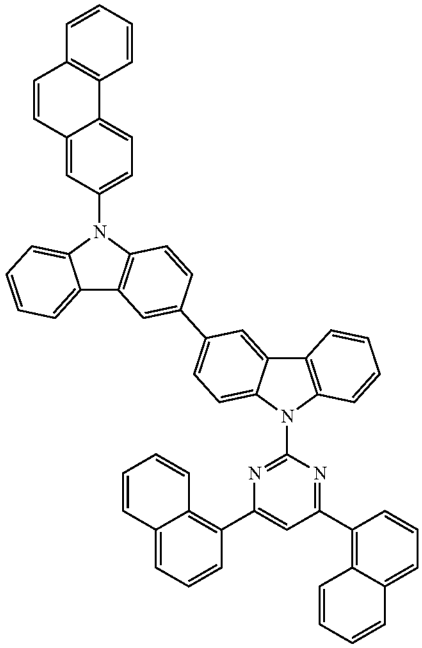
Compound 133
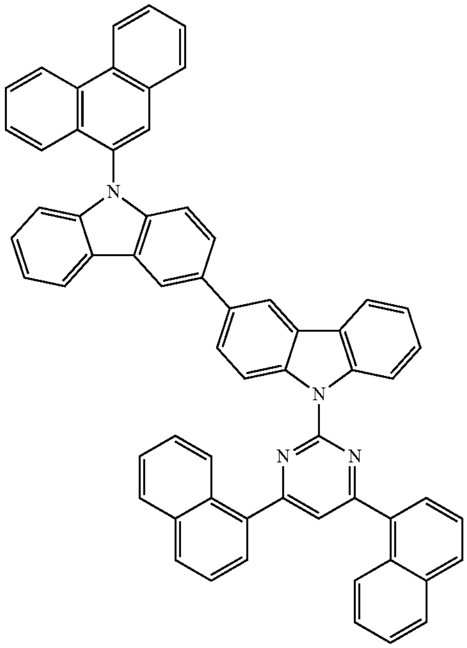
-continued -continued
Compound 134
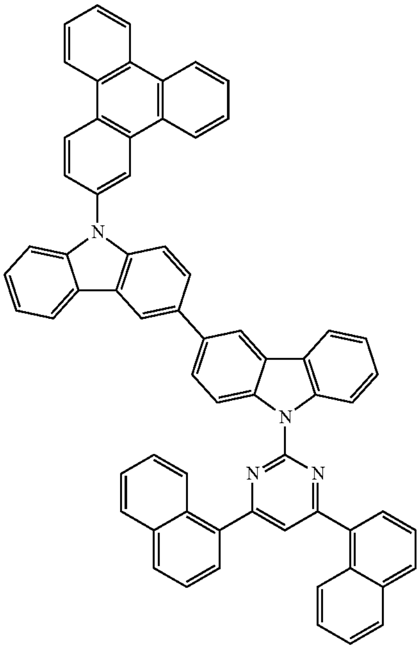
Compound 135
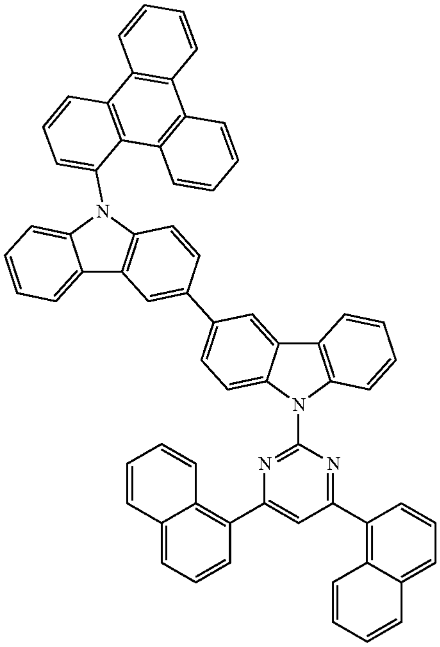
-continued
Compound 136
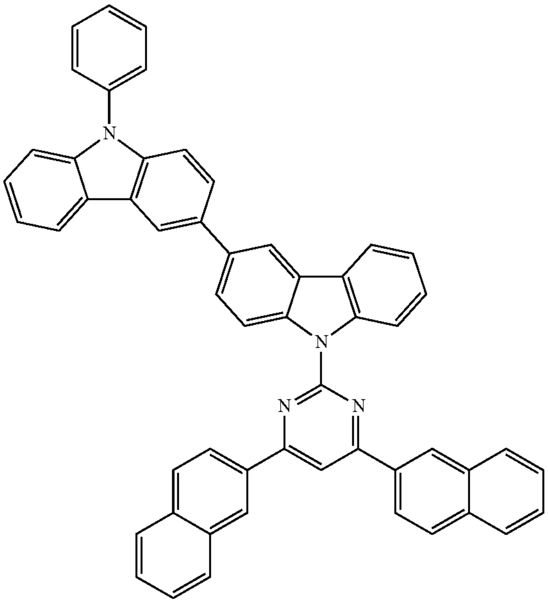
Compound 137
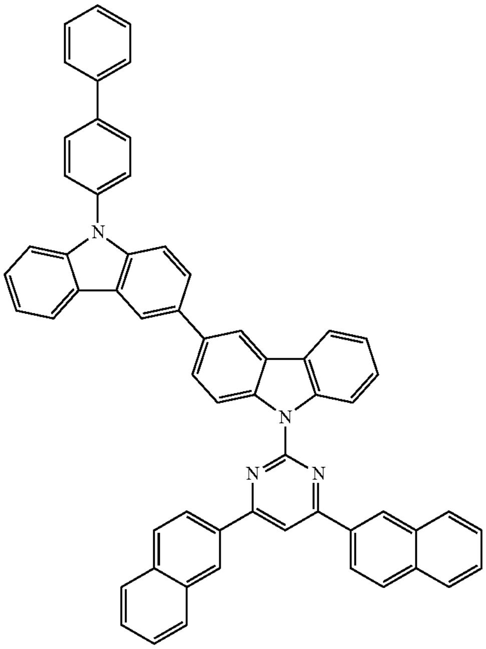

-continued
Compound 138
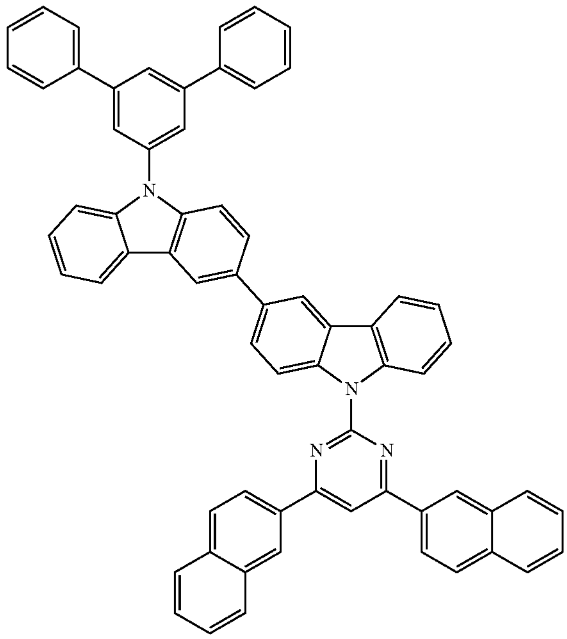
Compound 139
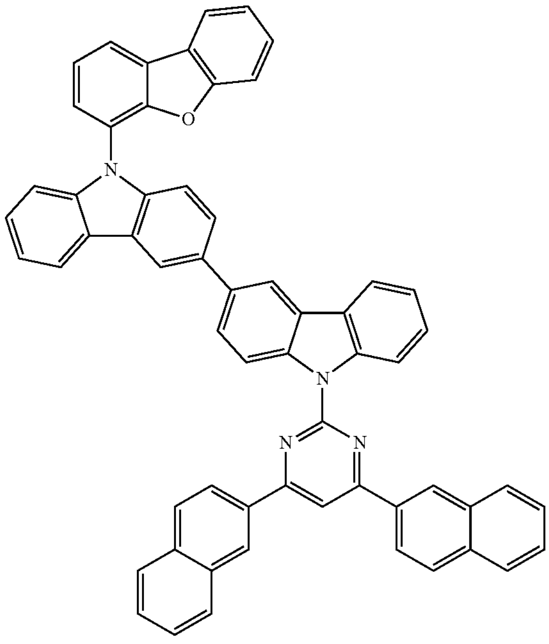
-continued
Compound 140
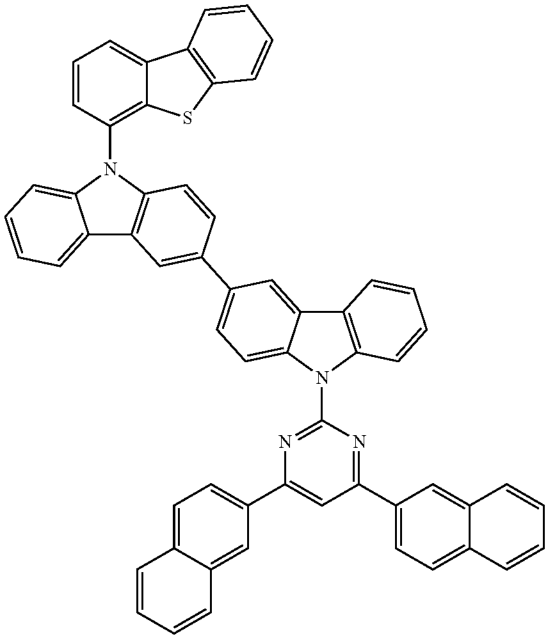
Compound 141
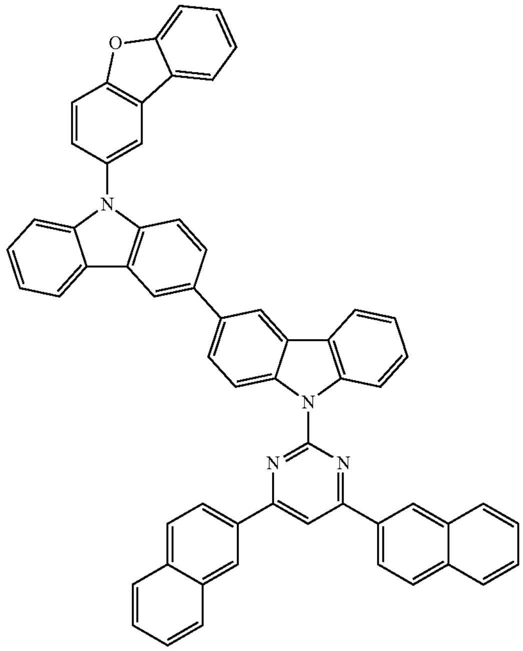

-continued
Compound 142
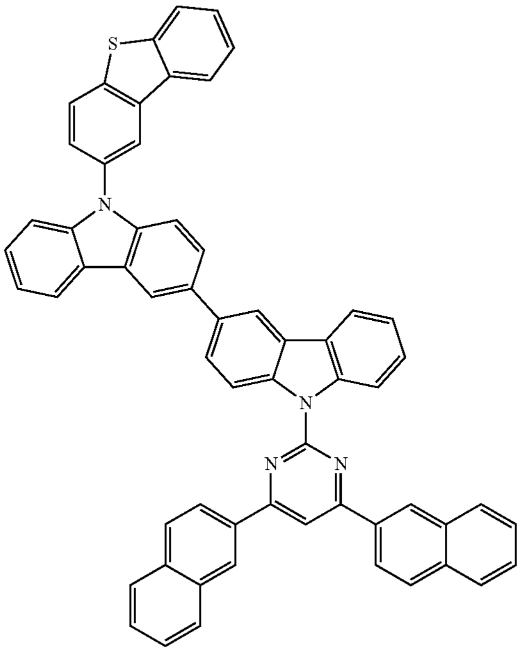
Compound 143
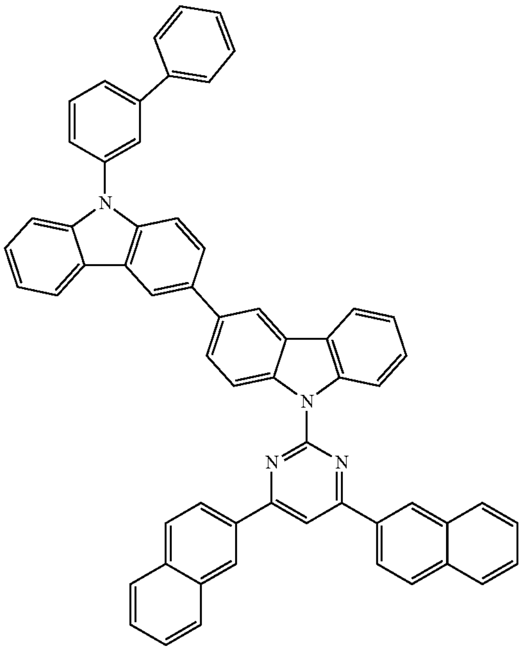
-continued
Compound 144
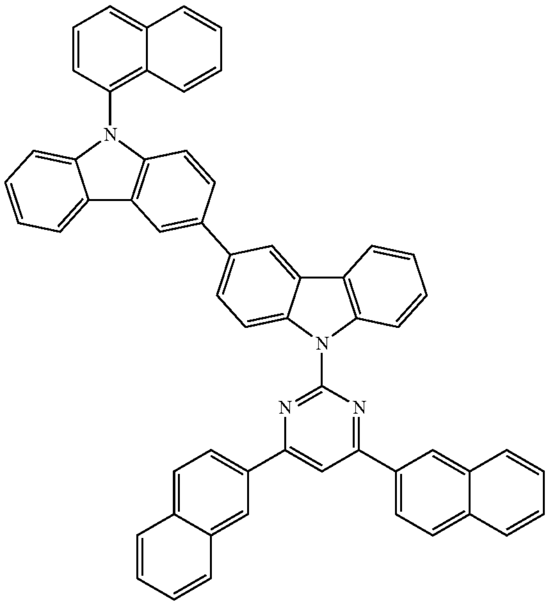
Compound 145
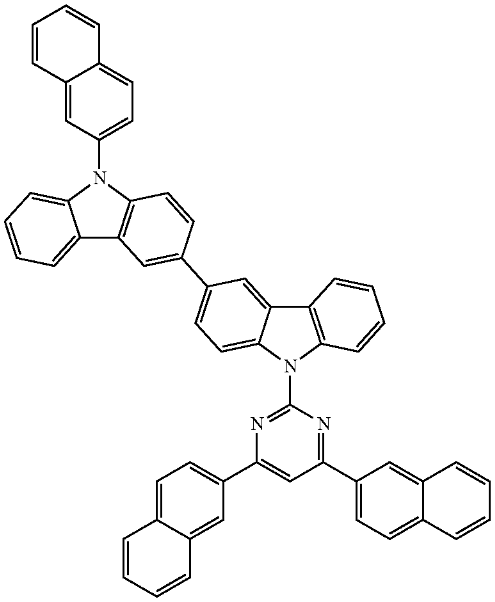

-continued
Compound 146
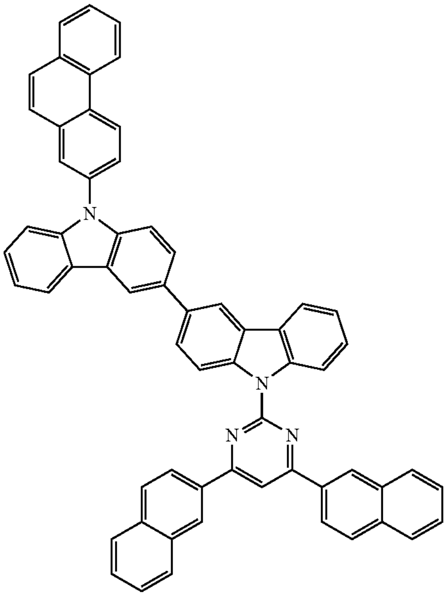
Compound 147
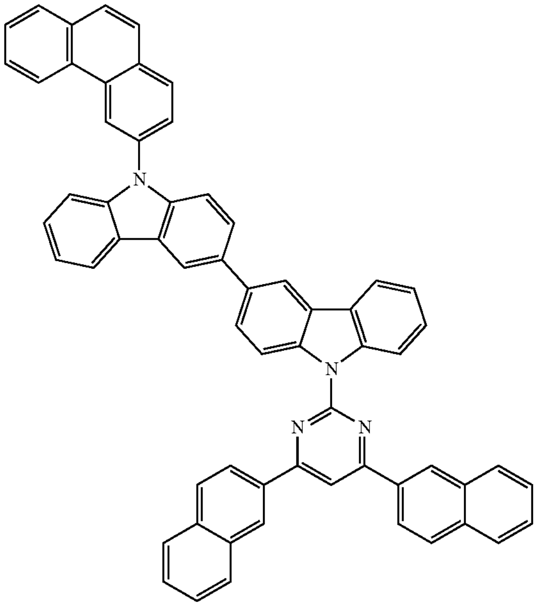
-continued
Compound 148
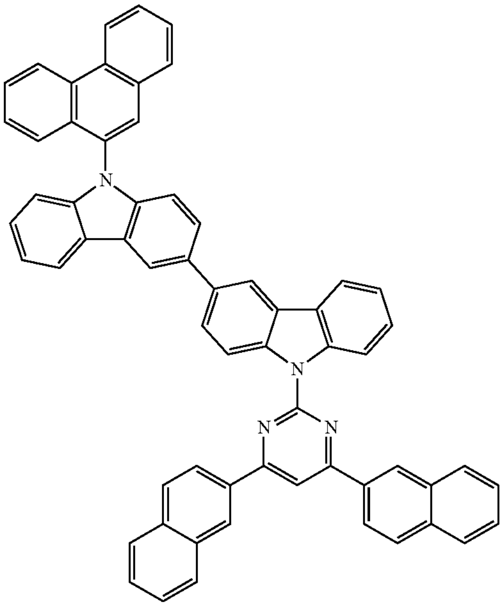
Compound 149
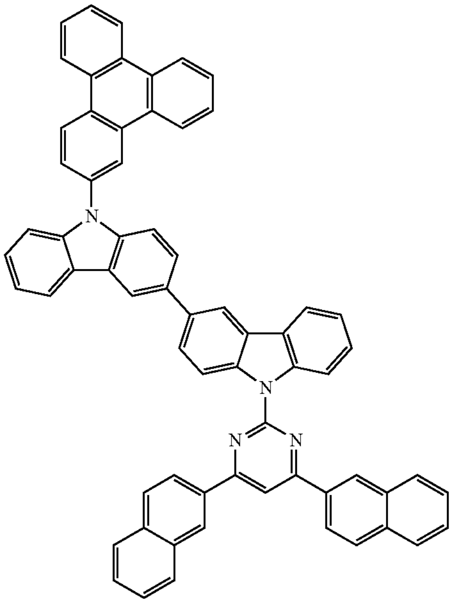

Compound 150
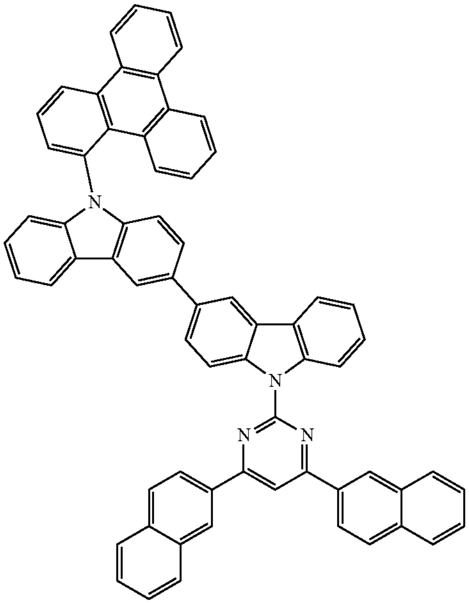
Compound 151
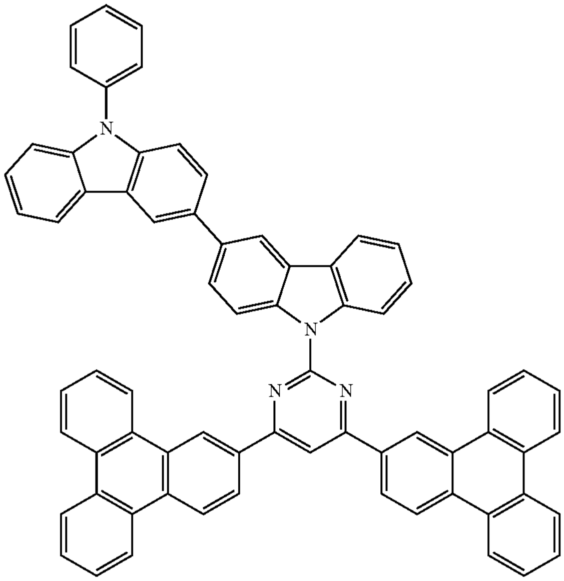
Compound 152
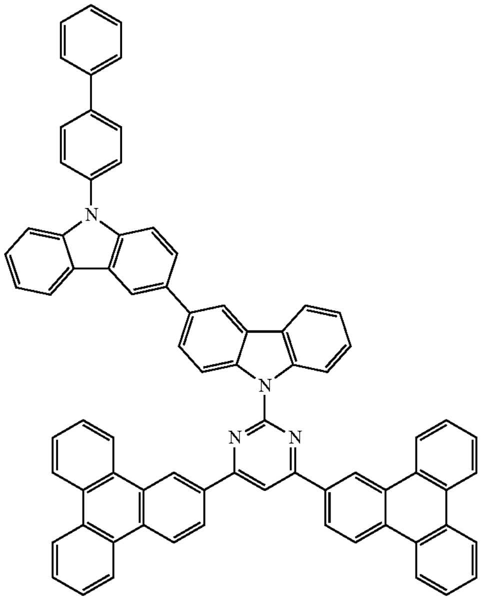
Compound 153
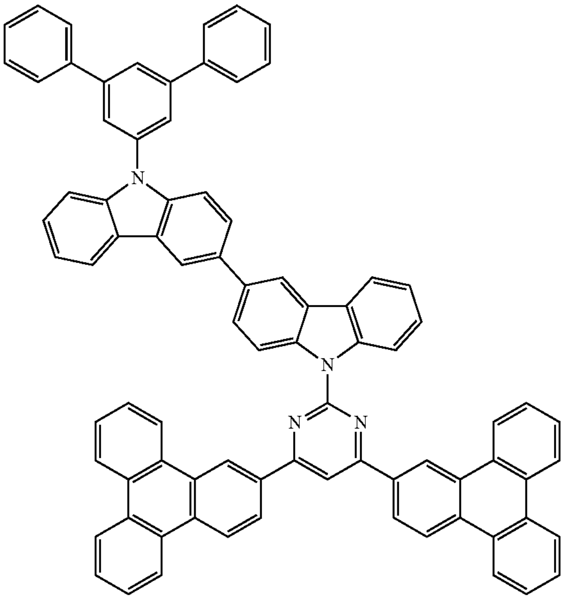

-continued
Compound 154
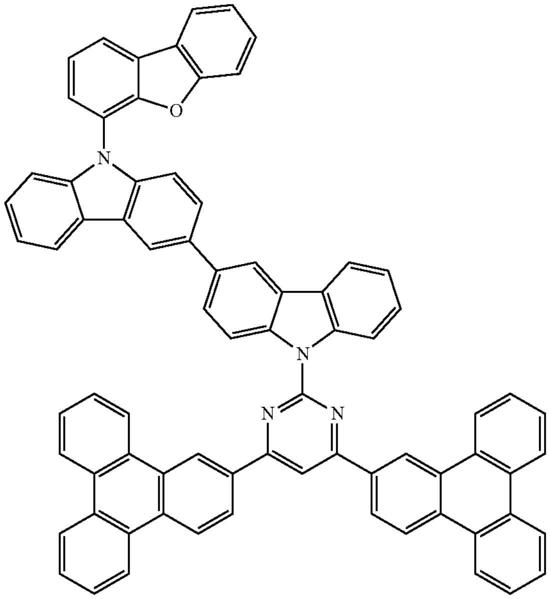
Compound 155
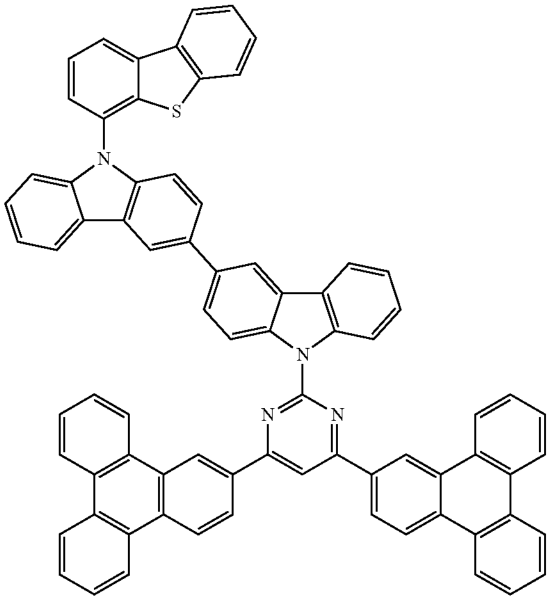
-continued
Compound 156
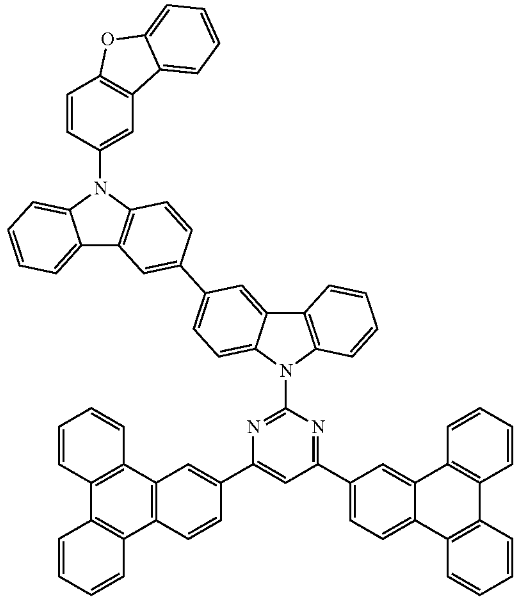
Compound 157
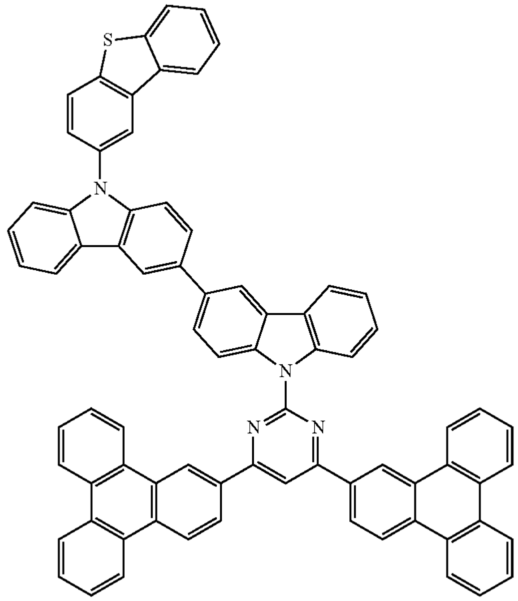

-continued
Compound 158
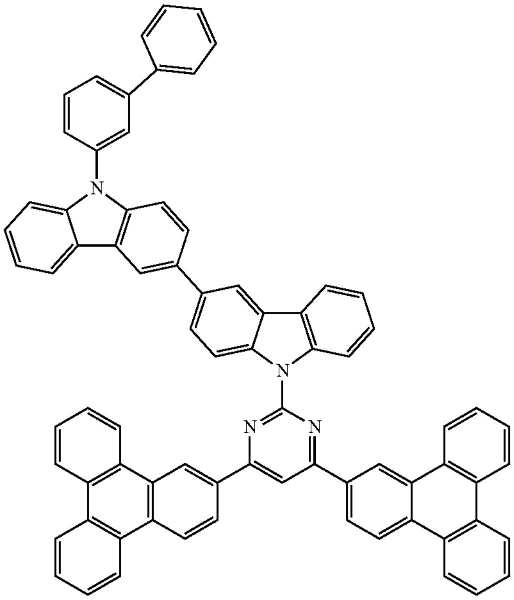
Compound 159
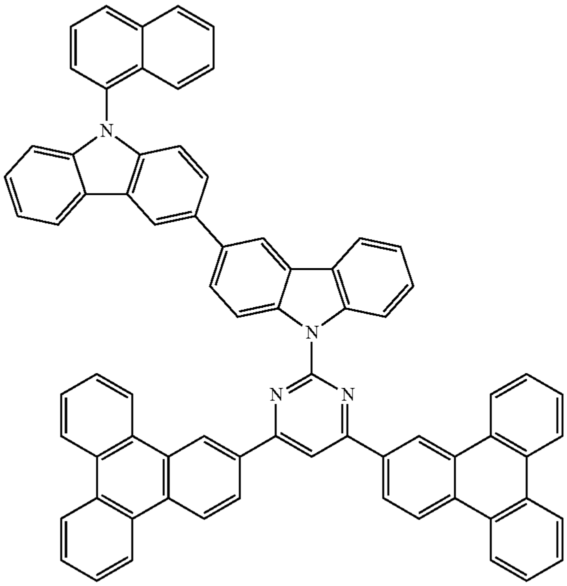
-continued
Compound 160
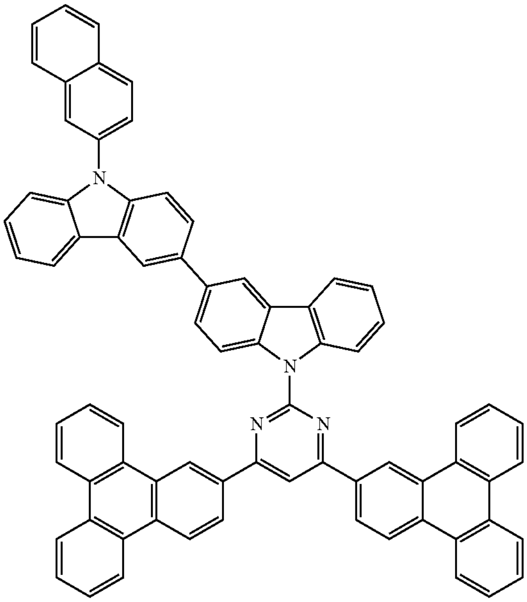
Compound 161
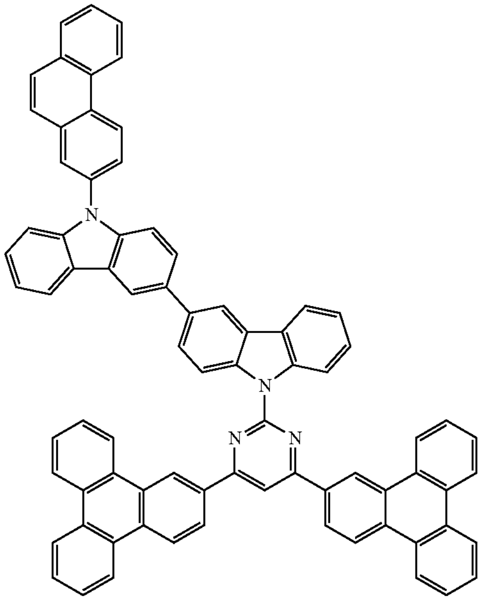

-continued
Compound 162
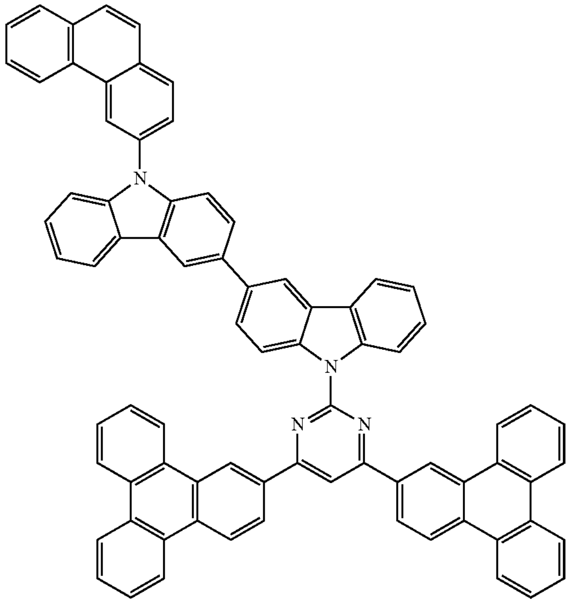
Compound 163
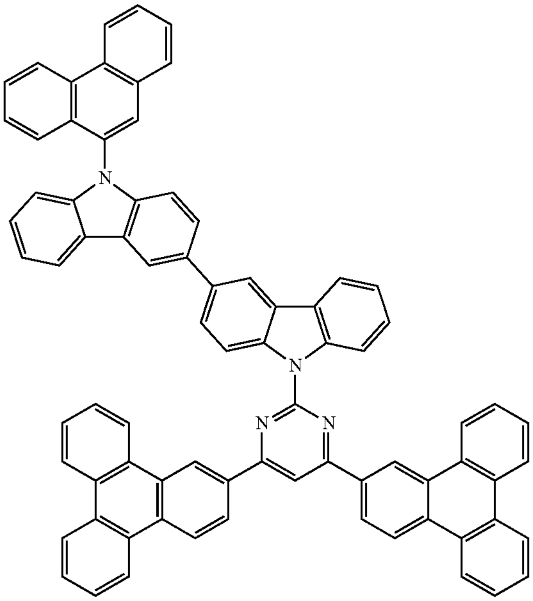
-continued
Compound 164
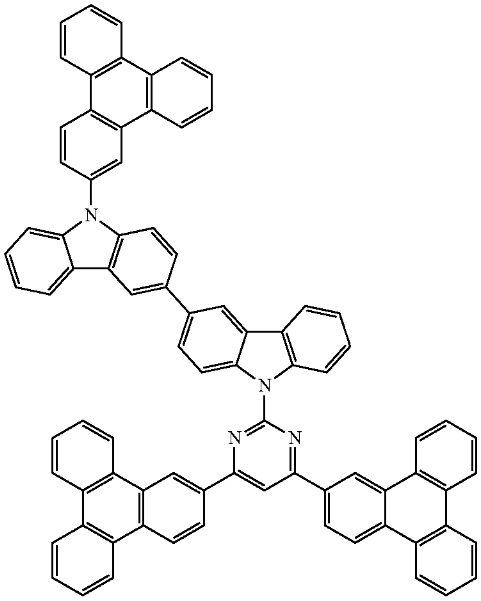
Compound 165
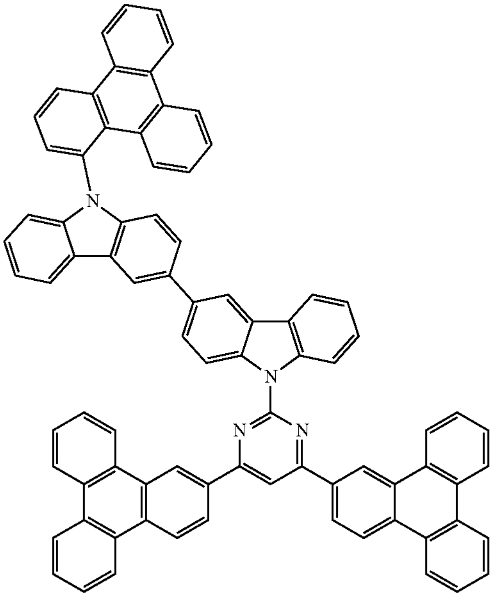

-continued
Compound 166
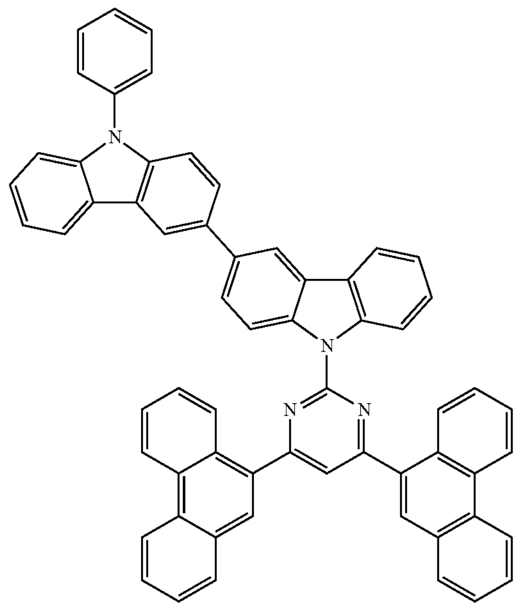
Compound 167
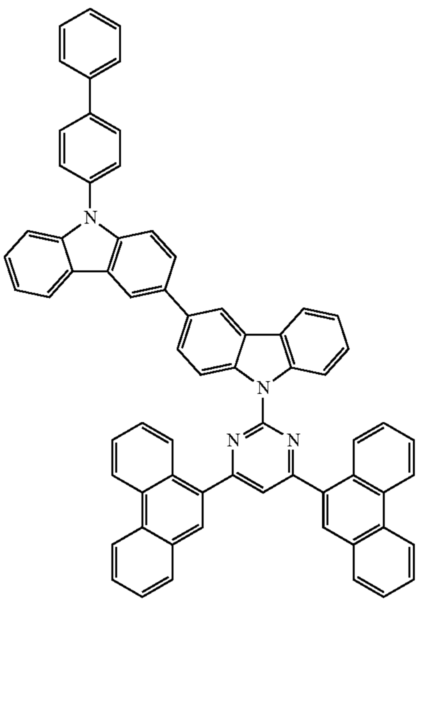
-continued
Compound 168
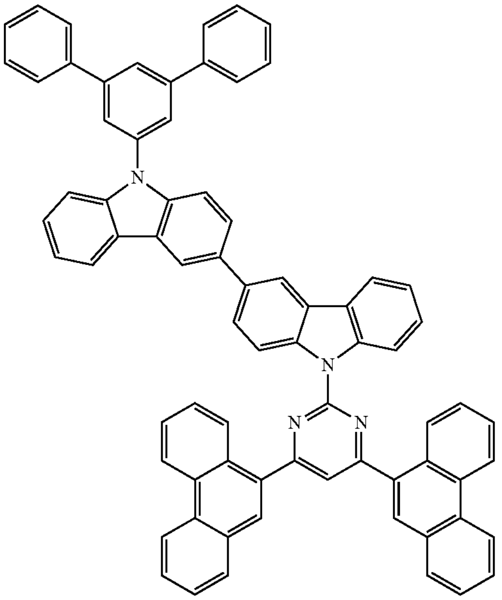
Compound 169
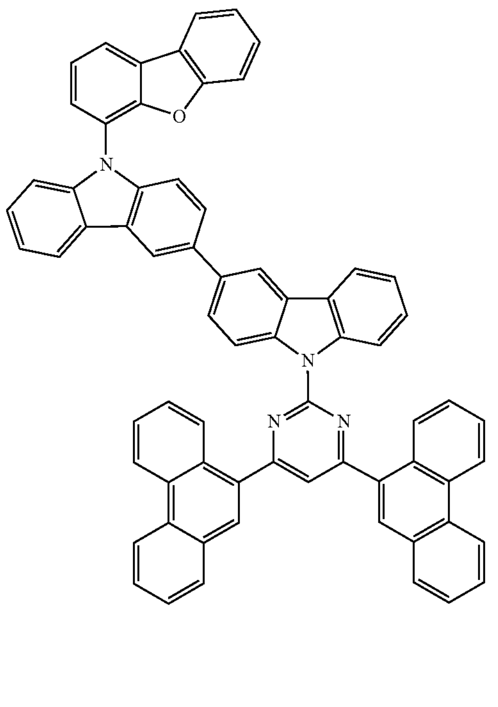

-continued
Compound 170
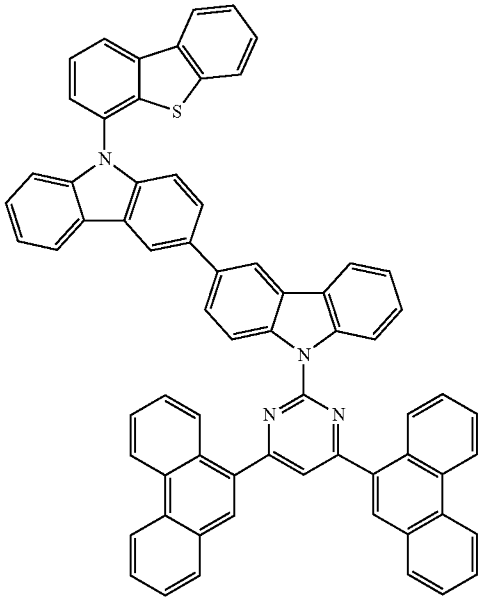
Compound 171
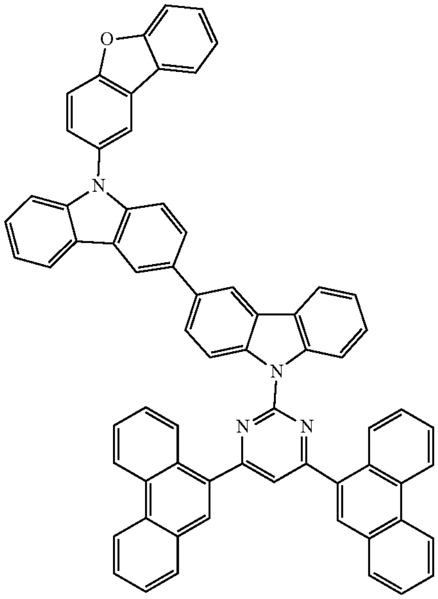
-continued
Compound 172
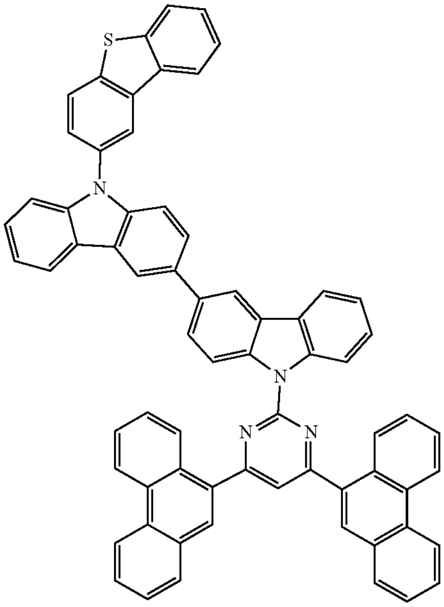
Compound 173
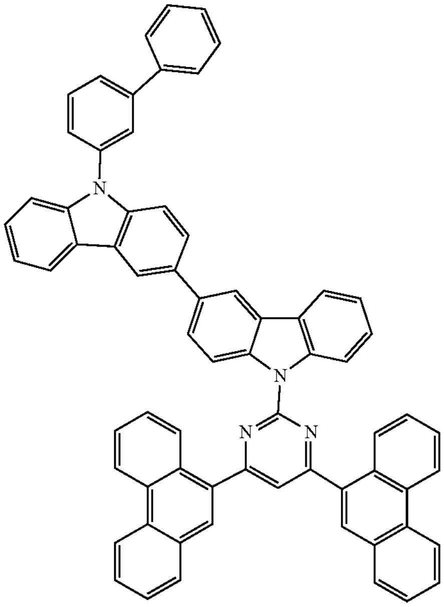

-continued
Compound 174
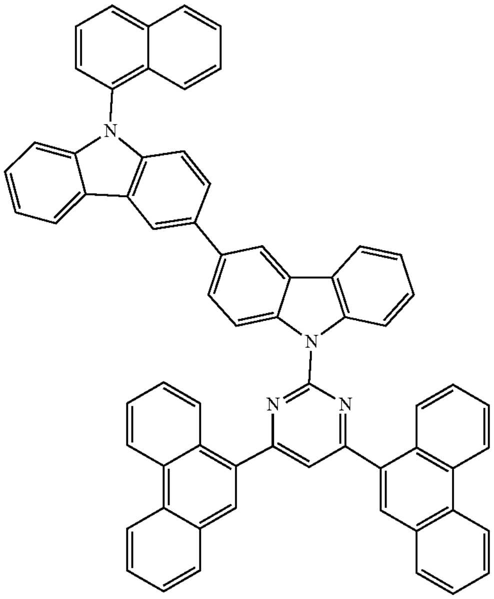
Compound 175
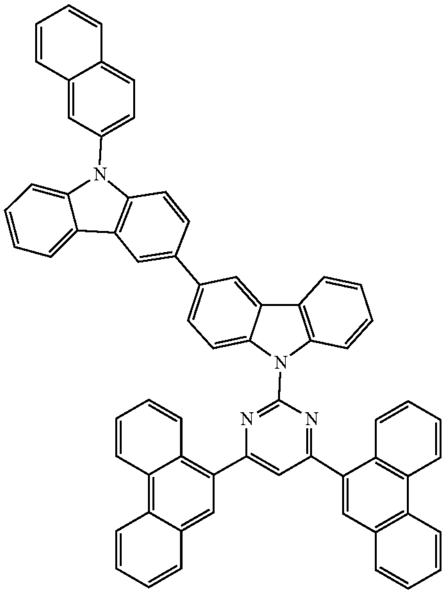
-continued
Compound 176
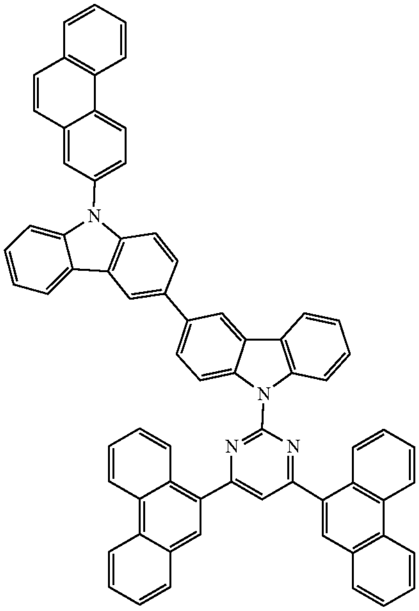
Compound 177
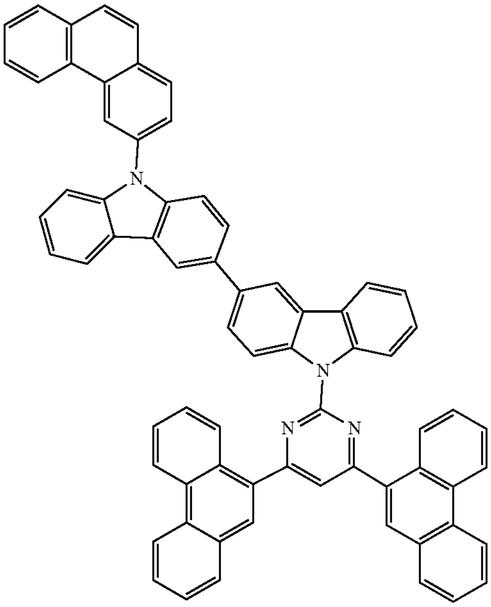

-continued
Compound 178
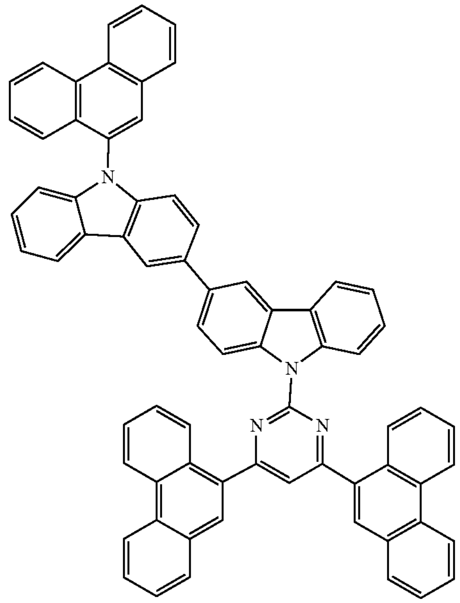
Compound 179
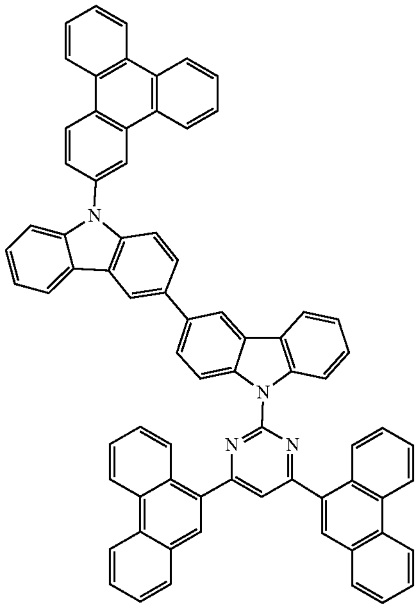
-continued
Compound 180
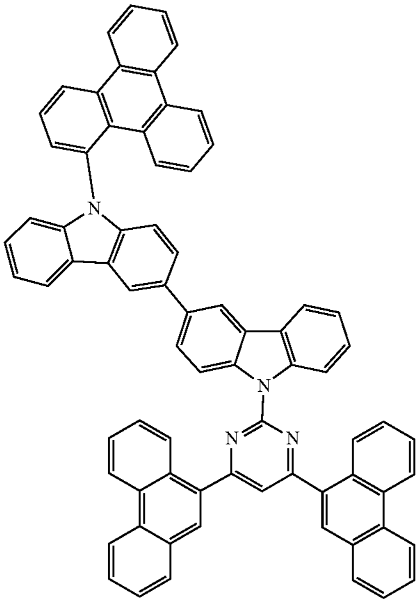
Compound 181
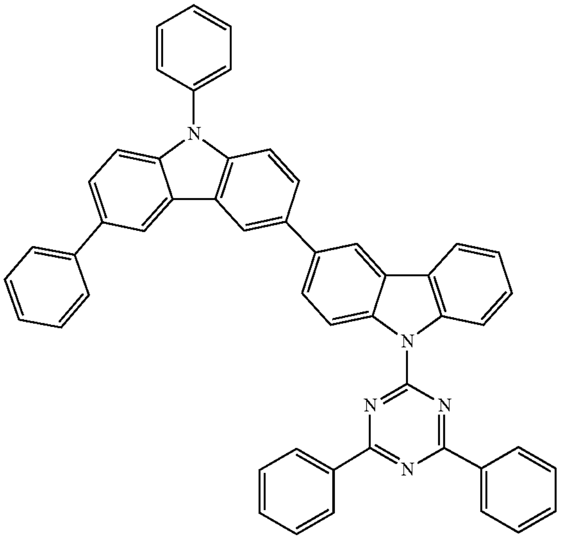

-continued

Compound 182

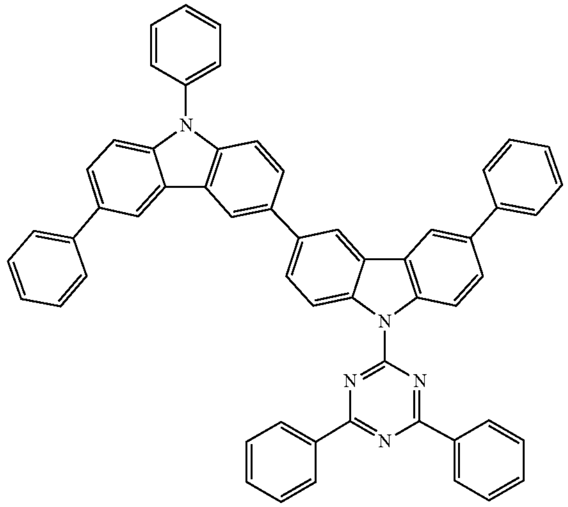

Compound 183

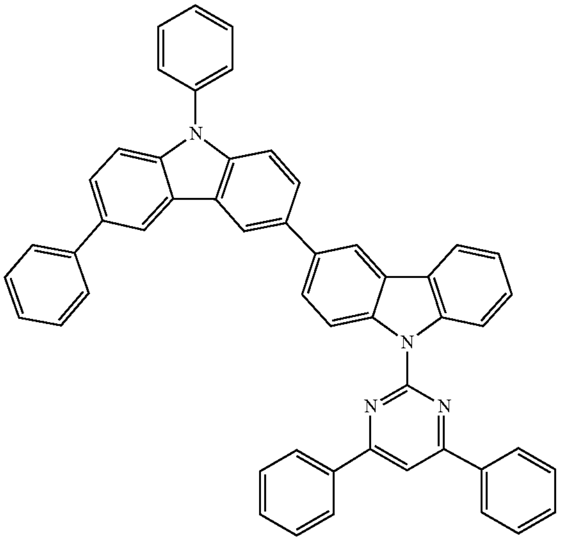

Compound 184

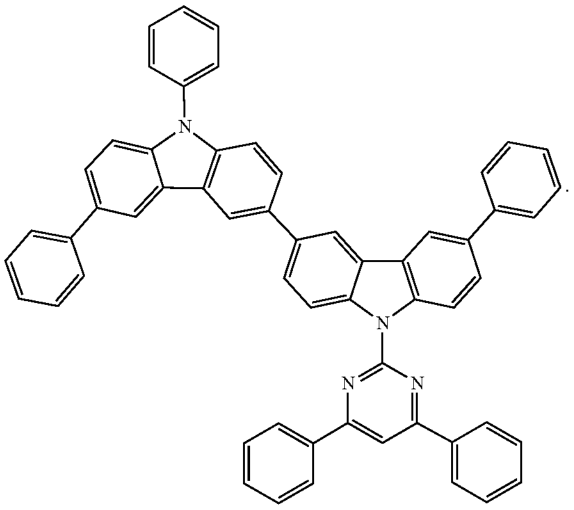

A first device comprising an organic light emitting device is also provided. The device further comprises an anode, a cathode, and an organic layer, disposed between the anode and the cathode. The organic layer comprises a compound having Formula I, as described above.

$R_1$, $R_2$, $R_3$, and $R_4$ may represent mono, di, tri, or tetra substitutions. $R_1$, $R_2$, $R_3$, and $R_4$ are independently selected from the group consisting of hydrogen, alkyl, alkoxy, amino, alkenyl, alkynyl, aryl and heteroaryl. $Ar_1$, $Ar_2$, and $Ar_3$ are independently selected from aryl or heteroaryl. $Ar_1$, $Ar_2$, and $Ar_3$ may be further substituted. X is C or N.

In one aspect, $Ar_1$, $Ar_2$, and $Ar_3$ are independently selected from the group consisting of phenyl, pyridine, naphthalene, biphenyl, terphenyl, fluorene, dibenzofuran, dibenzothiophene, phenanthrene, and triphenylene. $Ar_1$, $Ar_2$, and $Ar_3$ are independently further substituted with a substituent selected from the group consisting of hydrogen, alkyl, alkoxy, amino, alkenyl, alkynyl, aryl and heteroaryl, but the substituent is not an aryl or heteroaryl fused directly to $Ar_1$, $Ar_2$, and $Ar_3$. Preferably, $Ar_1$ and $Ar_2$ are independently selected from the group consisting of phenyl, pyridine, and naphthalene. Preferably, $Ar_3$ is selected from the group consisting of phenyl, biphenyl, dibenzofuran, and dibenzothiophene.

In another aspect, $R_1$, $R_2$, $R_3$, and $R_4$ are hydrogen.

Specific examples of devices containing compounds comprising bicarbazole are also provided. In particular, the compound is selected from the group consisting of Compound 1-Compound 184.

In one aspect, the organic layer is deposited using solution processing.

In one aspect, the organic layer is an emissive layer and the compound having Formula I is a host.

In another aspect, the organic layer further comprises an emissive dopant having the formula:

D1

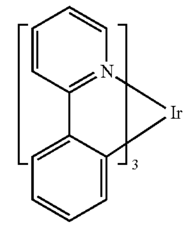

D2

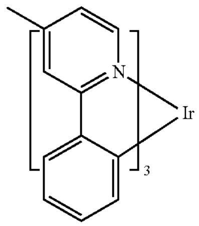

D3

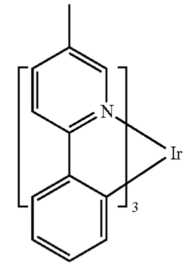

-continued
D4
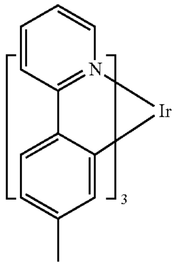
D5
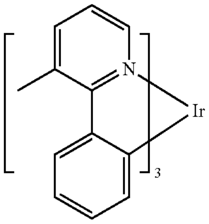
D6
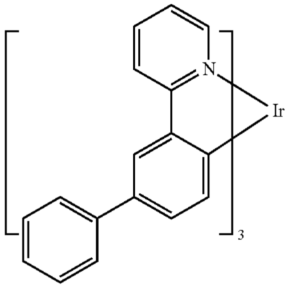
D7
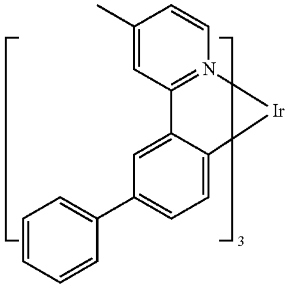
D8
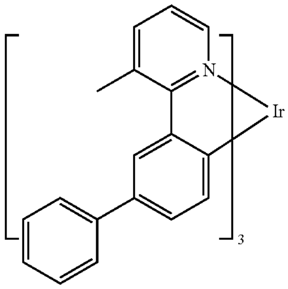
-continued
D9
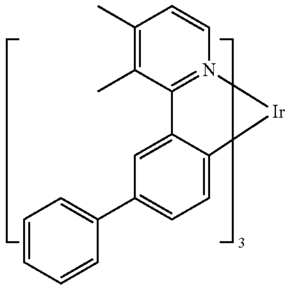
D10
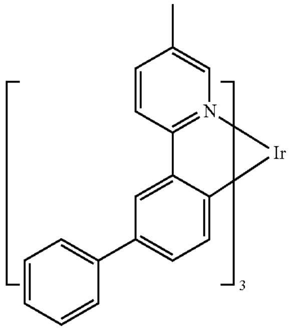
D11
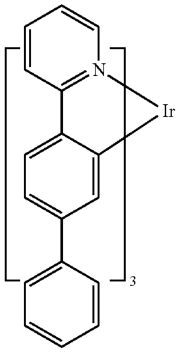
D12
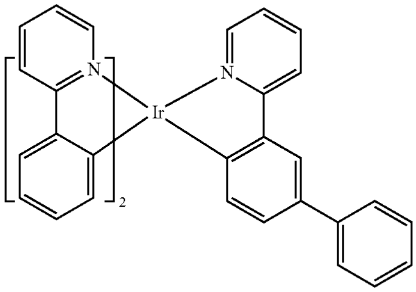
D13
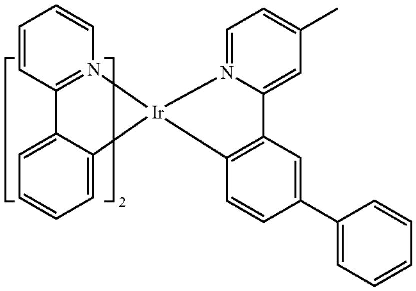

D14
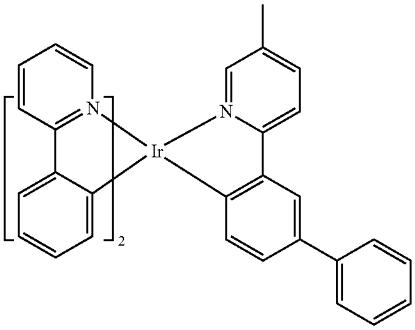
D15
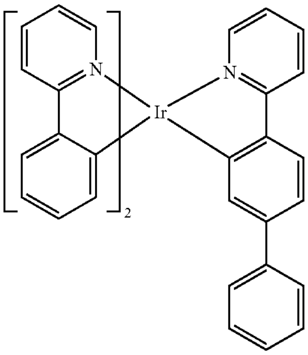
D16
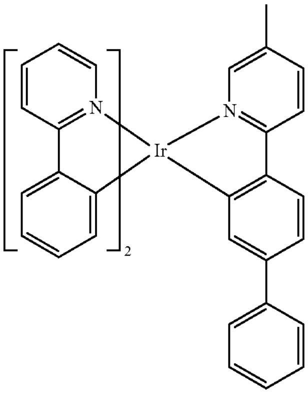
D17
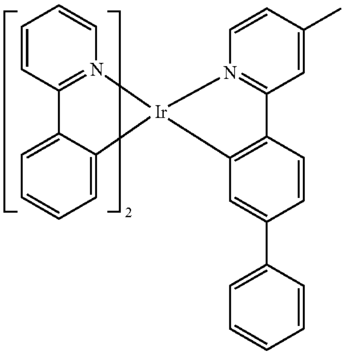
D18
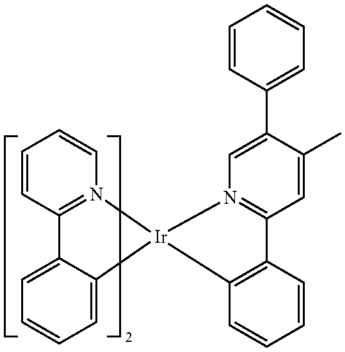
D19
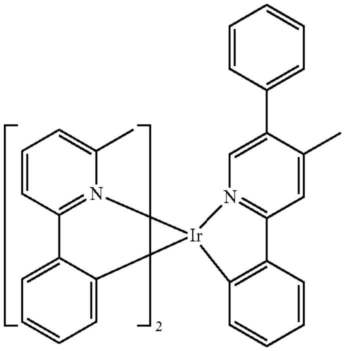
D20
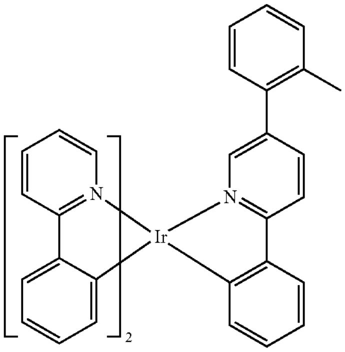
D21
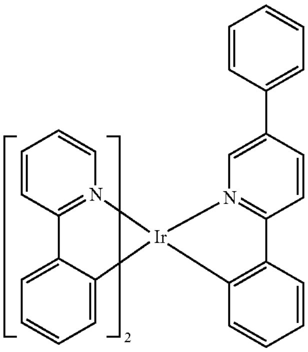

-continued
D22
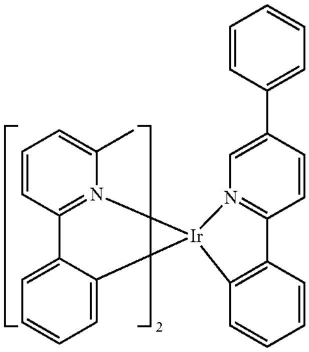
D23
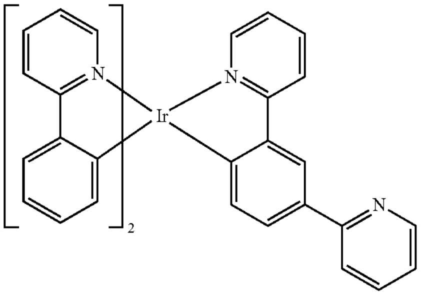
D24
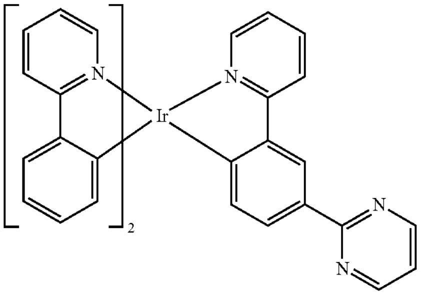
D25
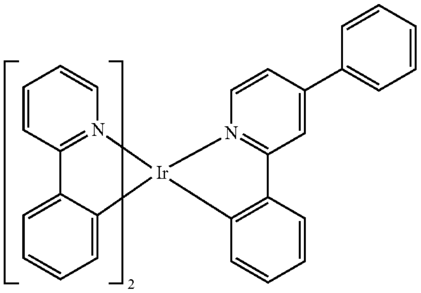
D26
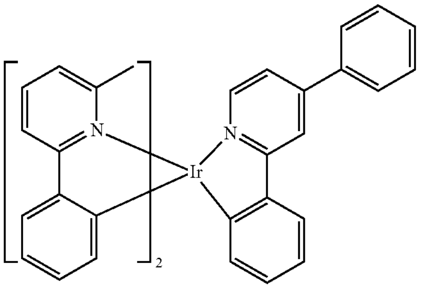
-continued
D27
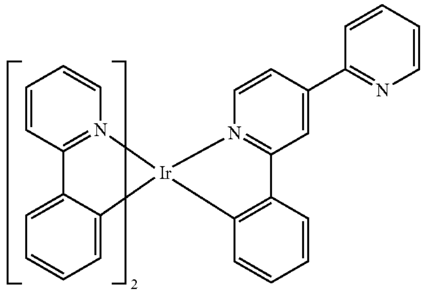
D28
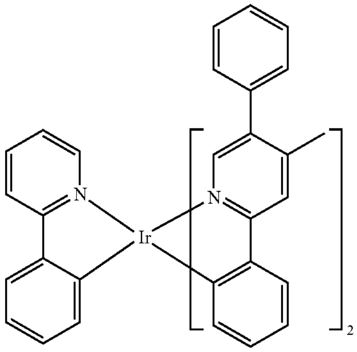
D29
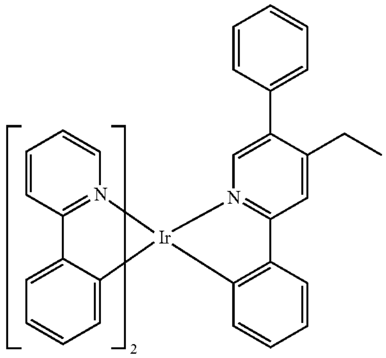
D30
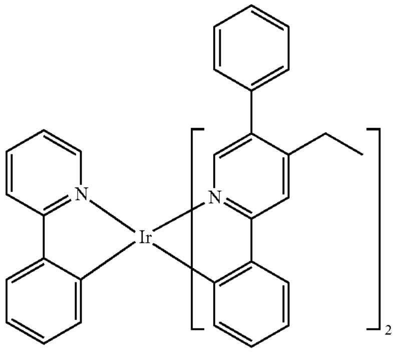
D31
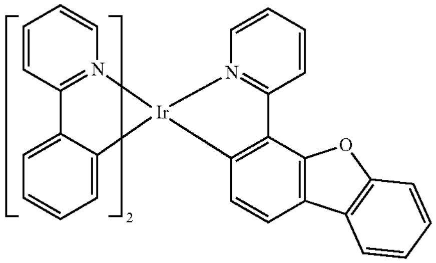

-continued
D32
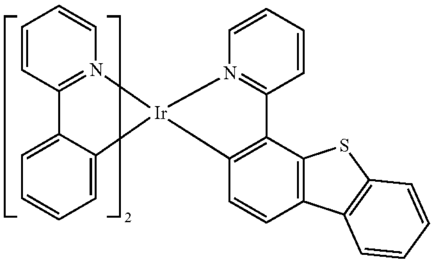
D33
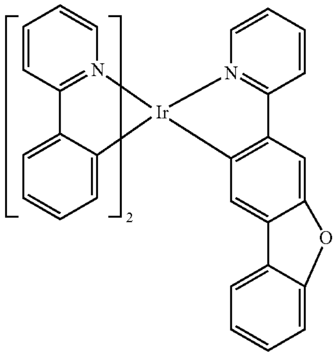
D34
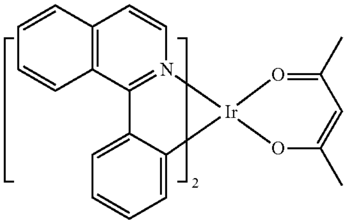
D35
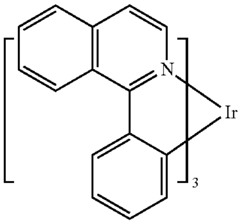
D36
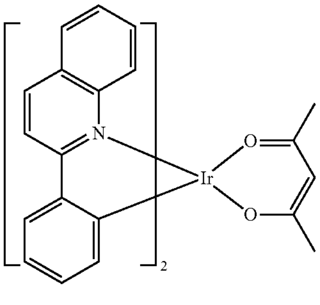
-continued
D37
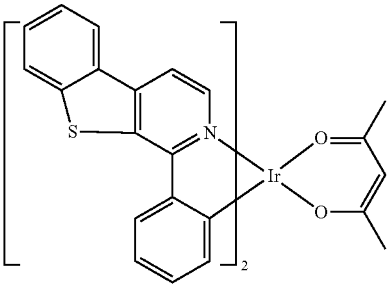
D38
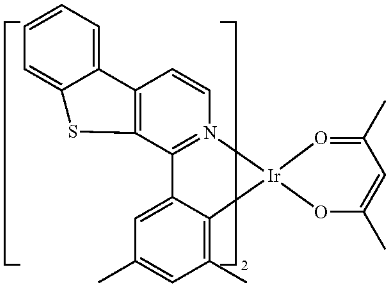
D39
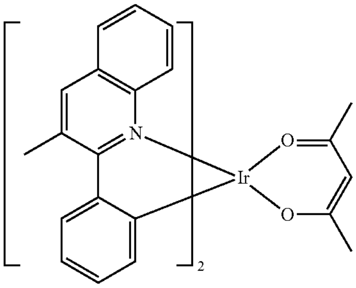
D40
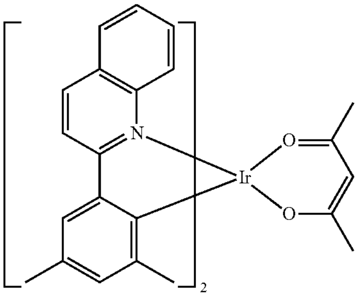
D41
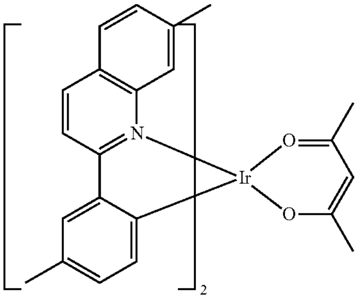

-continued

D42

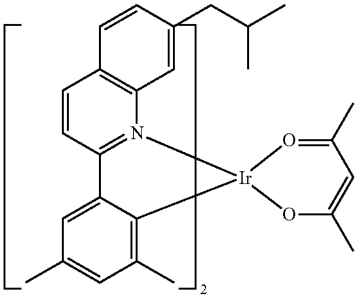

D43

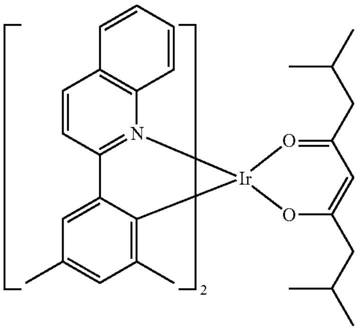

D44

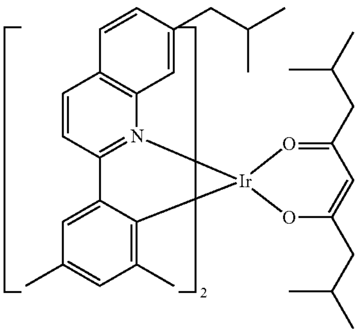

D45

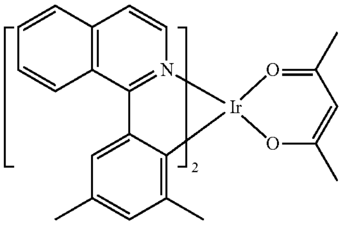

D46

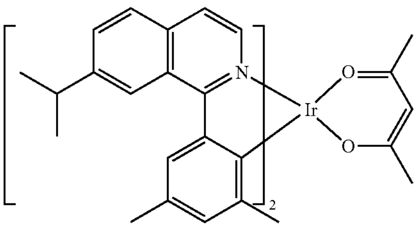

-continued

D47

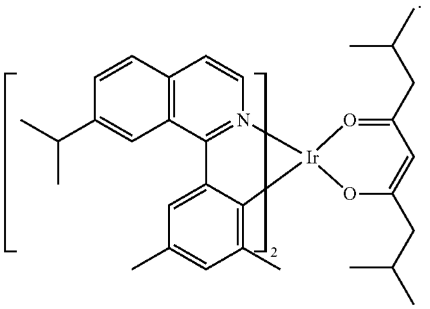

In one aspect, the first device is a consumer product. In another aspect, the first device is an organic light emitting device.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but not limit to: a phthalocyanine or porphryin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

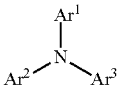

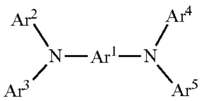

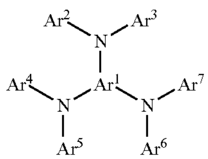

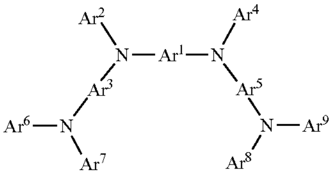

-continued

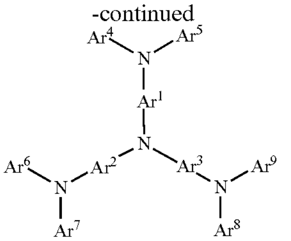

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, alkyl, alkoxy, amino, alkenyl, alkynyl, arylalkyl, heteroalkyl, aryl and heteroaryl.

In one aspect, $Ar^1$ to $Ar^9$ is independently selected from the group consisting

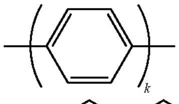
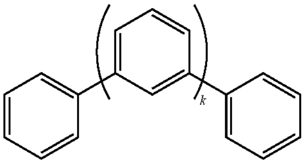
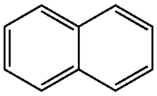
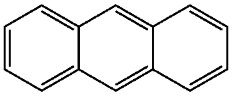
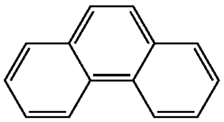
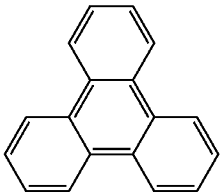

of:

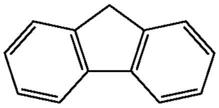
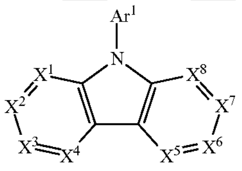

-continued

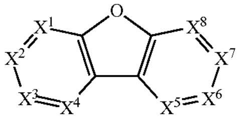
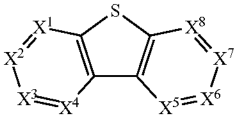

k is an integer from 1 to 20; $X^1$ to $X^8$ is CH or N; $Ar^1$ has the same group defined above.

Examples of metal complexes used in HIL or HTL include, but not limit to the following general formula:

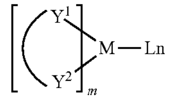

M is a metal, having an atomic weight greater than 40; $(Y^1\text{-}Y^2)$ is a bidentate ligand, Y1 and $Y^2$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, $(Y^1\text{-}Y^2)$ is a 2-phenylpyridine derivative.

In another aspect, $(Y^1\text{-}Y^2)$ is a carbene ligand.

In another aspect, M is selected from Ir, Pt, Os, and Zn.

In a further aspect, the metal complex has a smallest oxidation potential in solution vs. $Fc^+/Fc$ couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant.

Examples of metal complexes used as host are preferred to have the following general formula:

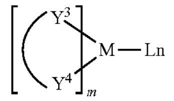

M is a metal; $(Y^3\text{-}Y^4)$ is a bidentate ligand, $Y^3$ and $Y^4$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, the metal complexes are:

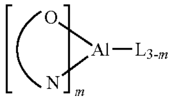
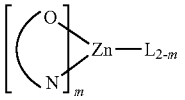

(O—N) is a bidentate ligand, having metal coordinated to atoms O and N.

In another aspect, M is selected from Ir and Pt.

In a further aspect, $(Y^3\text{-}Y^4)$ is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, alkyl, alkoxy, amino, alkenyl, alkynyl, arylalkyl, heteroalkyl, aryl and heteroaryl.

In one aspect, host compound contains at least one of the following groups in the molecule:

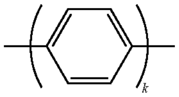
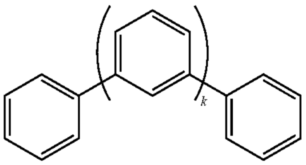
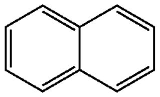
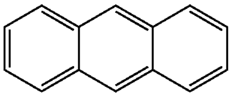
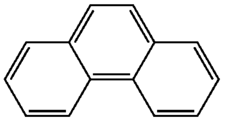
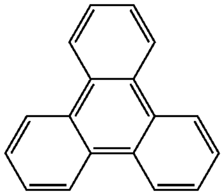
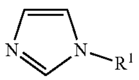
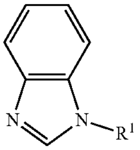
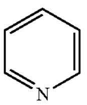
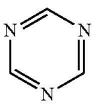
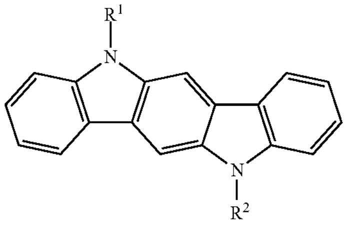

-continued

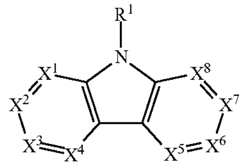
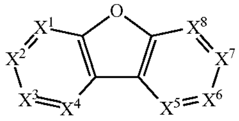
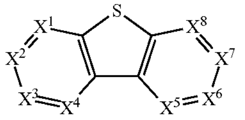
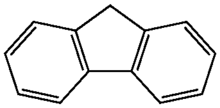
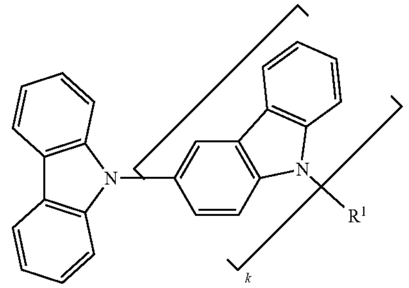
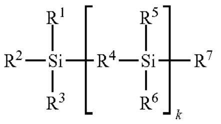
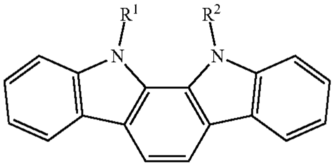

$R^1$ to $R^7$ is independently selected from the group consisting of hydrogen, alkyl, alkoxy, amino, alkenyl, alkynyl, arylalkyl, heteroalkyl, aryl and heteroaryl, when it is aryl or heteroaryl, it has the similar definition as Ar's mentioned above.

k is an integer from 0 to 20.

$X^1$ to $X^8$ is selected from CH or N.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule used as host described above.

In another aspect, compound used in HBL contains at least one of the following groups in the molecule:

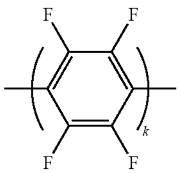
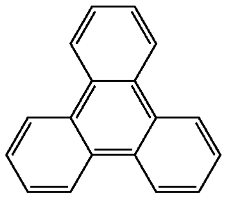
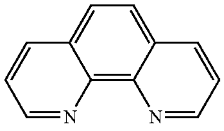
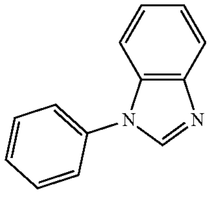

-continued

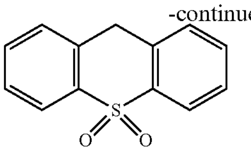 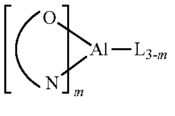

k is an integer from 0 to 20; L is an ancillary ligand, m is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

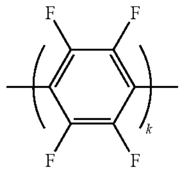 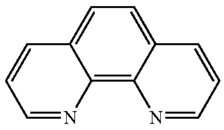 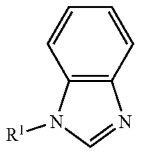

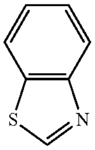 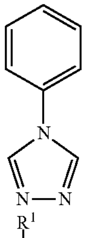 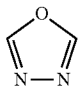 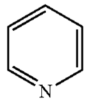 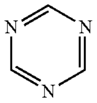

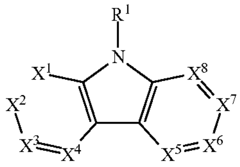 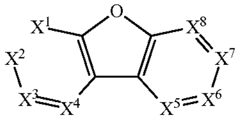

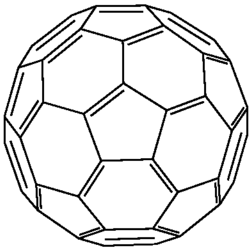 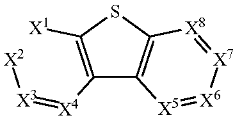

-continued

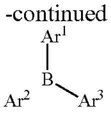

$R^1$ is selected from the group consisting of hydrogen, alkyl, alkoxy, amino, alkenyl, alkynyl, arylalkyl, heteroalkyl, aryl and heteroaryl, when it is aryl or heteroaryl, it has the similar definition as Ar's mentioned above.

$Ar^1$ to $Ar^a$ has the similar definition as Ar's mentioned above.

k is an integer from 0 to 20.

$X^1$ to $X^8$ is selected from CH or N.

In another aspect, the metal complexes used in ETL contains, but not limit to the following general formula:

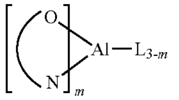 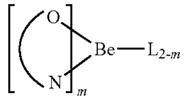

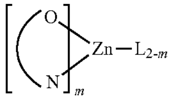 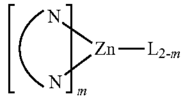

(O—N) or (N—N) is a bidentate ligand, having metal coordinated to atoms O, N or N, N; L is an ancillary ligand; m is an integer value from 1 to the maximum number of ligands that may be attached to the metal.

In any above-mentioned compounds used in each layer of OLED device, the hydrogen atoms attached to conjugated rings can be partially or fully deuterated.

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 1 below. Table 1 lists non-limiting classes of materials, non-limiting examples of compounds for each class, and references that disclose the materials.

TABLE 1
| MATERIAL | EXAMPLES OF MATERIAL | PUBLICATIONS |
|---|---|---|
| | Hole injection materials | |
| Phthalocyanine and porphryin compounds | 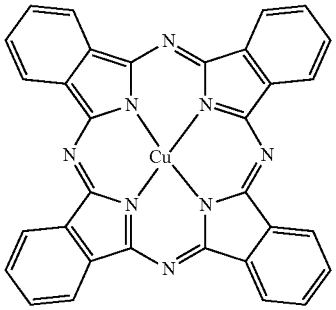 | Appl. Phys. Lett. 69, 2160 (1996) |
| Starburst triarylamines | 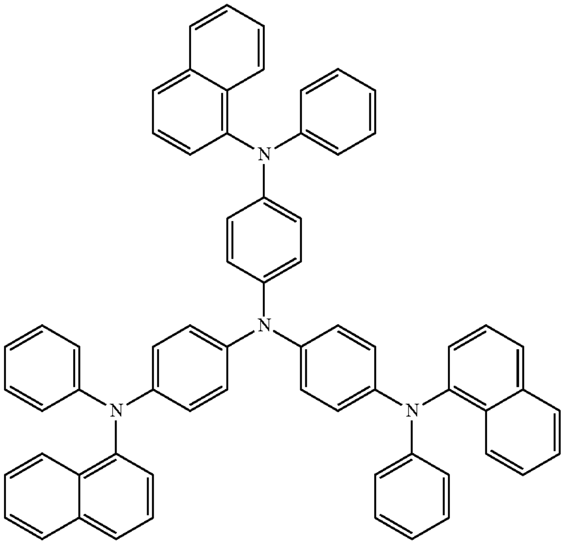 [SMILES: c1ccc(N(c2ccc(N(c3ccc(N(c4ccccc4)c4cccc5ccccc45)cc3)c3ccc(N(c4ccccc4)c4cccc5ccccc45)cc3)cc2)c2cccc3ccccc23)cc1] | J. Lumin. 72-74, 985 (1997) |
| $CF_x$ Fluorohydrocarbon polymer | $-[CH_xF_y]_n-$ | Appl. Phys. Lett. 78, 673 (2001) |

TABLE 1-continued
| MATERIAL | EXAMPLES OF MATERIAL | PUBLICATIONS |
|---|---|---|
| Conducting polymers (e.g., PEDOT:PSS, polyaniline, polypthiophene) | 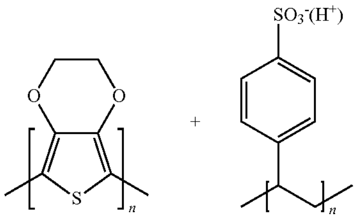 | Synth. Met. 87, 171 (1997) WO2007002683 |
| Phosphonic acid and sliane SAMs | 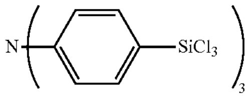 | US20030162053 |
| Triarylamine or polythiophene polymers with conductivity dopants | 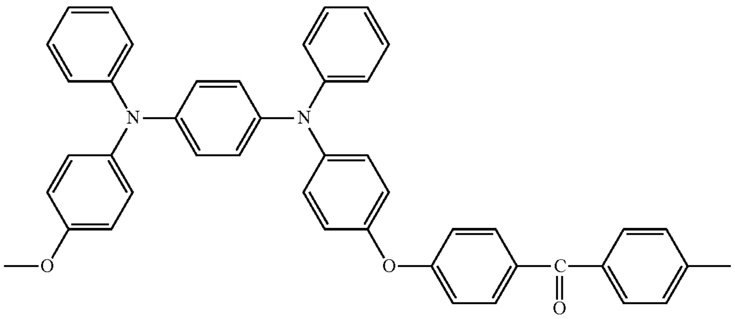 and 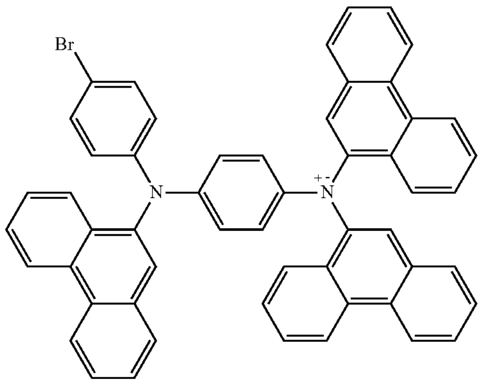 [SMILES: Brc1ccc(N(c2ccc(N(c3cc4ccccc4c4ccccc34)c3cc4ccccc4c4ccccc34)cc2)c2cc3ccccc3c3ccccc23)cc1] | EA01725079A1 |

TABLE 1-continued
| MATERIAL | EXAMPLES OF MATERIAL | PUBLICATIONS |
| --- | --- | --- |
| | 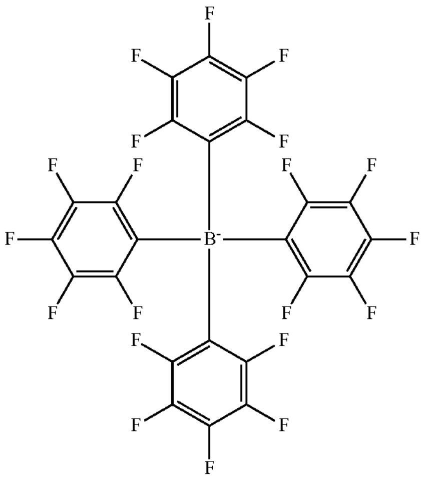 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F] | |
| Arylamines complexed with metal oxides such as molybdenum and tungsten oxides | 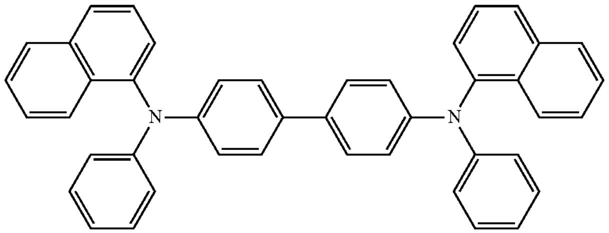 $+MoO_x$ | SID Symposium Digest, 37, 923 (2006) WO2009018009 |
| p-type semiconducting organic complexes | 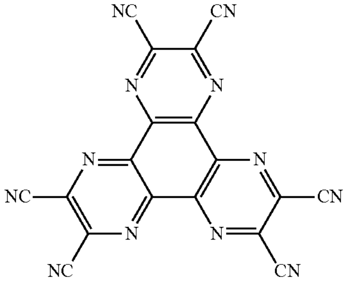 [SMILES: N#Cc1nc2c3nc(C#N)c(C#N)nc3c3nc(C#N)c(C#N)nc3c2nc1C#N] | US20020158242 |

TABLE 1-continued
| MATERIAL | EXAMPLES OF MATERIAL | PUBLICATIONS |
| --- | --- | --- |
| Metal organometallic complexes | 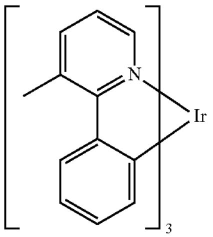 | US20060240279 |
| Cross-linkable compounds | 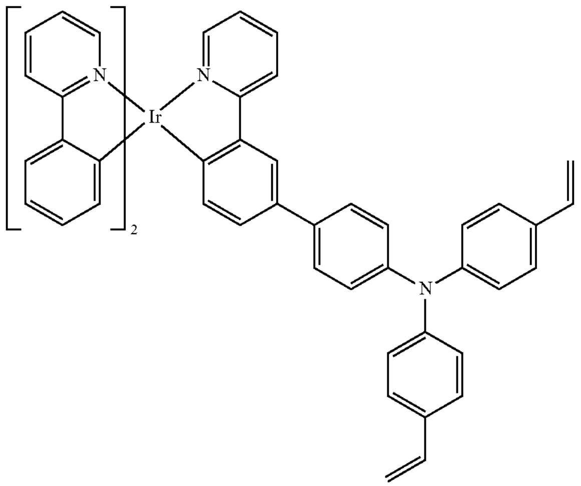 | US20080220265 |
| | Hole transporting materials | |
| Triarylamines (e.g., TPD, α-NPD) | 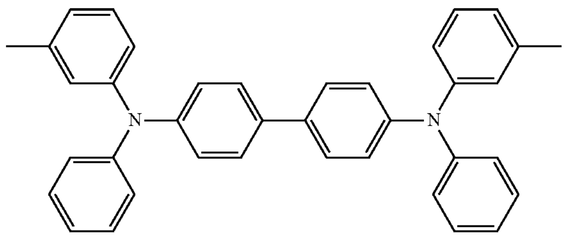 | Appl. Phys. Lett. 51, 913 (1987) |

TABLE 1-continued
| MATERIAL | EXAMPLES OF MATERIAL | PUBLICATIONS |
|---|---|---|
| | 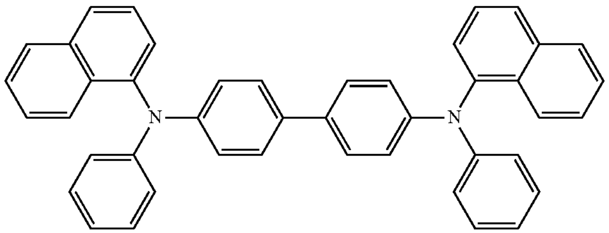 [SMILES: c1ccc(N(c2ccc(-c3ccc(N(c4ccccc4)c4cccc5ccccc45)cc3)cc2)c2cccc3ccccc23)cc1] | U.S. Pat. No. 5,061,569 |
| | 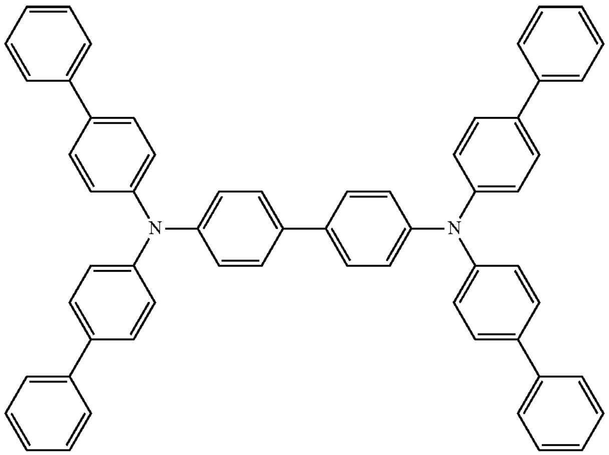 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |

TABLE 1-continued
| MATERIAL | EXAMPLES OF MATERIAL | PUBLICATIONS |
| --- | --- | --- |
| | 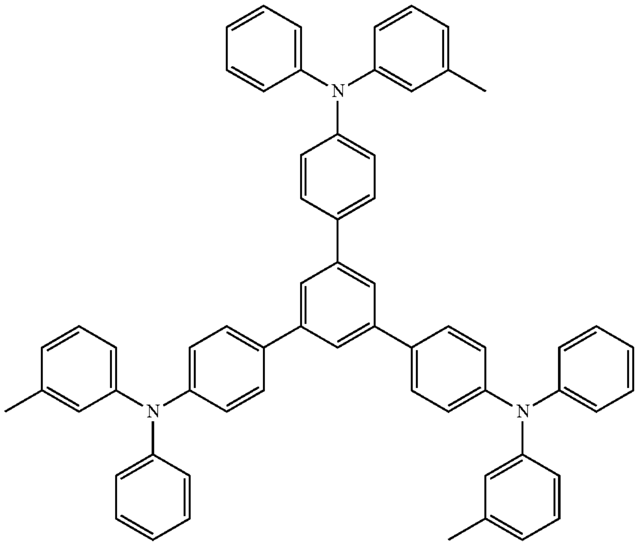 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |

TABLE 1-continued
| MATERIAL | EXAMPLES OF MATERIAL | PUBLICATIONS |
| --- | --- | --- |
| | 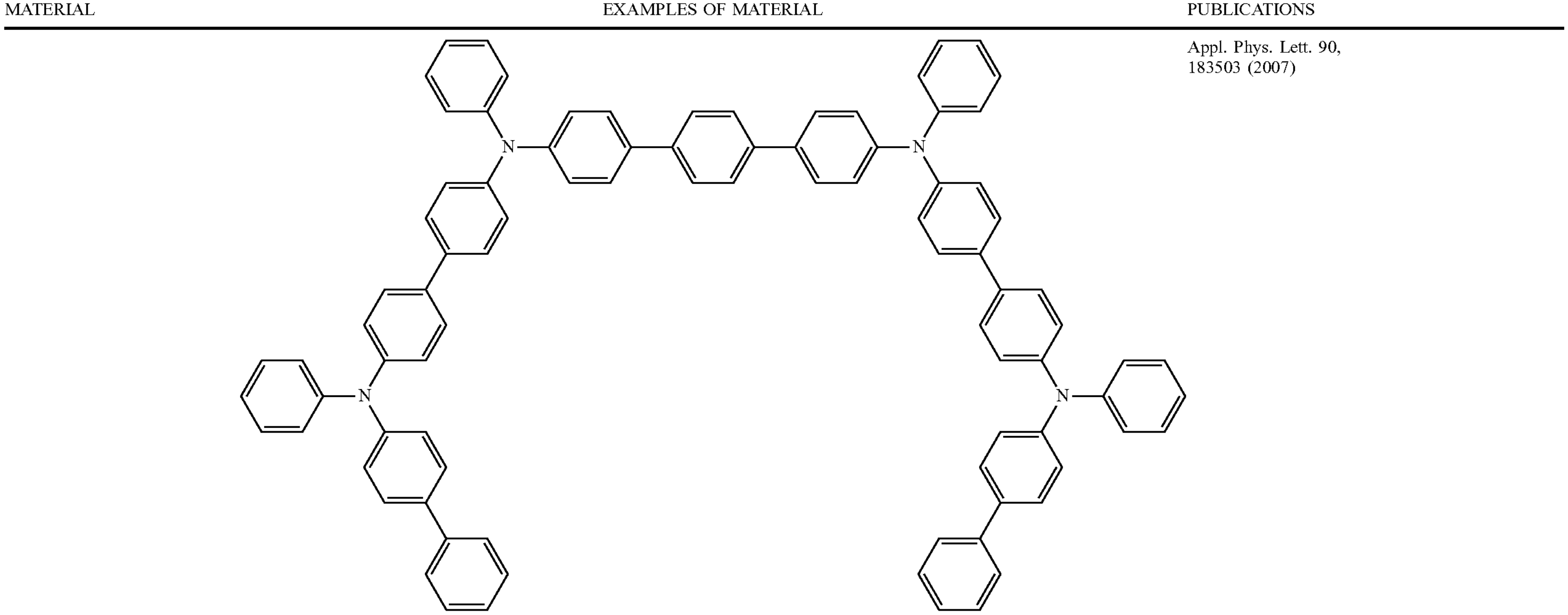 | Appl. Phys. Lett. 90, 183503 (2007) |

TABLE 1-continued
| MATERIAL | EXAMPLES OF MATERIAL | PUBLICATIONS |
|---|---|---|
| | 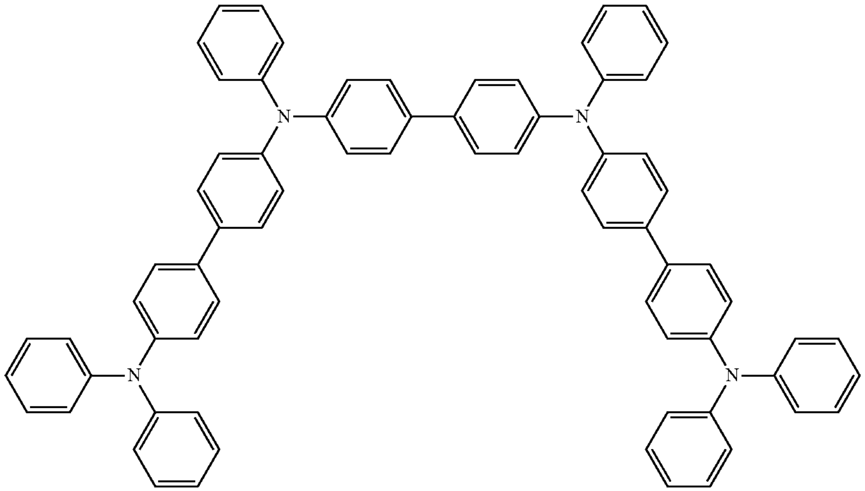 [SMILES: c1ccc(N(c2ccccc2)c2ccc(-c3ccc(N(c4ccccc4)c4ccc(-c5ccc(N(c6ccccc6)c6ccc(-c7ccc(N(c8ccccc8)c8ccccc8)cc7)cc6)cc5)cc4)cc3)cc2)cc1] | Appl. Phys. Lett. 90, 183503 (2007) |
| Triaylamine on spirofluorene core | 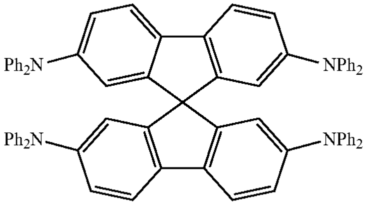 | Synth. Met. 91, 209 (1997) |

TABLE 1-continued
| MATERIAL | EXAMPLES OF MATERIAL | PUBLICATIONS |
|---|---|---|
| Arylamine carbazole compounds | 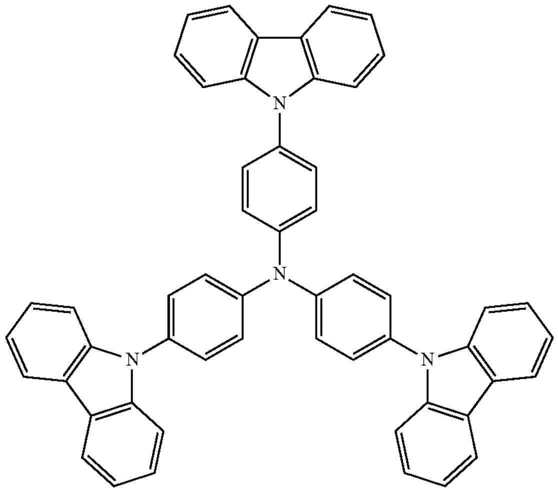 [SMILES: c1ccc2c(c1)c1ccccc1n2-c1ccc(N(c2ccc(-n3c4ccccc4c4ccccc43)cc2)c2ccc(-n3c4ccccc4c4ccccc43)cc2)cc1] | Adv. Mater. 6, 677 (1994), US20080124572 |
| Triarylamine with (di)benzothiophene/(di)benzofuran | 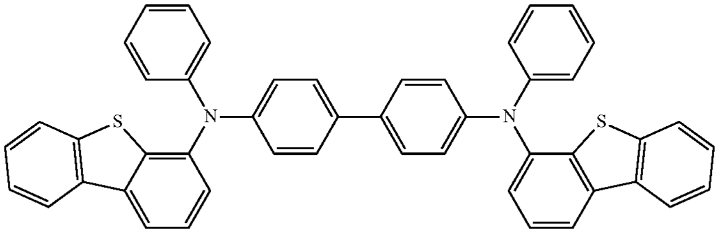 [SMILES: c1ccc(N(c2ccc(-c3ccc(N(c4ccccc4)c4cccc5c4sc4ccccc45)cc3)cc2)c2cccc3c2sc2ccccc23)cc1] | US20070278938, US20080106190 |

TABLE 1-continued
| MATERIAL | EXAMPLES OF MATERIAL | PUBLICATIONS |
|---|---|---|
| Indolocarbazoles | 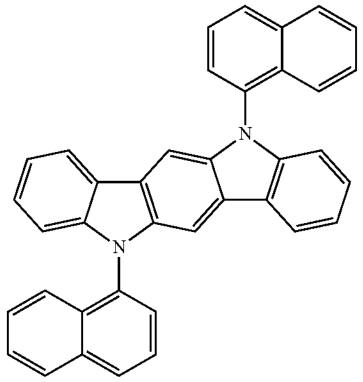 [SMILES: c1ccc2c(-n3c4ccccc4c4cc5c(cc43)c3ccccc3n5-c3cccc4ccccc34)cccc2c1] | Synth. Met. 111, 421 (2000) |
| Isoindole compounds | 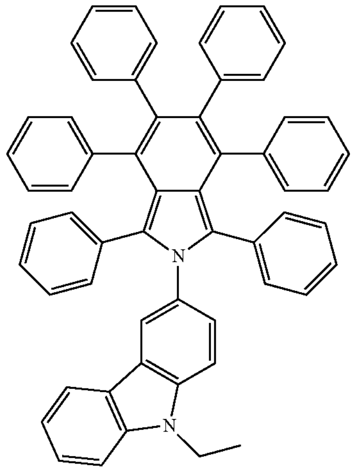 [SMILES: CCn1c2ccccc2c2cc(-n3c(-c4ccccc4)c4c(-c5ccccc5)c(-c5ccccc5)c(-c5ccccc5)c(-c5ccccc5)c4c3-c3ccccc3)ccc21] | Chem. Mater. 15, 3148 (2003) |

TABLE 1-continued
| MATERIAL | EXAMPLES OF MATERIAL | PUBLICATIONS |
|---|---|---|
| Metal carbene complexes | 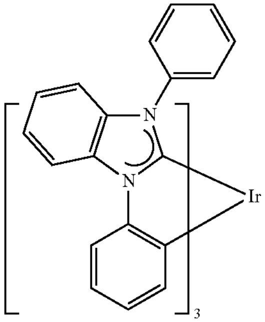 | US20080018221 |
| | Phosphorescent OLED host materials<br>Red hosts | |
| Arylcarbazoles | 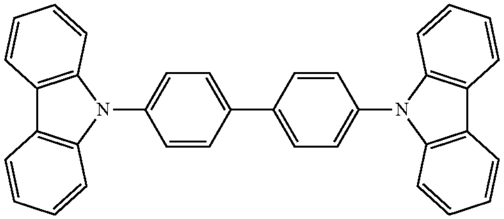 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
| Metal 8-hydroxyquinolates (e.g., $Alq_3$, BAlq) | 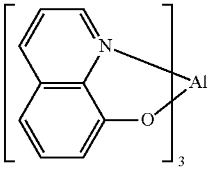 | Nature 395, 151 (1998) |
| | 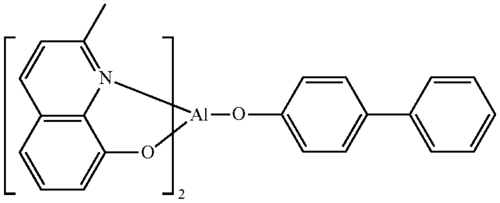 | US20060202194 |

TABLE 1-continued
| MATERIAL | EXAMPLES OF MATERIAL | PUBLICATIONS |
|---|---|---|
| | 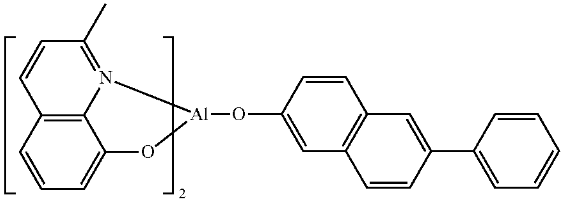 | WO2005014551 |
| | 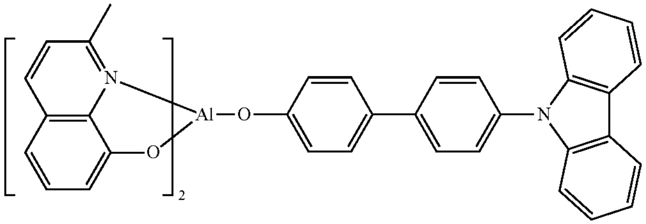 | WO2006072002 |
| Metal phenoxybenzothiazole compounds | 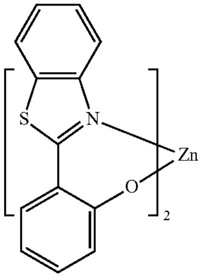 | Appl. Phys. Lett. 90, 123509 (2007) |
| Conjugated oligomers and polymers (e.g., polyfluorene) | 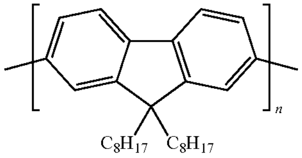 | Org. Electron. 1, 15 (2000) |

TABLE 1-continued
| MATERIAL | EXAMPLES OF MATERIAL | PUBLICATIONS |
|---|---|---|
| Aromatic fused rings | 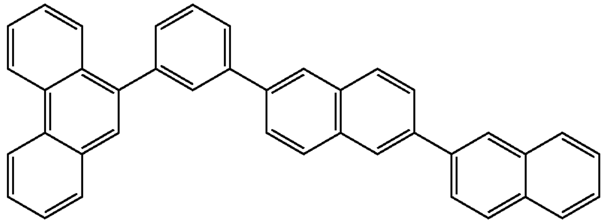 [SMILES: c1cc(-c2ccc3cc(-c4ccc5ccccc5c4)ccc3c2)cc(-c2cc3ccccc3c3ccccc23)c1] | WO2009066779, WO2009066778, WO2009063833, US20090045731, US20090045730, WO2009008311, US20090008605, US20090009065 |
| Zinc complexes | 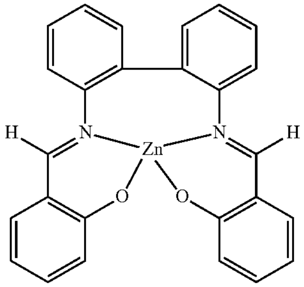 | WO2009062578 |
| | Green hosts | |
| Arylcarbazoles | 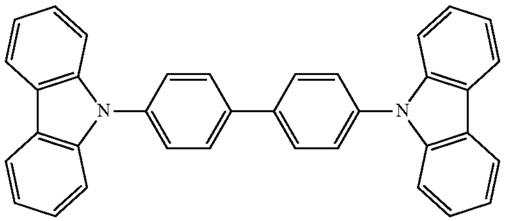 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
| | 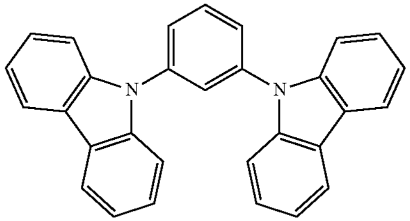 [SMILES: c1cc(-n2c3ccccc3c3ccccc32)cc(-n2c3ccccc3c3ccccc32)c1] | US20030175553 |

TABLE 1-continued
| MATERIAL | EXAMPLES OF MATERIAL | PUBLICATIONS |
|---|---|---|
| | 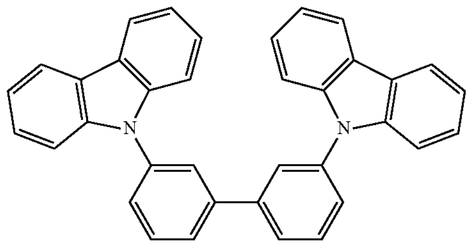 [SMILES: c1cc(-c2cccc(-n3c4ccccc4c4ccccc43)c2)cc(-n2c3ccccc3c3ccccc32)c1] | WO2001039234 |
| Aryltriphenylene compounds | 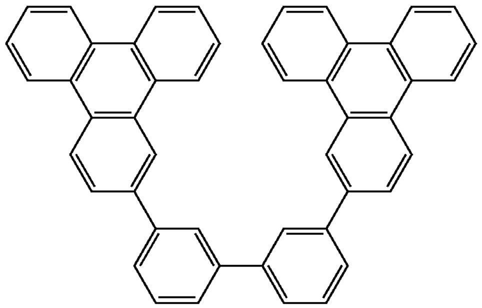 [SMILES: c1cc(-c2cccc(-c3ccc4c5ccccc5c5ccccc5c4c3)c2)cc(-c2ccc3c4ccccc4c4ccccc4c3c2)c1] | US20060280965 |
| | 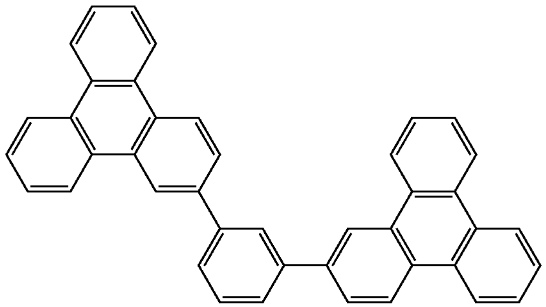 [SMILES: c1cc(-c2ccc3c4ccccc4c4ccccc4c3c2)cc(-c2ccc3c4ccccc4c4ccccc4c3c2)c1] | US20060280965 |

TABLE 1-continued
| MATERIAL | EXAMPLES OF MATERIAL | PUBLICATIONS |
| --- | --- | --- |
| | 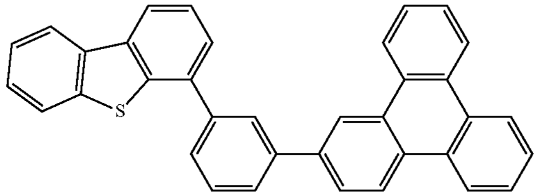 [SMILES: c1cc(-c2ccc3c4ccccc4c4ccccc4c3c2)cc(-c2cccc3c2sc2ccccc23)c1] | WO2009021126 |
| Donor acceptor type molecules | 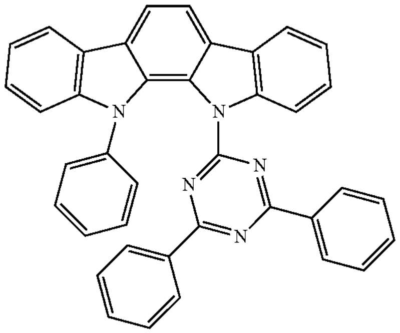 [SMILES: c1ccc(-c2nc(-c3ccccc3)nc(-n3c4ccccc4c4ccc5c6ccccc6n(-c6ccccc6)c5c43)n2)cc1] | WO2008056746 |
| Aza-carbazole/DBT/DBF | 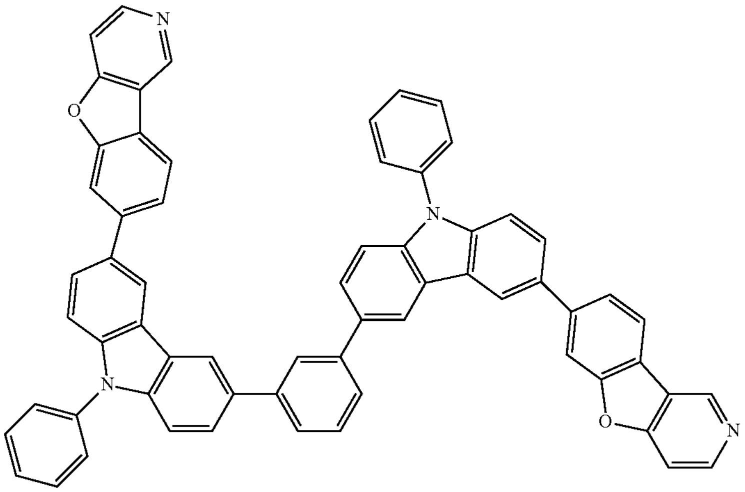 [SMILES: c1ccc(-n2c3ccc(-c4cccc(-c5ccc6c(c5)c5cc(-c7ccc8c(c7)oc7ccncc78)ccc5n6-c5ccccc5)c4)cc3c3cc(-c4ccc5c(c4)oc4ccncc45)ccc32)cc1] | JP2008074939 |

TABLE 1-continued
| MATERIAL | EXAMPLES OF MATERIAL | PUBLICATIONS |
|---|---|---|
| Polymers (e.g., PVK) | 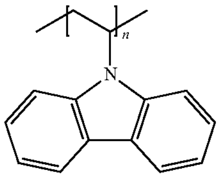 | Appl. Phys. Lett. 77, 2280 (2000) |
| Spirofluorene compounds | 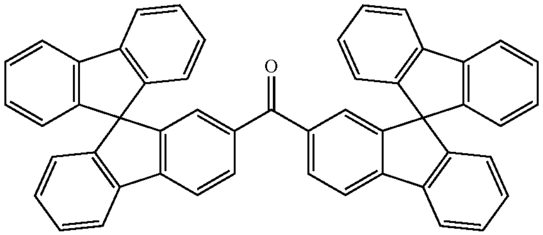 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |
| Metal phenoxybenzooxazole compounds | 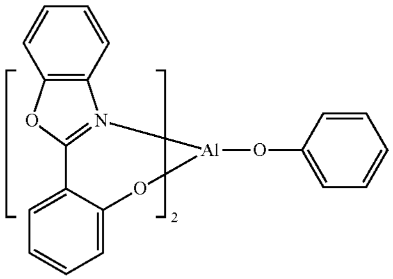 | WO2005089025 |
| | 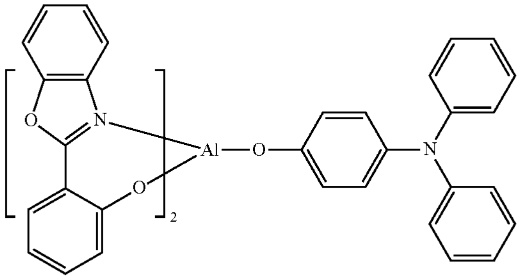 | WO2006132173 |

TABLE 1-continued
| MATERIAL | EXAMPLES OF MATERIAL | PUBLICATIONS |
|---|---|---|
| | 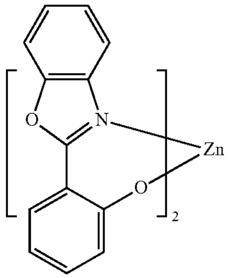 | JP200511610 |
| Spirofluorene-carbazole compounds | 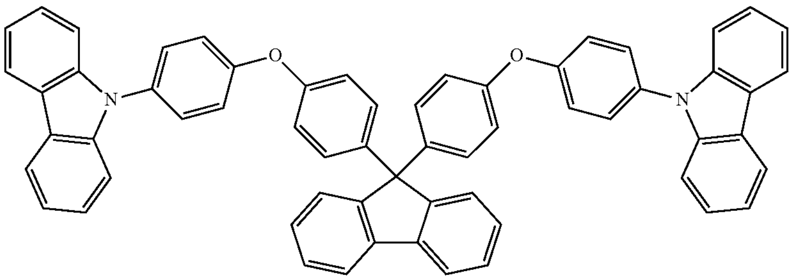 [SMILES: c1ccc2c(c1)-c1ccccc1C2(c1ccc(Oc2ccc(-n3c4ccccc4c4ccccc43)cc2)cc1)c1ccc(Oc2ccc(-n3c4ccccc4c4ccccc43)cc2)cc1] | JP2007254297 |
| | 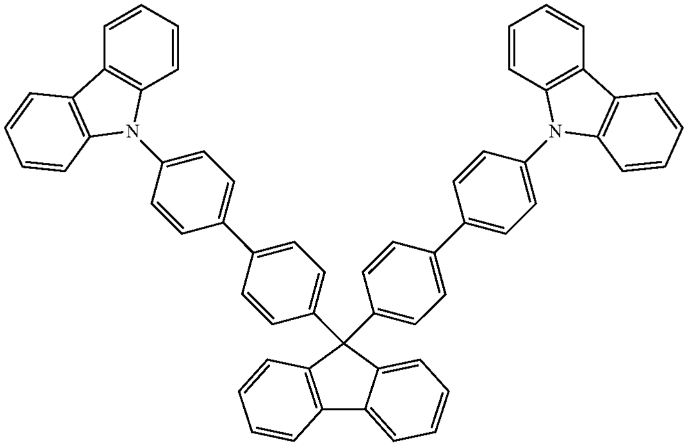 [SMILES: c1ccc2c(c1)-c1ccccc1C2(c1ccc(-c2ccc(-n3c4ccccc4c4ccccc43)cc2)cc1)c1ccc(-c2ccc(-n3c4ccccc4c4ccccc43)cc2)cc1] | JP2007254297 |

TABLE 1-continued
| MATERIAL | EXAMPLES OF MATERIAL | PUBLICATIONS |
|---|---|---|
| Indolocabazoles | 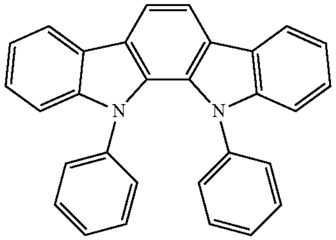 [SMILES: c1ccc(-n2c3ccccc3c3ccc4c5ccccc5n(-c5ccccc5)c4c32)cc1] | WO2007063796 |
| | 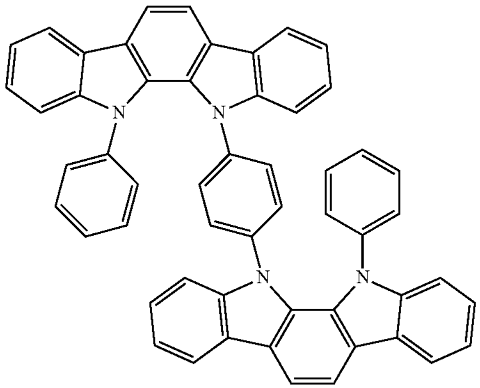 [SMILES: c1ccc(-n2c3ccccc3c3ccc4c5ccccc5n(-c5ccc(-n6c7ccccc7c7ccc8c9ccccc9n(-c9ccccc9)c8c76)cc5)c4c32)cc1] | WO2007063754 |
| 5-member ring electron deficient heterocycles (e.g., triazole, oxadiazole) | 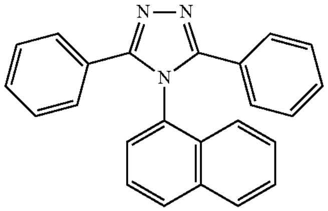 [SMILES: c1ccc(-c2nnc(-c3ccccc3)n2-c2cccc3ccccc23)cc1] | J. Appl. Phys. 90, 5048 (2001) |

TABLE 1-continued
| MATERIAL | EXAMPLES OF MATERIAL | PUBLICATIONS |
|---|---|---|
| | 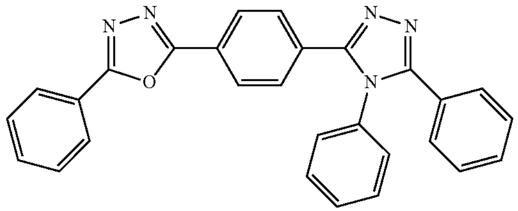 [SMILES: c1ccc(-c2nnc(-c3ccc(-c4nnc(-c5ccccc5)n4-c4ccccc4)cc3)o2)cc1] | WO2004107822 |
| Tetraphenylene complexes | 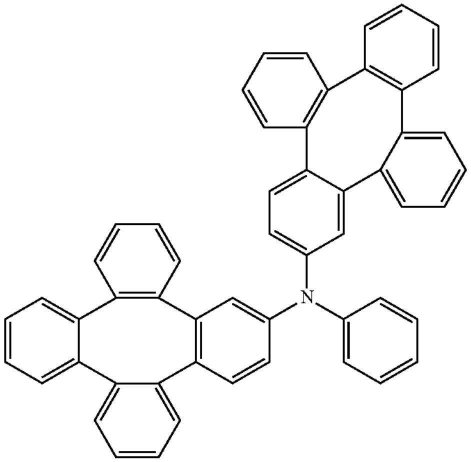 [SMILES: c1ccc(N(c2ccc3c(c2)-c2ccccc2-c2ccccc2-c2ccccc2-3)c2ccc3c(c2)-c2ccccc2-c2ccccc2-c2ccccc2-3)cc1] | US20050112407 |
| Metal phenoxypyridine compounds | 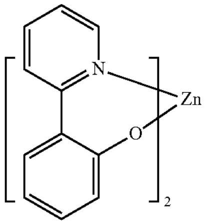 | WO2005030900 |

TABLE 1-continued
| MATERIAL | EXAMPLES OF MATERIAL | PUBLICATIONS |
|---|---|---|
| Metal coordination complexes (e.g., Zn, Al with N^N ligands) | 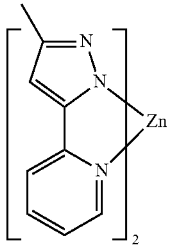 | US20040137268, US20040137267 |
| | Blue hosts | |
| Arylcarbazoles | 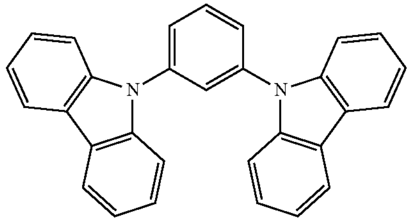 [SMILES: c1cc(-n2c3ccccc3c3ccccc32)cc(-n2c3ccccc3c3ccccc32)c1] | Appl. Phys. Lett, 82, 2422 (2003) |
| | 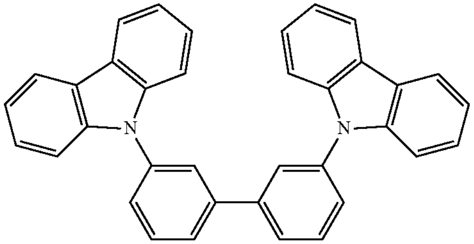 [SMILES: c1cc(-c2cccc(-n3c4ccccc4c4ccccc43)c2)cc(-n2c3ccccc3c3ccccc32)c1] | US20070190359 |
| Dibenzothiophene/ Dibenzofuran- carbazole compounds | 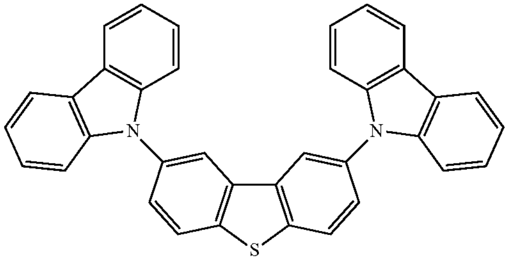 [SMILES: c1ccc2c(c1)c1ccccc1n2-c1ccc2sc3ccc(-n4c5ccccc5c5ccccc54)cc3c2c1] | WO2006114966, US20090167162 |

TABLE 1-continued
| MATERIAL | EXAMPLES OF MATERIAL | PUBLICATIONS |
|---|---|---|
| | 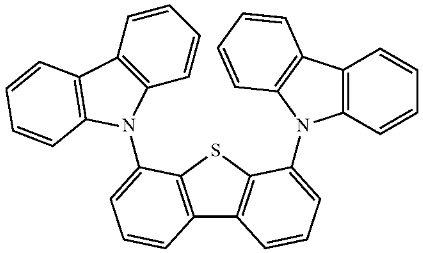 [SMILES: c1cc(-n2c3ccccc3c3ccccc32)c2sc3c(-n4c5ccccc5c5ccccc54)cccc3c2c1] | US20090167162 |
| | 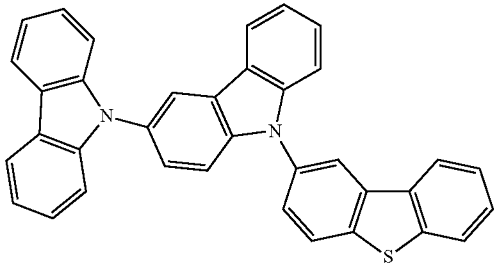 [SMILES: c1ccc2c(c1)sc1ccc(-n3c4ccccc4c4cc(-n5c6ccccc6c6ccccc65)ccc43)cc12] | WO2009086028 |
| | 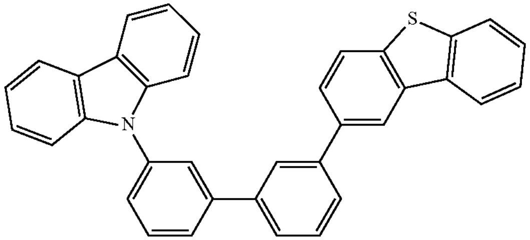 [SMILES: c1cc(-c2cccc(-n3c4ccccc4c4ccccc43)c2)cc(-c2ccc3sc4ccccc4c3c2)c1] | US20090030202, US20090017330 |

TABLE 1-continued
| MATERIAL | EXAMPLES OF MATERIAL | PUBLICATIONS |
|---|---|---|
| Silicon aryl compounds | 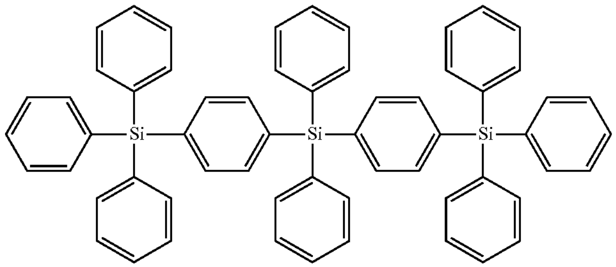 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 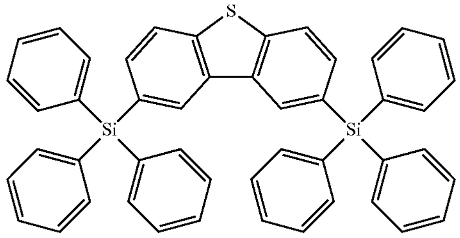 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |
| Silicon/Germanium aryl compounds | 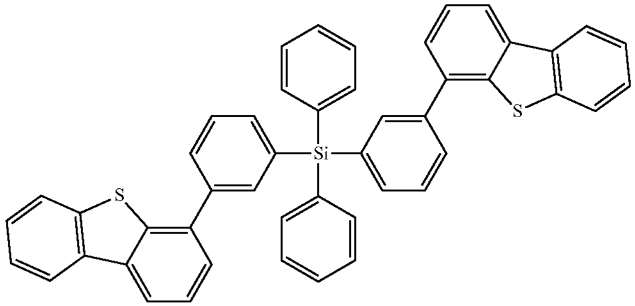 [SMILES: c1ccc([Si](c2ccccc2)(c2cccc(-c3cccc4c3sc3ccccc34)c2)c2cccc(-c3cccc4c3sc3ccccc34)c2)cc1] | EP2034538A |
| Aryl benzoyl ester | 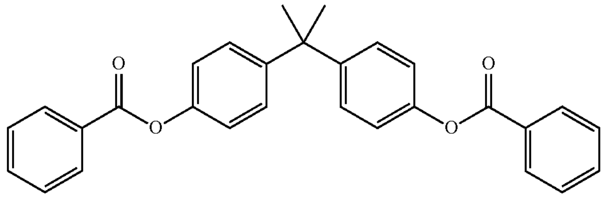 [SMILES: CC(C)(c1ccc(OC(=O)c2ccccc2)cc1)c1ccc(OC(=O)c2ccccc2)cc1] | WO2006100298 |

TABLE 1-continued
| MATERIAL | EXAMPLES OF MATERIAL | PUBLICATIONS |
|---|---|---|
| High triplet metal organometallic complex | 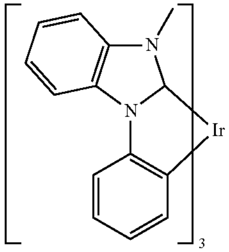 | U.S. Pat. No. 7,154,114 |
| | Phosphorescent dopants<br>Red dopants | |
| Heavy metal porphyrins (e.g., PtOEP) | 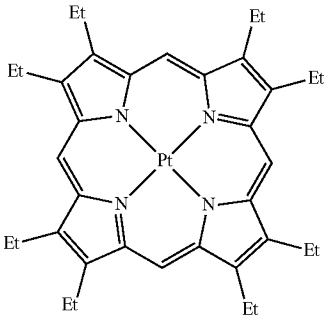 | Nature 395, 151 (1998) |
| Iridium(III) organometallic complexes | 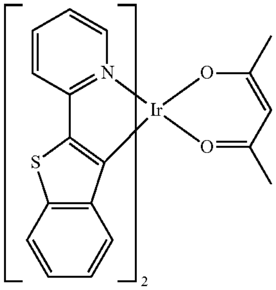 | Appl. Phys. Lett. 78, 1622 (2001) |

TABLE 1-continued
| MATERIAL | EXAMPLES OF MATERIAL | PUBLICATIONS |
|---|---|---|
| | 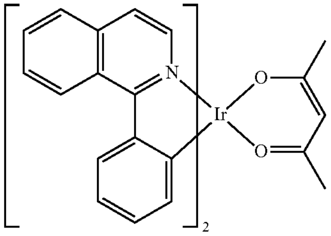 | US2006835469 |
| | 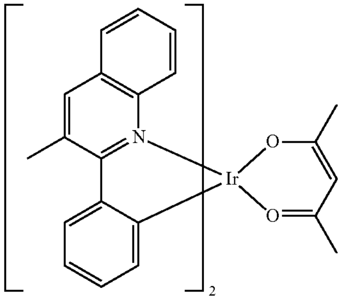 | US2006835469 |
| | 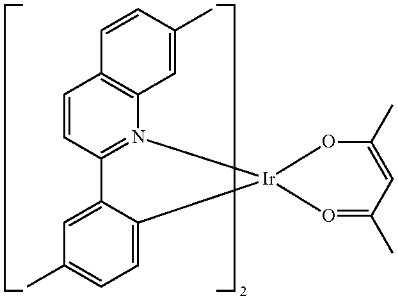 | US20060202194 |

TABLE 1-continued
| MATERIAL | EXAMPLES OF MATERIAL | PUBLICATIONS |
|---|---|---|
| | 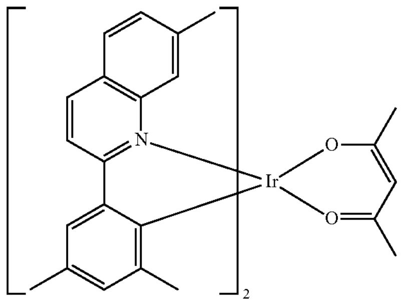 | US20060202194 |
| | 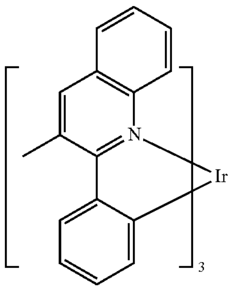 | US20070087321 |
| | 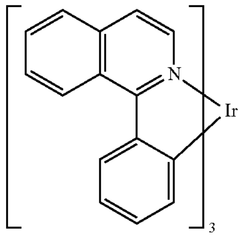 | US20070087321 |

TABLE 1-continued
| MATERIAL | EXAMPLES OF MATERIAL | PUBLICATIONS |
|---|---|---|
| | 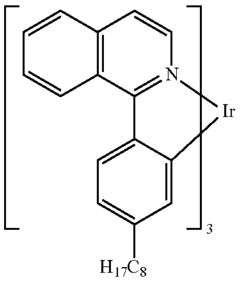 | Adv. Mater. 19, 739 (2007) |
| | 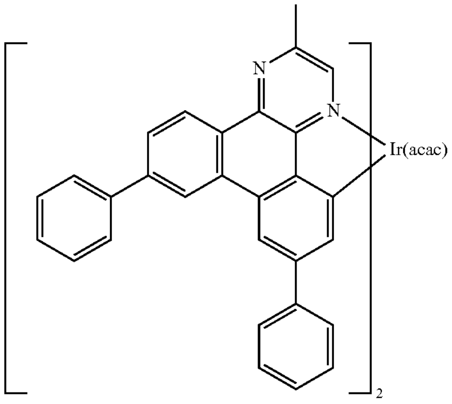 | WO2009100991 |
| | 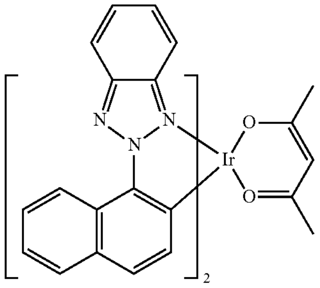 | WO2008101842 |

TABLE 1-continued
| MATERIAL | EXAMPLES OF MATERIAL | PUBLICATIONS |
|---|---|---|
| Platinum(II) organometallic complexes | 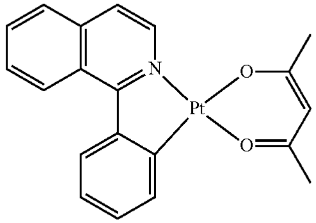 | WO2003040257 |
| Osminum(III) complexes | 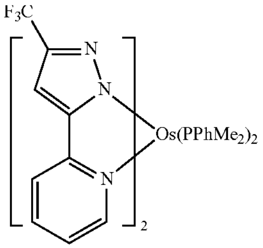 | Chem. Mater. 17, 3532 (2005) |
| Ruthenium(II) complexes | 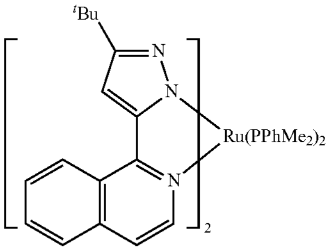 | Adv. Mater. 17, 1059 (2005) |
| Rhenium (I), (II), and (III) complexes | 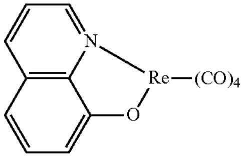 | US20050244673 |

TABLE 1-continued
| MATERIAL | EXAMPLES OF MATERIAL | PUBLICATIONS |
|---|---|---|
| | Green dopants | |
| Iridium(III) organometallic complexes | 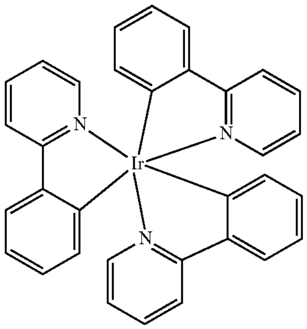 and its derivatives | Inorg. Chem. 40, 1704 (2001) |
| | 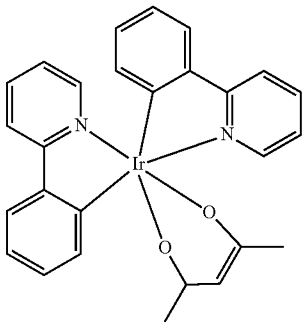 | US20020034656 |

TABLE 1-continued
| MATERIAL | EXAMPLES OF MATERIAL | PUBLICATIONS |
|---|---|---|
| | 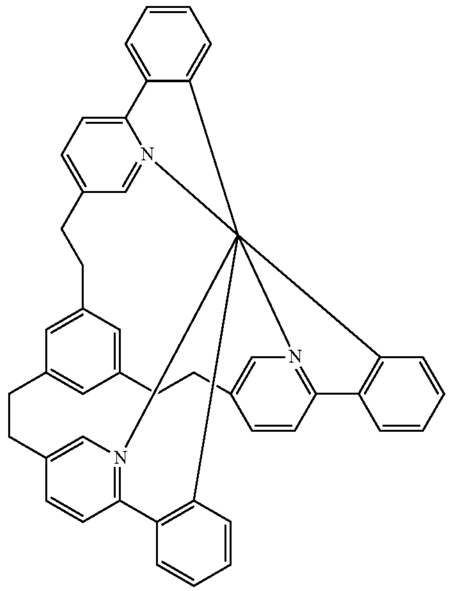 | U.S. Pat. No. 7,332,232 |
| | 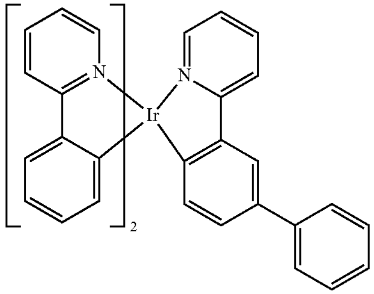 | US20090108737 |

TABLE 1-continued
| MATERIAL | EXAMPLES OF MATERIAL | PUBLICATIONS |
|---|---|---|
| | 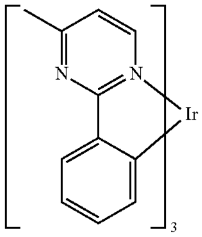 | US20090039776 |
| | 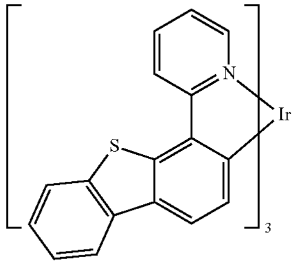 | U.S. Pat. No. 6,921,915 |
| | 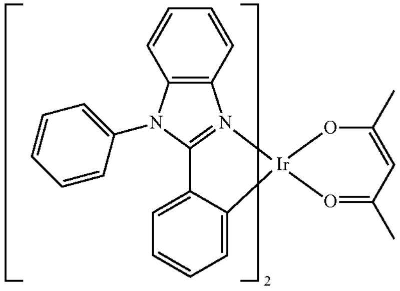 | U.S. Pat. No. 6,687,266 |

TABLE 1-continued
| MATERIAL | EXAMPLES OF MATERIAL | PUBLICATIONS |
|---|---|---|
| | 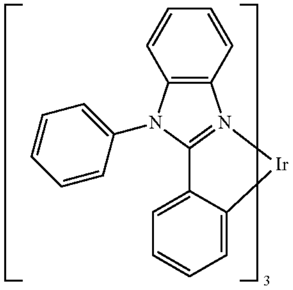 | Chem. Mater. 16, 2480 (2004) |
| | 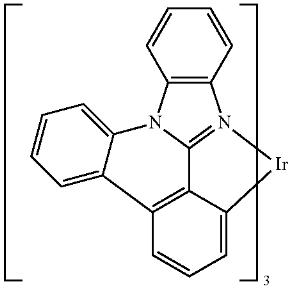 | US20070190359 |
| | 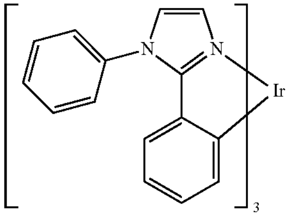 | US 20060008670 JP2007123392 |
| | 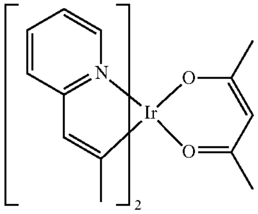 | Adv. Mater. 16, 2003 (2004) |

TABLE 1-continued
| MATERIAL | EXAMPLES OF MATERIAL | PUBLICATIONS |
|---|---|---|
| | 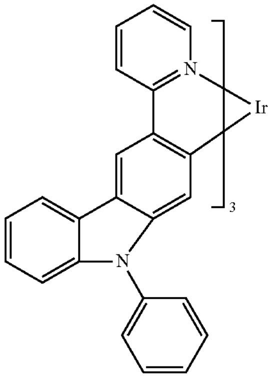 | Angew. Chem. Int. Ed. 2006, 45, 7800 |
| | 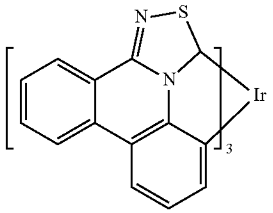 | WO2009050290 |
| | 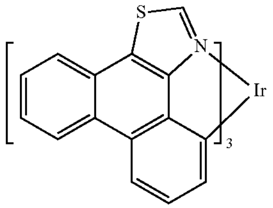 | US20090165846 |

TABLE 1-continued
| MATERIAL | EXAMPLES OF MATERIAL | PUBLICATIONS |
|---|---|---|
| | 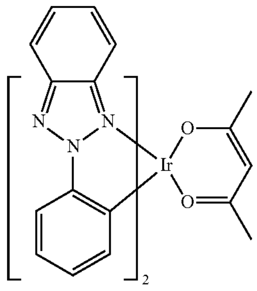 | US20080015355 |
| Monomer for polymeric metal organometallic compounds | 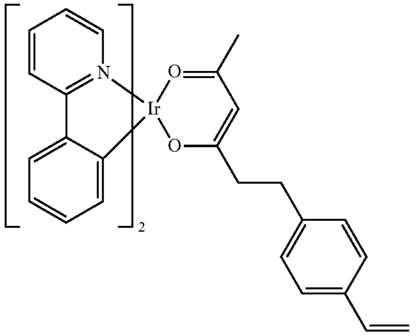 | U.S. Pat. No. 7,250,226, U.S. Pat. No. 7,396,598 |
| Pt(II) organometallic complexes, including polydentated ligands | 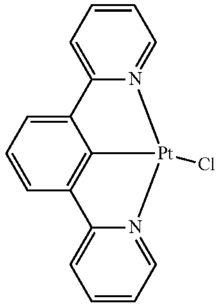 | Appl. Phys. Lett. 86, 153505 (2005) |

TABLE 1-continued
| MATERIAL | EXAMPLES OF MATERIAL | PUBLICATIONS |
|---|---|---|
| | 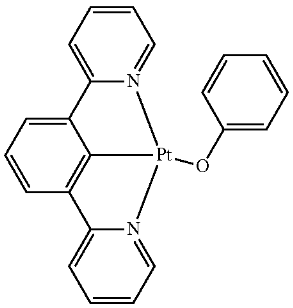 | Appl. Phys. Lett. 86, 153505 (2005) |
| | 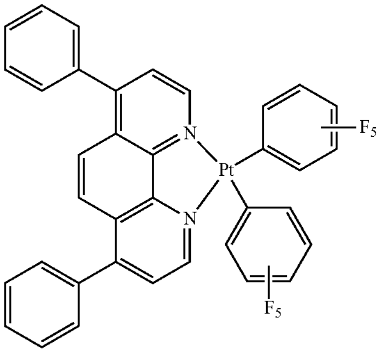 | Chem. Lett. 34, 592 (2005) |
| | 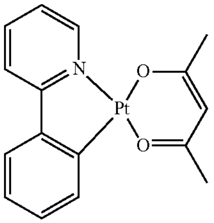 | WO2002015645 |

TABLE 1-continued
| MATERIAL | EXAMPLES OF MATERIAL | PUBLICATIONS |
|---|---|---|
| | 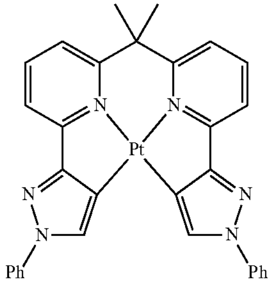 | US20060263635 |
| Cu complexes | 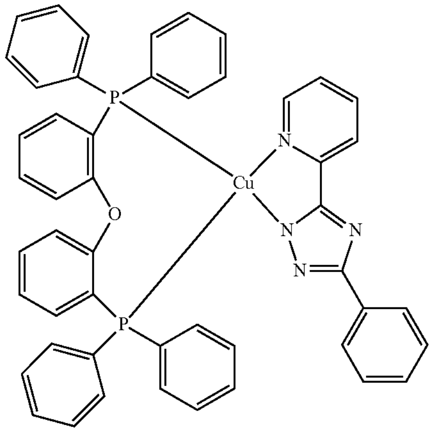 | WO2009000673 |
| Gold complexes | 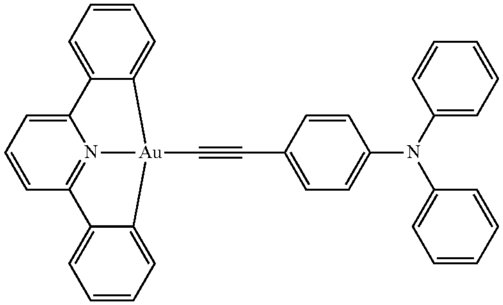 | Chem. Commun. 2906 (2005) |

TABLE 1-continued
| MATERIAL | EXAMPLES OF MATERIAL | PUBLICATIONS |
|---|---|---|
| Rhenium(III) complexes | 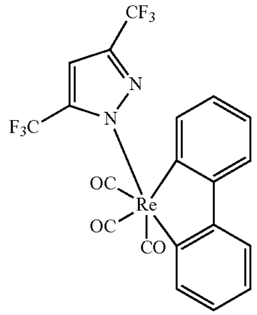 | Inorg. Chem. 42, 1248 (2003) |
| Deuterated organometallic complexes | 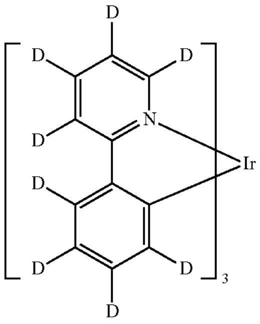 | US20030138657 |
| Organometallic complexes with two or more metal centers | 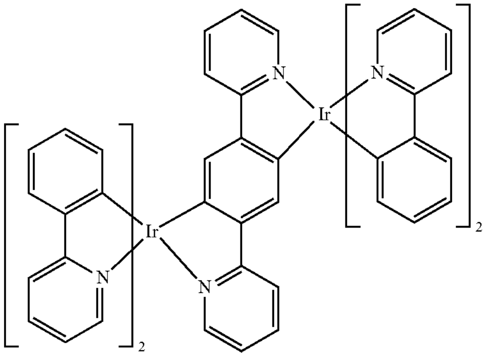 | US20030152802 |

TABLE 1-continued
| MATERIAL | EXAMPLES OF MATERIAL | PUBLICATIONS |
|---|---|---|
| | 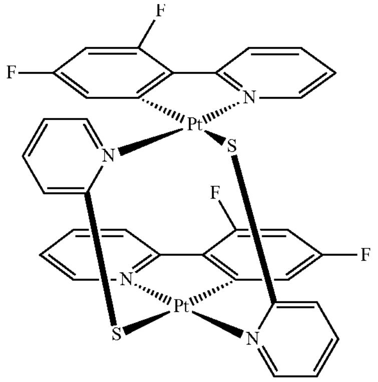 | U.S. Pat. No. 7,090,928 |
| | Blue dopants | |
| Iridium(III) organometallic complexes | 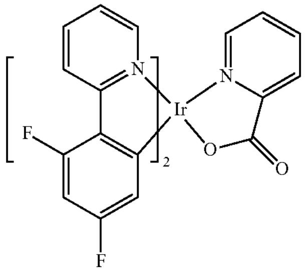 | WO2002002714 |
| | 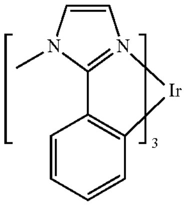 | WO2006009024 |

TABLE 1-continued
| MATERIAL | EXAMPLES OF MATERIAL | PUBLICATIONS |
|---|---|---|
| | 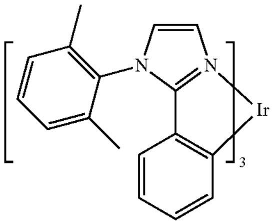 | US20060251923 |
| | 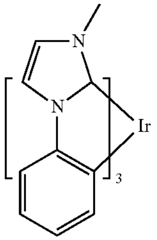 | U.S. Pat. No. 7,393,599, WO2006056418, US20050260441, WO2005019373 |
| | 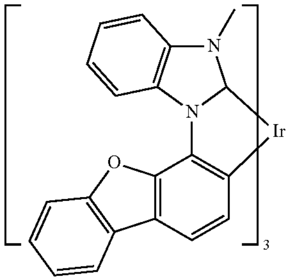 | U.S. Pat. No. 7,534,505 |

TABLE 1-continued
| MATERIAL | EXAMPLES OF MATERIAL | PUBLICATIONS |
|---|---|---|
| | 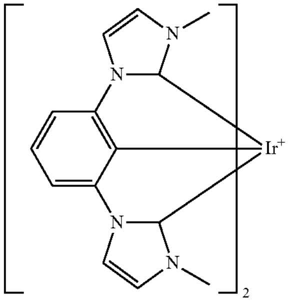 | U.S. Pat. No. 7,445,855 |
| | 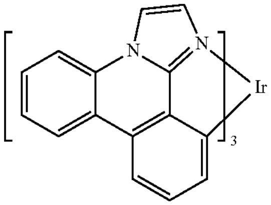 | US20070190359, US20080297033 |
| | 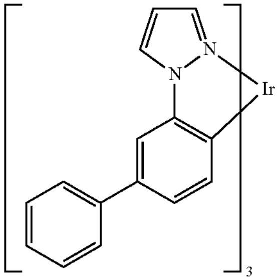 | U.S. Pat. No. 7,338,722 |
| | 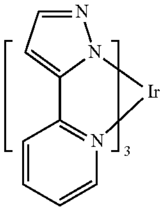 | US20020134984 |

TABLE 1-continued
| MATERIAL | EXAMPLES OF MATERIAL | PUBLICATIONS |
|---|---|---|
| | 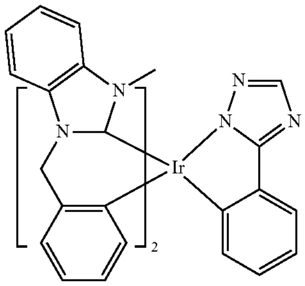 | Angew. Chem. Int. Ed. 47, 1 (2008) |
| | 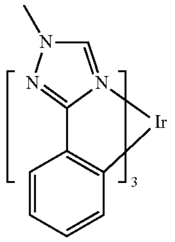 | Chem. Mater. 18, 5119 (2006) |
| | 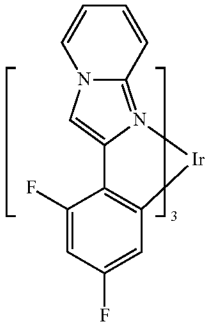 | Inorg. Chem. 46, 4308 (2007) |

TABLE 1-continued
| MATERIAL | EXAMPLES OF MATERIAL | PUBLICATIONS |
| --- | --- | --- |
| | 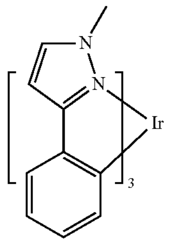 | WO2005123873 |
| | 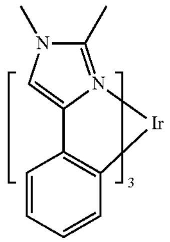 | WO2005123873 |
| | 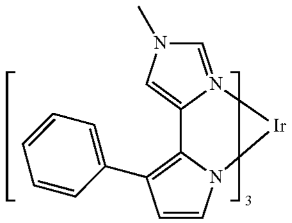 | WO2007004380 |

TABLE 1-continued
| MATERIAL | EXAMPLES OF MATERIAL | PUBLICATIONS |
|---|---|---|
| | 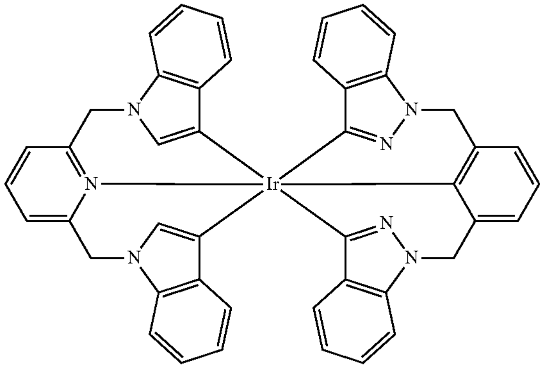 | WO2006082742 |
| Osmium(II) complexes | 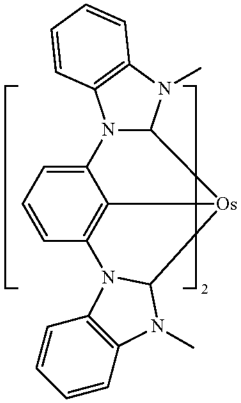 | U.S. Pat. No. 7,279,704 |
| | 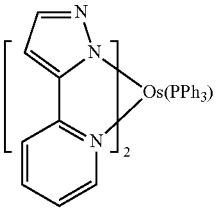 | Organometallics 23, 3745 (2004) |

TABLE 1-continued
| MATERIAL | EXAMPLES OF MATERIAL | PUBLICATIONS |
|---|---|---|
| Gold complexes | 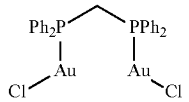 | Appl. Phys. Lett. 74, 1361 (1999) |
| Platinum(II) complexes | 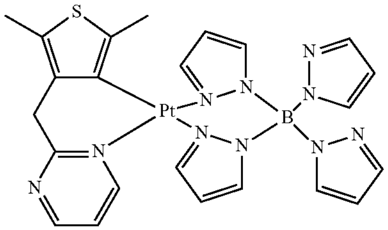 | WO2006098120, WO2006103874 |
| | Exciton/hole blocking layer materials | |
| Bathocuprine compounds (e.g., BCP, BPhen) | 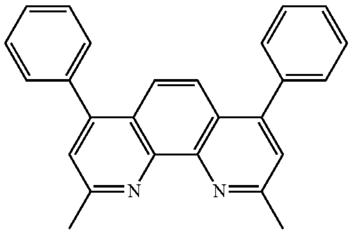 [SMILES: Cc1cc(-c2ccccc2)c2ccc3c(-c4ccccc4)cc(C)nc3c2n1] | Appl. Phys. Lett. 75, 4 (1999) |
| | 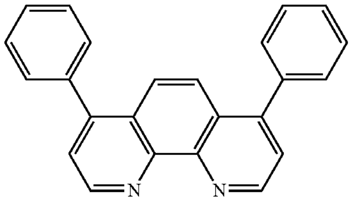 [SMILES: c1ccc(-c2ccnc3c2ccc2c(-c4ccccc4)ccnc23)cc1] | Appl. Phys. Lett. 79, 449 (2001) |
| Metal 8-hydroxyquinolates (e.g., BAlq) | 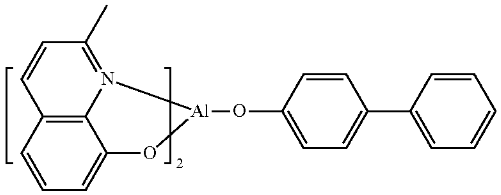 | Appl. Phys. Lett. 81, 162 (2002) |

TABLE 1-continued
| MATERIAL | EXAMPLES OF MATERIAL | PUBLICATIONS |
|---|---|---|
| 5-member ring electron deficient heterocycles such as triazole, oxadiazole, imidazole, benzoimidazole | 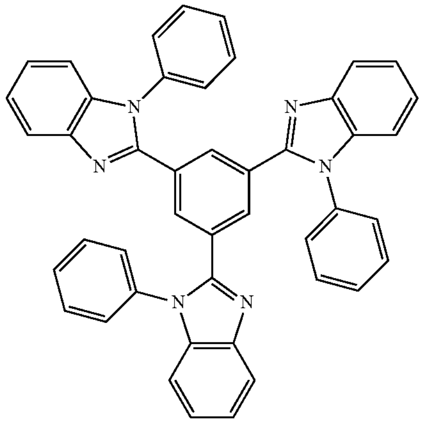 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |
| Triphenylene compounds | 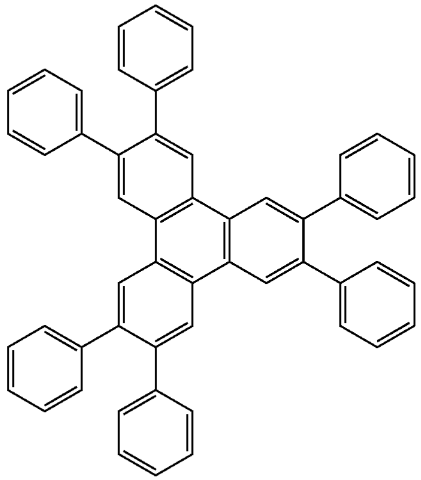 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |

TABLE 1-continued
| MATERIAL | EXAMPLES OF MATERIAL | PUBLICATIONS |
| --- | --- | --- |
| Fluorinated aromatic compounds | 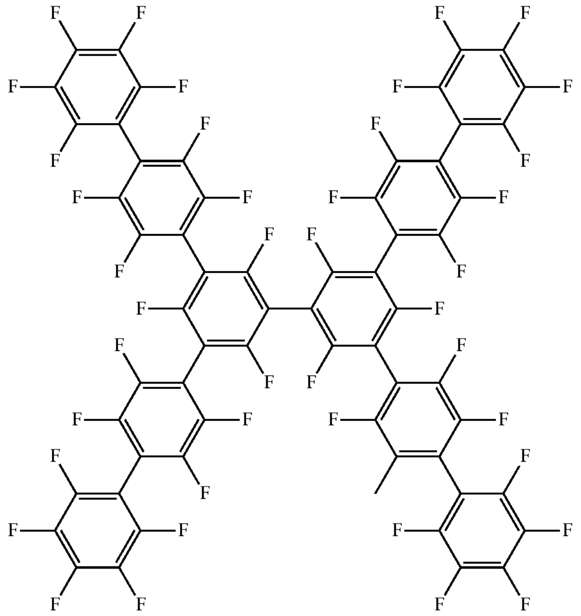 [SMILES: Cc1c(F)c(-c2c(F)c(-c3c(F)c(F)c(-c4c(F)c(F)c(F)c(F)c4F)c(F)c3F)c(F)c(-c3c(F)c(-c4c(F)c(F)c(-c5c(F)c(F)c(F)c(F)c5F)c(F)c4F)c(F)c(-c4c(F)c(F)c(-c5c(F)c(F)c(F)c(F)c5F)c(F)c4F)c3F)c2F)c(F)c(F)c1-c1c(F)c(F)c(F)c(F)c1F] | Appl. Phys. Lett. 79, 156 (2001) |
| Phenothiazine-S-oxide | 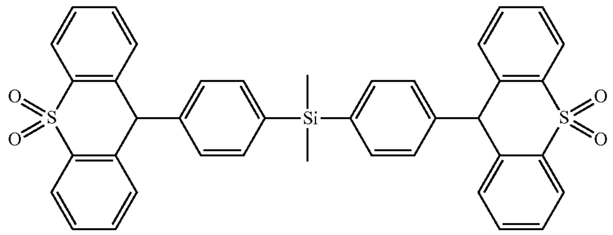 [SMILES: C[Si](C)(c1ccc(C2c3ccccc3S(=O)(=O)c3ccccc32)cc1)c1ccc(C2c3ccccc3S(=O)(=O)c3ccccc32)cc1] | WO2008132085 |

TABLE 1-continued
| MATERIAL | EXAMPLES OF MATERIAL | PUBLICATIONS |
|---|---|---|
| | Electron transporting materials | |
| Anthracene-benzoimidazole compounds | 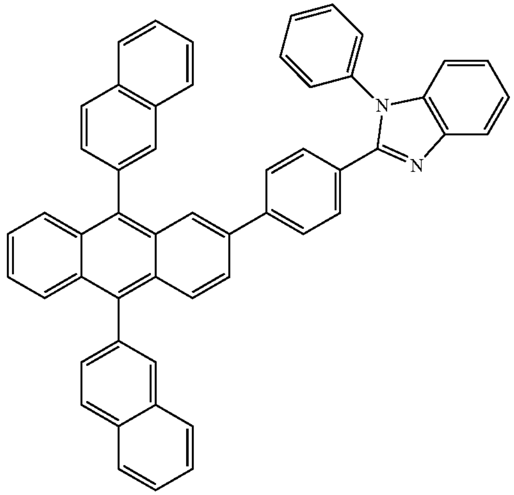 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] | WO2003060956 |
| | 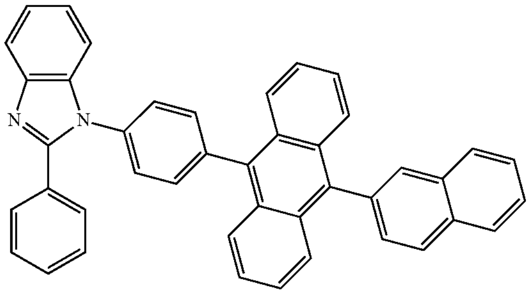 [SMILES: c1ccc(-c2nc3ccccc3n2-c2ccc(-c3c4ccccc4c(-c4ccc5ccccc5c4)c4ccccc34)cc2)cc1] | US20090179554 |

TABLE 1-continued
| MATERIAL | EXAMPLES OF MATERIAL | PUBLICATIONS |
|---|---|---|
| Aza triphenylene derivatives | 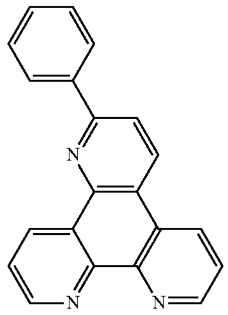 [SMILES: c1ccc(-c2ccc3c4cccnc4c4ncccc4c3n2)cc1] | US20090115316 |
| Anthracene-benzothiazole compounds | 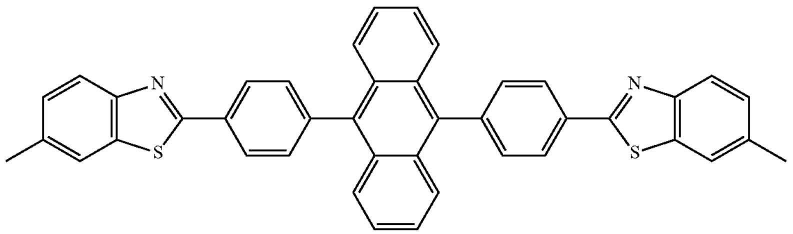 | Appl. Phys. Lett. 89, 063504 (2006) |
| Metal 8-hydroxyquinolates (e.g., $Alq_3$, $Zrq_4$) | 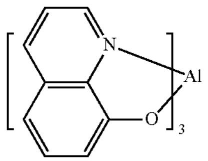 | Appl. Phys. Lett. 51, 913 (1987)<br>U.S. Pat. No. 7,230,107 |
| Metal hydroxybenoquinolates | 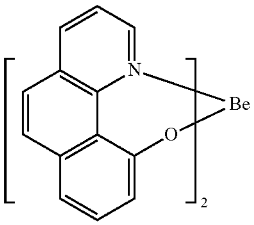 | Chem. Lett. 5, 905 (1993) |

TABLE 1-continued
| MATERIAL | EXAMPLES OF MATERIAL | PUBLICATIONS |
|---|---|---|
| Bathocuprine compounds such as BCP, BPhen, etc | 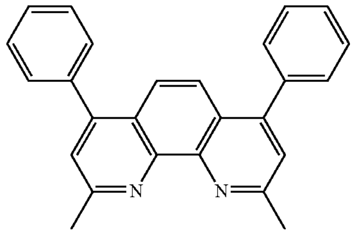 [SMILES: Cc1cc(-c2ccccc2)c2ccc3c(-c4ccccc4)cc(C)nc3c2n1] | Appl. Phys. Lett. 91, 263503 (2007) |
| | 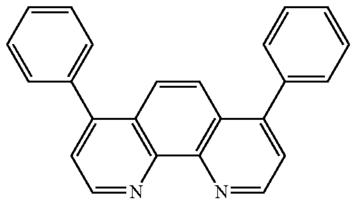 [SMILES: c1ccc(-c2ccnc3c2ccc2c(-c4ccccc4)ccnc23)cc1] | Appl. Phys. Lett. 79, 449 (2001) |
| 5-member ring electron deficient heterocycles (e.g., triazole, oxadiazole, imidazole, benzoimidazole) | 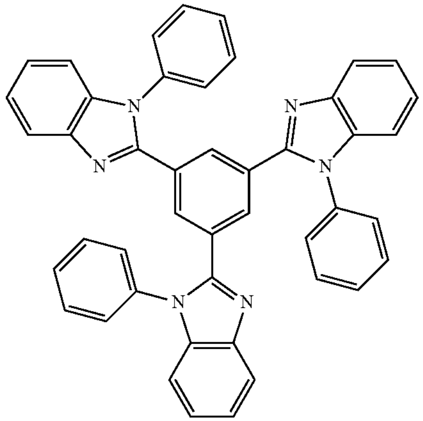 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 74, 865 (1999) |
| | 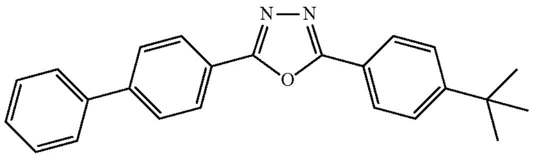 [SMILES: CC(C)(C)c1ccc(-c2nnc(-c3ccc(-c4ccccc4)cc3)o2)cc1] | Appl. Phys. Lett. 55, 1489 (1989) |

TABLE 1-continued
| MATERIAL | EXAMPLES OF MATERIAL | PUBLICATIONS |
| --- | --- | --- |
| | 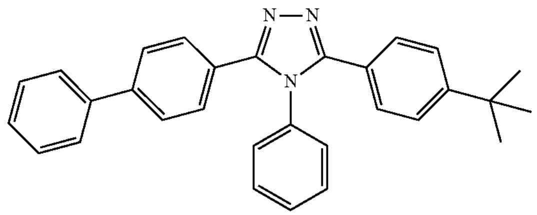 [SMILES: CC(C)(C)c1ccc(-c2nnc(-c3ccc(-c4ccccc4)cc3)n2-c2ccccc2)cc1] | Jpn. J. Apply. Phys. 32, L917 (1993) |
| Silole compounds | 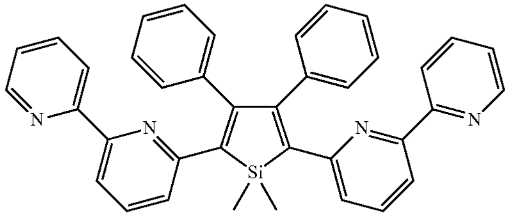 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 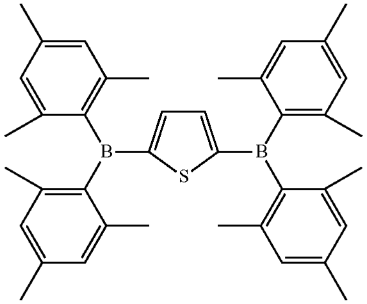 | J. Am. Chem. Soc. 120, 9714 (1998) |
| Fluorinated aromatic compounds | 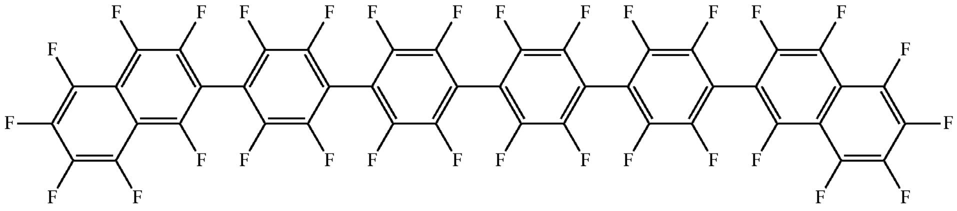 [SMILES: Fc1c(F)c(-c2c(F)c(F)c(-c3c(F)c(F)c4c(F)c(F)c(F)c(F)c4c3F)c(F)c2F)c(F)c(F)c1-c1c(F)c(F)c(-c2c(F)c(F)c(-c3c(F)c(F)c4c(F)c(F)c(F)c(F)c4c3F)c(F)c2F)c(F)c1F] | J. Am. Chem. Soc. 122, 1832 (2000) |

TABLE 1-continued
| MATERIAL | EXAMPLES OF MATERIAL | PUBLICATIONS |
|---|---|---|
| Fullerene (e.g., C60) | 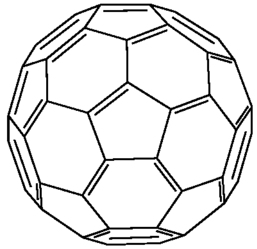 [SMILES: c1cc2c3ccc4c5ccc6c7ccc8c9ccc%10c1c1c2c2c3c4c3c5c6c4c7c8c5c9c%10c1c1c2c3c4c51] | US20090101870 |
| Triazine complexes | 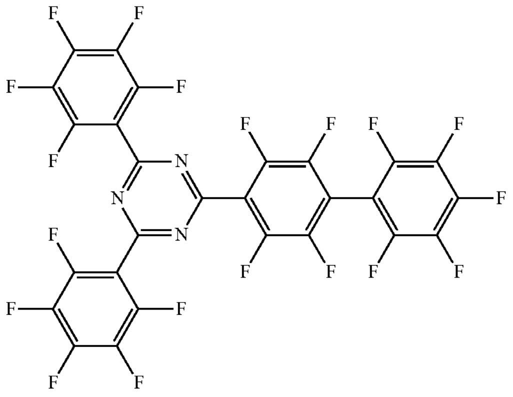 [SMILES: Fc1c(F)c(F)c(-c2nc(-c3c(F)c(F)c(F)c(F)c3F)nc(-c3c(F)c(F)c(-c4c(F)c(F)c(F)c(F)c4F)c(F)c3F)n2)c(F)c1F] | US20040036077 |
| Zn (N^N) complexes | 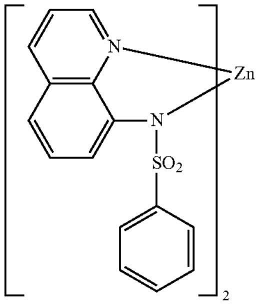 | U.S. Pat. No. 6,528,187 |

EXPERIMENTAL

Compound Examples

Example 1. Synthesis of Compound 1

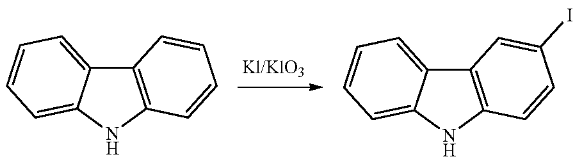 [SMILES: c1ccc2c(c1)[nH]c1ccccc12 ; Ic1ccc2[nH]c3ccccc3c2c1]

Synthesis of 3-iodo-9H-carbazole. To a solution of 9H-carbazole (5.57 g, 33.3 mmol) and KI (3.68 g, 22.2 mmol) in AcOH (92 mL) was heated to 100° C. for 1 h. $KIO_3$ (3.57 g, 16.7 mmol) was added in portions to the solution, and the resulting mixture was stirred for another 2 h at 100° C. The mixture was poured into water (500 mL) and the precipitation was collected by filtration and washed with hot water. Recrystallization was made in DCM to afford 6.8 g (70%) of product as a white solid.

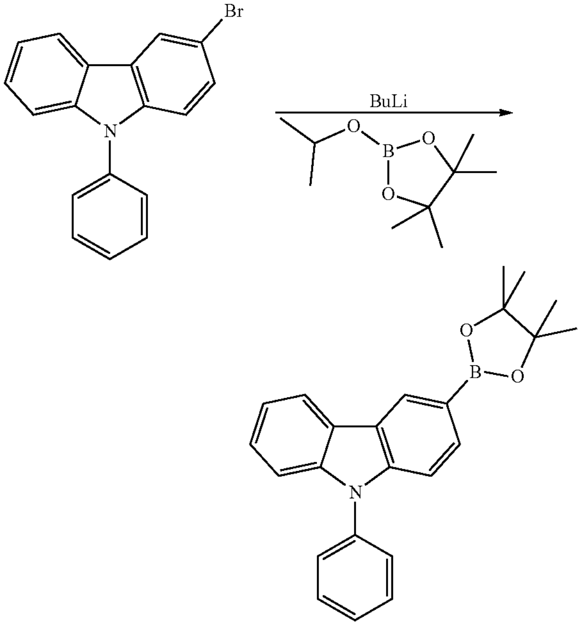

Synthesis of 9-phenyl-3-(4,4,5,5-tetramethyl-1,3,2-dioxaborolan-2-yl)-9H-carbazole. To a solution of 3-bromo-9-phenyl-9H-carbazole (20.3 g, 63 mmol) in THF (150 mL) at −78° C. was added 47.25 mL (75.8 mmol) of n-butyllithium (1.6 M in hexane). The mixture was stirred at −78° C. for 1 h. 21 mL (100 mmol) of 2-isopropoxy-4,4,5,5-tetramethyl-[1,3,2]-dioxaborolane was added to the solution, and the resulting mixture was warmed to room temperature and stirred for 8 h. The mixture was poured into water and extracted with dichloromethane. The organic extracts were washed with brine and dried over magnesium sulfate. The solvent was removed by rotary evaporation, and recrystallization was made in hexane to afford 19.3 g (83%) of product as a white solid.

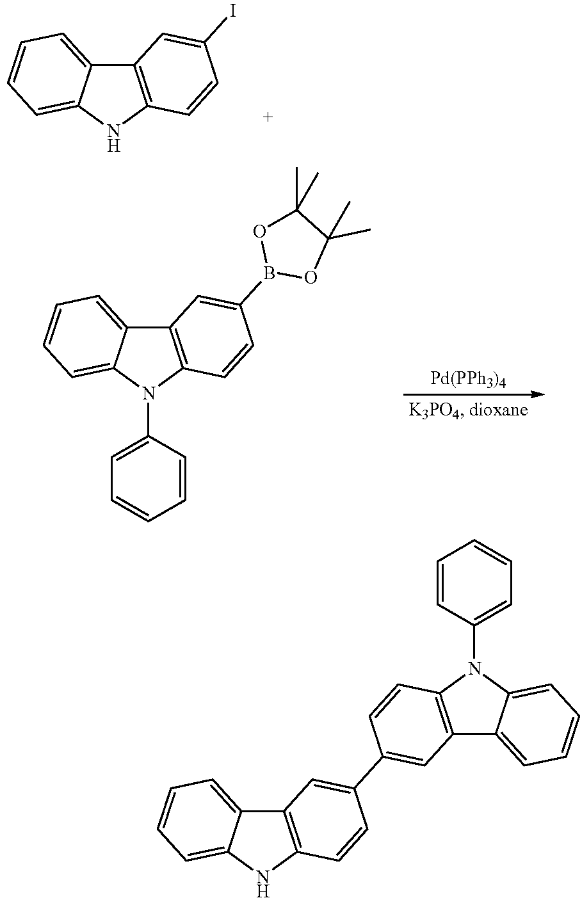

Synthesis of 3-(9-phenyl-9H-carbazol-3-yl)-9H-carbazole. To a solution of 3-iodo-9H-carbazole (879 mg, 3.0 mmol), $Pd(PPh_3)_4$ (165 mg, 0.15 mmol), 9-phenyl-3-(4,4,5,5-tetramethyl-1,3,2-dioxaborolan-2-yl)-9H-carbazole (1.29 g, 4.5 mmol) and $K_3PO_4$ (1.8 g, 18.0 mmol) in dioxane (5 mL). The solution was heated to 85° C. with vigorous stirring for 48 h under argon atmosphere. The mixture was poured into water and extracted with DCM. The organic extracts were washed with brine and dried over $MgSO_4$. The solvent was removed by rotary evaporation, and recrystallization was made in DCM to afford 900 mg (74%) of product.

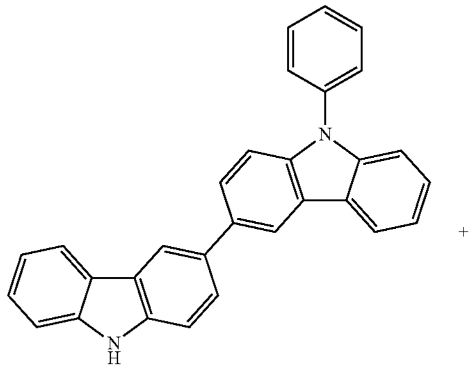

-continued

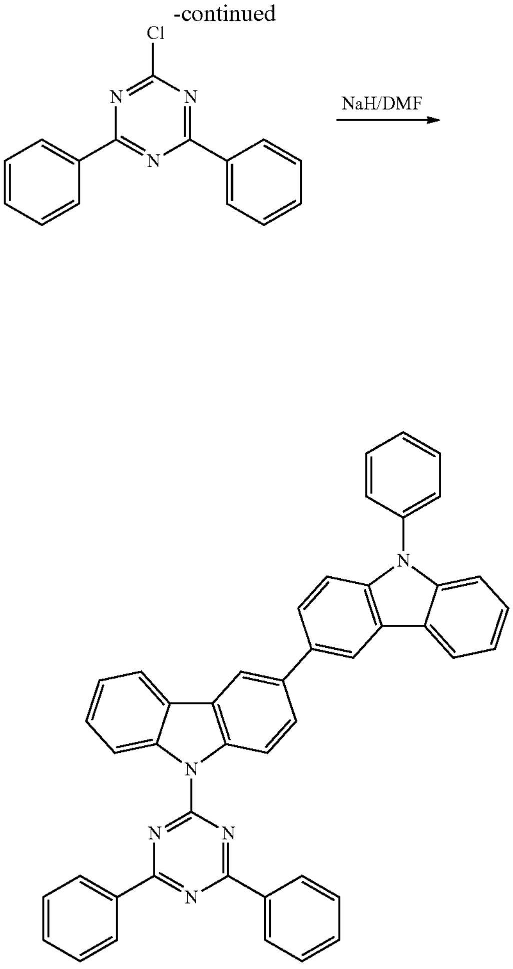

Compound 1

Synthesis of 9-(4,6-diphenyl-1,3,5-triazin-2-yl)-3-(9-phenyl-9H-carbazol-3-yl)-9H-carbazole (Compound 1). To a solution of sodium hydride (100 mg, 3.0 mmol) and 3-(9-phenyl-9H-carbazol-3-yl)-9H-carbazole (816 mg, 2.0 mmol) in dry DMF (40 mL) was stirred at room temperature for 1 h under argon atmosphere. 2-Chloro-4,6-diphenyl-1,3,5-triazine (448 mg, 1.67 mmol) was added to the solution at room temperature, then refluxed overnight. The mixture was poured into water and the precipitation was collected by filtration and washed with water, methanol and DCM to get 800 mg (75%) yellow solid.

Device Examples

All device examples were fabricated by high vacuum (<$10^{-7}$ Torr) thermal evaporation. The anode electrode is 800 Å of indium tin oxide (ITO). The cathode consisted of 10 Å of LiF followed by 1000 Å of Al. All devices were encapsulated with a glass lid sealed with an epoxy resin in a nitrogen glove box (<1 ppm of $H_2O$ and $O_2$) immediately after fabrication, and a moisture getter was incorporated inside the package.

As used herein, the following compounds have the following structures:

H1

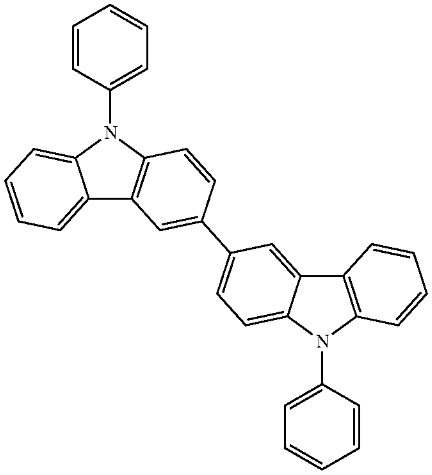

E1

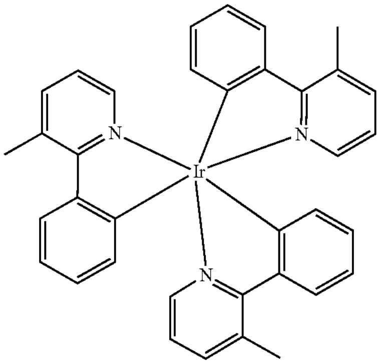

H2

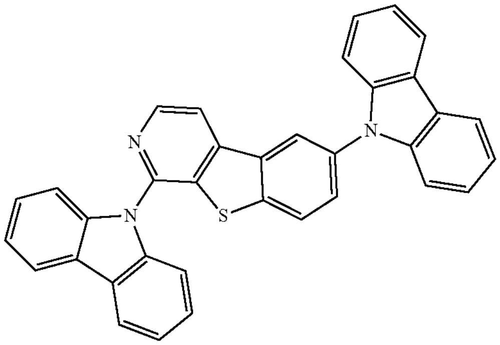

H3

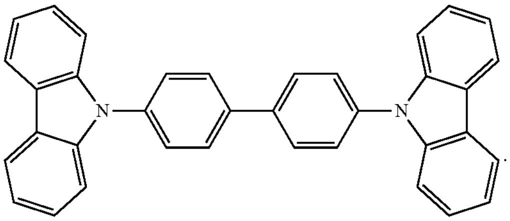

Particular devices are provided. The organic stack of the Device Examples 1 and 2 consisted of sequentially, from the ITO surface, 100 Å of E1 as the hole injection layer (HIL), 300 Å of 4,4'-bis[N-(1-naphthyl)-N-phenylamino]biphenyl (α-NPD) as the hole transporting layer (HTL), 300 Å of host doped with E1 as the emissive layer (EML), 100 Å of H2 as the blocking layer (BL), and 400 Å of Alq as the electron transporting layer (ETL).

Comparative Device Examples 1 and 2 were fabricated similarly to Device Examples 1 and 2, except H3 was used as host.

Device structures for Device Examples 1 and 2 are provided in Table 2 and the corresponding measured device data is provided in Table 3.

TABLE 2

| VTE PHOLEDs | | | | | | |
|---|---|---|---|---|---|---|
| Example | HIL | HTL | EML (doping %) | | BL | ETL |
| Example 1 | E1 | NPD | Compound 1 | E1 5% | H2 | Alq |
| Example 2 | E1 | NPD | Compound 1 | E1 10% | H2 | Alq |
| Comparative Example 1 | E1 | NPD | H3 | E1 5% | H2 | Alq |
| Comparative Example 2 | E1 | NPD | H3 | E1 10% | H2 | Alq |

TABLE 3

| VTE device data | | | | | | | | | | | |
|---|---|---|---|---|---|---|---|---|---|---|---|
| | | | | | | At 1000 nits | | | | At 40 mA/cm$^2$ | |
| | 1931 CIE | | | FWHM | Voltage | LE | EQE | PE | | $L_0$ | LT80 |
| Example | x | y | $\lambda_{max}$ | (nm) | (V) | (Cd/A) | (%) | (lm/W) | | (nits) | % (h) |
| Example 1 | 0.324 | 0.623 | 520 | 66 | 5.7 | 40.6 | 11.3 | 22.2 | | 12,769 | 86 |
| Example 2 | 0.336 | 0.619 | 522 | 69 | 5.6 | 47.4 | 13.2 | 26.4 | | 15,048 | 83 |
| Comp. Example 1 | 0.316 | 0.628 | 520 | 64 | 5.7 | 45.5 | 12.7 | 25.1 | | 12,635 | 46 |
| Comp. Example 2 | 0.317 | 0.630 | 520 | 64 | 5.2 | 54.4 | 15.1 | 32.6 | | 16,264 | 29 |

Device Examples 1 and 2 showed green PHOLEDs with Compound 1 as host with different E1 doping concentrations. The comparative examples used H3 (i.e., CBP, a commonly used PHOLED host) as the host. As can be seen from the table, devices with Compound 1 as host had comparative operating voltage, slightly lower efficiency than devices with H3 as the host. However, the device operating lifetime was much higher than comparative examples. Device Example 1 almost doubled the lifetime of Comparative Example 1 (86 h vs 46 h) and Device Example 2 almost tripled the lifetime of Comparative Example 2 (83 h vs. 29 h). Therefore, Compound 1 is an excellent host material for phosphorescent OLEDs.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore includes variations from the particular examples and preferred embodiments described herein, as will be apparent to one of skill in the art. It is understood that various theories as to why the invention works are not intended to be limiting.

The invention claimed is:

1. A compound having the formula:

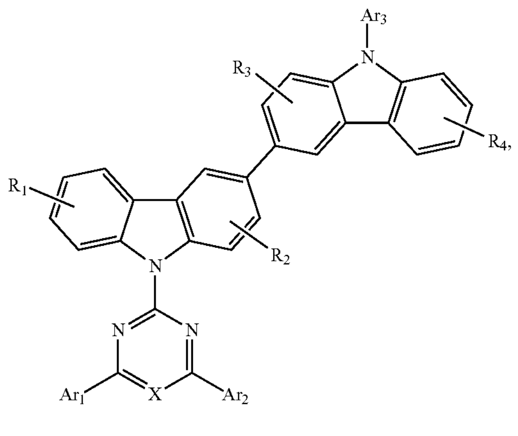

wherein $R_1$, $R_2$, $R_3$, and $R_4$ may represent mono- up to the maximum substitutions, or no substitutions;

wherein each $R_1$, $R_2$, $R_3$, and $R_4$ is independently selected from the group consisting of hydrogen, alkyl, alkoxy, amino, alkenyl, alkynyl, aryl and heteroaryl;

wherein $Ar_1$ and $Ar_2$ are independently selected from aryl or heteroaryl; and wherein X is C or N; and wherein $Ar_3$ is a polycyclic fused aryl system.

2. The compound of claim 1, wherein $Ar_1$, $Ar_2$, and $Ar_3$ are further substituted.

3. The compound of claim 1, wherein $Ar_1$ and $Ar_2$ are independently selected from the group consisting of phenyl, pyridine, naphthalene, biphenyl, terphenyl, fluorene, dibenzofuran, dibenzothiophene, phenanthrene, and triphenylene; and wherein $Ar_1$ and $Ar_2$ are independently further substituted with a substituent selected from the group consisting of hydrogen, alkyl, alkoxy, amino, alkenyl, alkynyl, aryl and heteroaryl, wherein the substituent is not an aryl or heteroaryl fused directly to $Ar_1$ and $Ar_2$.

4. The compound of claim 1, wherein $Ar_1$ and $Ar_2$ are independently selected from the group consisting of phenyl, pyridine, and naphthalene.

5. The compound of claim 1, wherein $Ar_3$ is selected from the group consisting of naphthalene, phenanthrene, and triphenylene.

6. The compound of claim 1, wherein $R_1$, $R_2$, $R_3$, and $R_4$ are hydrogen.
7. The compound of claim 1, wherein the compound is selected from the group consisting of:
Compound 9
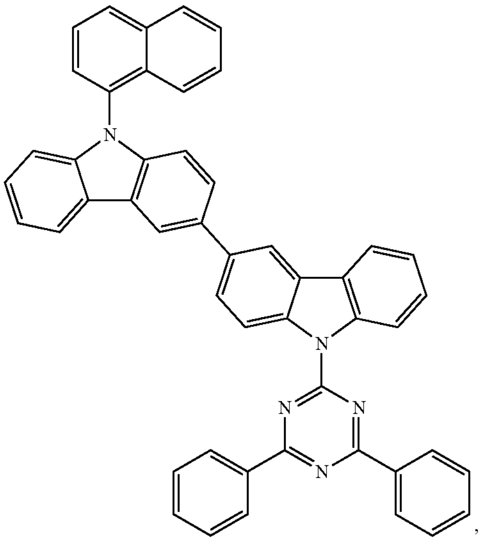
Compound 10
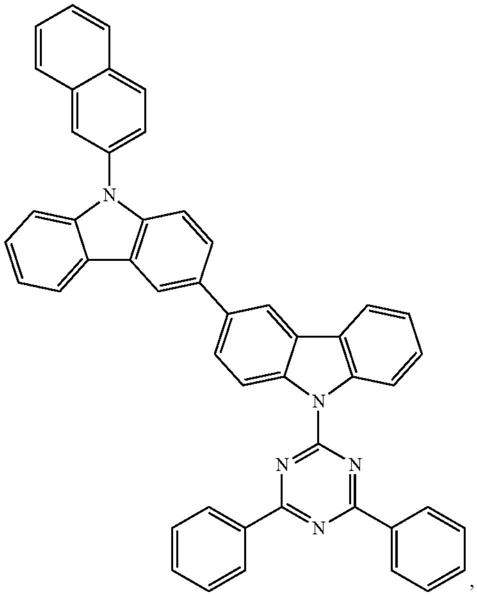
-continued
Compound 11
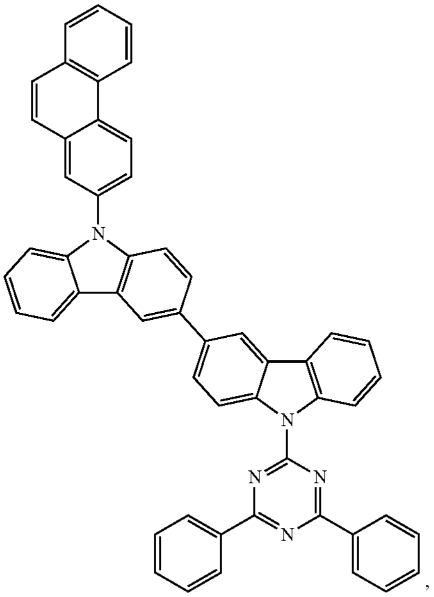
Compound 12
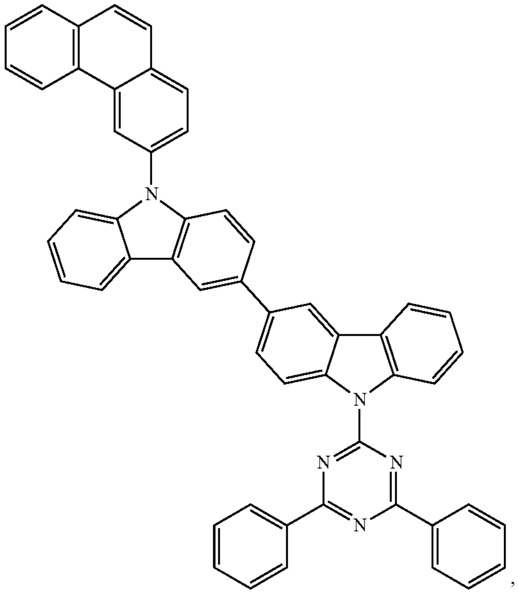

-continued
Compound 13
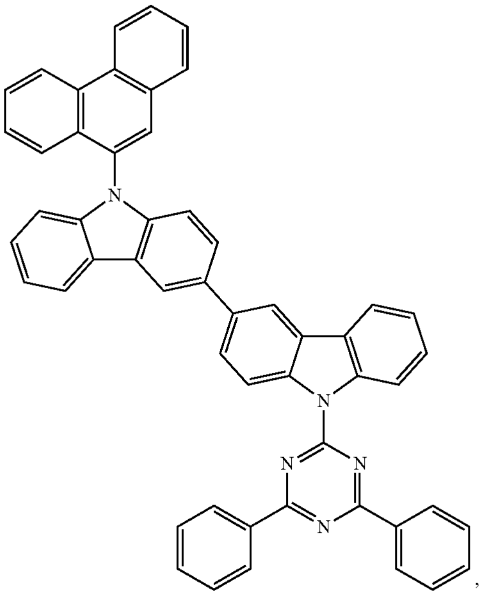
,
Compound 14
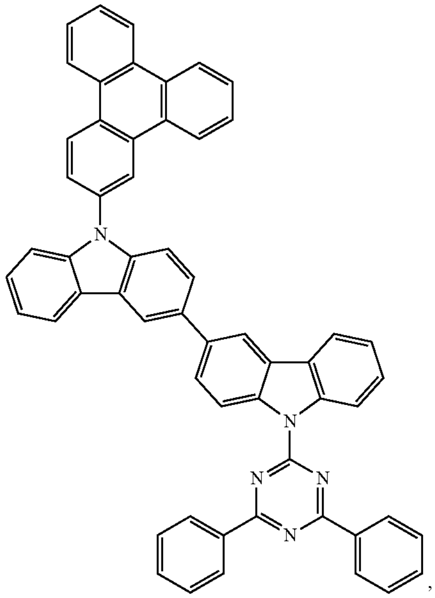
,
-continued
Compound 15
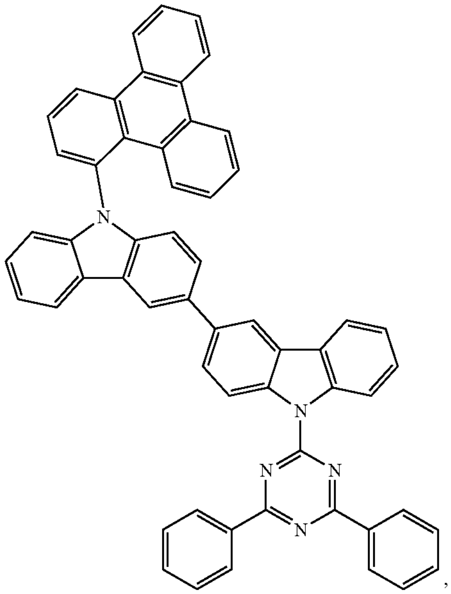
,
Compound 24
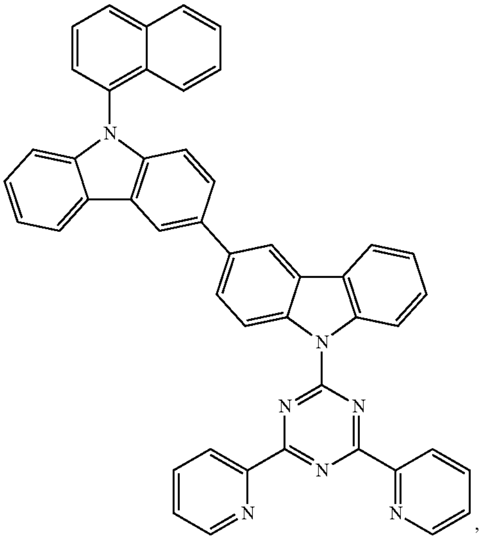
, -continued
Compound 25
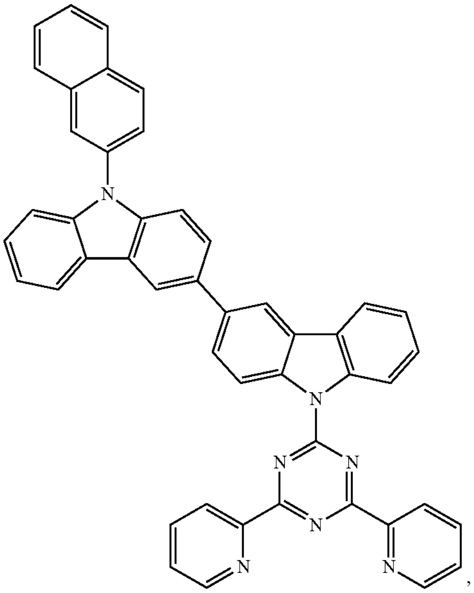
,
-continued
Compound 27
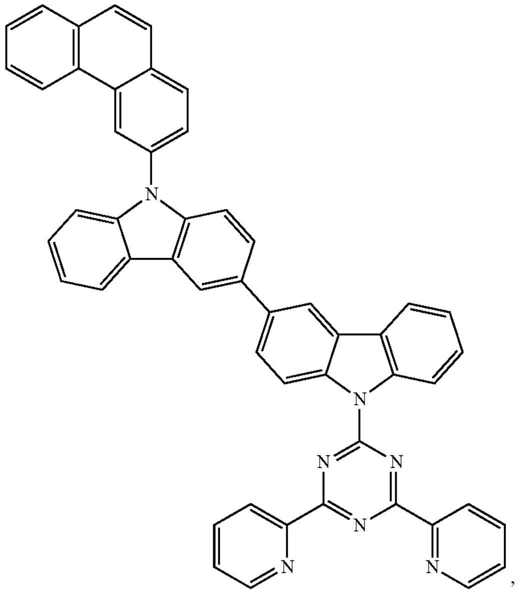
,
Compound 26
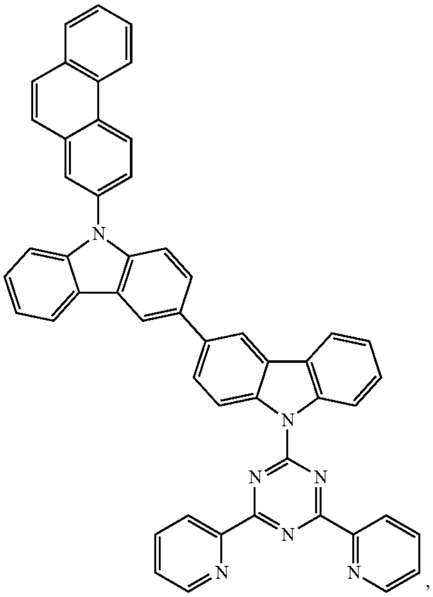
,
Compound 28
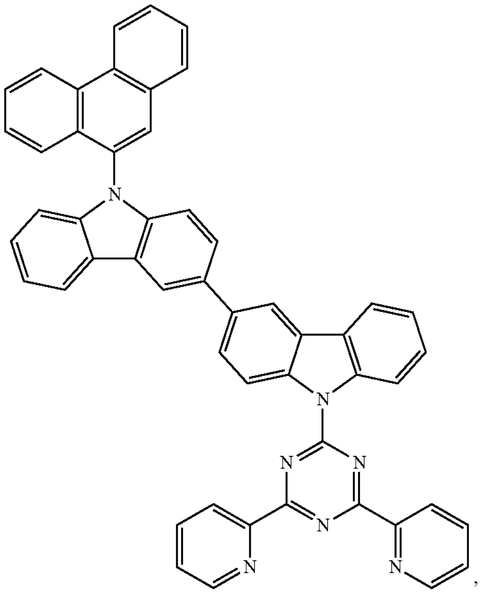
, -continued
Compound 29
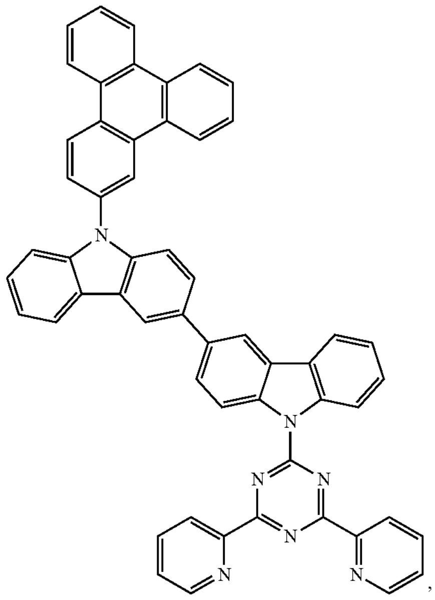
,
Compound 30
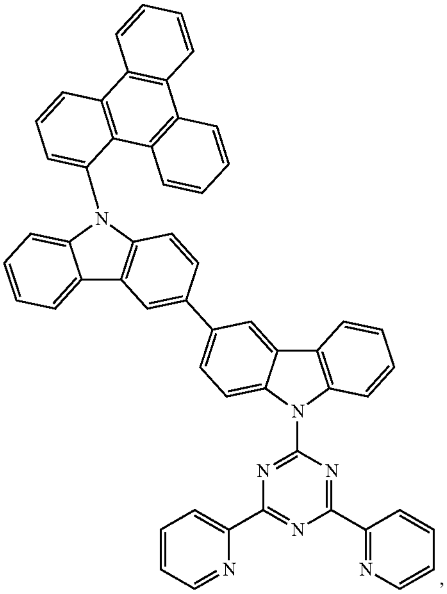
,
-continued
Compound 39
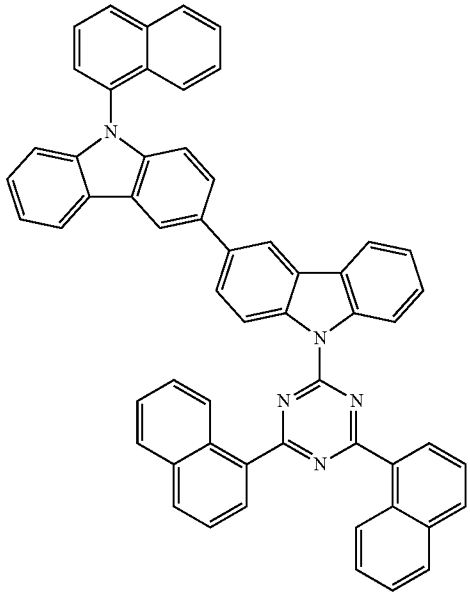
,
Compound 40
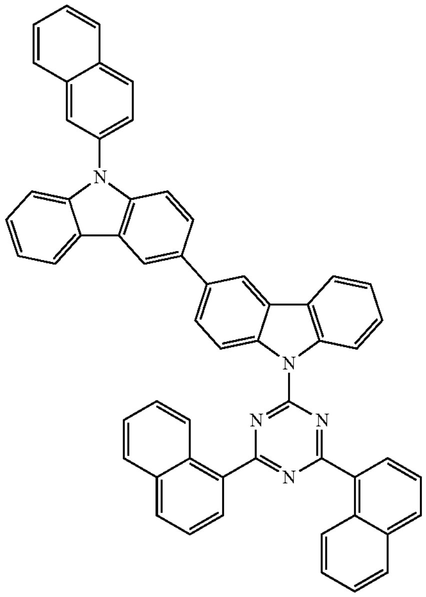
, -continued
Compound 41
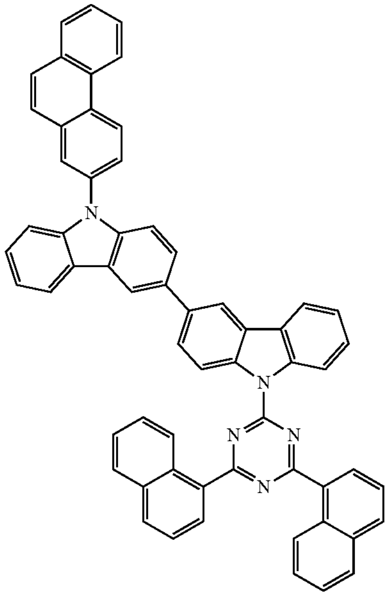
,
Compound 42
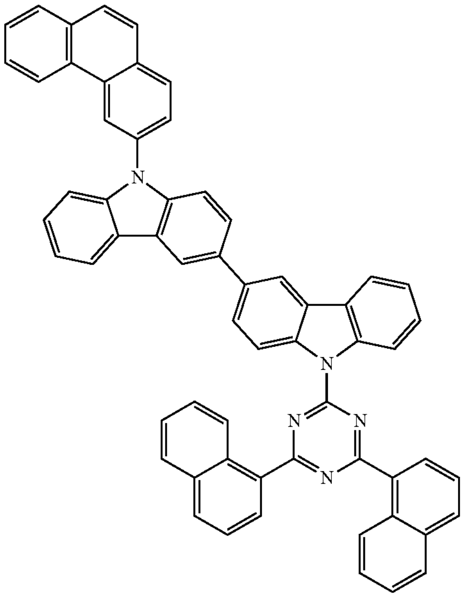
,
-continued
Compound 43
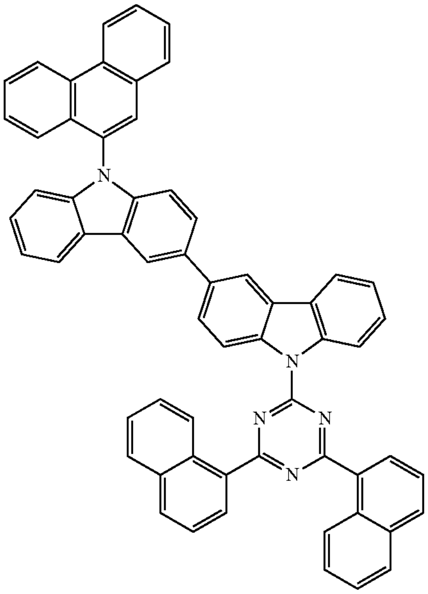
,
Compound 44
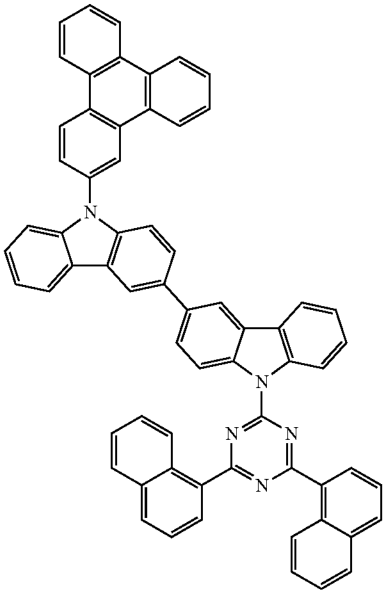
, -continued
Compound 45
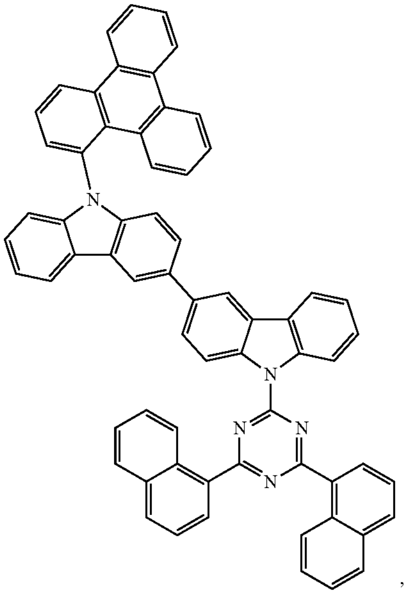
,
Compound 54
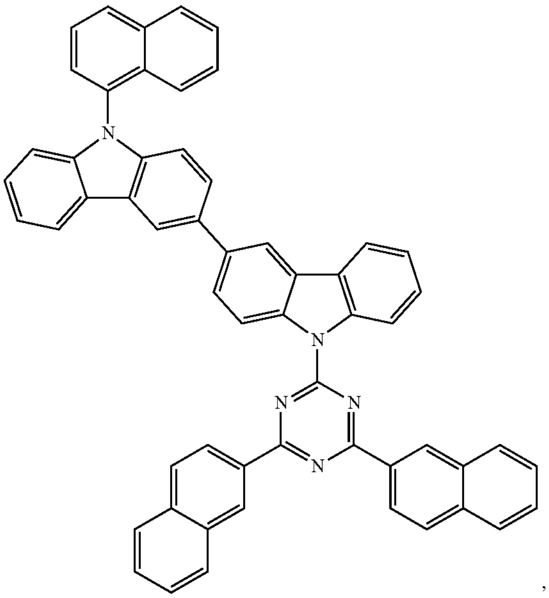
,
Compound 55
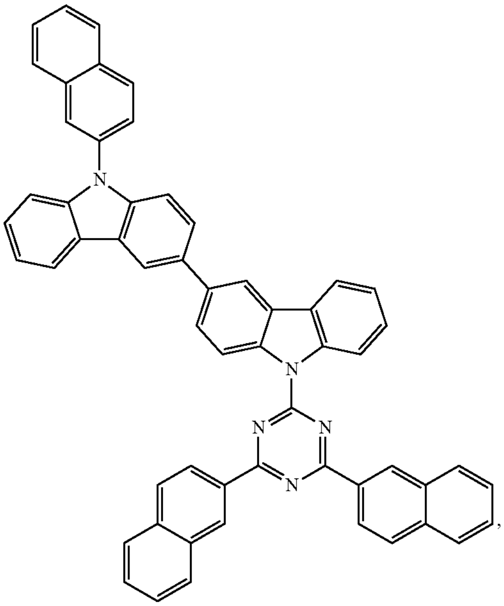
,
Compound 56
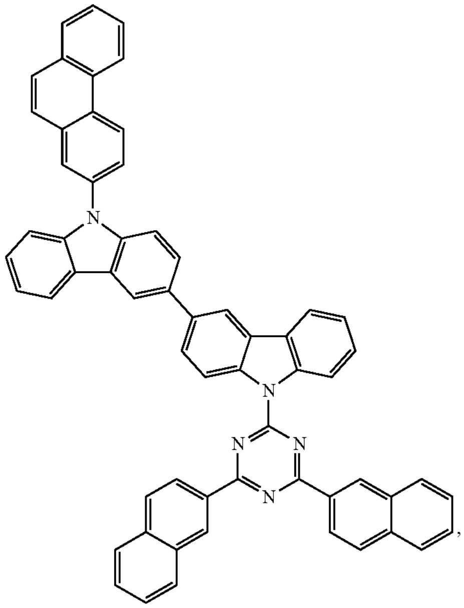
, Compound 57
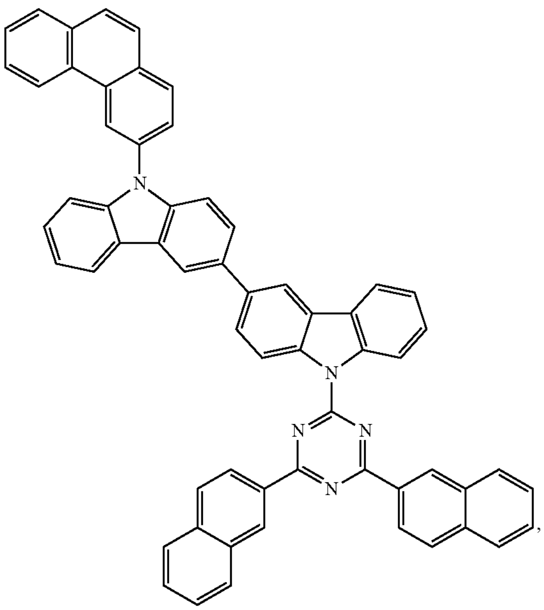
,
Compound 58
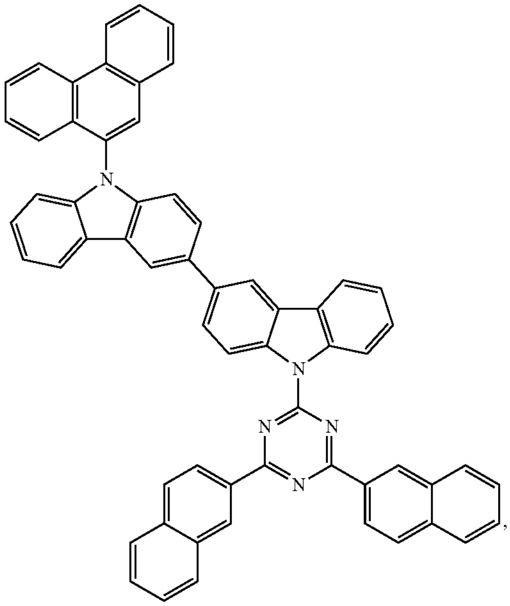
,
Compound 59
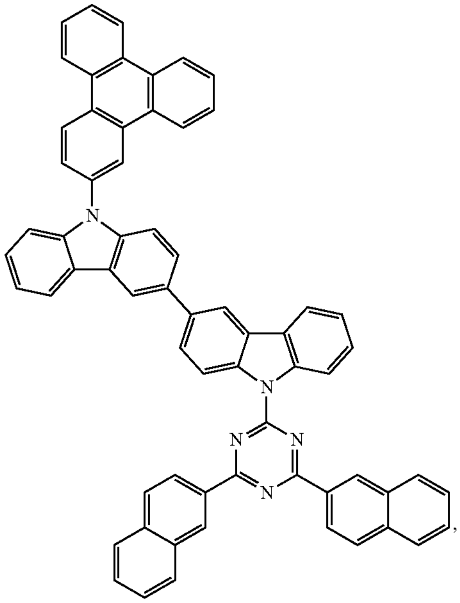
,
Compound 60
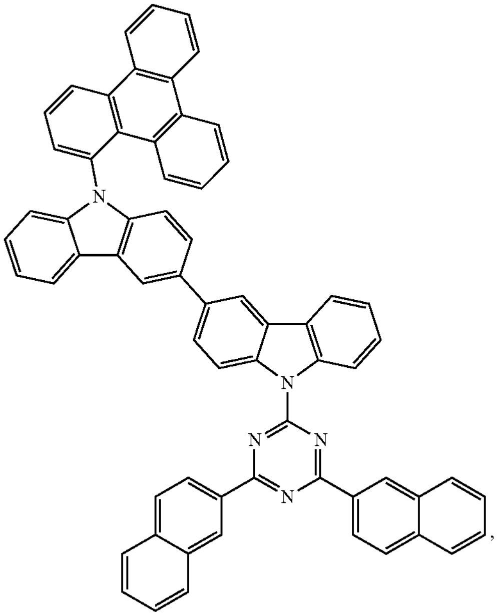
, -continued
Compound 69
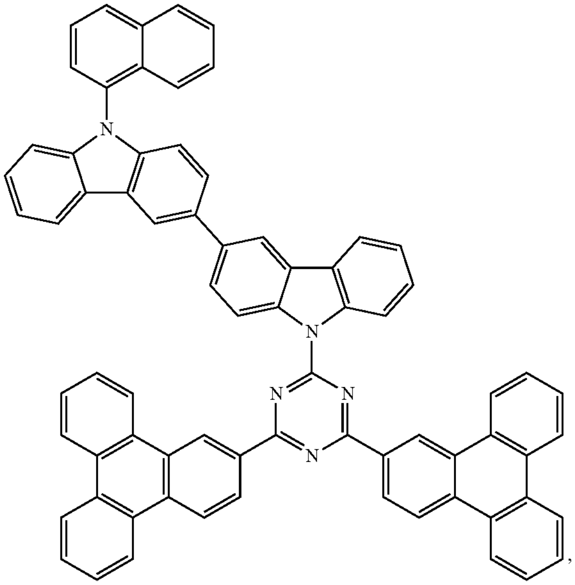
,
Compound 70
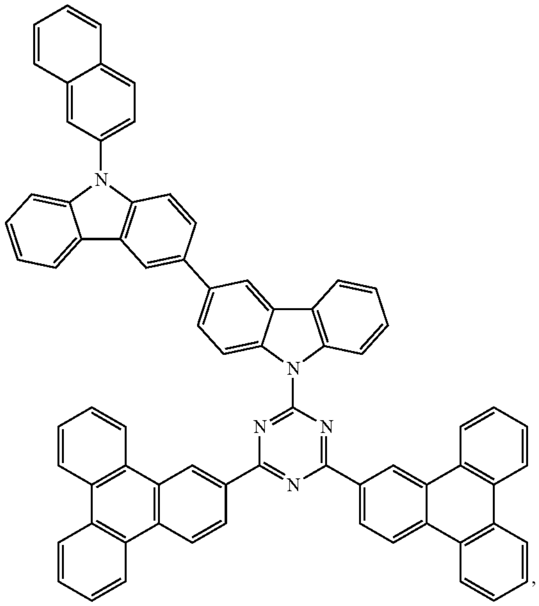
,
-continued
Compound 71
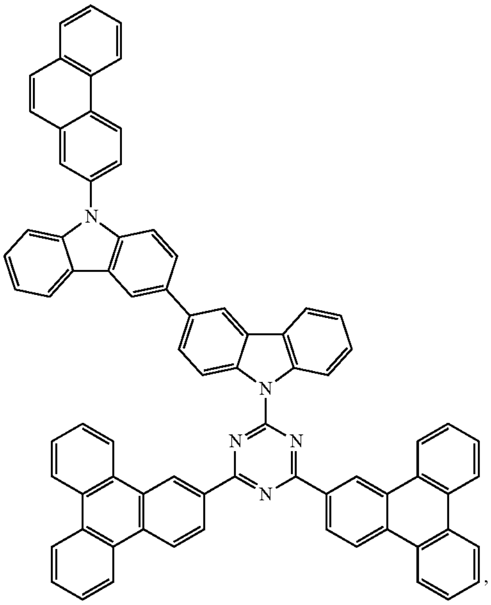
,
Compound 72
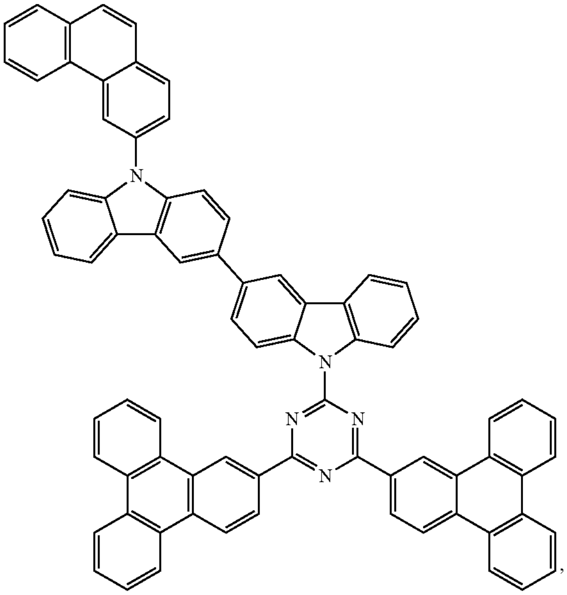
, -continued
Compound 73
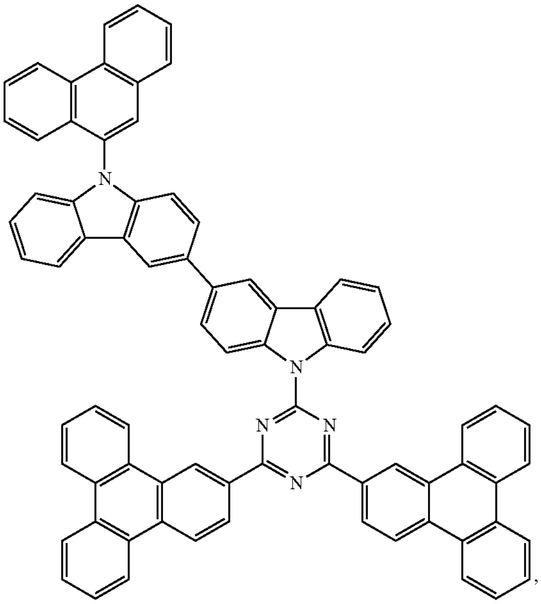
,
Compound 74
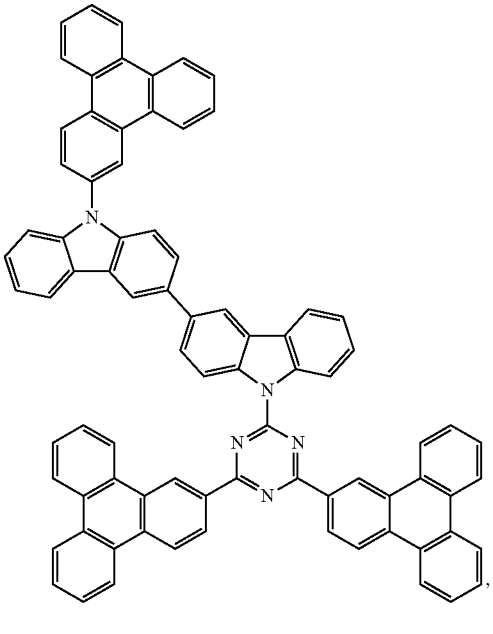
,
-continued
Compound 75
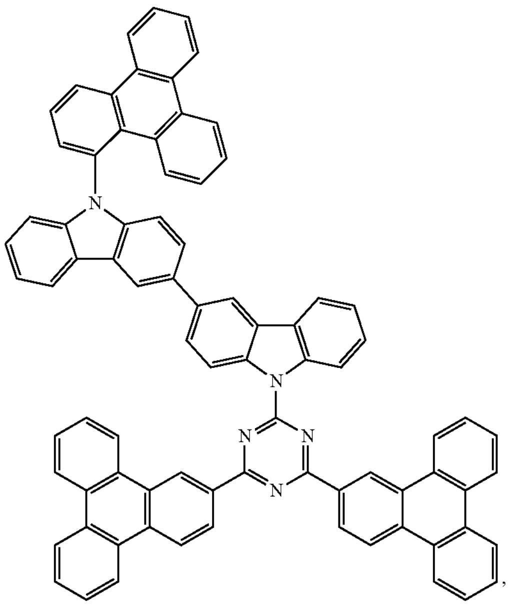
,
Compound 84
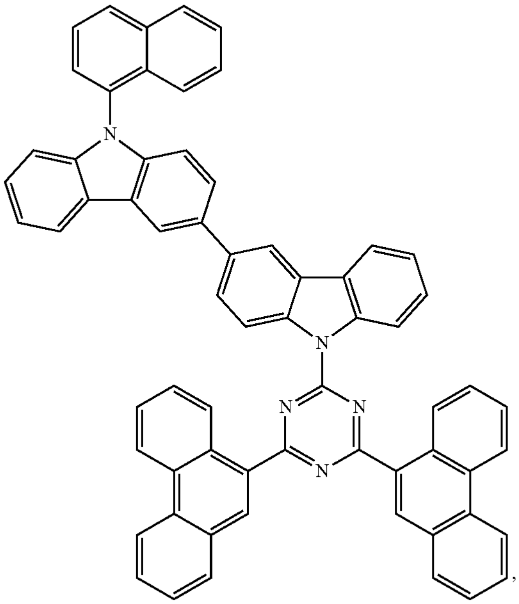
, Compound 85
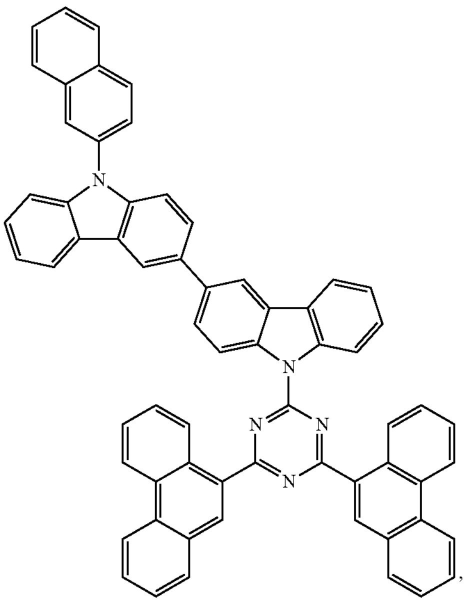
Compound 86
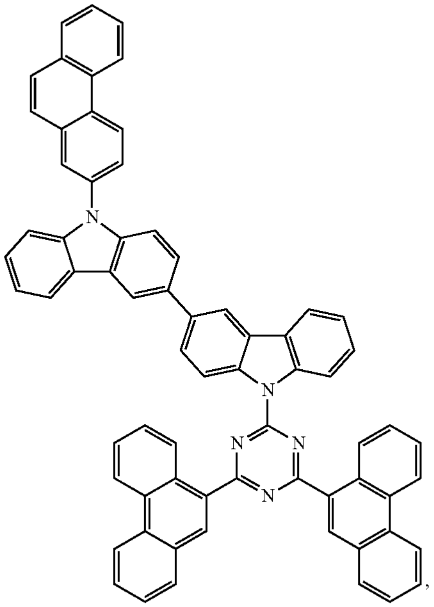
Compound 87
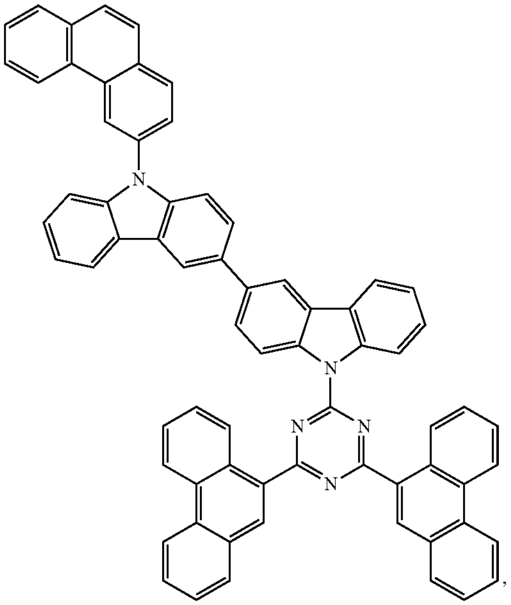
Compound 88
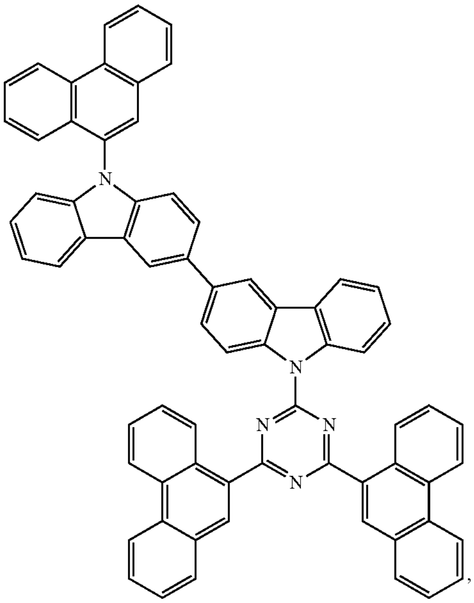

-continued
Compound 89
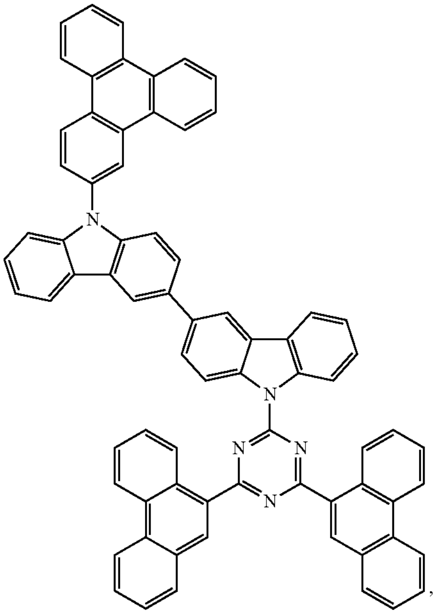
,
Compound 90
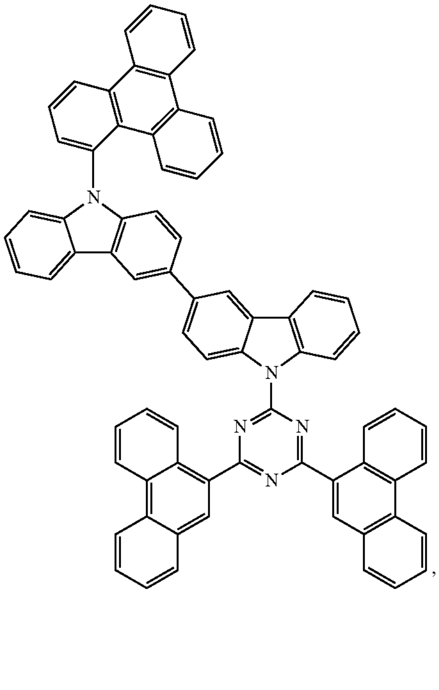
,
-continued
Compound 99
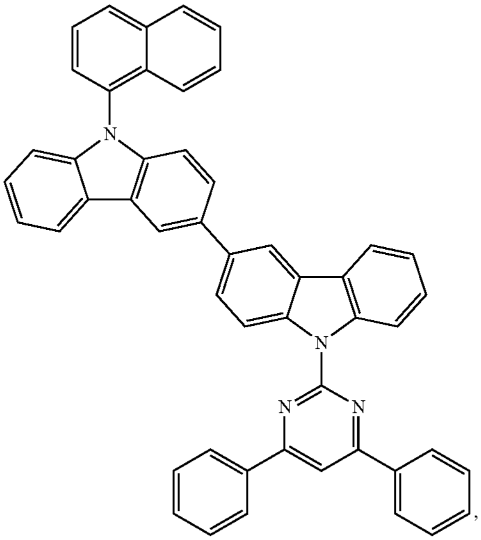
,
Compound 100
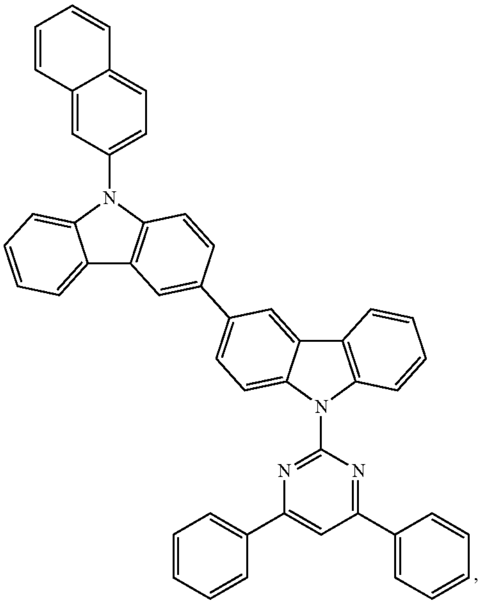
, -continued
Compound 101
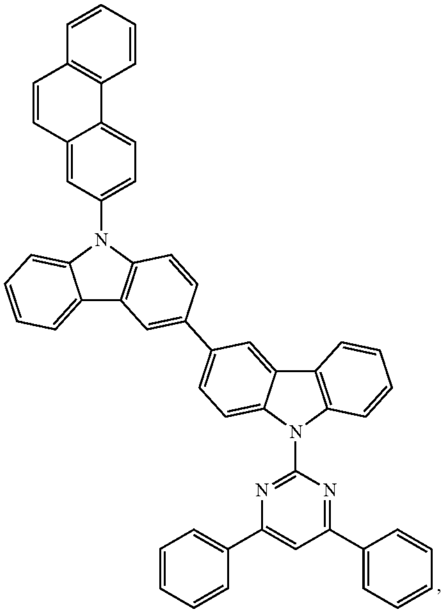
,
Compound 103
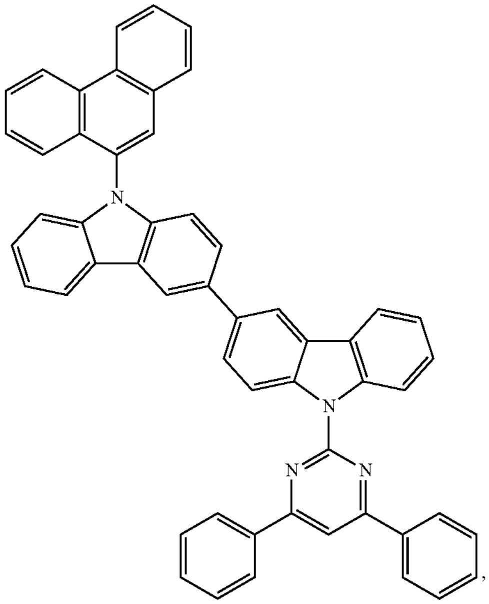
,
Compound 102
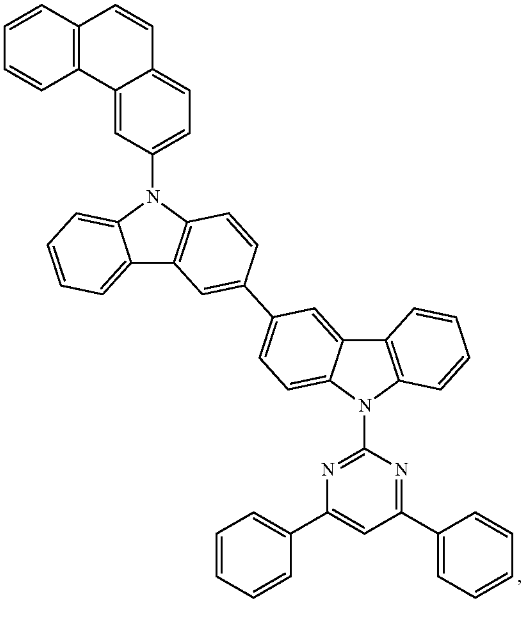
,
Compound 104
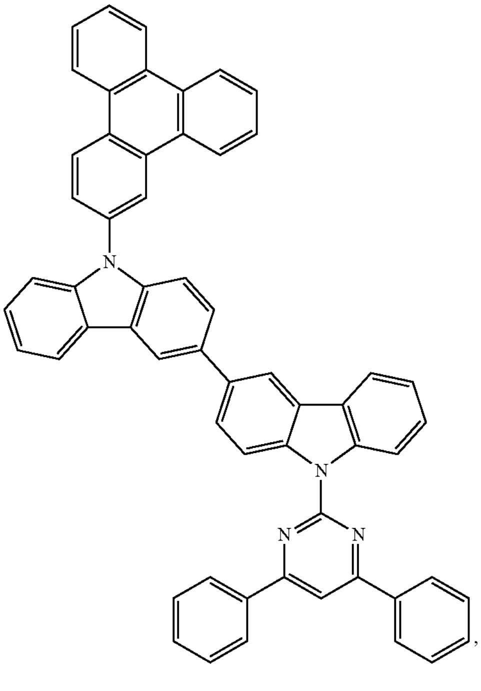
, -continued
Compound 105
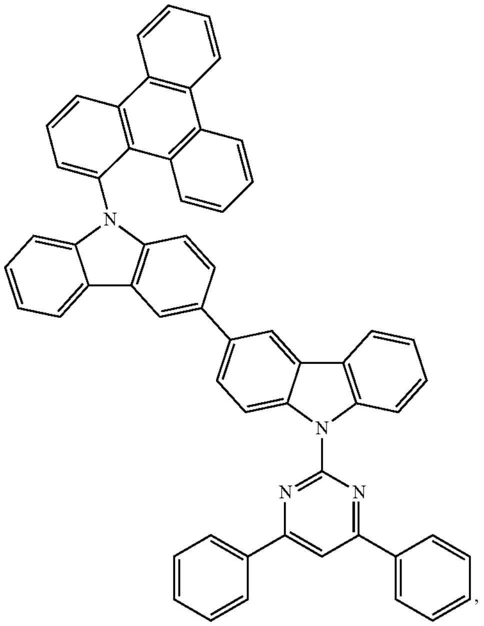
Compound 114
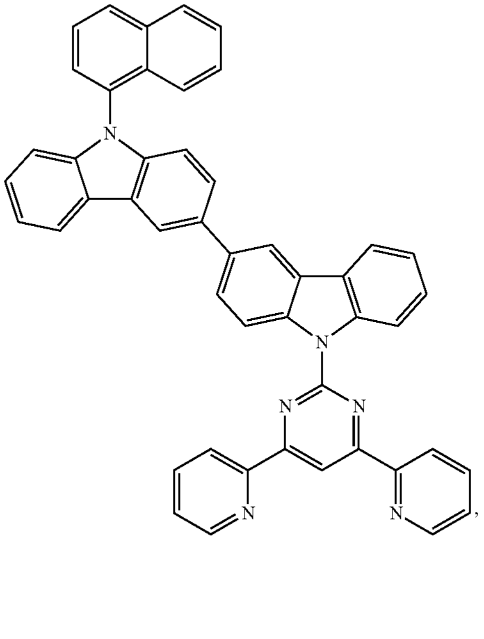
-continued
Compound 115
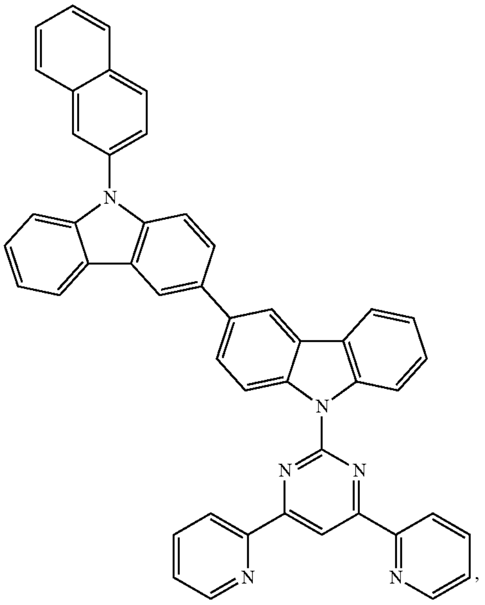
Compound 116
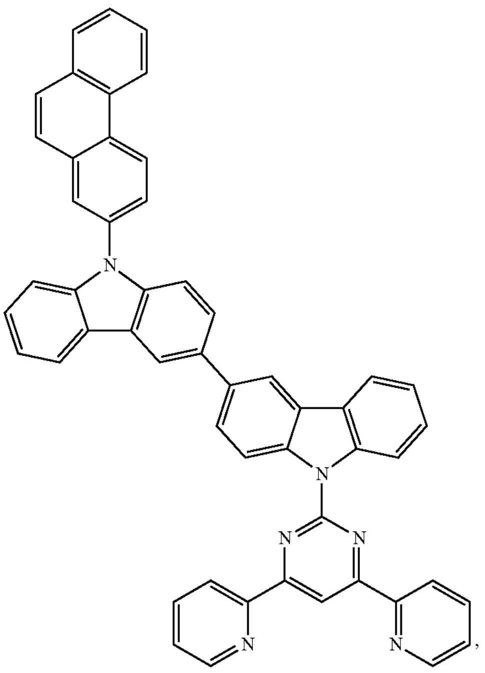

-continued
Compound 117
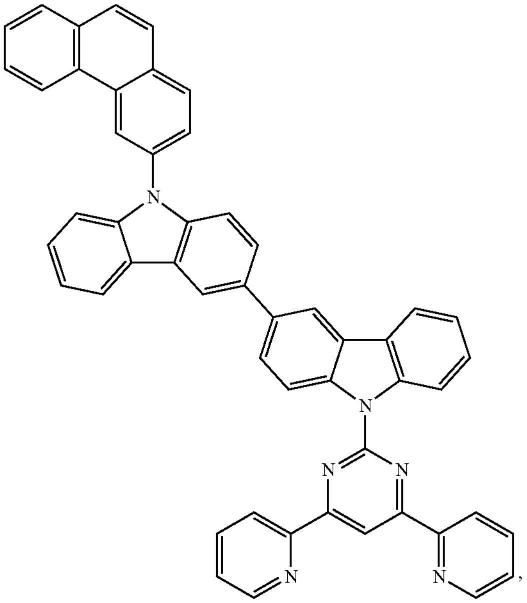
Compound 118
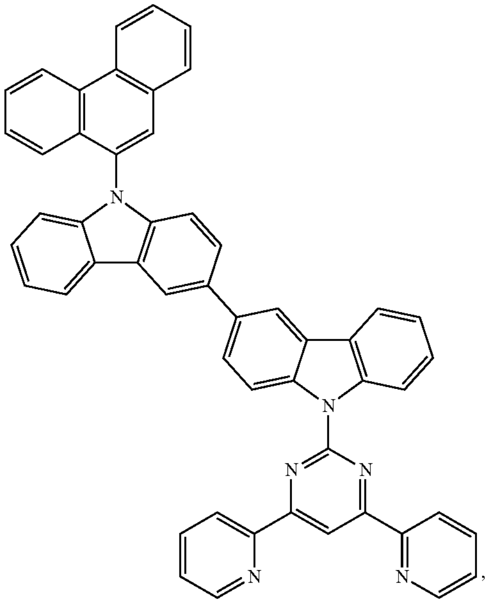
-continued
Compound 119
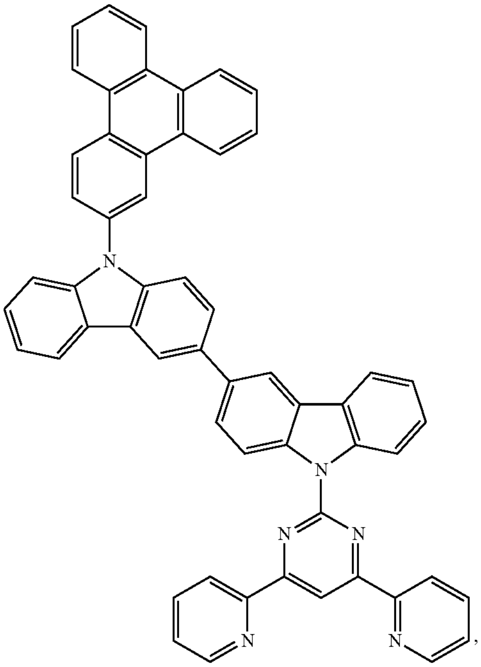
Compound 120
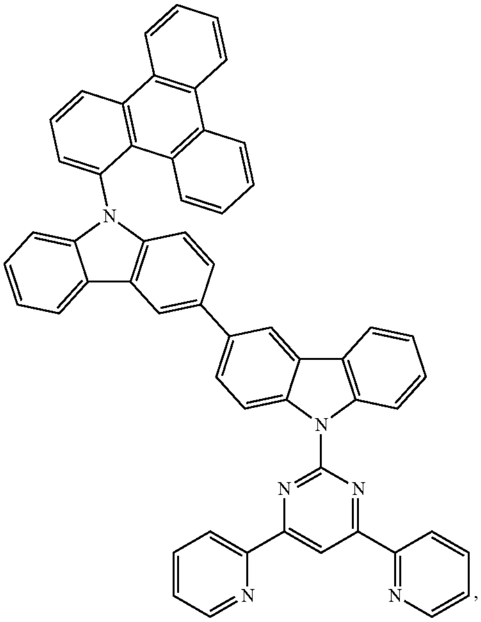

-continued
Compound 129
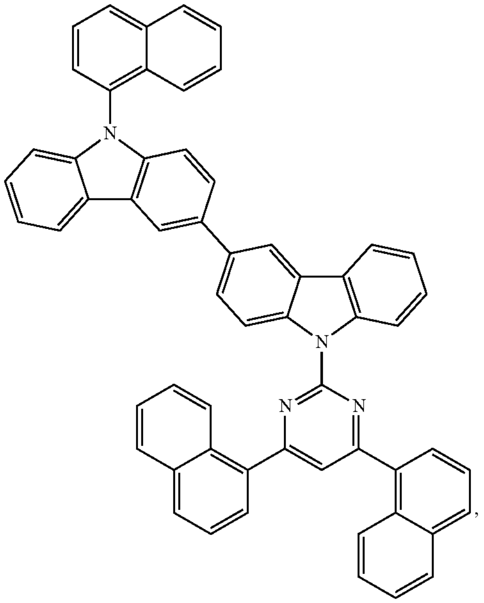
,
Compound 130
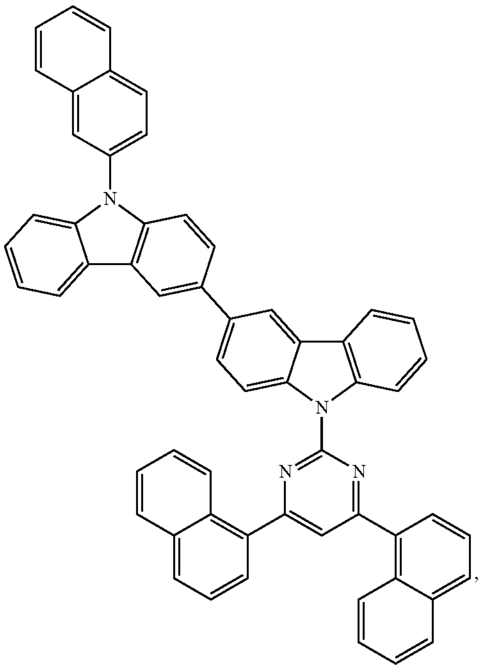
,
-continued
Compound 131
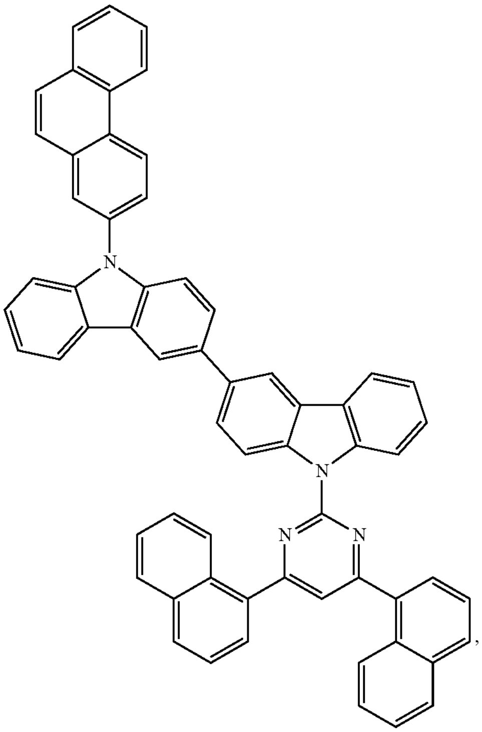
,
Compound 132
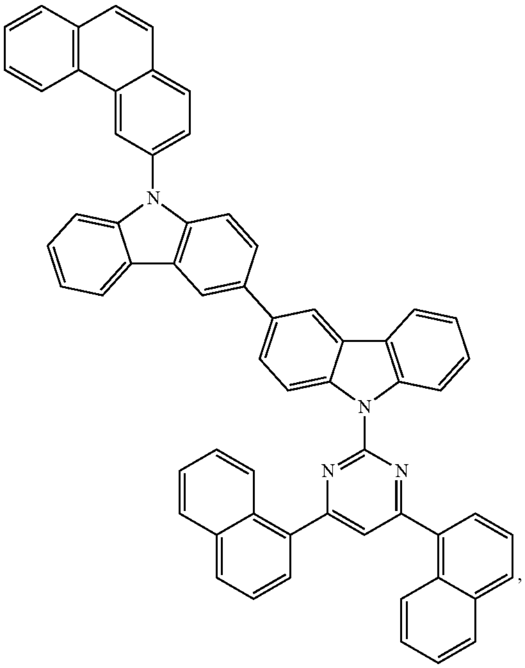
, -continued
Compound 133
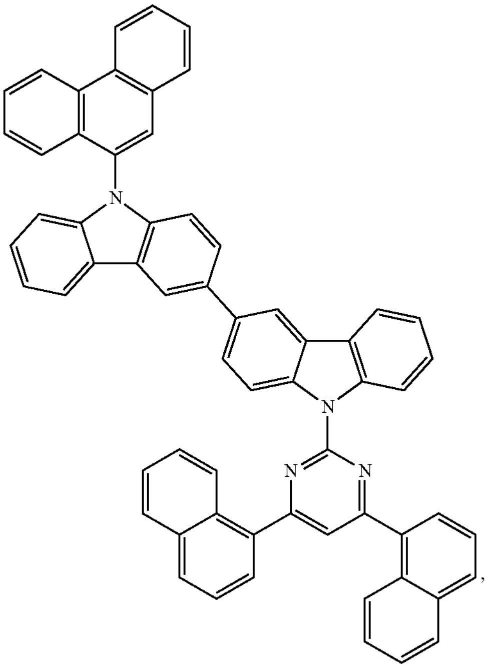
,
Compound 134
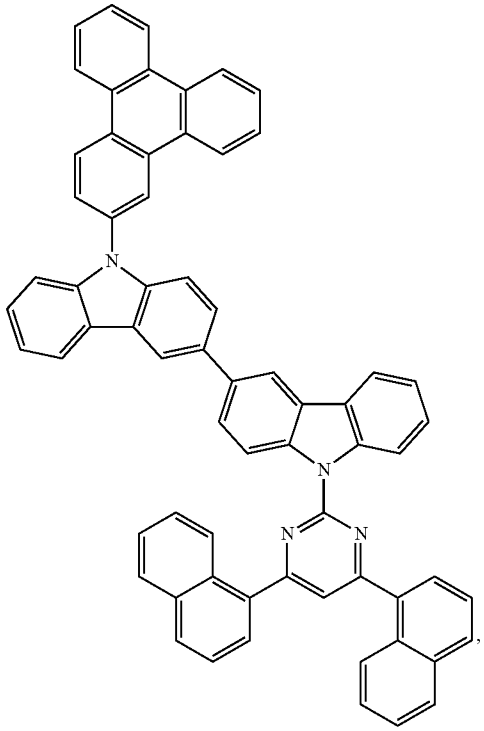
,
-continued
Compound 135
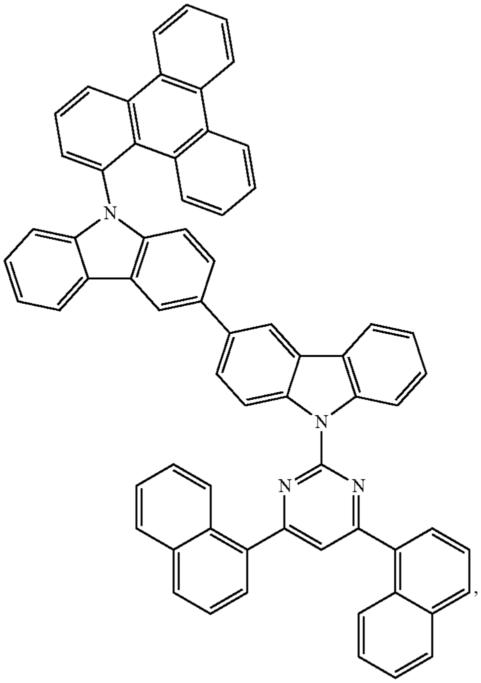
,
Compound 144
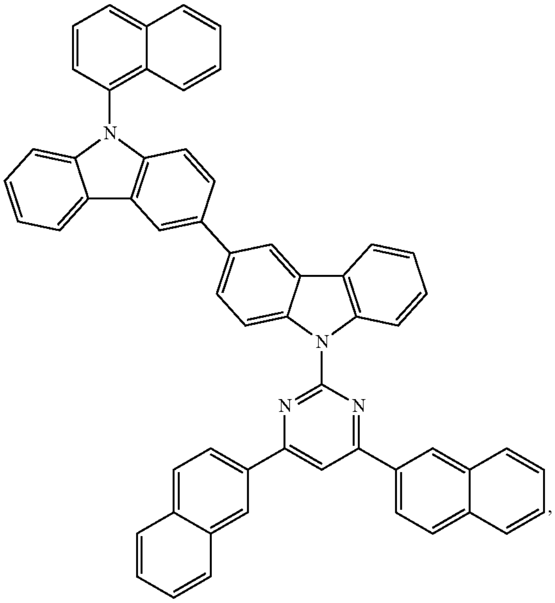
, Compound 145
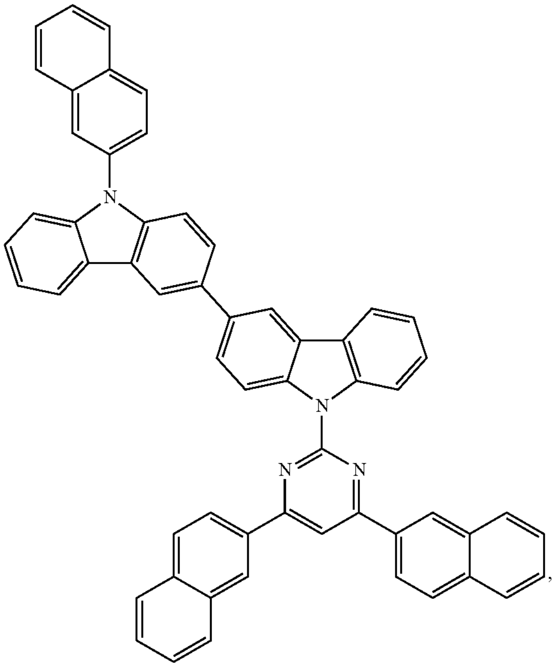
,
Compound 146
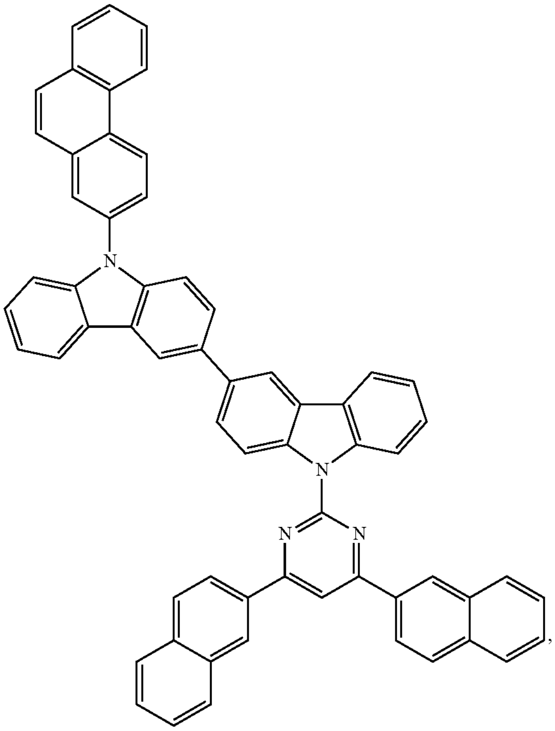
,
Compound 147
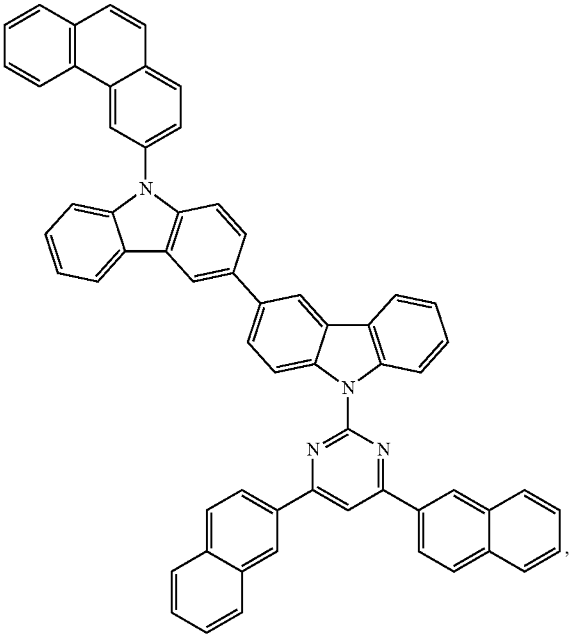
,
Compound 148
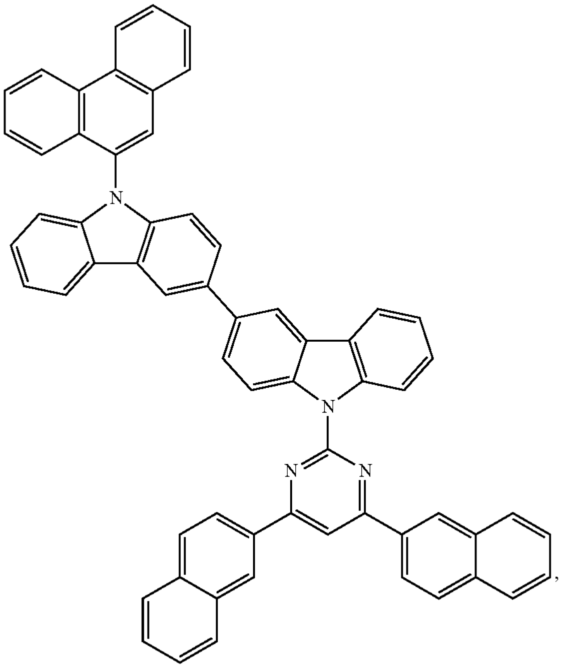
, -continued
Compound 149
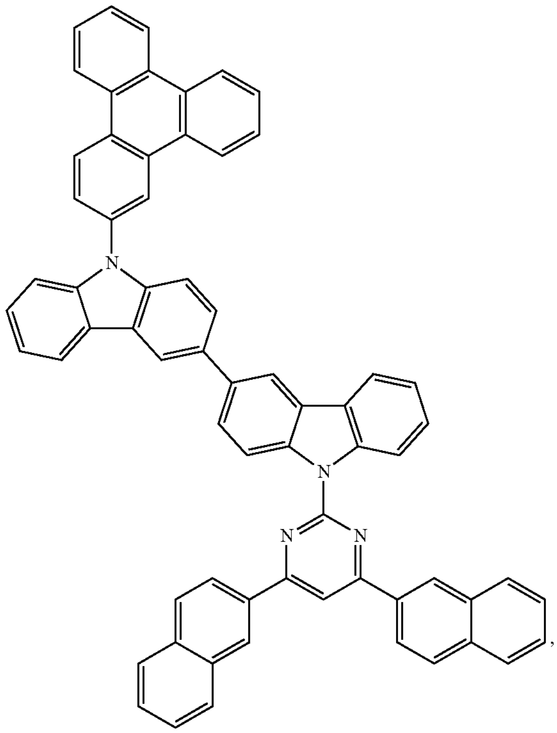
,
Compound 159
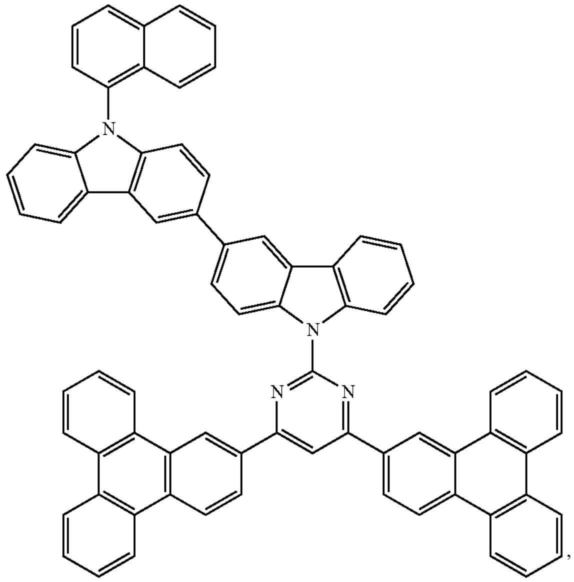
,
Compound 150
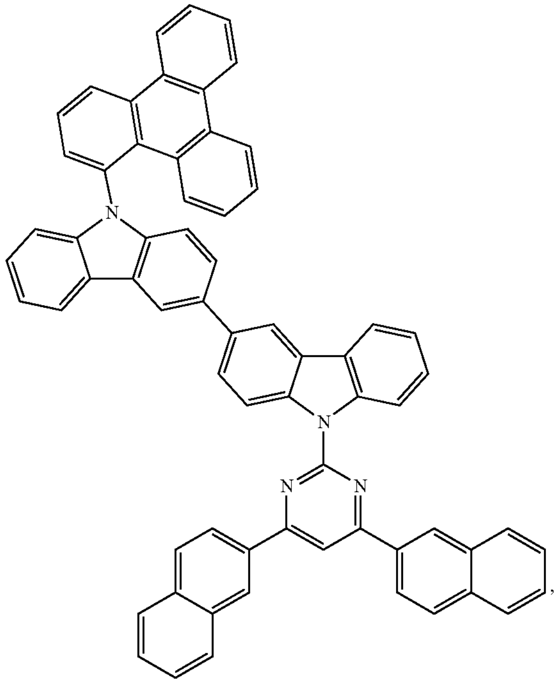
,
Compound 160
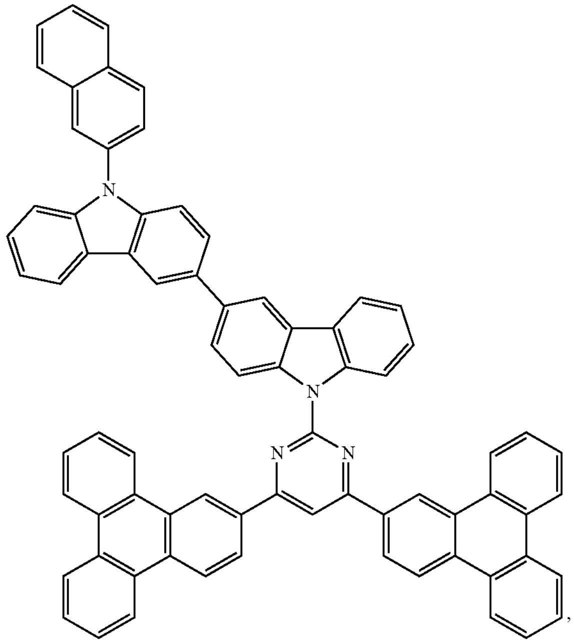
, -continued
Compound 161
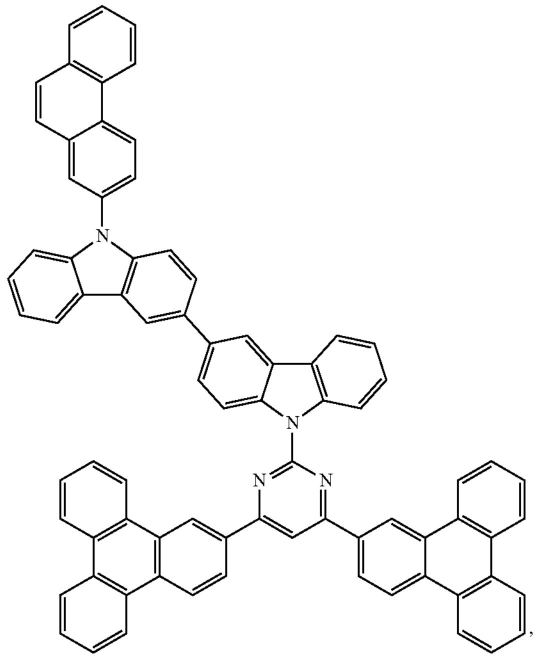
Compound 162
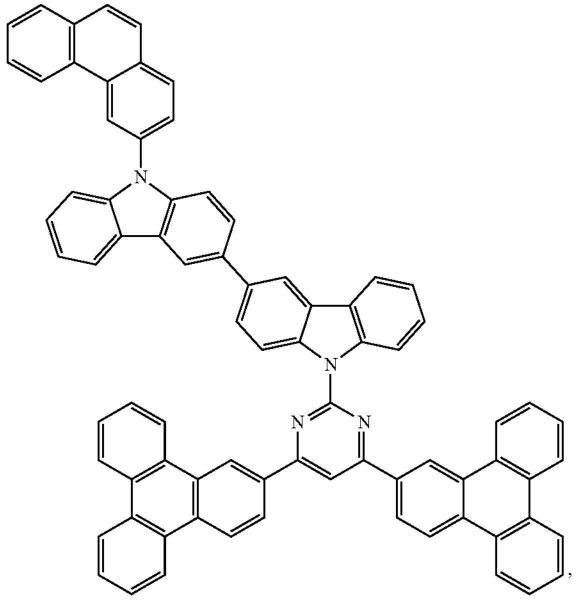
-continued
Compound 163
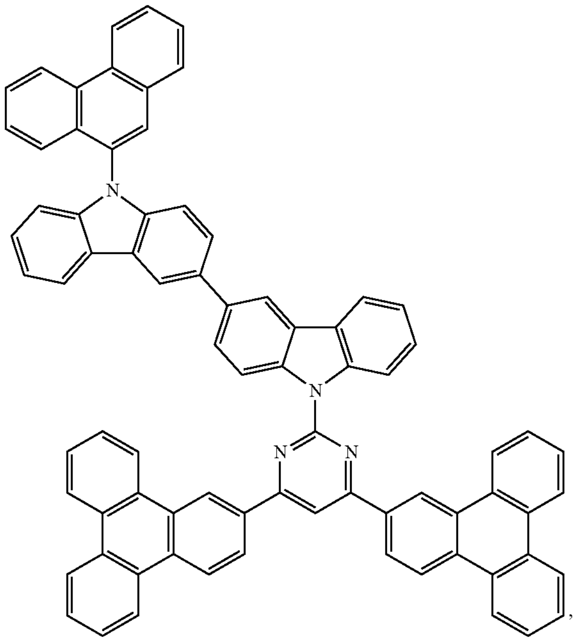
Compound 164
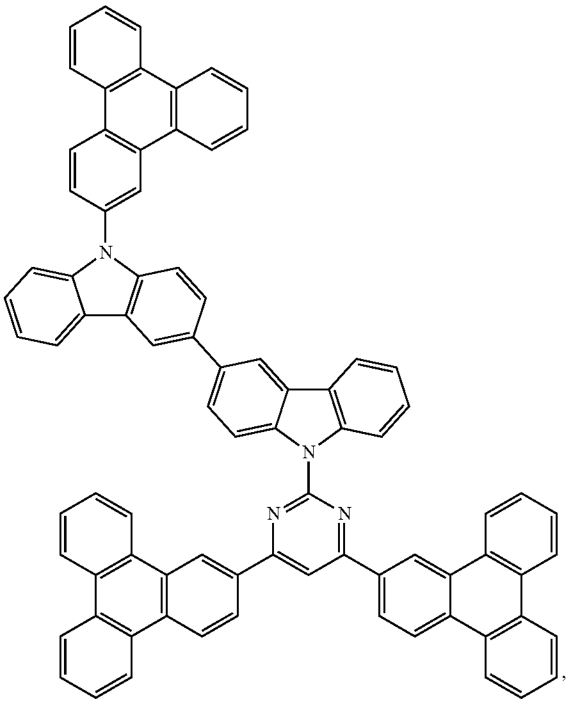

-continued
Compound 165
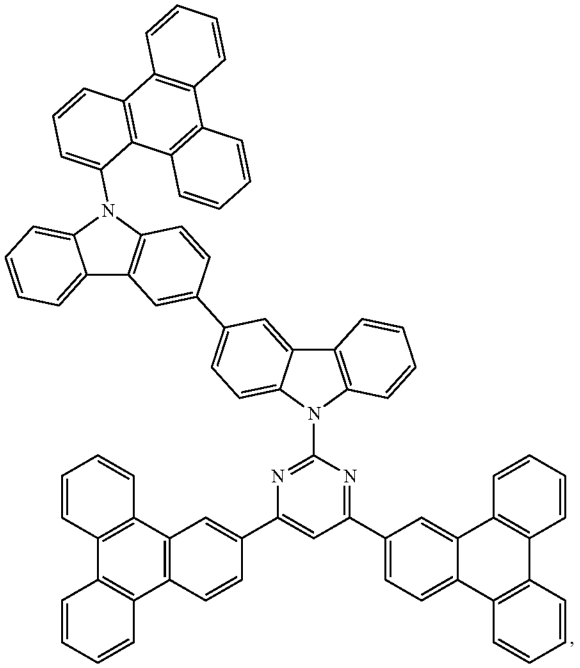
Compound 174
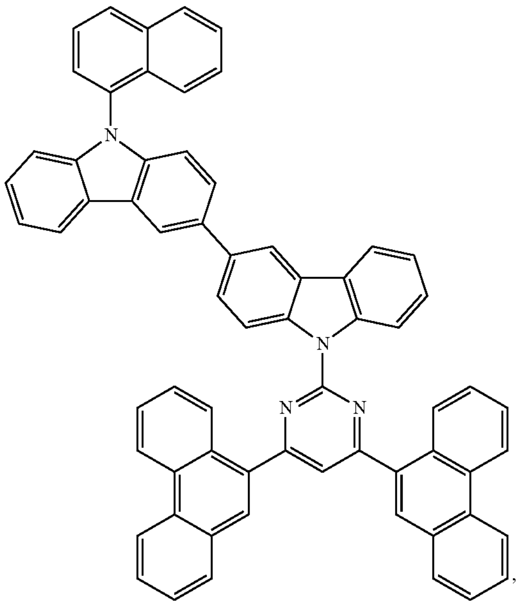
-continued
Compound 175
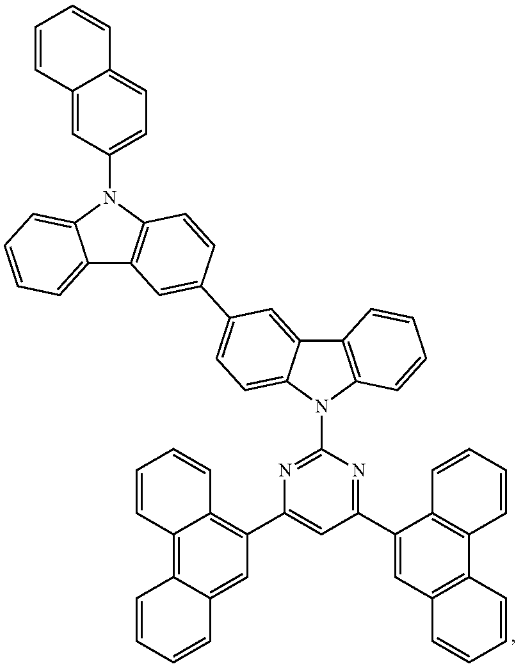
Compound 176
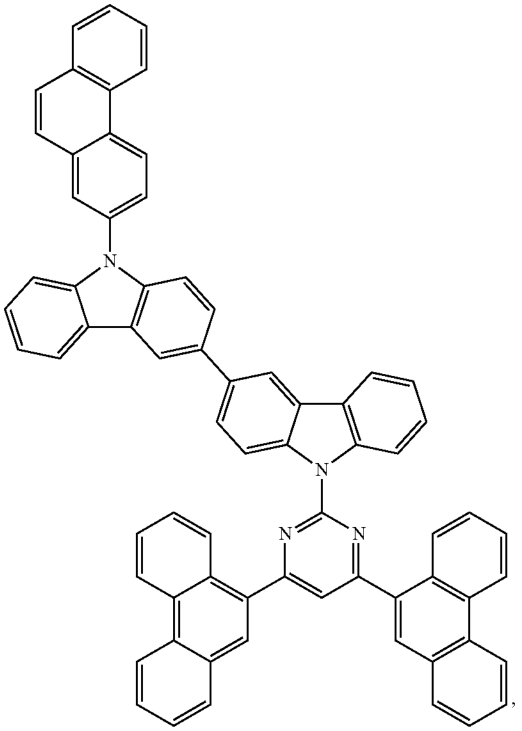

-continued
Compound 177
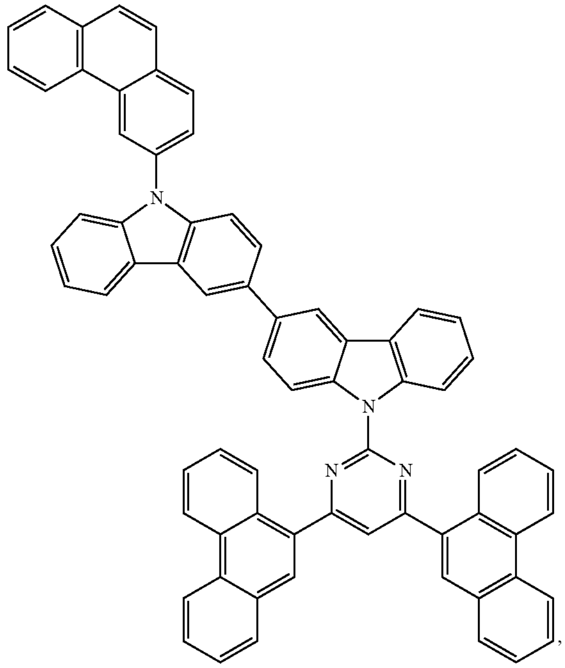
,
Compound 178
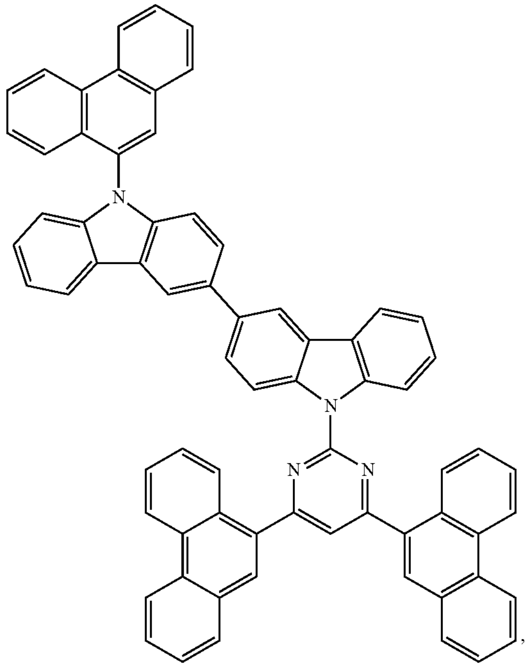
,
-continued
Compound 179
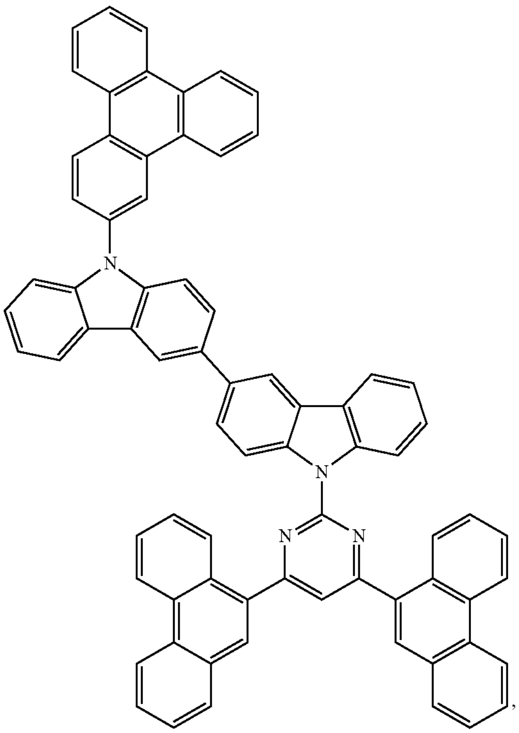
, and
Compound 180
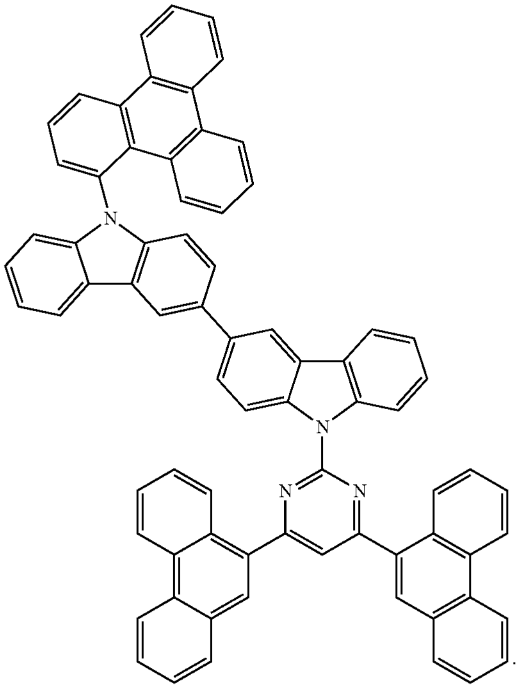
.
8. A first device comprising an organic light emitting device, organic light emitting device comprising:
an anode;
a cathode; and
an organic layer, disposed between the anode and the cathode, wherein the organic layer comprises a compound having the formula:

Formula I

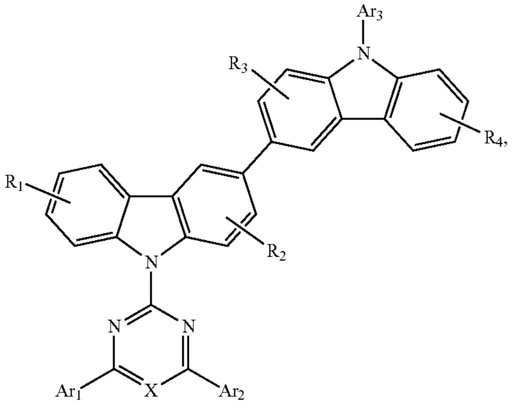

wherein $R_1$, $R_2$, $R_3$, and $R_4$ may represent mono, di, tri, or tetra substitutions;

wherein $R_1$, $R_2$, $R_3$, and $R_4$ are independently selected from the group consisting of hydrogen, alkyl, alkoxy, amino, alkenyl, alkynyl, aryl and heteroaryl;

wherein $Ar_1$ and $Ar_2$ are independently selected from aryl or heteroaryl; and wherein X is C or N; and wherein $Ar_3$ is a polycyclic fused aryl system.

9. The device of claim 8, wherein $Ar_1$, $Ar_2$, and $Ar_3$ are further substituted.

10. The device of claim 8, wherein $Ar_1$ and $Ar_2$ are independently selected from the group consisting of phenyl, pyridine, naphthalene, biphenyl, terphenyl, fluorene, dibenzofuran, dibenzothiophene, phenanthrene, and triphenylene; and wherein $Ar_1$ and $Ar_2$ are independently further substituted with a substituent selected from the group consisting of hydrogen, alkyl, alkoxy, amino, alkenyl, alkynyl, aryl and heteroaryl, wherein the substituent is not an aryl or heteroaryl fused directly to $Ar_1$ and $Ar_2$.

11. The device of claim 8, wherein $Ar_1$ and $Ar_2$ are independently selected from the group consisting of phenyl, pyridine, and naphthalene.

12. The device of claim 8, wherein $Ar_3$ is selected from the group consisting of naphthalene, phenanthrene, and triphenylene.

13. The device of claim 8, wherein $R_1$, $R_2$, $R_3$, and $R_4$ are hydrogen.

14. The device of claim 8, wherein the organic layer is deposited using solution processing.

15. The device of claim 8, wherein the organic layer is an emissive layer and the compound having Formula I is a host.

16. The device of claim 15, wherein the organic layer further comprises an emissive dopant having the structure:

D1

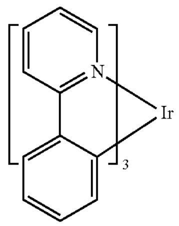

-continued

D2

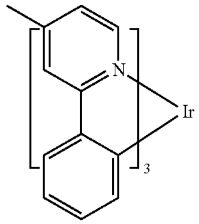

D3

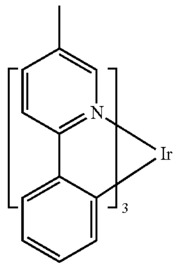

D4

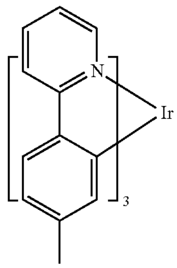

D5

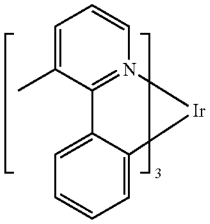

D6

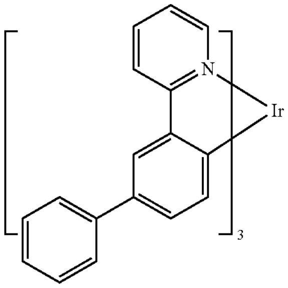

D7

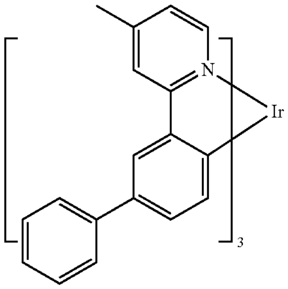

-continued
D8
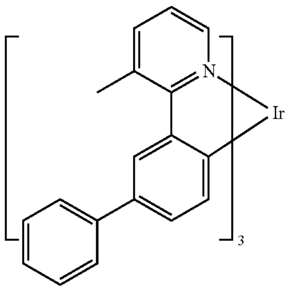
D9
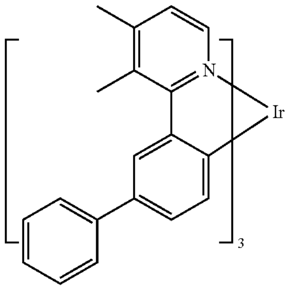
D10
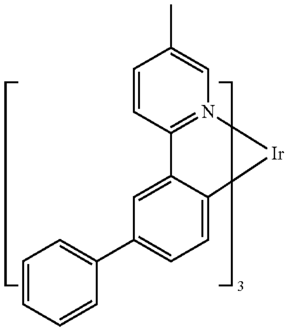
D11
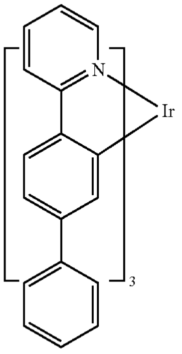
D12
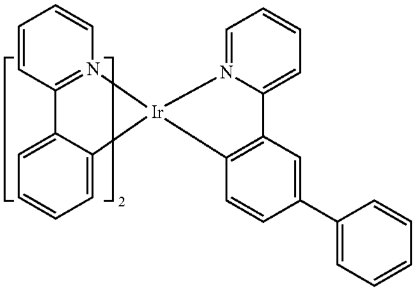
-continued
D13
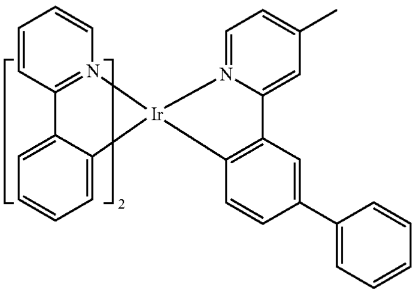
D14
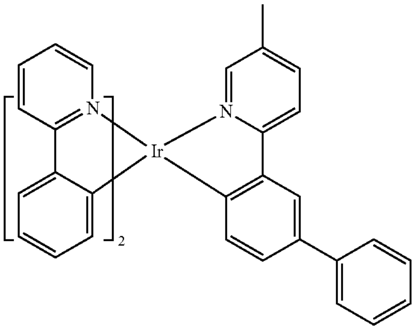
D15
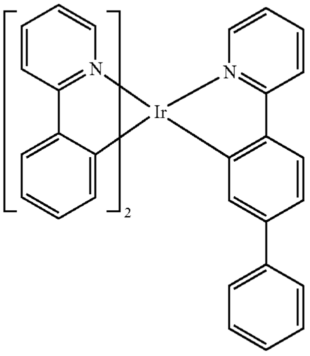
D16
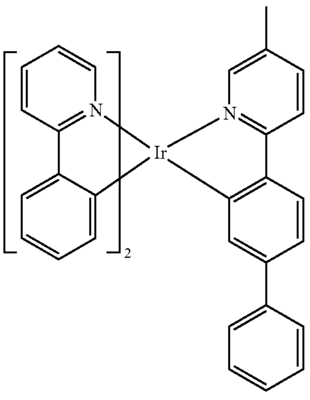

-continued
D17
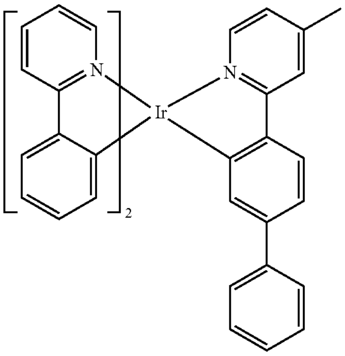
D18
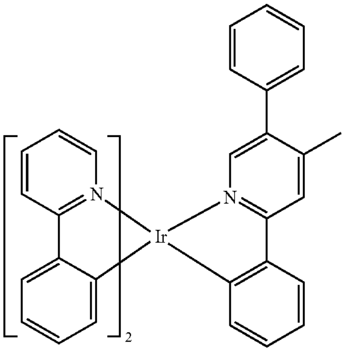
D19
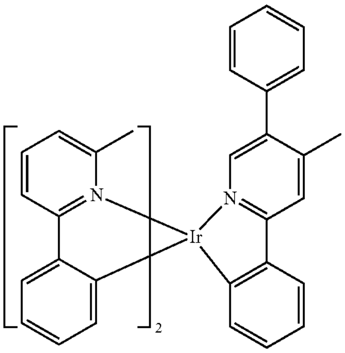
D20
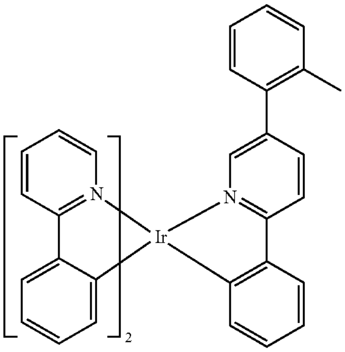
-continued
D21
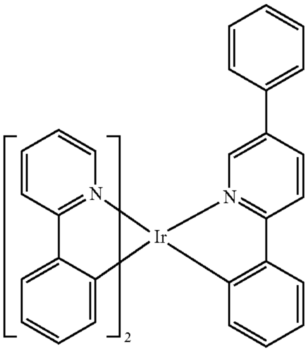
D22
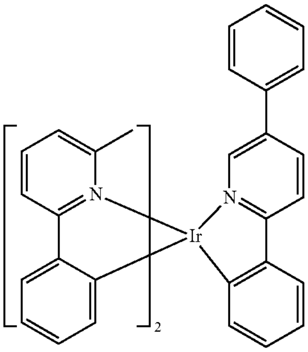
D23
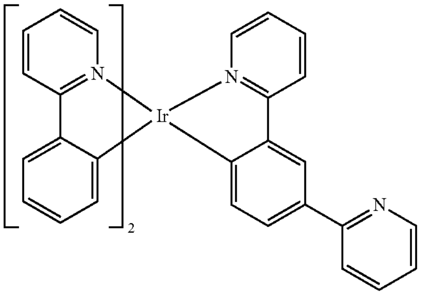
D24
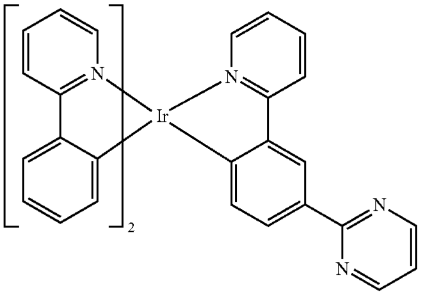
D25
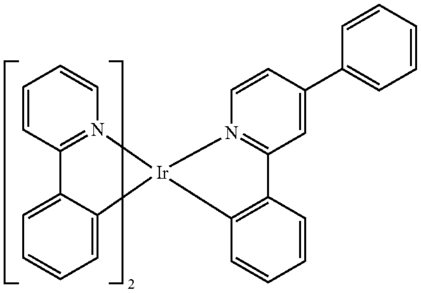

-continued
D26
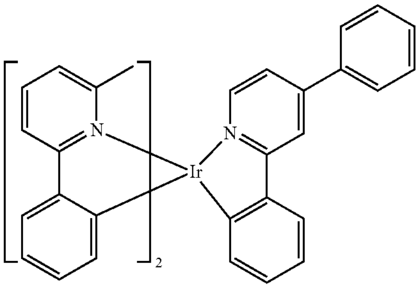
D27
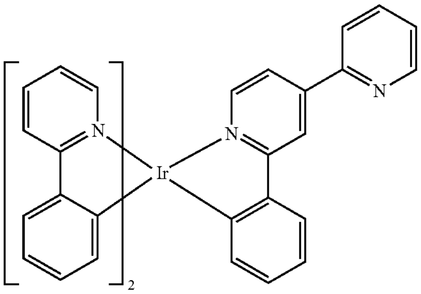
D28
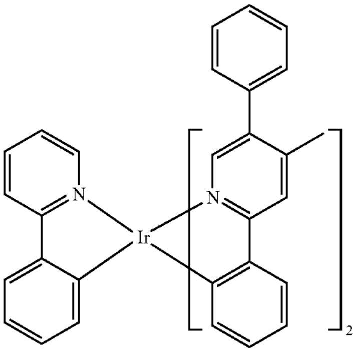
D29
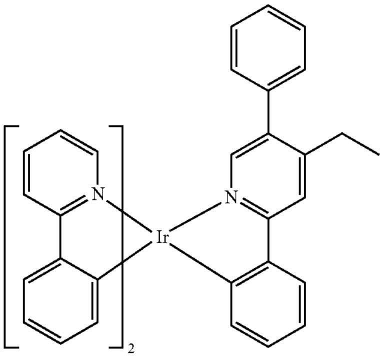
-continued
D30
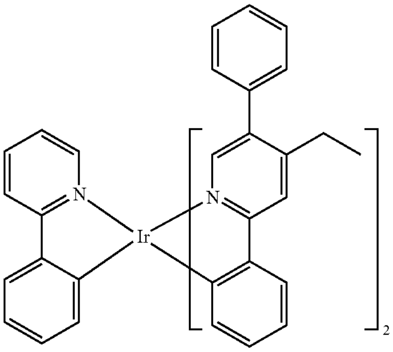
D31
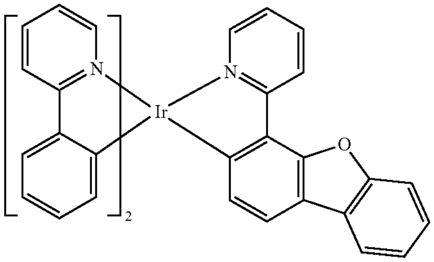
D32
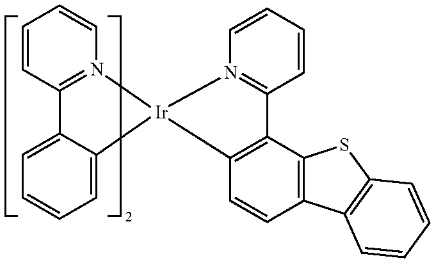
D33
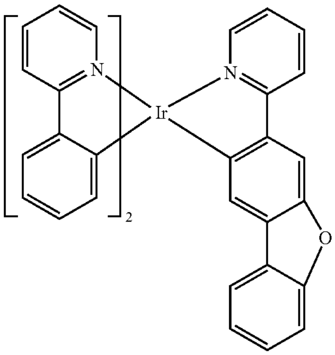
D34
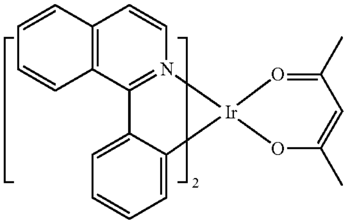

-continued
D35
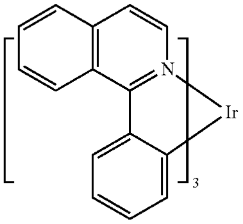
D36
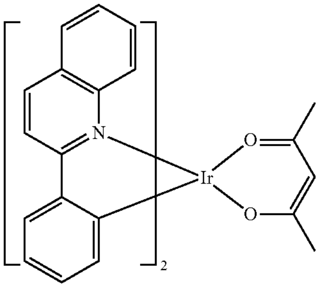
D37
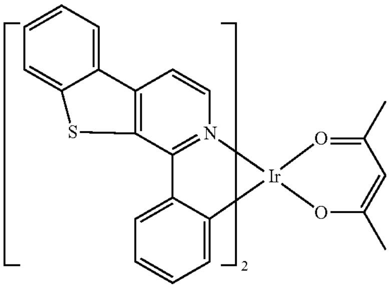
D38
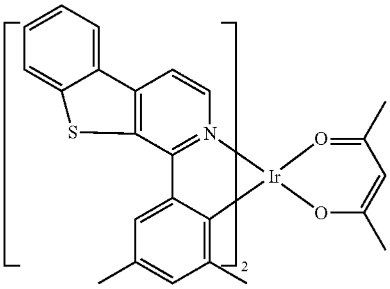
D39
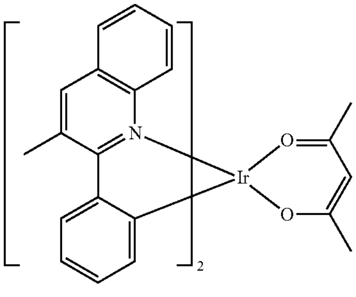
-continued
D40
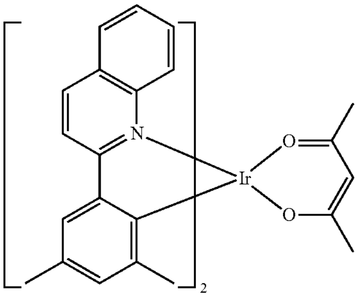
D41
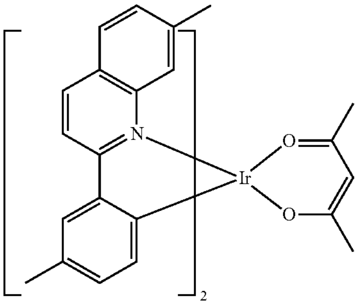
D42
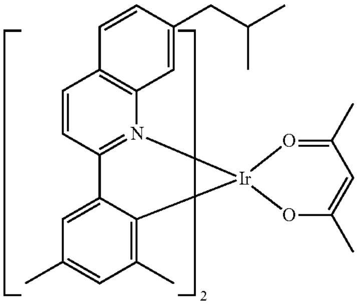
D43
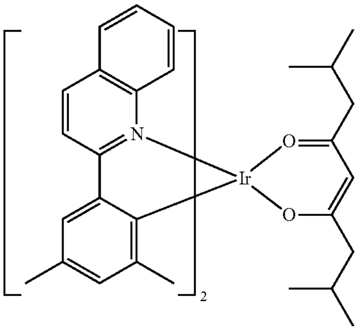
D44
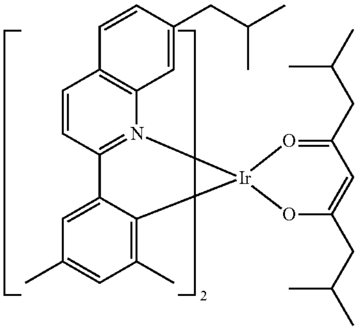

-continued
D45
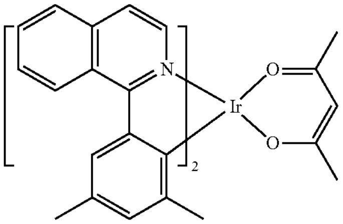
D46
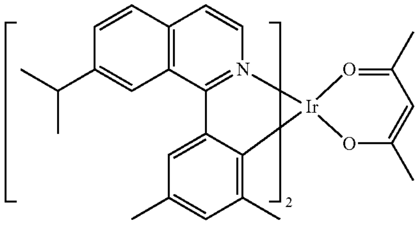
D47
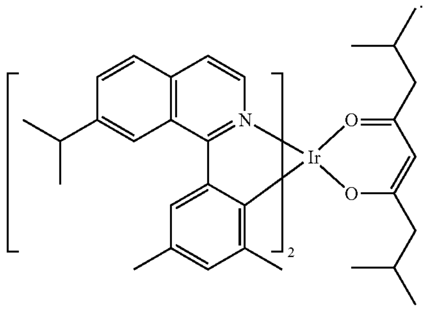
17. The device of claim 8, wherein the first device is an organic light emitting device.
18. The device of claim 8, wherein the compound is selected from the group consisting of:
Compound 9
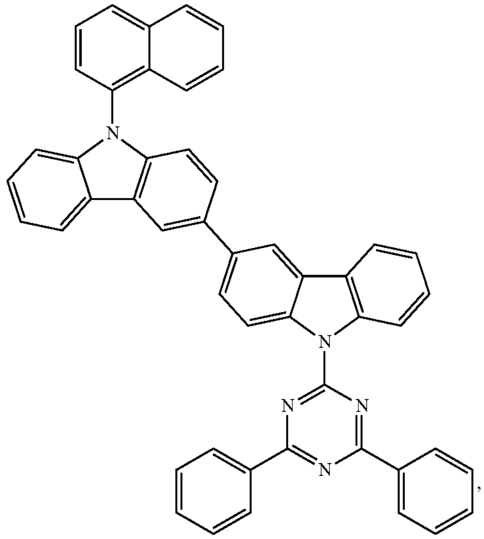
,
-continued
Compound 10
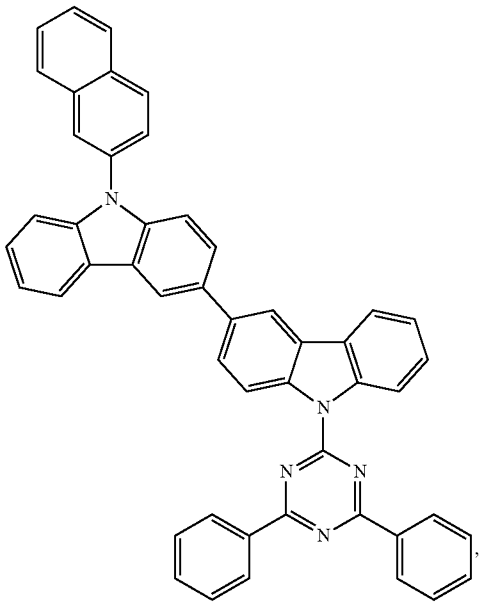
,
Compound 11
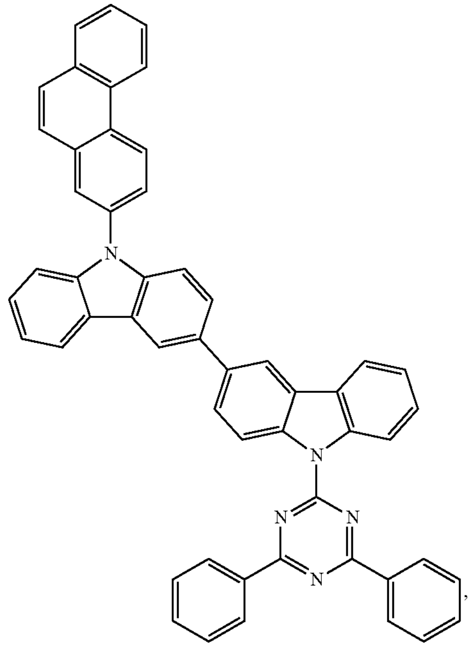
, -continued
Compound 12
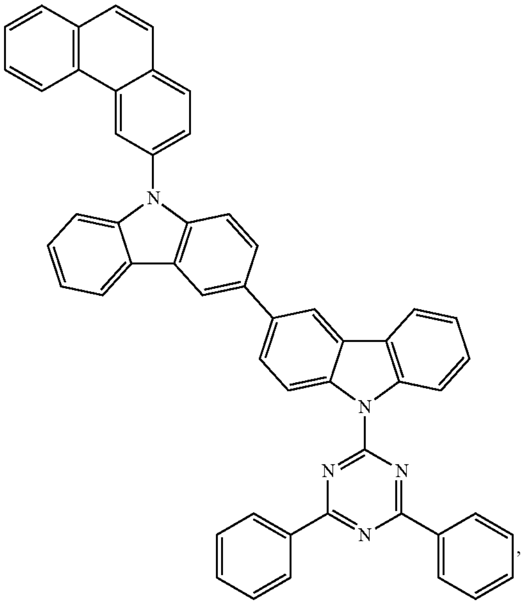
Compound 13
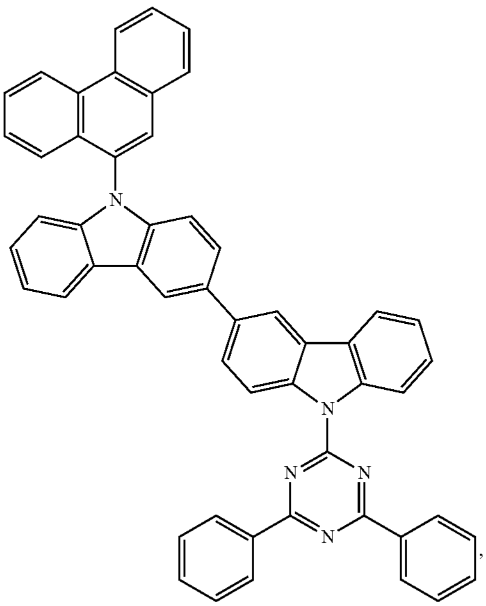
-continued
Compound 14
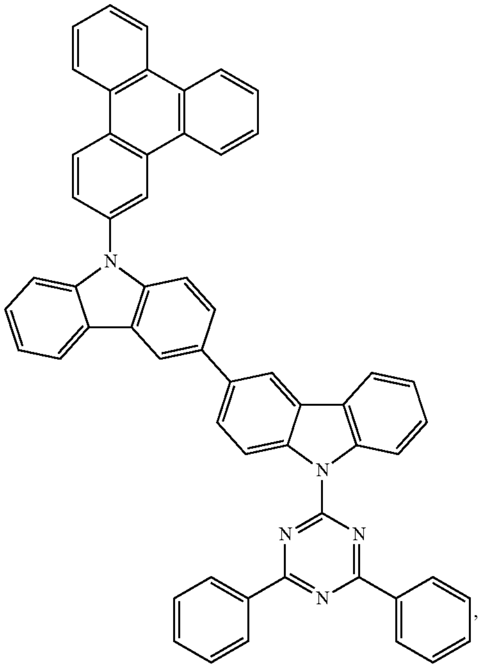
Compound 15
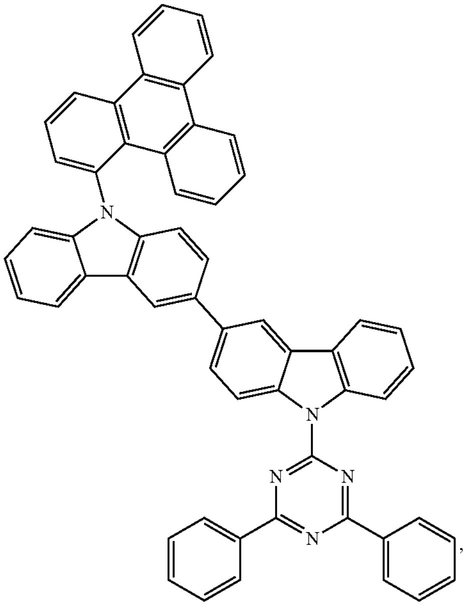

-continued
Compound 24
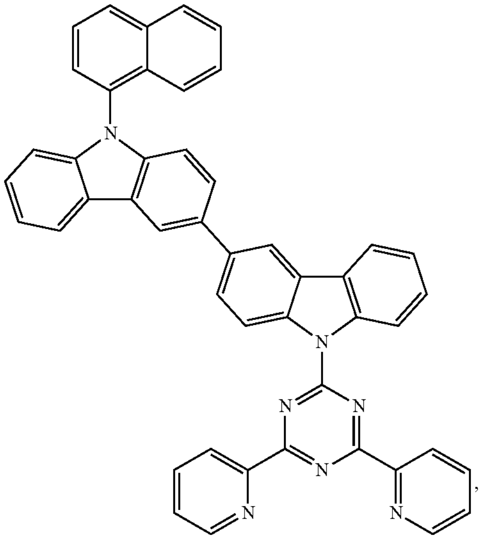
Compound 25
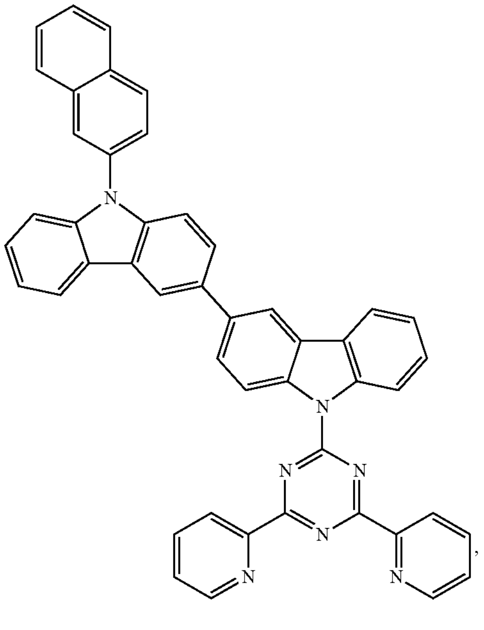
-continued
Compound 26
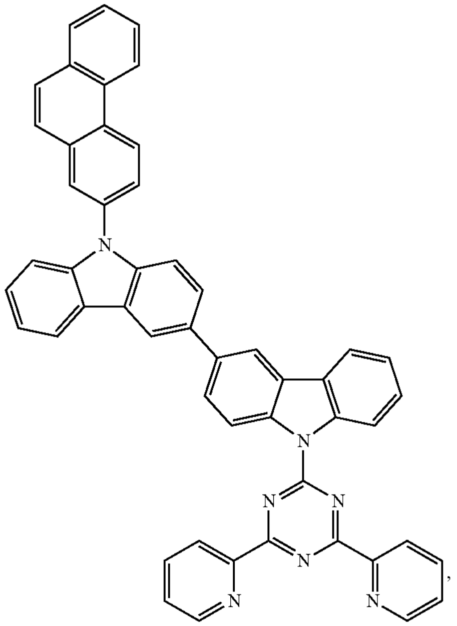
Compound 27
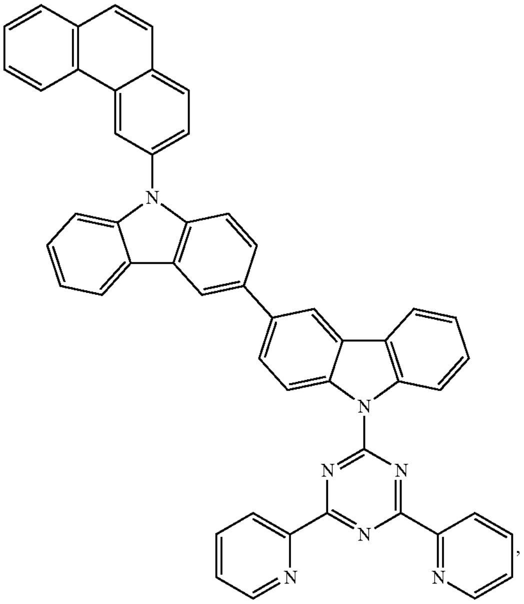

-continued
Compound 28
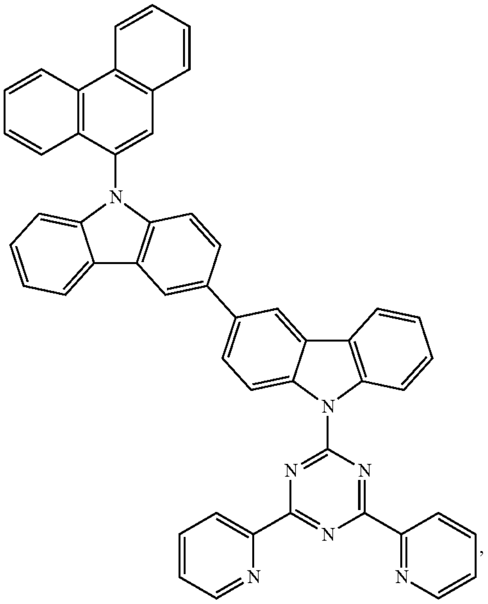
Compound 29
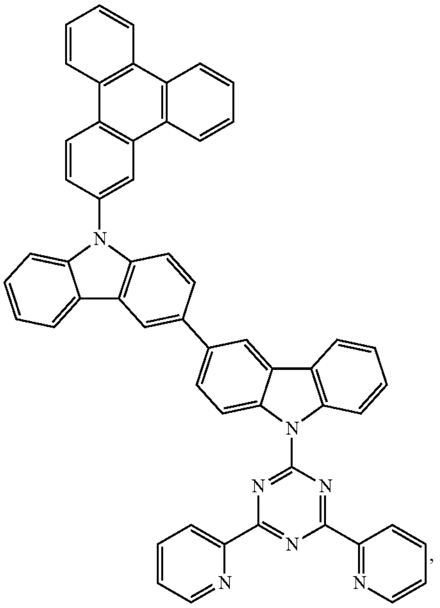
-continued
Compound 30
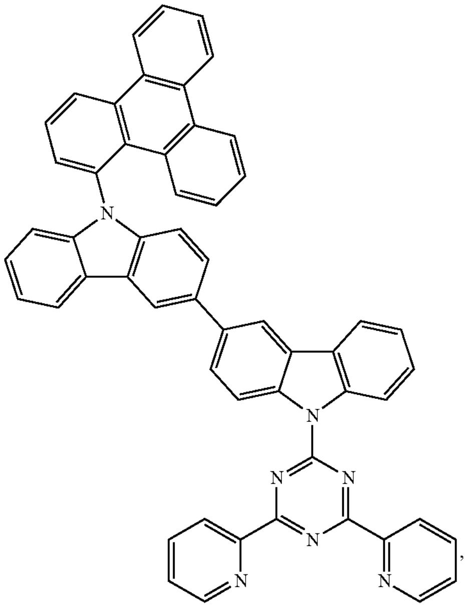
Compound 39
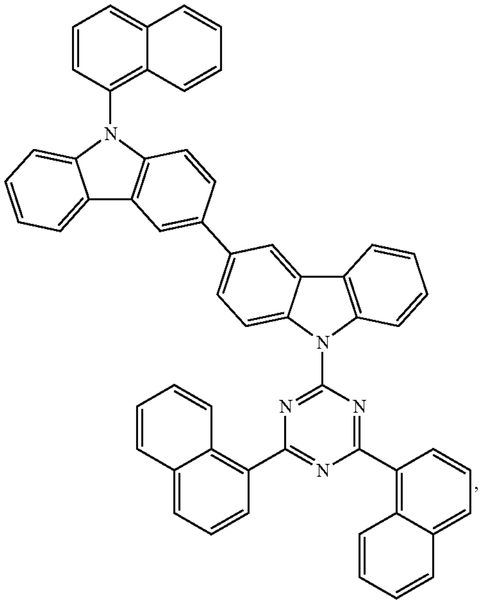

-continued
Compound 40
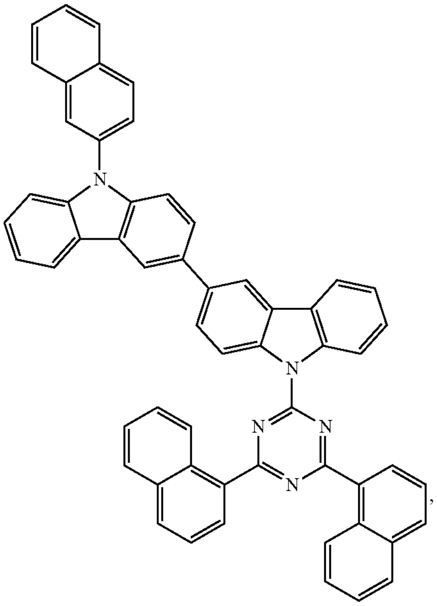
Compound 41
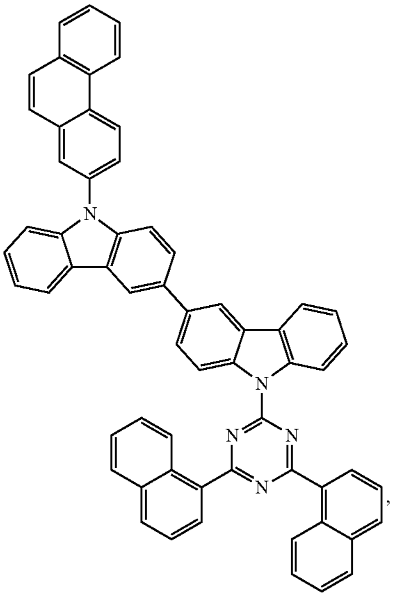
-continued
Compound 42
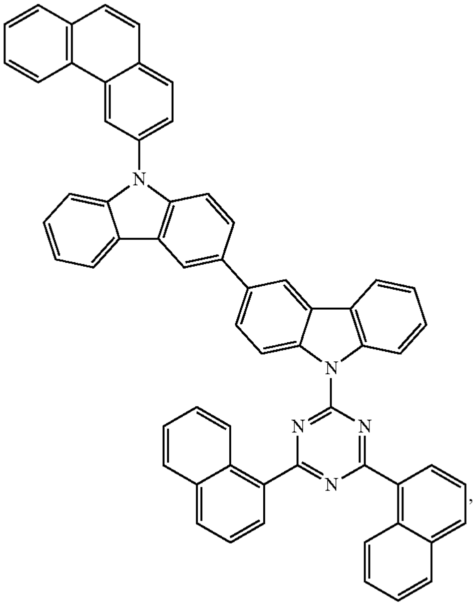
Compound 43
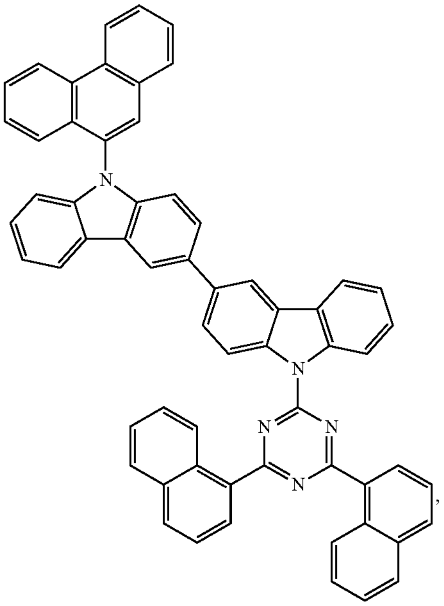

-continued
Compound 44
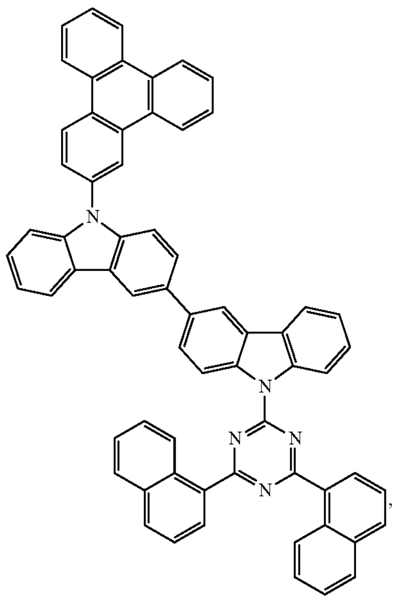
Compound 45
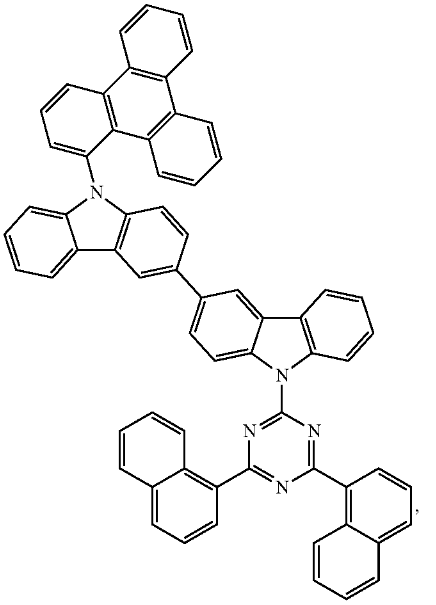
-continued
Compound 54
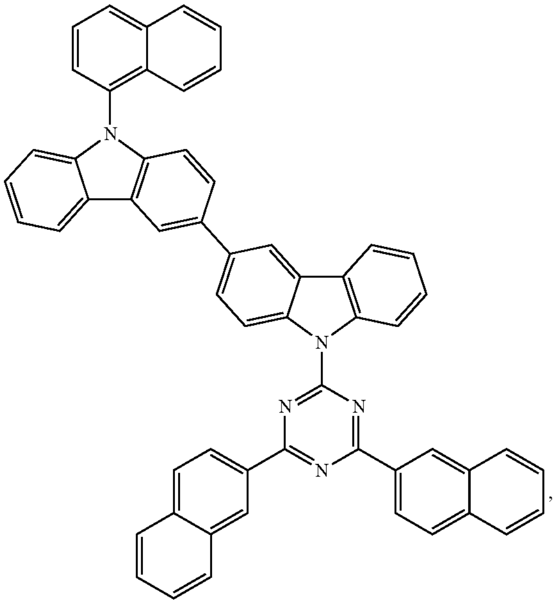
Compound 55
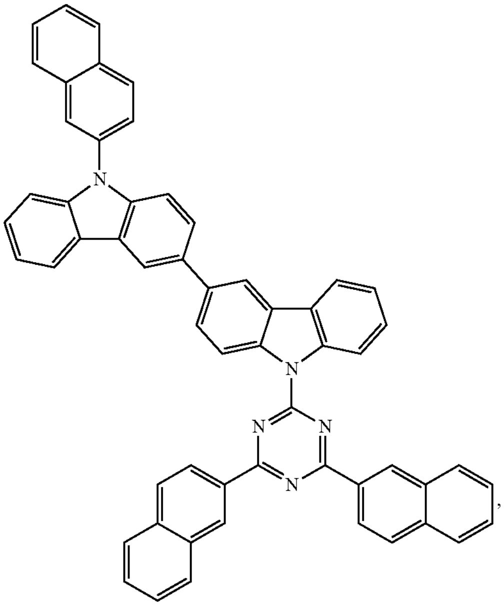

-continued
Compound 56
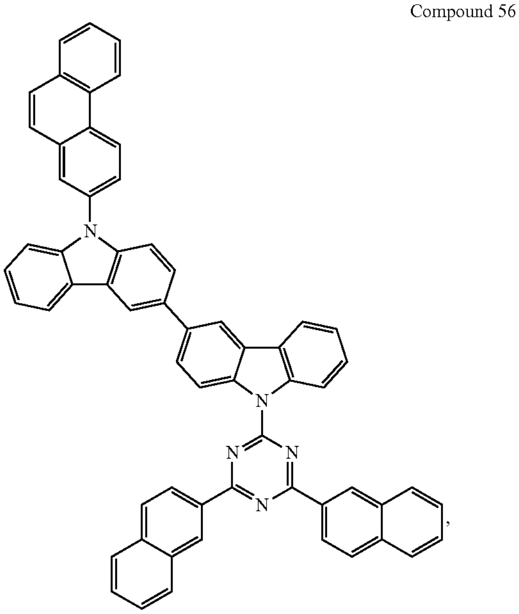
,
Compound 57
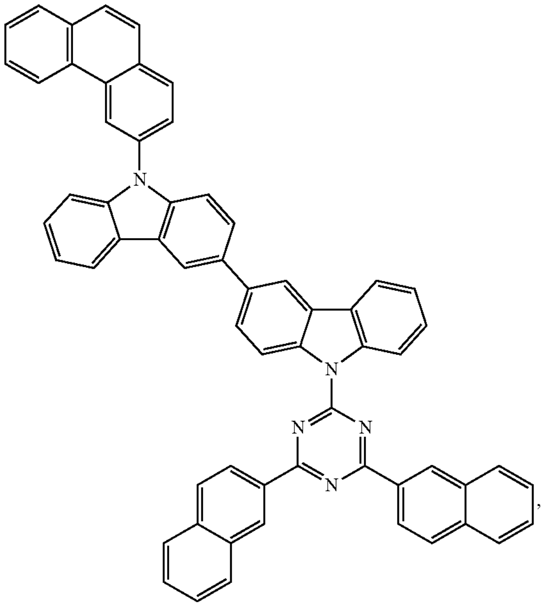
,
-continued
Compound 58
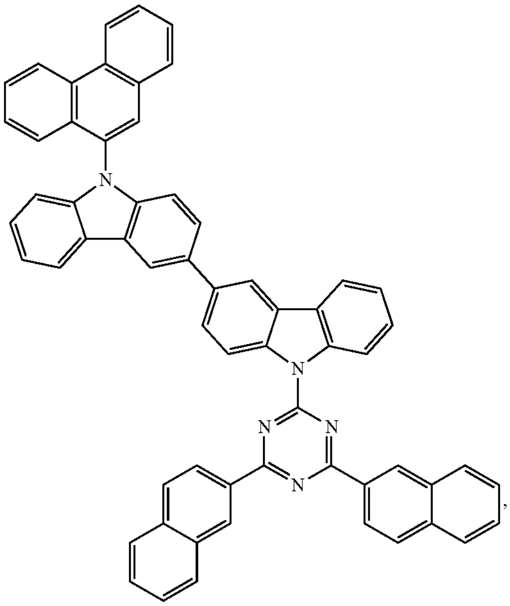
,
Compound 59
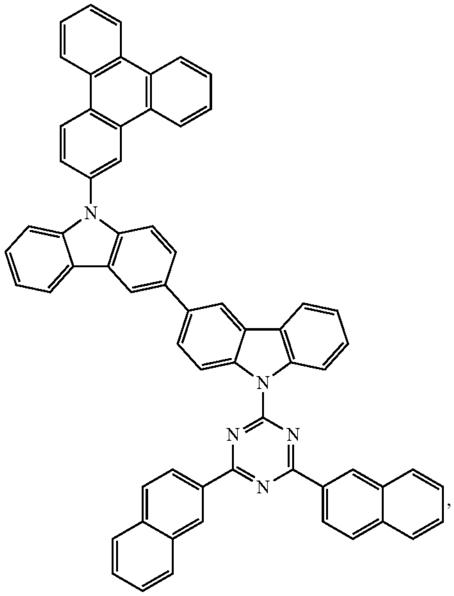
, -continued
Compound 60
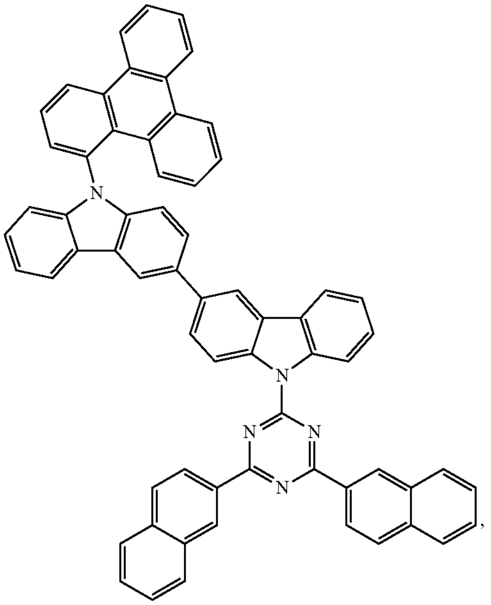
Compound 69
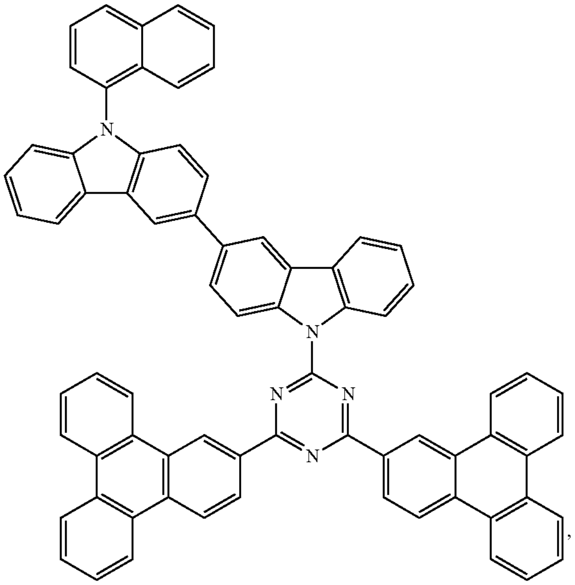
-continued
Compound 70
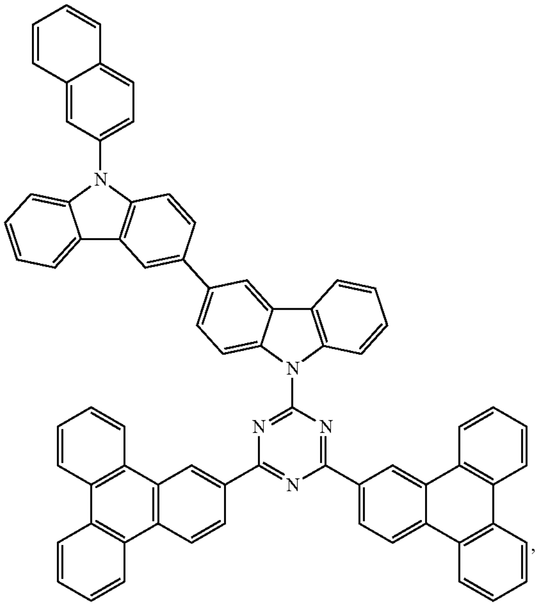
Compound 71
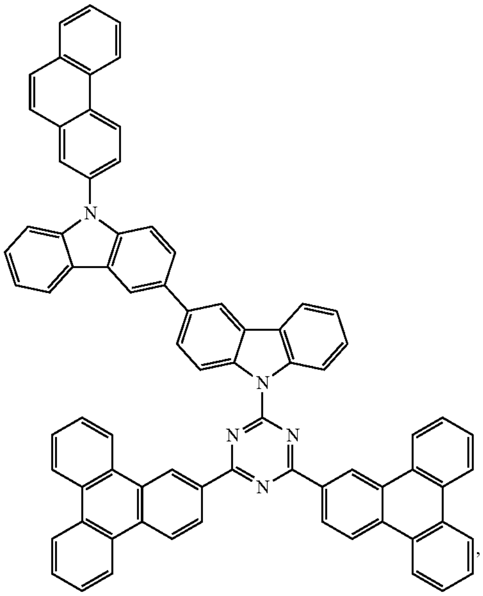

-continued
Compound 72
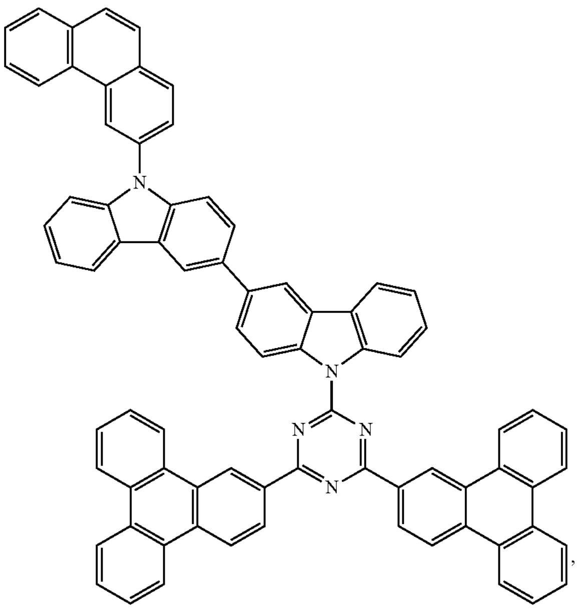
,
Compound 73
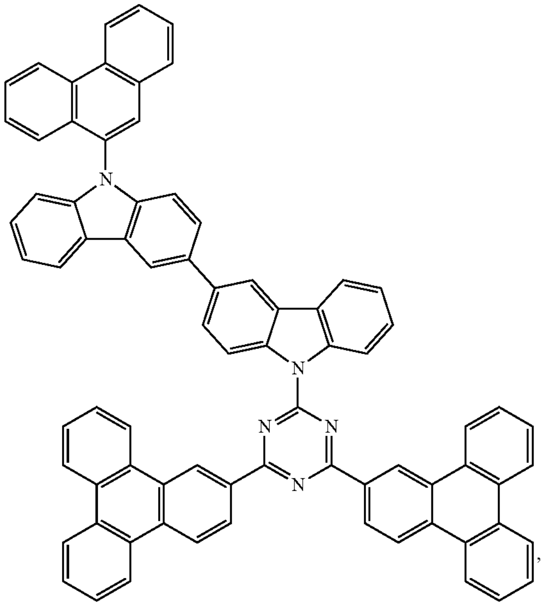
,
-continued
Compound 74
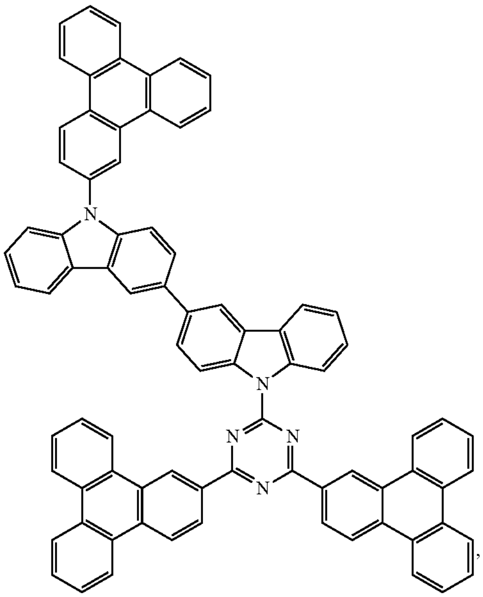
,
Compound 75
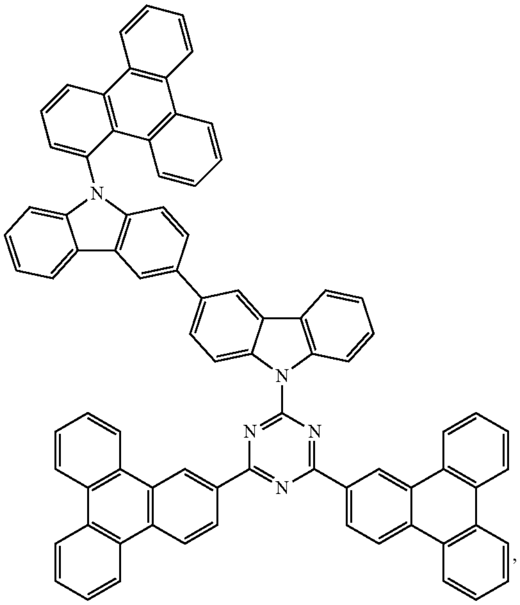
, -continued
Compound 84
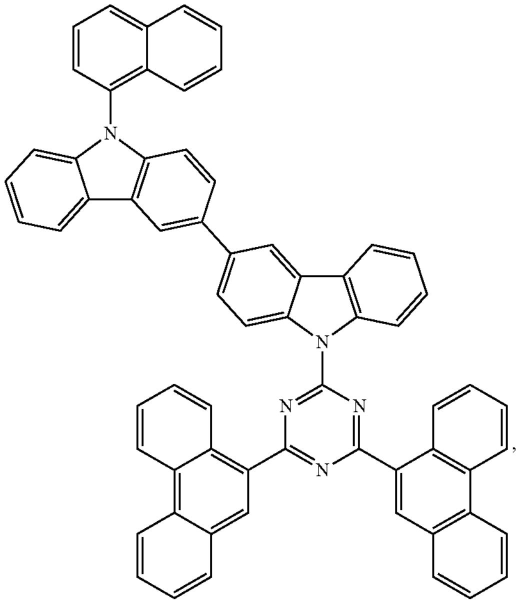
,
Compound 85
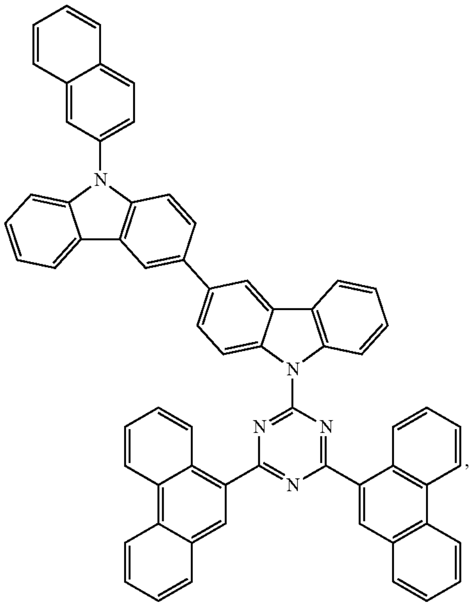
,
-continued
Compound 86
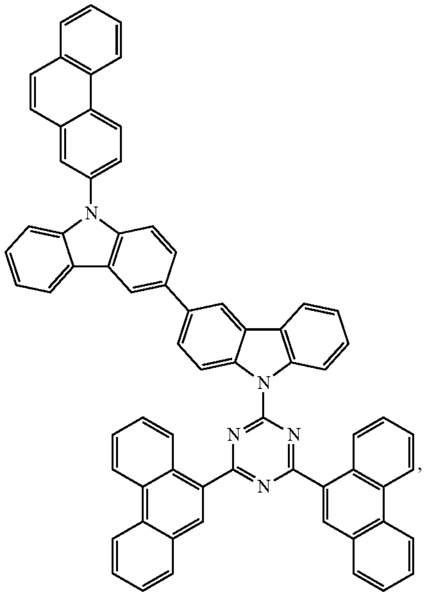
,
Compound 87
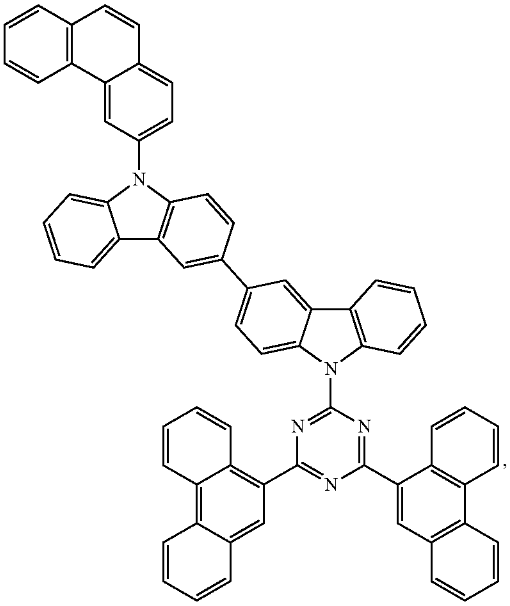
, -continued
Compound 88
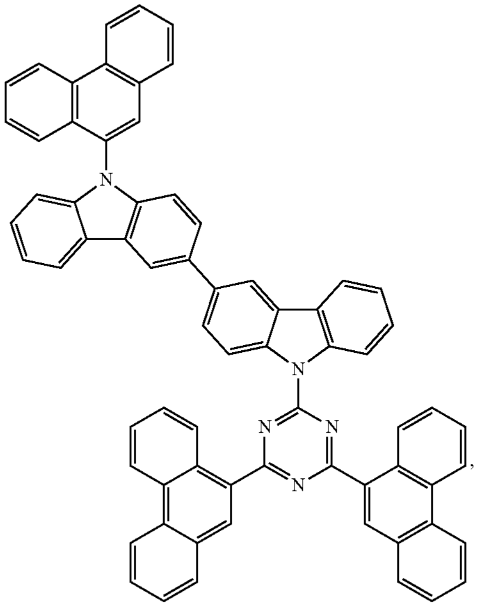
Compound 89
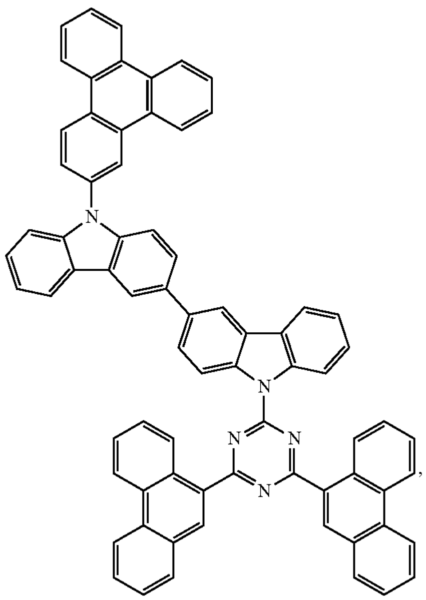
-continued
Compound 90
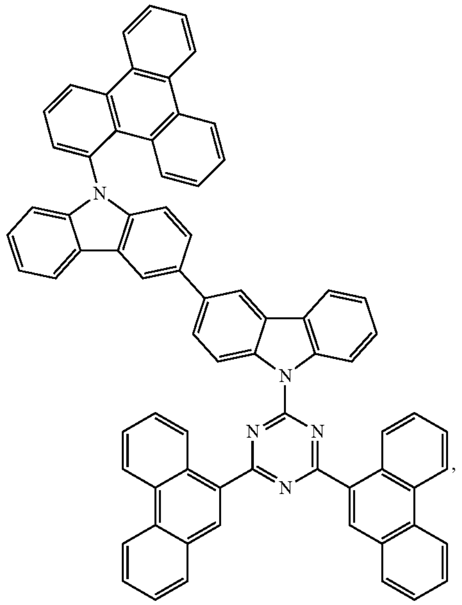
Compound 99
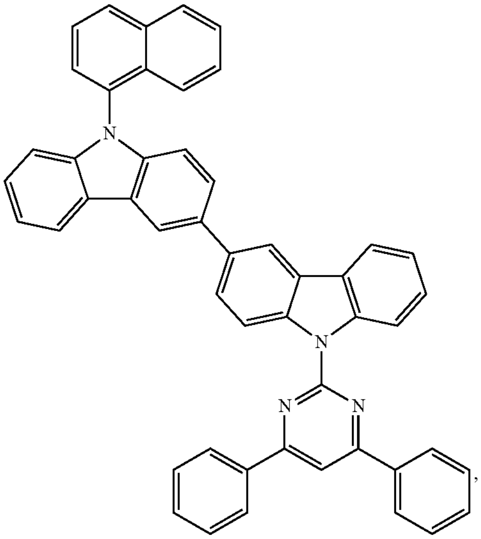

-continued
Compound 100
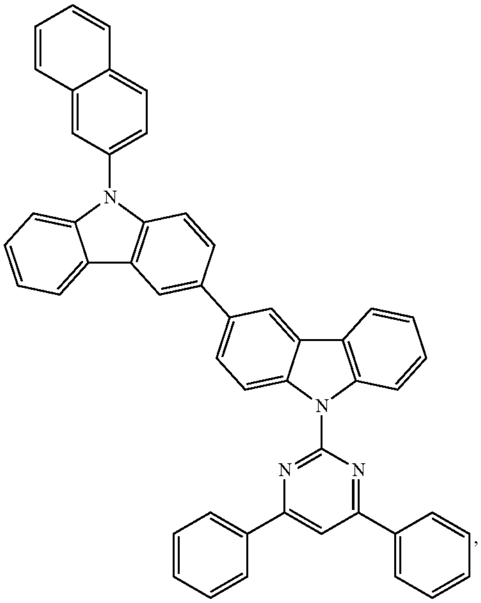
,
Compound 101
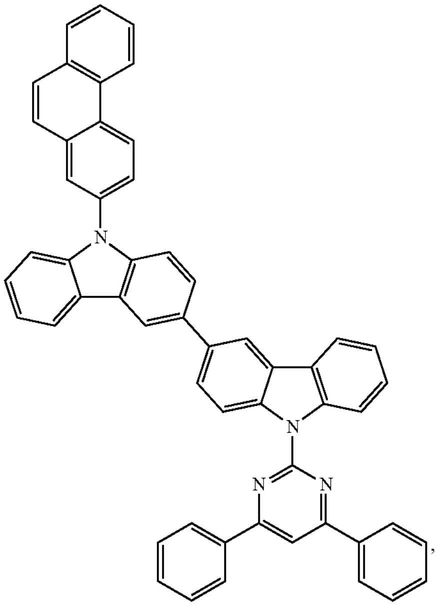
,
-continued
Compound 102
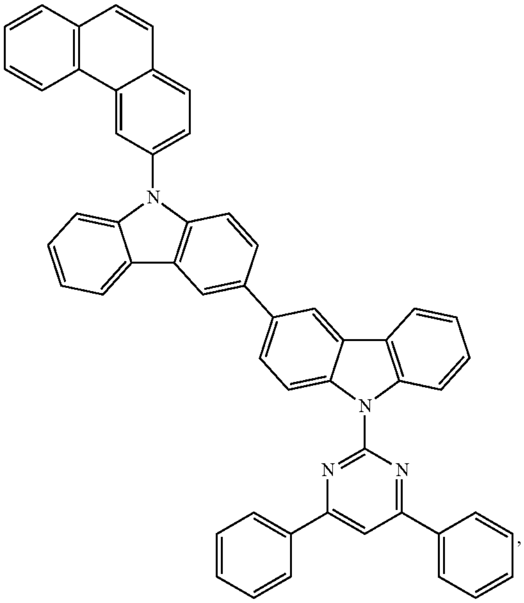
,
Compound 103
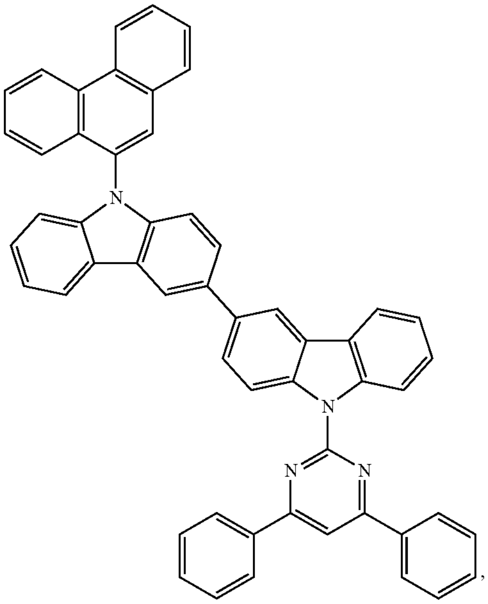
, -continued
Compound 104
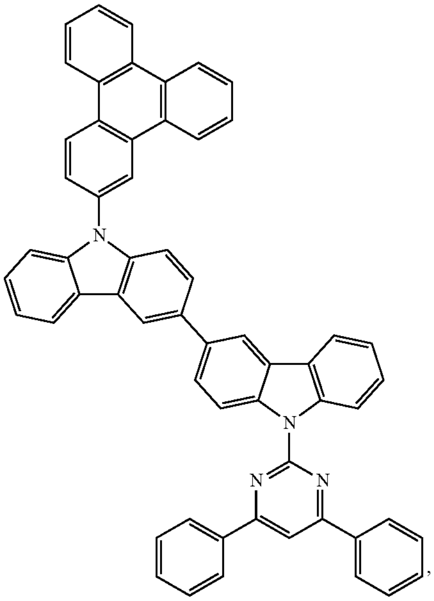
,
Compound 105
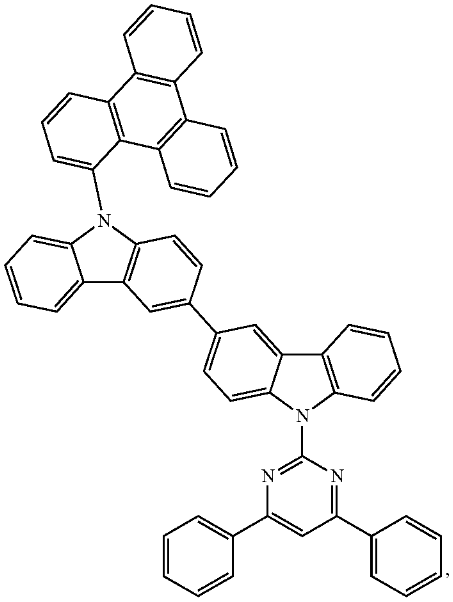
,
-continued
Compound 114
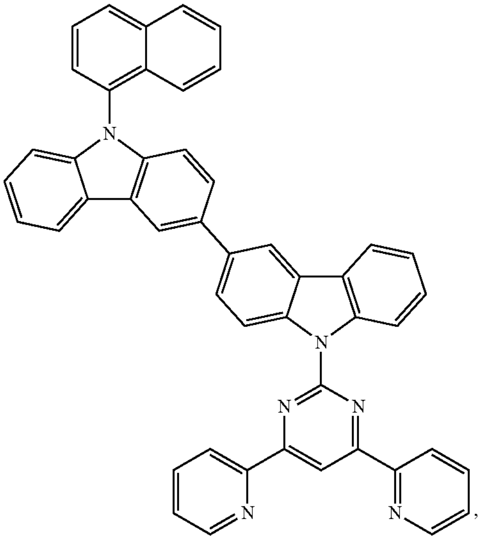
,
Compound 115
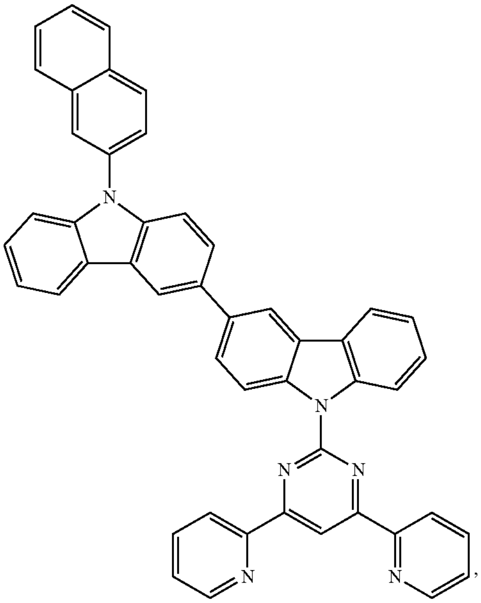
, -continued
Compound 116
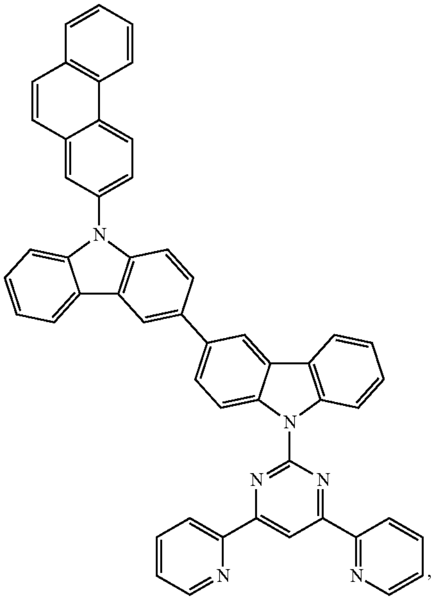
Compound 117
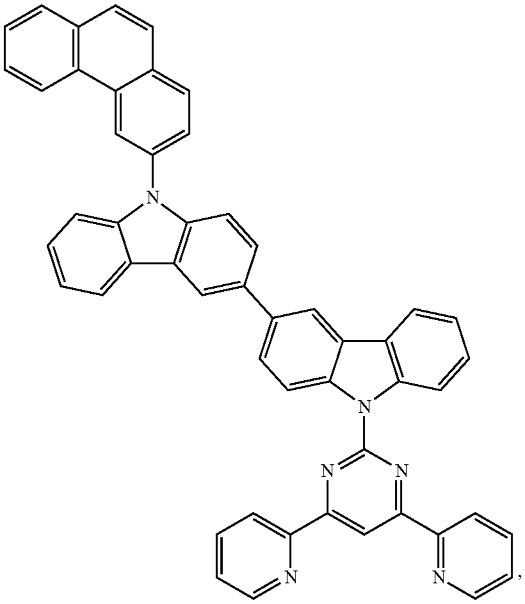
-continued
Compound 118
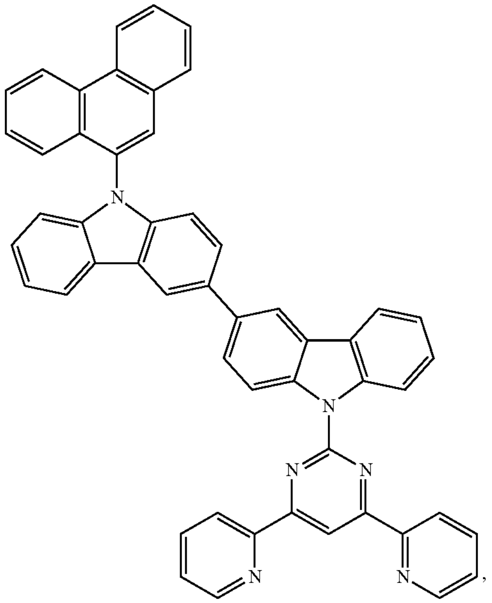
Compound 119
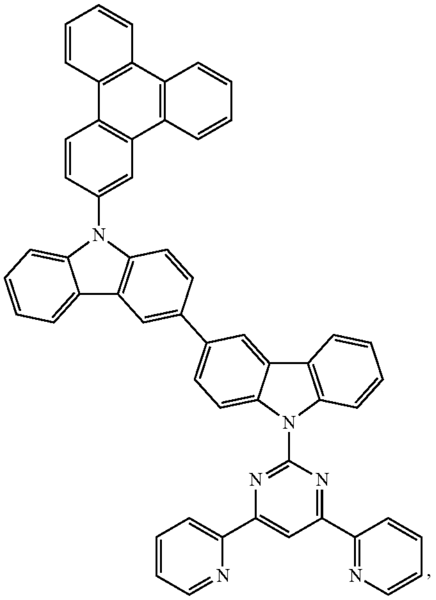

-continued
Compound 120
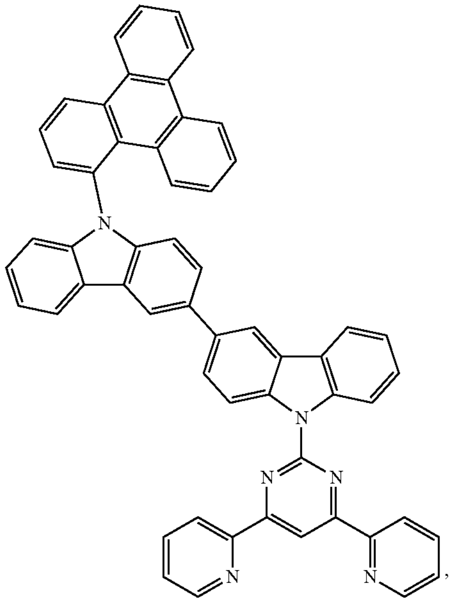
Compound 129
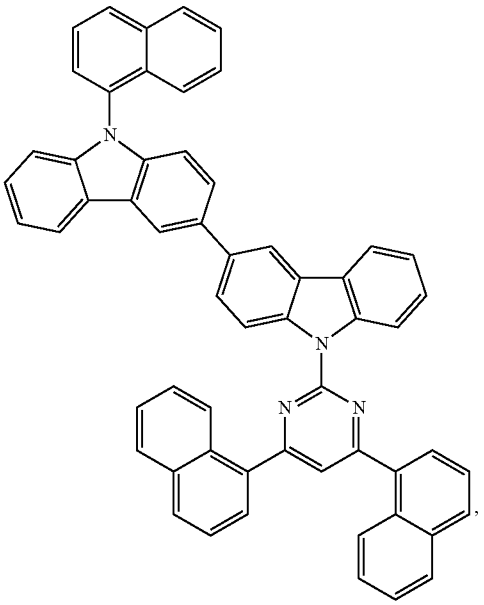
-continued
Compound 130
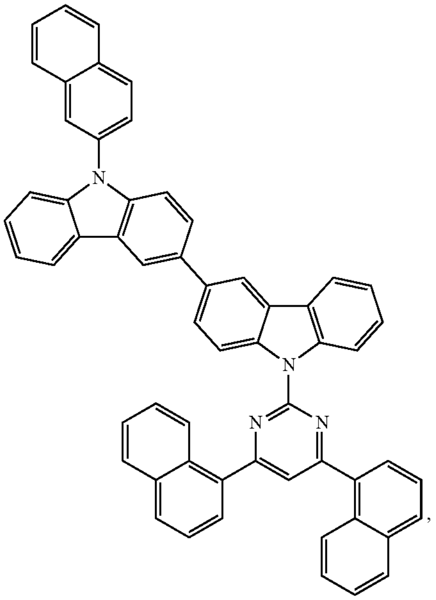
Compound 131
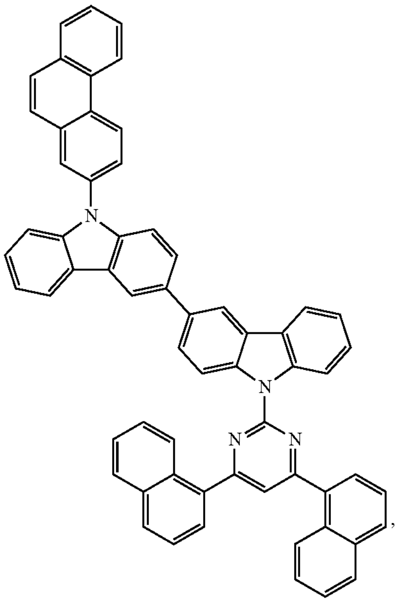

-continued
Compound 132
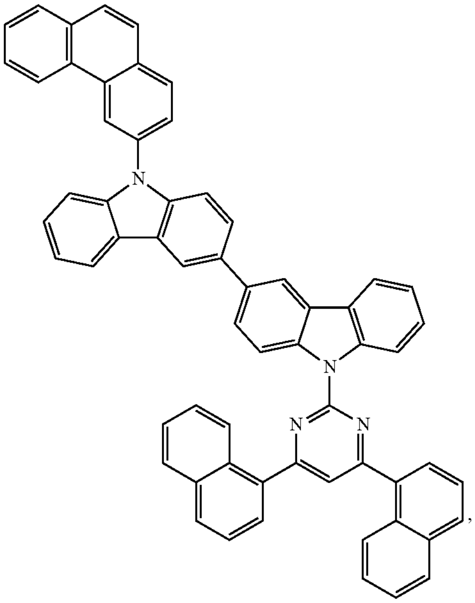
,
Compound 133
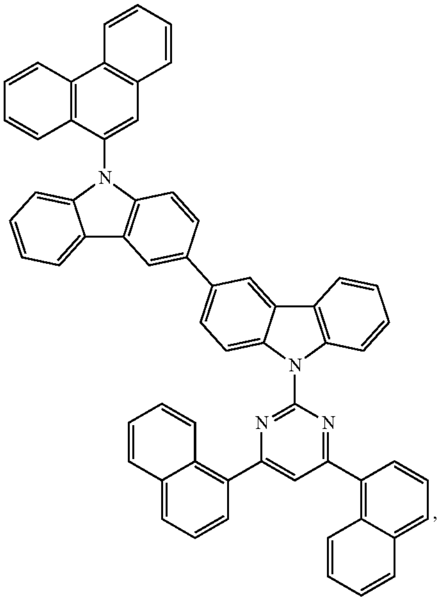
,
-continued
Compound 134
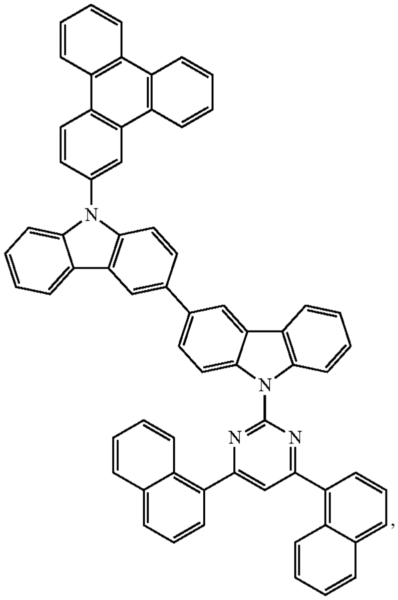
,
Compound 135
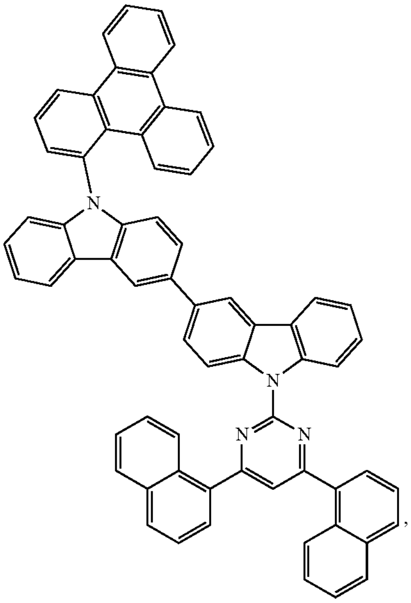
, -continued
Compound 144
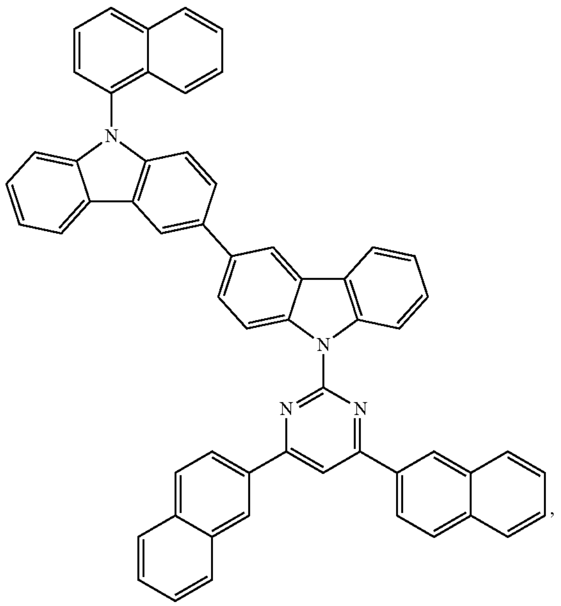
Compound 145
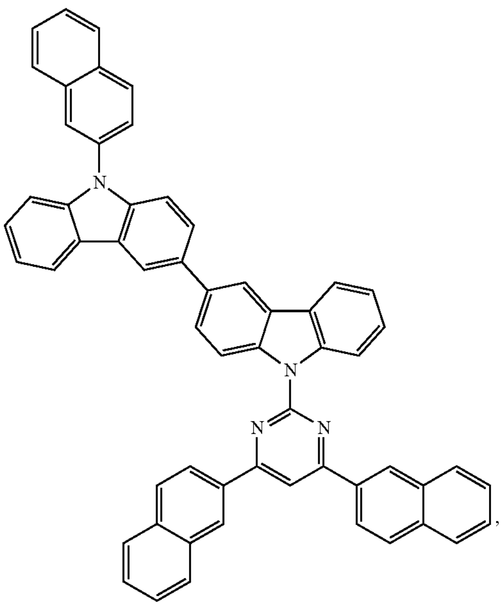
-continued
Compound 146
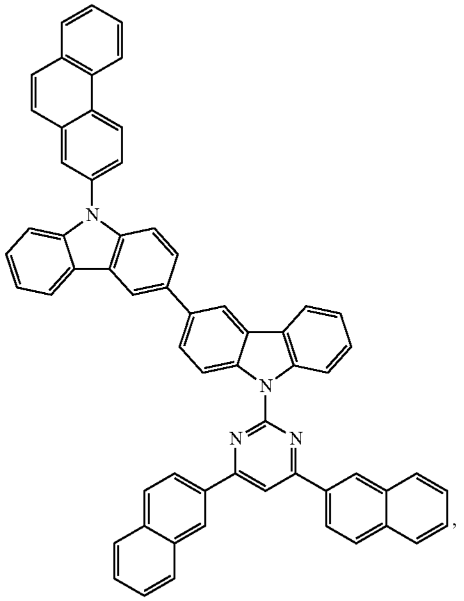
Compound 147
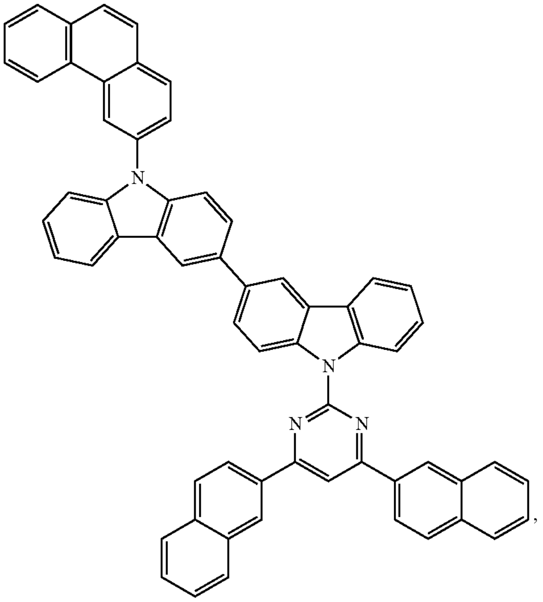

-continued
Compound 148
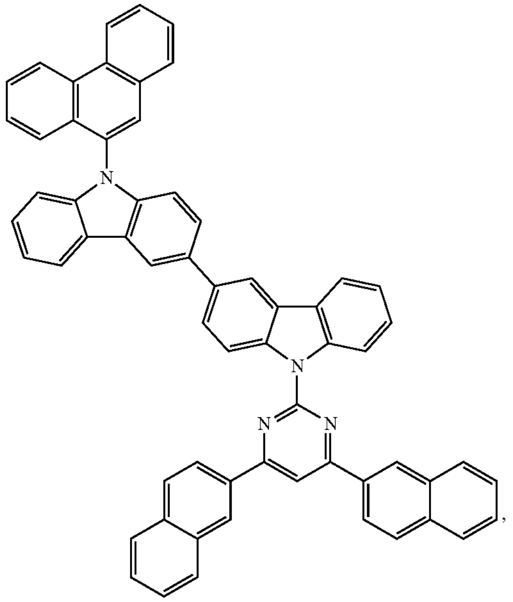
Compound 149
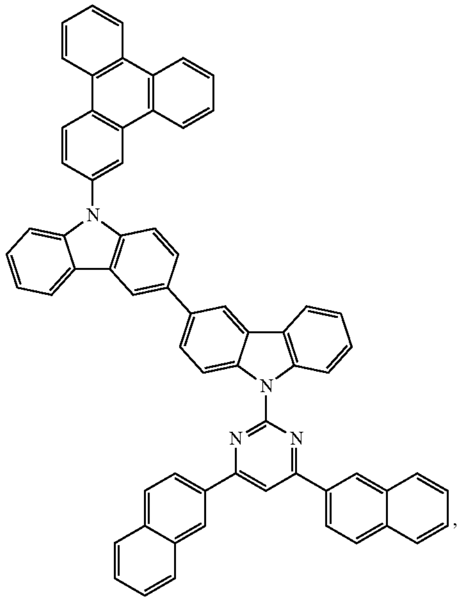
-continued
Compound 150
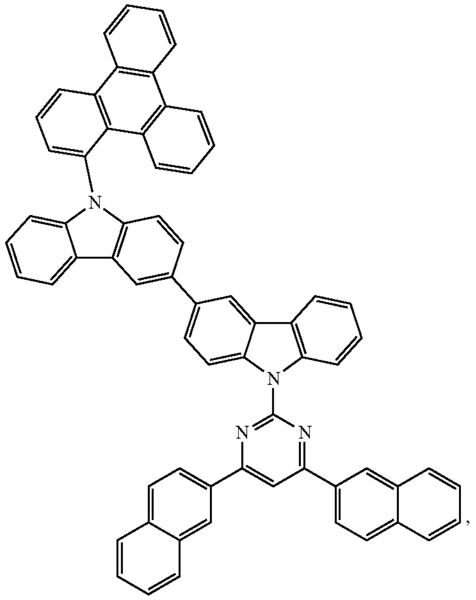
Compound 159
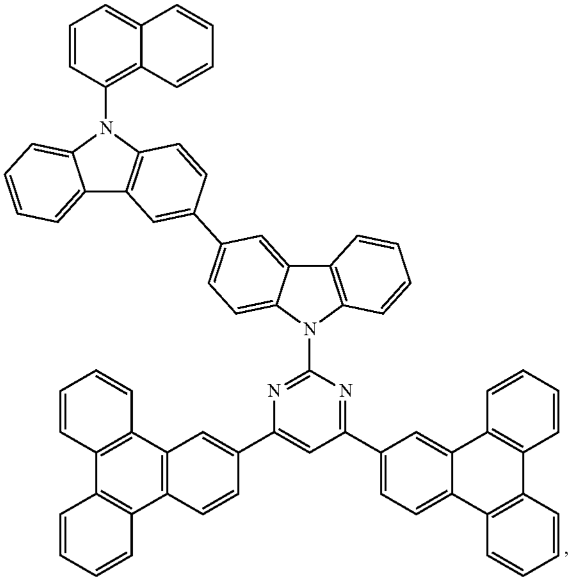

-continued
Compound 160
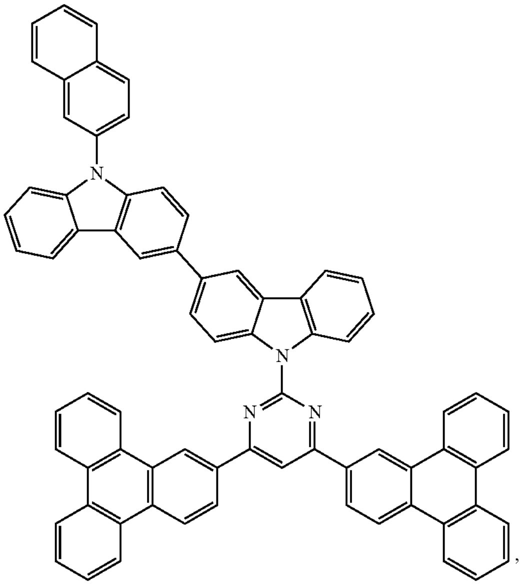
,
Compound 161
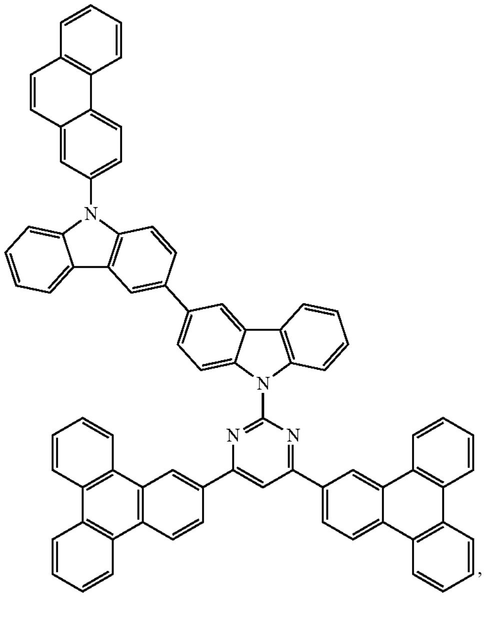
,
-continued
Compound 162
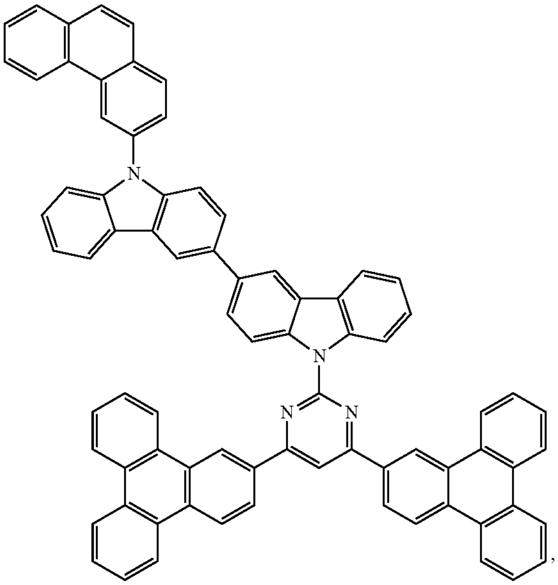
,
Compound 163
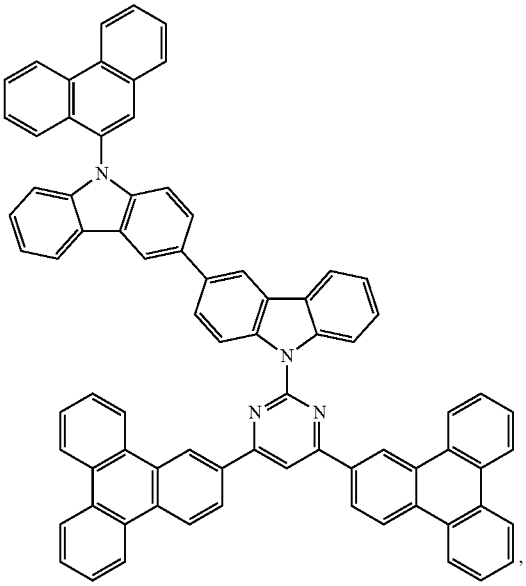
, -continued
Compound 164
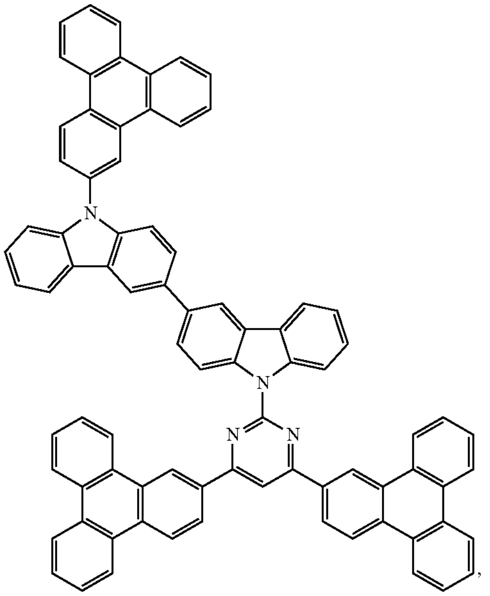
Compound 165
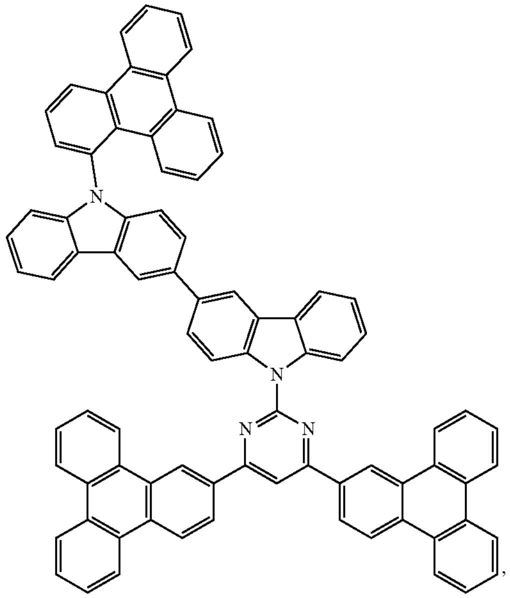
-continued
Compound 174
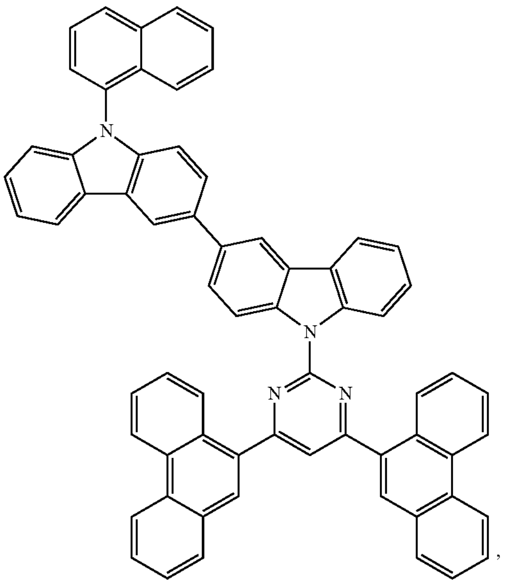
Compound 175
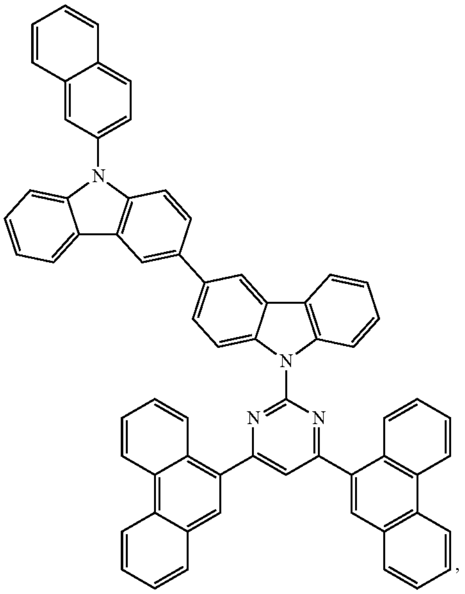

-continued
Compound 176
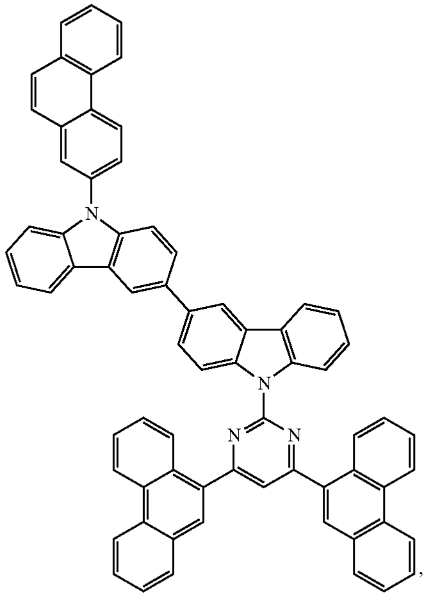
,
Compound 177
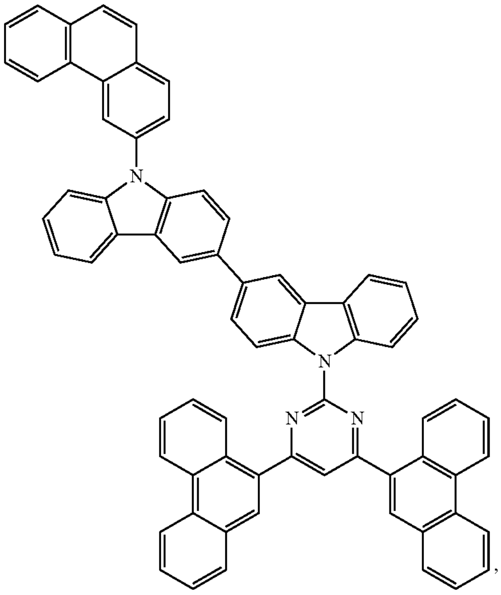
,
-continued
Compound 178
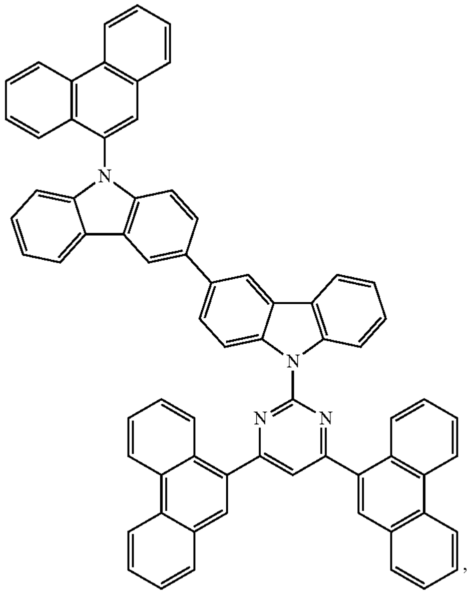
,
Compound 179
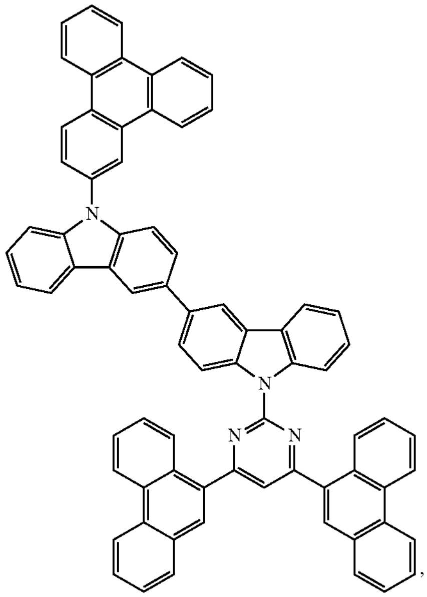
, and -continued Compound 180

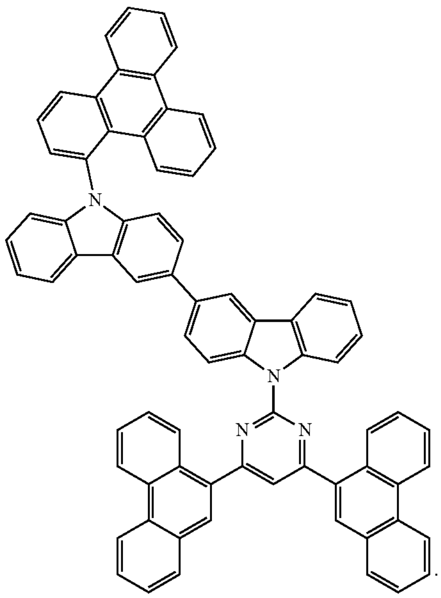

19. A consumer product comprising an organic light emitting device, the organic light emitting device comprising:

an anode;

a cathode; and an organic layer, disposed between the anode and the cathode, wherein the organic layer comprises a compound having the formula:

Formula I

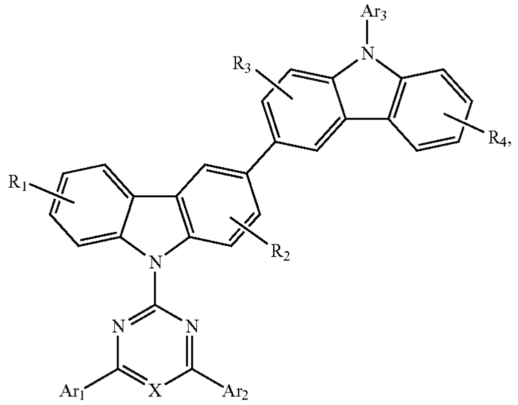

wherein $R_1$, $R_2$, $R_3$, and $R_4$ may represent mono, di, tri, or tetra substitutions;

wherein $R_1$, $R_Z$, $R_3$, and $R_4$ are independently selected from the group consisting of hydrogen, alkyl, alkoxy, amino, alkenyl, alkynyl, aryl and heteroaryl;

wherein $Ar_1$ and $Ar_2$ are independently selected from aryl or heteroaryl; and wherein X is C or N; and wherein $Ar_3$ is a polycyclic fused aryl system.

20. The consumer product of claim 19, wherein the consumer product is selected from the group consisting of flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a wall, theater or stadium screen, and a sign.

* * * * *